United States Patent
Granger et al.

(10) Patent No.: US 9,771,419 B2
(45) Date of Patent: *Sep. 26, 2017

(54) ANTAGONISTIC HUMAN LIGHT-SPECIFIC HUMAN MONOCLONAL ANTIBODIES

(71) Applicants: Kyowa Hakko Kirin Co., Limited, Tokyo (JP); La Jolla Institute for Allergy and Immunology, La Jolla, CA (US)

(72) Inventors: Steven W. Granger, Encinitas, CA (US); Shinichiro Kato, Chiba (JP); Carl F. Ware, Solana Beach, CA (US)

(73) Assignees: KYOWA HAKKO KIRIN CO., LIMITED, Tokyo (JP); LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 14/611,965

(22) Filed: Feb. 2, 2015

(65) Prior Publication Data

US 2015/0337046 A1    Nov. 26, 2015

Related U.S. Application Data

(63) Continuation of application No. 13/889,608, filed on May 8, 2013, now Pat. No. 8,974,787, which is a continuation of application No. 13/240,356, filed on Sep. 22, 2011, now Pat. No. 8,461,307, which is a continuation of application No. 12/439,518, filed as application No. PCT/US2007/018832 on Aug. 24, 2007, now Pat. No. 8,058,402.

(60) Provisional application No. 60/897,875, filed on Jan. 25, 2007, provisional application No. 60/840,774, filed on Aug. 28, 2006.

(51) Int. Cl.
| | |
|---|---|
| C07K 16/00 | (2006.01) |
| C07K 16/24 | (2006.01) |
| C07K 16/28 | (2006.01) |
| A61K 39/00 | (2006.01) |

(52) U.S. Cl.
CPC .......... *C07K 16/24* (2013.01); *C07K 16/2875* (2013.01); *A61K 2039/505* (2013.01); *C07K 2317/21* (2013.01); *C07K 2317/34* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,140,467 A | 10/2000 | Ware | |
| 6,235,878 B1 | 5/2001 | Nishi et al. | |
| 6,346,388 B1 | 2/2002 | Brigham-Burke et al. | |
| 6,479,254 B2 | 11/2002 | Ebner et al. | |
| 6,495,520 B2 | 12/2002 | Ebner et al. | |
| 6,590,090 B1 | 7/2003 | Nishi et al. | |
| 6,635,743 B1 | 10/2003 | Ebner et al. | |
| 6,998,108 B1 | 2/2006 | Ware | |
| 7,118,742 B2 | 10/2006 | Ware | |
| 7,541,441 B2 | 6/2009 | Rosen et al. | |
| 7,575,745 B2 | 8/2009 | Ware | |
| 8,058,402 B2 * | 11/2011 | Granger ............. | C07K 16/2875 530/387.3 |
| 8,461,307 B2 * | 6/2013 | Granger ............. | C07K 16/2875 530/387.3 |
| 8,974,787 B2 * | 3/2015 | Granger ............. | C07K 16/2875 424/133.1 |
| 2003/0060605 A1 | 3/2003 | Ware | |
| 2003/0215442 A1 | 11/2003 | Fraser et al. | |
| 2004/0009147 A1 | 1/2004 | Ebner et al. | |
| 2004/0038349 A1 | 2/2004 | Hilbert et al. | |
| 2004/0176320 A1 | 9/2004 | Natunen et al. | |
| 2005/0129614 A1 | 6/2005 | Rosen | |

(Continued)

FOREIGN PATENT DOCUMENTS

| | | |
|---|---|---|
| JP | 2004-515230 | 5/2004 |
| JP | 2005-517384 | 6/2005 |

(Continued)

OTHER PUBLICATIONS

George et al. (Circulation. 1998; 97: 900-906).*
Lippincott-Schwartz (Current Protocols in Cell Biology, 16.0.1-16.0.2, 2002).*
ABCAM—Product Information for Cat. No. ab17716—Rabbit Anti-LIGHT Polyclonal Antibody (Biotin) (2006).
ABCAM—Product Information for Cat. No. ab18881—Rabbit Anti-LIGHT Polyclonal Antibody (2006).
Abnova Corporation—Product Information for Cat. No. H00008740-M01—Mouse Monoclonal Anti-TNFSF14 (LIGHT), Clone 4E3 (2008).

(Continued)

*Primary Examiner* — Brad Duffy
(74) *Attorney, Agent, or Firm* — Wenderoth, Lind & Ponack, L.L.P.

(57) ABSTRACT

Provided herein are antibodies that immunospecifically bind to an hLIGHT polypeptide; isolated nucleic acids encoding the antibodies; vectors and host cells comprising nucleic acids encoding the antibodies; methods of making the antibodies; and a method of treating a hLIGHT-mediated disease in a subject comprising administering to the subject the antibodies. In preferred embodiments, the anti-hLIGHT antibodies provided herein will ameliorate, neutralize or otherwise inhibit hLIGHT biological activity in vivo (e.g., the hLIGHT-mediated production or secretion of CCL20, IL-8 or RANTES from a cell expressing a hLIGHT receptor). Also provided herein is a method for the detection of hLIGHT in a sample as well as a method for ameliorating, neutralizing or otherwise inhibiting hLIGHT activity, e.g., in a human subject suffering from a disorder in which hLIGHT activity is detrimental.

18 Claims, 41 Drawing Sheets

(56) References Cited

U.S. PATENT DOCUMENTS

| | | |
|---|---|---|
| 2005/0163747 A1 | 7/2005 | Hilbert et al. |
| 2005/0202462 A1 | 9/2005 | Matsui et al. |
| 2005/0287605 A1 | 12/2005 | Matsui et al. |

FOREIGN PATENT DOCUMENTS

| | | |
|---|---|---|
| RU | 2252786 C2 | 8/2004 |
| WO | WO 97/34911 | 9/1997 |
| WO | WO 98/03648 | 1/1998 |
| WO | WO 99/02563 | 1/1999 |
| WO | WO 99/35262 | 7/1999 |
| WO | WO 99/42584 | 8/1999 |
| WO | WO 00/71151 | 11/2000 |
| WO | WO 01/79496 | 10/2001 |
| WO | WO 02/20615 A2 | 3/2002 |
| WO | 02/43478 | 6/2002 |
| WO | WO 02/066050 | 8/2002 |
| WO | 03/016468 | 2/2003 |
| WO | 03/089579 | 10/2003 |
| WO | WO 03/089575 | 10/2003 |
| WO | WO 2006/063067 | 6/2006 |

OTHER PUBLICATIONS

Antigenix America Inc.—Product Information for Cat. No. RHF928—Anti-Human LIGHT Polyclonal Antibody, Unconjugated (2006).
Antigenix America Inc.—Product Information for Cat. No. RHF928B—Anti-Human Light Polyclonal Antibody, Biotin Conjugated (2006).
Banks et al., "Lymphotoxin-Alpha-Deficient Mice. Effects on Secondary Lymphoid Organ Development and Humoral Immune Responsiveness," *J Immunol.* 155(4):1685-1693 (1995).
Biolegend—Product Information for Cat. No. 318701/318702—Purified Anti-Human CD258 (LIGHT) (2007).
Biolegend—Product Information for Cat. No. 318703/318704—Biotin Anti-Human CD258 (LIGHT) (2007).
Biolegend—Product Information for Cat. No. 318705/318706—PE Anti-Human CD258 (LIGHT) (2007).
Biolegend—Product Information for Cat. No. 318801/318802—Purified anti-human HVEM (TR2) (2010).
Biovision—Product Information for Cat. No. 5607-100—Rabbit Anti-LIGHT Polyclonal Antibody, Unconjugated (2005).
Brown et al., "IL-12 Independent Light Signaling Enhances MHC Class II Disparate CD4+ T Cell Alloproliferation, IFN-γ Responses, and Intestinal Graft-versus-Host Disease," *J. Immunol.* 174:4688-4695 (2005).
Browning et al., "Characterization of Lymphotoxin-Alpha Beta Complexes on the Surface of Mouse Lymphocytes," *J Immunol.* 159(7):3288-3298 (1997).
Bruggermann et al., "Designer Mice: the Production of Human Antibody Repertoires in Transgenic Animals," *Year Immunol.* 7:33-40 (1993).
Castellano et al., "Mechanisms Regulating Expression of the Tumor Necrosis Factor-Related Light Gene. Role of Calcium-Signaling Pathway in the Transcriptional Control," *J Biol Chem.* 277(45):42841-42851 (2002).
Cheung et al., "Evolutionarily Divergent Herpesviruses Modulate T Cell Activation by Targeting the Herpesvirus Entry Mediator Cosignaling Pathway," *Proc Natl Acad Sci U S A* 102(37):13218-13223 (2005).
Clark and Ledbetter "How B and T Cells Talk to Each Other," *Nature* 367(6462):425-428 (1994).
Clark et al., "Cultured Human Follicular Dendritic Cells. Growth Characteristics and Interactions with B Lymphocytes," *J Immunol.* 148(11):3327-3335 (1992).
Cohavy et al., "LIGHT Expression by Mucosal T Cells May Regulate IFN-γ Expression in the Intestine," *J. Immunol.* 173:251-258 (2004).
Cohavy et al., "LIGHT is Constitutively Expressed on T and NK Cells in the Human Gut and Can Be Induced by CD2-Mediated Signaling," *J. Immunol.* 174:646-653 (2005).
Crowe et al., "A Lymphotoxin-Beta-Specific Receptor," *Science* 264(5159):707-710 (1994).
De Togni et al., "Abnormal Development of Peripheral Lymphoid Organs in Mice Deficient in Lymphotoxin," *Science.* 264(5159):703-707 (1994).
Dohi et al., "Elimination of Colonic Patches with Lymphotoxin Beta Receptor-Ig Prevents Th2 Cell-Type Colitis," *J Immunol.* 167(5):2781-2790 (2001).
eBIOSCIENCE—Product Information for Cat. No. 14-6969—Affinity Purified Rabbit anti-Human LIGHT Polyclonal Antibody (2006).
Fava et al., "A Role for the Lymphotoxin/LIGHT Axis in the Pathogenesis of Murine Collagen-Induced Arthritis," *J. Immunol.* 171(1):115-126 (2003).
Forster et al., "A putative Chemokine Receptor, BLR1, Directs B Cell Migration to Defined Lymphoid Organs and Specific Anatomic Compartments of the Spleen," *Cell* 87(6):1037-1047 (1996).
Gommerman et al., "A Role for Surface Lymphotoxin in Experimental Autoimmune Encephalomyelitis Independent of LIGHT," *J. Clin. Invest.* 112(5):755-767 (2003).
Granger and Ware, "Turning on LIGHT," *J. Clin. Invest.* 108(12):1741-1742 (2001).
Granger et al., "Genomic Characterization of LIGHT Reveals Linkage to an Immune Response Locus on Chromosome 19p13.3 and Distinct Isoforms Generated by Alternate Splicing or Proteolysis," *J. Immunol.* 167(9):5122-5128 (2001).
Guo et al., "Cutting Edge: Membrane Lymphotoxin Regulates CD8(+) T Cell-Mediated Intestinal Allograft Rejection," *J. Immunol.* 167(9):4796-4800 (2001).
Hsu et al., "Attenuation of Th1 Response in Decoy Receptor 3 Transgenic Mice," *J. Immunol.* 175(8):5135-5145 (2005).
Jakobovits et al., "Analysis of homozygous mutant chimeric mice: deletion of the immunoglobulin heavy-chain joining region blocks B-cell development and antibody production," *Proc Natl Acad Sci U S A* 15;90(6):2551-2555 (1993).
Karre, "Immunology. A Perfect Mismatch," *Science* 295(5562):2029-2031 (2002).
Kunkel et al., "Chemokines in Lymphocyte Trafficking and Intestinal Immunity," *Microcirculation* 10(3-4):313-323 (2003).
Kwon et al., "Colonic Epithelial Cells Are a Major Site of Macrophage Inflammatory Protein 3alpha (MIP-3alpha) Production in Normal Colon and Inflammatory Bowel Disease," *Gut* 51(6):818-826 (2002).
Lama and Ware, "Human Immunodeficiency Virus Type 1 Nef Mediates Sustained Membrane Expression of Tumor Necrosis Factor and the Related Cytokine LIGHT on Activated T Cells," *J. Virol.* 74(20):9396-9402 (2000).
Liu et al., "LIGHT-Deficiency Impairs CD8+ T Cell Expansion, But Not Effector Function," *Int. Immunol.* 15(7):861-870 (2003).
Low et al., "Inflammatory Bowel Disease Is Linked to 19p13 and Associated with ICAM-1," *Inflamm Bowel Dis.* 10(3):173-181 (2004).
Lugering et al., "Lymphoid Precursors in Intestinal Cryptopatches Express CCR6 and Undergo Dysregulated Development in the Absence of CCR6," *J Immunol.* 171(5):2208-2215 (2003).
Mähler et al., "Differential Susceptibility of Inbred Mouse Strains to Dextran Sulfate Sodium-Induced Colitis," *Am. J. Physiol.* 274(3 Pt 1):G544-G551 (1998).
Matsui et al., "LIGHT, a Member of the Tumor Necrosis Factor Ligand Superfamily, Prevents Tumor Necrosis Factor-α-Mediated Human Primary Hepatocyte Apoptosis, But Not Fas-Mediated Apoptosis," *J. Biol. Chem.* 277(51):50054-50061 (2002).
Matsumoto et al., "Role of Lymphotoxin and the Type I TNF Receptor in the Formation of Germinal Centers," *Science* 271(5253):1289-1291 (1996).
Montgomery et al.," Herpes Simplex virus-1 Entry into Cells Mediated by a Novel Member of the TNF/NGF Receptor Family" *Cell* 87(3):427-436 (1996).
Morrissey et al., "CD4+ T Cells That Express High Levels of CD45RB Induce Wasting Disease When Transferred into Congenic

(56) References Cited

OTHER PUBLICATIONS

Severe Combined Immunodeficient Mice. Disease Development Is Prevented by Cotransfer of Purified CD4+ T Cells," *J. Exp. Med.* 178(1):237-244 (1993).
Neurath et al., "Antibodies to Interleukin 12 Abrogate Established Experimental Colitis in Mice," *J. Exp. Med.* 182(5):1281-1290 (1995).
Novus Biologicals—Product Information for Cat. No. ab17716—Rabbit Anti-LIGHT Polyclonal Antibody, Unconjugated (2006).
Novus Biologicals—Product Information for Cat. No. H00008740-M01—Mouse Monoclonal Anti-TNFSF14 (LIGHT) (2006).
Otterdal et al., "Platelet-Derived Light Induces Inflammatory Responses in Endothelial Cells and Monocytes," Blood 108(3):928-935 (2006).
Peprotech—Product Information for Cat. No. 315-12—Recombinant Murine LIGHT (2006).
Peprotech—Product Information for Cat. No. 500-P179—Rabbit Polyclonal Anti-human LIGHT (2006).
Peprotech—Product Information for Cat. No. 500-P179Bt—Biotinylated Rabbit Polyclonal Anti-human LIGHT (2006).
Pulendran et al., "Immunological Tolerance in Germinal Centres," *Immunol Today* 18(1):27-32 (1997).
Puleston et al., "A Distinct Subset of Chemokines Dominates the Mucosal Chemokine Response in Inflammatory Bowel Disease," *Aliment. Pharmacol.Ther.* 21(2):109-120 (2005).
R&D Systems—Product Information for Cat. No. 1794-LT—Recombinant Mouse LIGHT/TNFSF14 (2004).
R&D Systems—Product Information for Cat. No. 1794-LT/CF—Recombinant Mouse LIGHT/TNFSF14 (Carrier Free) (2004).
R&D Systems—Product Information for Cat. No. 664-LI—Recombinant Human LIGHT/TNFSF14 (2005).
R&D Systems—Product Information for Cat. No. 664—LI/CF Recombinant Human LIGHT/TNFSF14 (Carrier Free) (2000).
R&D Systems—Product Information for Cat. No. AF1794—Goat Anti-mouse LIGHT/TNFSF14 Antibody (2004).
R&D Systems—Product Information for Cat. No. AF664—Goat Anti-human LIGHT/TNFSF14 Antibody (2005).
R&D Systems—Product Information for Cat. No. BAF1794—Biotinylated Goat Anti-mouse LIGHT/TNFSF14 Antibody (2004).
R&D Systems—Product Information for Cat. No. BAF664—Biotinylated Goat Anti-human LIGHT/TNFSF14 Antibody (2001).
R&D Systems—Product Information for Cat. No. DLITOO—Human LIGHT/TNFSF14 Quantikine ELISA Kit (2002).
R&D Systems—Product Information for Cat. No. DY664—Human LIGHT/TNFSF14 DuoSetELISA Development Kit (2006).
R&D Systems—Product Information for Cat. No. FAB664A—Mouse Monoclonal Anti-human LIGHT/TNFSF14/CD258—Allophycocyanin Antibody (2005).
R&D Systems—Product Information for Cat. No. FAB664P—Mouse Monoclonal Anti-human LIGHT/TNFSF14/CD258-Phycoerythrin Antibody (2005).
R&D Systems—Product Information for Cat. No. MAB1794—Rat Monoclonal Anti-Mouse LIGHT/TNFSF14 Antibody (2005).
R&D Systems—Product Information for Cat. No. MAB664—Mouse Monoclonal Anti-Human Light/TNFSF14 Antibody (2004).
R&D Systems—Product Information for Cat. No. RDP-122-025—human LIGHT/TNFSF14 PCR Primer Pair (2001).
Rioux et al., "Genomewide Search in Canadian Families with Inflammatory Bowel Disease Reveals Two Novel Susceptibility Loci," *Am J Hum Genet.* 66(6):1863-1870 (2000).
Rooney et al., "The Lymphotoxin-Beta Receptor Is Necessary and Sufficient for LIGHT-Mediated Apoptosis of Tumor Cells," *J. Biol. Chem.* 275(19):14307-14315 (2000).
Santa Cruz Biotechnology, Inc.—Product Information for Cat. No. sc-34119—Goat Polyclonal Antihuman Light, clone A-20 (2008).
Santa Cruz Biotechnology, Inc.—Product Information for Cat. No. sc-7767—Goat Polyclonal Antihuman Light, clone C-20 (2008).
Santa Cruz Biotechnology, Inc.—Product Information for Cat. No. sc-34117—Goat Polyclonal Antihuman Light, clone E-13 (2008).
Santa Cruz Biotechnology, Inc.—Product Information for Cat. No. sc-28880—Rabbit Polyclonal Anti-human LIGHT, clone FL-240 (2008).
Santa Cruz Biotechnology, Inc.—Product Information for Cat. No. sc-34120—Goat Polyclonal Anti-human LIGHT, clone 1-12 (2008).
Santa Cruz Biotechnology, Inc.—Product Information for Cat. No. sc-80161—Mouse Monoclonal Anti-human LIGHT, clone JQ07 (2008).
Santa Cruz Biotechnology, Inc.—Product Information for Cat. No. sc-7768—Goat Polyclonal Anti-human LIGHT, clone N-19 (2008).
Santa Cruz Biotechnology, Inc.—Product Information for Cat. No. sc-57350—Rat Monoclonal Anti-human LIGHT, clone Laury-1 (2008).
Santa Cruz Biotechnology, Inc.—Product Information for Cat. No. sc-22707—Goat Polyclonal Antihuman LIGHT, clone P-18 (2008).
Santa Cruz Biotechnology, Inc.—Product Information for Cat. No. sc-73397—Mouse Monoclonal Anti-human Light, clone T5-39 (2008).
Sarrias et al., "Inhibition of Herpes Simplex Virus gD and Lymphotoxin-α Binding to HveA by Peptide Antagonists," *J. Virol.* 73(7):5681-5687 (1999).
Shaikh et al., "Constitutive Expression of Light on T Cells Leads to Lymphocyte Activation, Inflammation, and Tissue Destruction," J. Immunol. 167(11):6330-6337 (2001).
Shi et al., "Death Decoy Receptor TR6/DcR3 Inhibits T Cell Chemotaxis In Vitro and In Vivo," *J. Immunol.* 171(7):3407-3414 (2003).
Stopfer et al., "Blocking Lymphotoxin-Beta Receptor Activation Diminishes Inflammation via Reduced Mucosal Addressin Cell Adhesion Molecule-1 (MAdCAM-1) Expression and Leucocyte Margination in Chronic DSS-Induced Colitis," *Clin Exp Immunol.* 136(1):21-29 (2004).
Stopfer et al., "Lymphotoxin-β Receptor Activation by Activated T Cells Induces Cytokine Release from Mouse Bone Marrow-Derived Mast Cells," *J. Immunol.* 172(12):7459-7465 (2004).
Tamada et al., "Blockade of LIGHT/Ltβ and CD40 Signaling Induces Allospecific T Cell Anergy, Preventing Graft-versus-Host Disease," *J. Clin. Invest.* 109(4):549-557 (2002).
Tamada et al., "Cutting Edge: Selective Impairment of CD8+0 T Cell Function in Mice Lacking the TNF Superfamily Member LIGHT," *J. Immunol.* 168(10):4832-4835 (2002).
Tamada et al., "LIGHT, a TNF-Like Molecule, Costimulates T Cell Proliferation and Is Required for Dendritic Cell-Mediated Allogeneic T Cell Response," *J Immunol* 164(8):4105-4110 (2000).
Varona et al., "CCR6 Has a Non-Redundant Role in the Development of Inflammatory Bowel Disease," *Eur J Immunol.* 33(10):2937-2946 (2003).
Wan et al., "A TNF Family Member LIGHT Transduces Costimulatory Signals into Human T Cells," *J. Immunol.* 169(12):6813-6821 (2002).
Wang and Fu et al., "LIGHT (a Cellular Ligand for Herpes Virus Entry Mediator and Lymphotoxin Receptor)-Mediated Thymocyte Deletion Is Dependent on the Interaction between TCR and MHC/Self-Peptide," *J. Immunol.* 170(8):3986-3993 (2003).
Wang and Fu, "Tumor Necrosis Factor Family Members and Inflammatory Bowel Disease," *Immunol. Rev.* 204:144-155 (2005).
Wang et al., "Dysregulated LIGHT Expression on T Cells Mediates Intestinal Inflammation and Contributes to IgA Nephropathy," *J. Clin. Invest.* 113(6):826-835 (2004).
Wang et al., "Stimulating Lymphotoxin β Receptor on the Dendritic Cells Is Critical for Their Homeostasis and Expansion," *J. Immunol.* 175(10):6997-7002 (2005).
Wang et al., "The Critical Role of LIGHT in Promoting Intestinal Inflammation and Crohn's Disease," *J. Immunol.* 174(12):8173-8182 (2005).
Wang et al., "The Critical Role of LIGHT, a TNF Family Member, in T Cell Development," *J Immunol.* 167(9):5099-5105 (2001).
Wang et al., "The Regulation of T Cell Homeostasis and Autoimmunity by T cell-Derived LIGHT," *J. Clin. Invest.* 108(12):1771-1780 (2001).
Wang et al., "The Role of Herpesvirus Entry Mediator as a Negative Regulator of T Cell-Mediated Responses," *J. Clin. Invest.* 115(3):711-717 (2005).

(56) References Cited

OTHER PUBLICATIONS

Watanabe et al., "CD52 Is a Novel Costimulatory Molecule for Induction of CD4+ Regulatory T Cells," *Clin Immunol.* 120(3):247-259 (2006).
Watts and Gommerman, "The LIGHT and DARC Sides of Herpesvirus Entry Mediator," *Proc. Natl. Acad. Sci. USA* 102(38):13365-13366 (2005).
Written Opinion of the International Searching Authority for PCT/US2007/018832 mailed Mar. 12, 2009.
Xu et al., "Selective Targeting of the LIGHT-HVEM Costimulatory System for the Treatment of Graft-Versus-Host Disease," *Blood* 109(9):4097-4104 (2007).
Yu et al., "A Newly Identified Member of Tumor Necrosis Factor Receptor Superfamily (TR6) Suppresses LIGHT-Mediated Apoptosis," *J Biol Chem.* 274(20):13733-13736 (1999).
An et al., "Lymphotoxin β Receptor-Ig Ameliorates TNBS-Induced Colitis via Blocking LIGHT/HVEM Signaling," *Pharmacol. Res.* 52(3):234-244 (2005).
Bonen and Cho "The Genetics of Inflammatory Bowel Disease," *Gastroenterology* 124(2):521-536 (2003).
Fishwild et al., "High-Avidity Human IgG kappa Monoclonal Antibodies from a Novel Strain of Minilocus Transgenic Mice," Nat Biotechnol. 14(7):845-851 (1996).
Ishida et al., "Production of Human Monoclonal and Polyclonal Antibodies in TransChromo Animals," Cloning Stem Cells 4(1):91-102 (2002).
Kang et al., "Signaling via LTbetaR on the lamina propria stromal cells of the gut is required for IgA production," *Nat Immunol.* 3(6):576-582 (2002).
Kaser et al., "Increased Expression of CCL20 in Human Inflammatory Bowel Disease," *J. Clin. Immunol.* 24(1):74-85 (2004).
Kosuge et al., "Attenuation of Graft Arterial Disease by Manipulation of the LIGHT Pathway," *Arterioscler. Thromb. Vasc. Biol.* 24(8):1409-1415 (2004).
MacKay et al., "Both the Lymphotoxin and Tumor Necrosis Factor Pathways Are Involved in Experimental Murine Models of Colitis," *Gastroenterology* 115(6):1464-1475 (1998).
Marks et al., "By-Passing Immunization. Human Antibodies from V-Gene Libraries Displayed on Phage," *J Mol Biol.* 222(3):581-597 (1991).
Matsumoto et al., "Affinity Maturation without Germinal Centres in Lymphotoxin-Alpha-Deficient Mice," *Nature* 382(6590):462-466 (1996).
Schutyser et al., "The CC Chemokine CCL20 and Its Receptor CCR6," *Cytokine Growth Factor Rev.* 14(5):409-426 (2003).
Shi et al., "Mouse T Cells Receive Costimulatory Signals from LIGHT, a TNF Family Member," *Blood* 100(9):3279-3286 (2002).
Rooney et al., "Expression of Lymphotoxins and Their Receptor-Fc Fusion Proteins by Baculovirus," *Methods Enzymol.* 322:345-363 (2000).
An et al., "Lymphotoxin β Receptor-Ig Protects from T-Cell-Mediated Liver Injury in Mice through Blocking LIGHT/HVEM Signaling," *Biol. Pharm. Bull.* 29(10): 2025-2030 (2006).
Mauri et al., "LIGHT, a New Member of the TNF Superfamily, and Lymphotoxin α are Ligands for Herpesvirus Entry Mediator," *Immunity* 8(1):21-30 (1998).
Varona et al., "CCR6-Deficient Mice Have Impaired Leukocyte Homeostasis and Altered Contact Hypersensitivity and Delayed-Type Hypersensitivity Responses," *J.Clin. Investig.* 107: R37-R45 (2001).
Mariuzza et al. (Annu. Rev. Biophys. Biophys. Chem. 1987;16:139-159).
Gussow et al. (Methods in Enzymology. 1991;203:99-121).
Winkler et al. (J. Imm., 265:4505-4514, 2000).
Kellermann et al. (Cur. Opin. Biotech., 13:593-597, 2002.
Office action from counterpart application in Honduras, Honduran Patent Appln. No. 2009-000414, dated Jan. 19, 2010.
Examination report from corresponding New Zealand Patent Application No. 575136 dated Mar. 9, 2011.
Examination report from corresponding Israeli Patent Application No. 197158, dated May 26, 2011.
Tamada et al., "Modulation of T-Cell-Mediated Immunity in Tumor and Graft-Versus-Host Disease Models through the LIGHT Co-Stimulatory Pathway," *Nat Med.* 6(3):283-9 (2000).
International Search Report mailed May 28, 2008 in counterpart PCT Application No. PCT/US2007/018832.
NCBI Database; GenBank Accession No. AAL10826 (Aug. 19, 2002).
NCBI Database; GenBank Accession No. AAY33445 (Aug. 5, 2005).
NCBI Database; GenBank Accession No. AAM46399 (Jun. 2, 2002).
NCBI Database; GenPept Accession No. PIR: B27594 (Jan. 21, 2000).
Extended European Search Report dated Oct. 21, 2011, from the European Patent Office in corresponding European Application No. 10172151.2.
Office Action dated Oct. 26, 2011, from the Chinese Patent Office in corresponding Chinese Application No. 200780040270.3 and English translation.
Fundamental Immunology p. 242, William E. Paul, M.D. ed., 3d ed; 1993.
Extended European Search Report dated Jul. 11, 2012, from the European Patent Office in corresponding European Application No. 12162958.8.
Japanese Office Action dated Oct. 9, 2012, from the Japanese Patent Office in corresponding Japanese Applicatoin No. 2009-526670, and English translation.
Fan, K. et al., Preparation and Characterization of a Monoclonal Antibody Against the Protein LIGHT, Hybridoma, 2005, vol. 24, No. 6, pp. 309-313.
Morel, Y. et al., Reciprocal Expression of the TNF Family Receptor Herpes Virus Entry Mediator and its Ligand LIGHT on Activated T Cells: LIGHT Down-Regulates Its Own Receptor, J. Immunol., 2000, vol. 165, pp. 4397-4404.
Office Action dated Aug. 22, 2013, from the Ukrainian Patent Office in corresponding Ukrainian Application No. 201206234, and English translation.
Canadian Office Action issued Aug. 27, 2015 in corresponding Canadian Application No. 2,661,782.
Beerli, Roger R. et al., "Mining Human antibody repertoires", *mAbs*, vol. 2, 2010, pp. 365-378.

\* cited by examiner

FIG. 3

| Name | Binding to HuLIGHT on EL4GFP HuLIGHT Cells | | Blocking Cell Surface LIGHT Binding to HVEM-Fc | | | | Blocking Cell Surface LIGHT Binding to LTBR-Fc | | | | Blocking CCL20 | Isotype | Epitope Group |
|---|---|---|---|---|---|---|---|---|---|---|---|---|---|
| | relative affinity | EC50 (µg/ml) | Human | IC50 (µg/ml) | Mouse | IC50 (µg/ml) | Human | IC50 (µg/ml) | Mouse | IC50 (µg/ml) | | | |
| 124E 63 | +++ | 0.1 | ++++ | 0.19 | - | - | ++++ | 1.3 | +++ | 0.43 | + | IgG3 | A |
| 124E 1 | +++ | 0.32 | ++++ | 0.2 | +++ | 0.64 | +++ | 1.7 | +++ | 2.8 | + | IgG1 | A |
| 124F 23 | +++ | 0.18 | +++ | 0.29 | - | - | +++ | 2.1 | - | - | + | IgG4 | B |
| 124E13 | +++ | 0.3 | ++ | 0.41 | NA | NA | +++ | 1.8 | +++ | NA | + | IgG1 | A |
| 124F 19 | +++ | 0.21 | NA | NA | NA | NA | ++ | 4.2 | ++ | 3.9 | + | IgG1 | B |

FIG. 4

| Pre-Inc. mAb | Coat mAb | | | | |
|---|---|---|---|---|---|
| | E1 | E13 | E63 | F19 | F23 |
| E1 | 95 | 82 | 89 | 0 | 0 |
| E13 | 98 | 97 | 98 | 0 | 0 |
| E63 | 87 | 90 | 84 | 0 | 22 |
| F19 | 0 | 0 | 0 | 98 | 98 |
| F23 | 0 | 0 | 0 | 53 | 87 |

| hLIGHT Epitope #1 ("E antibodies") | E1, E13, E63 |
|---|---|
| hLIGHT Epitope #2 ("F antibodies") | F19, F23 |

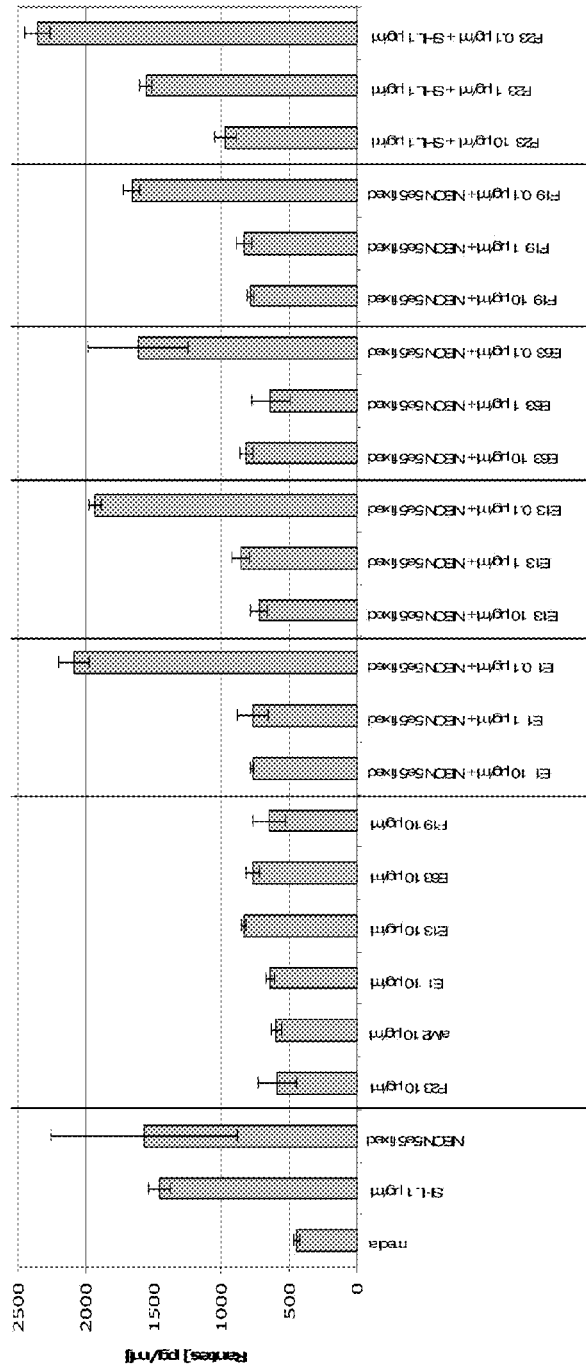
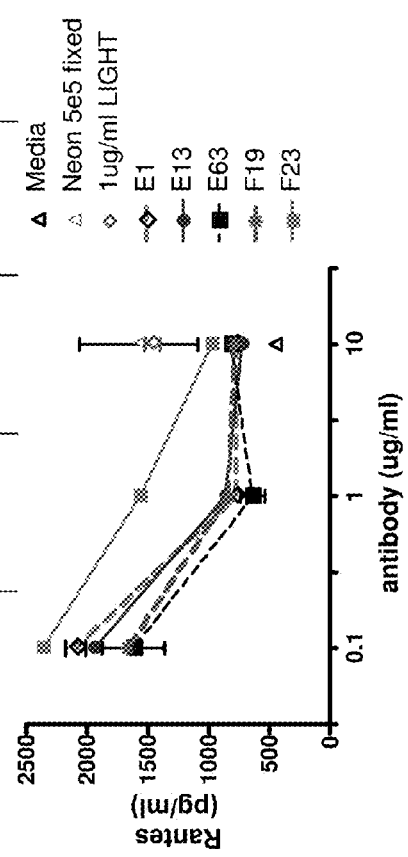
FIG. 10A
FIG. 10B

FIG. 11

| Soluble Ab | E1 | B12 | Coated Ab F19 | R&D mAb | Abnova | E45 |
|---|---|---|---|---|---|---|
| E1 | 94 | 22 | 15 | 99 | 0 | 99 |
| B12 | 17 | 97 | 16 | 0 | 61 | 11 |
| F19 | 4 | 0 | 99 | 99 | 0 | 7 |
| R&D mAb | 47 | 0 | 86 | 92 | 0 | 78 |
| Abnova | 30 | 97 | 15 | 38 | 89 | 64 |
| E45 | 60 | 5 | 8 | 99 | 64 | 98 |
| AntiM2 | 0 | 0 | 0 | 0 | 0 | 0 |

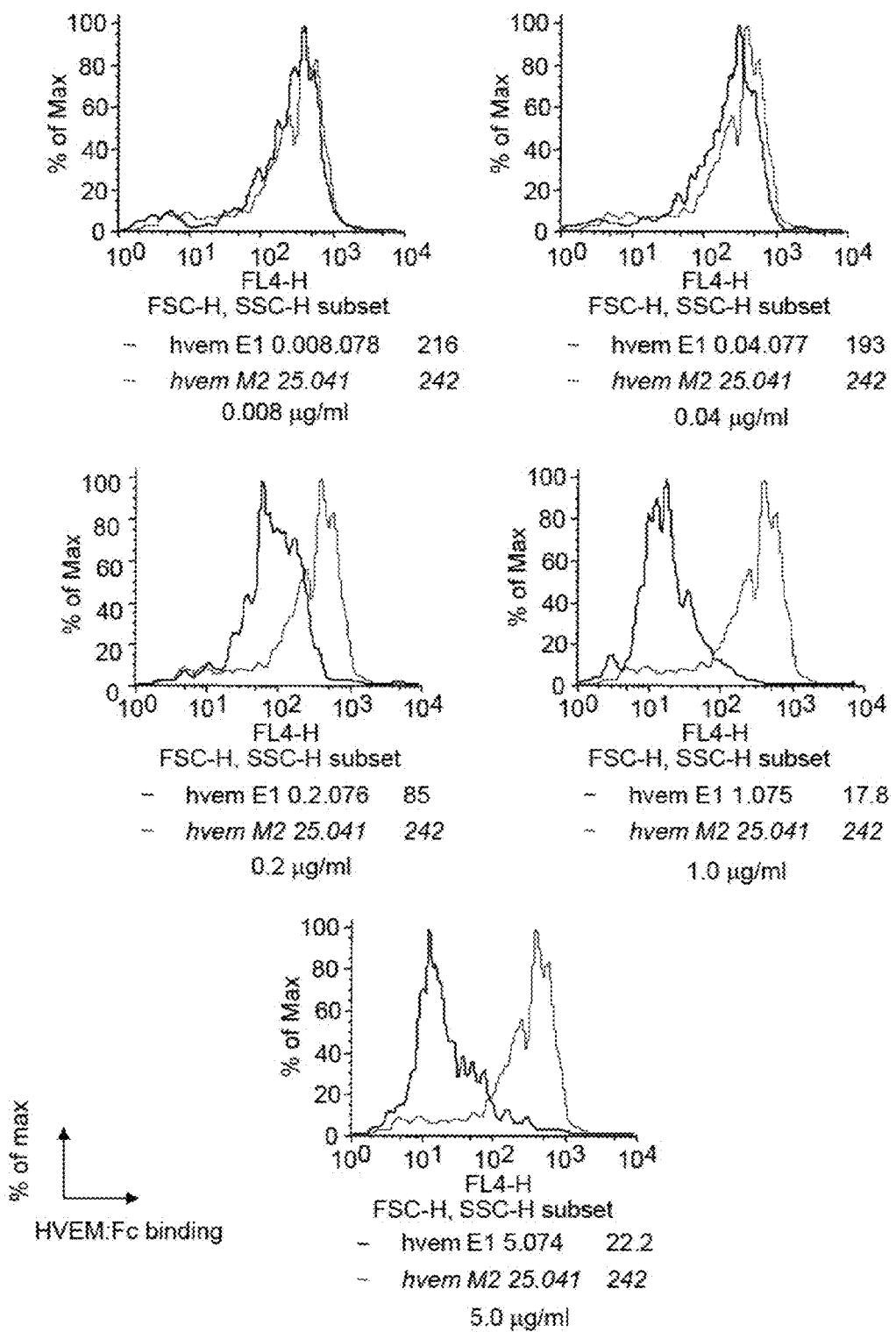

FIG. 12D
Monoclonal Abs - R&D
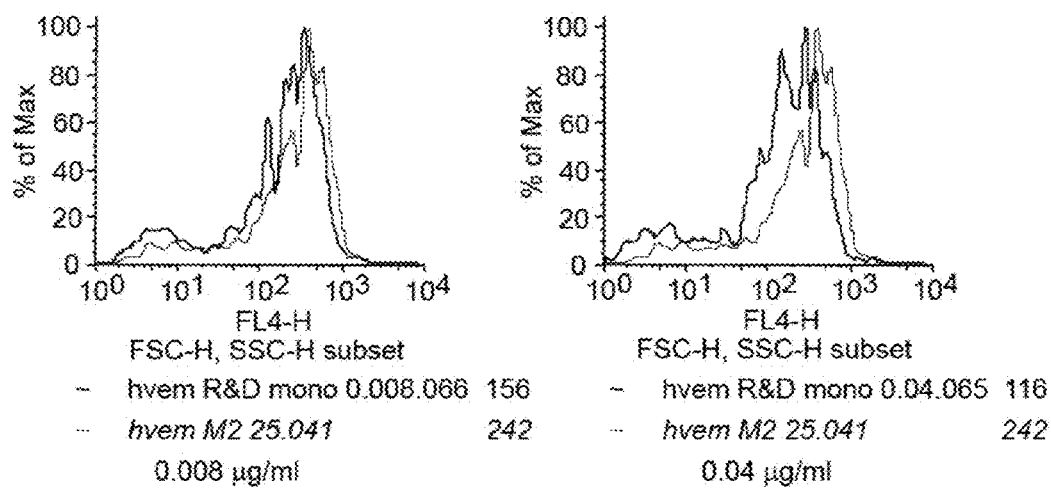
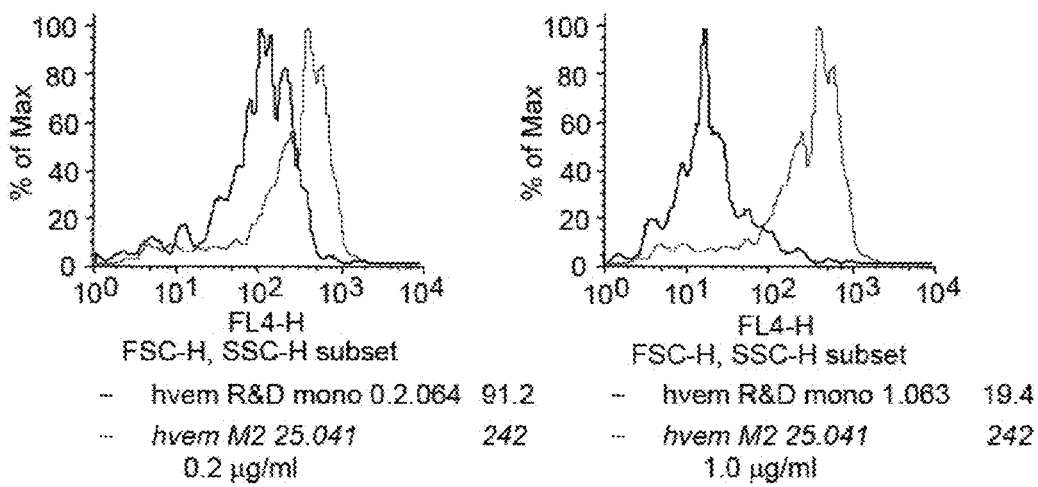
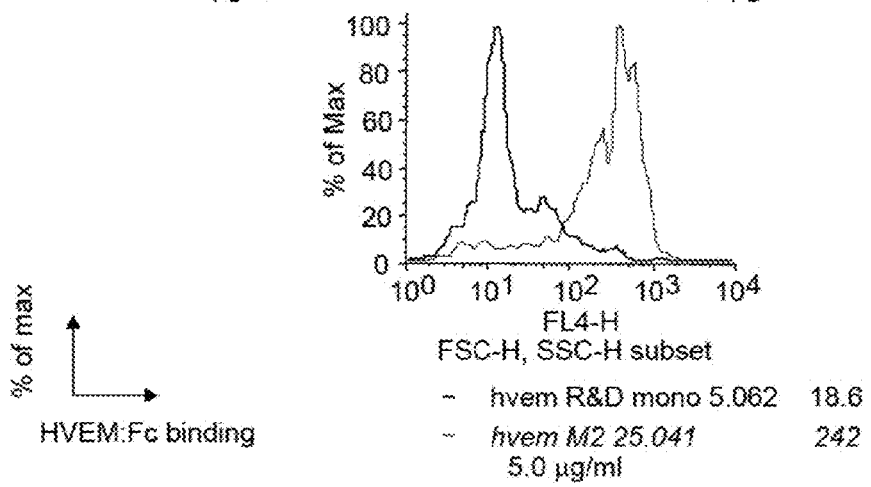

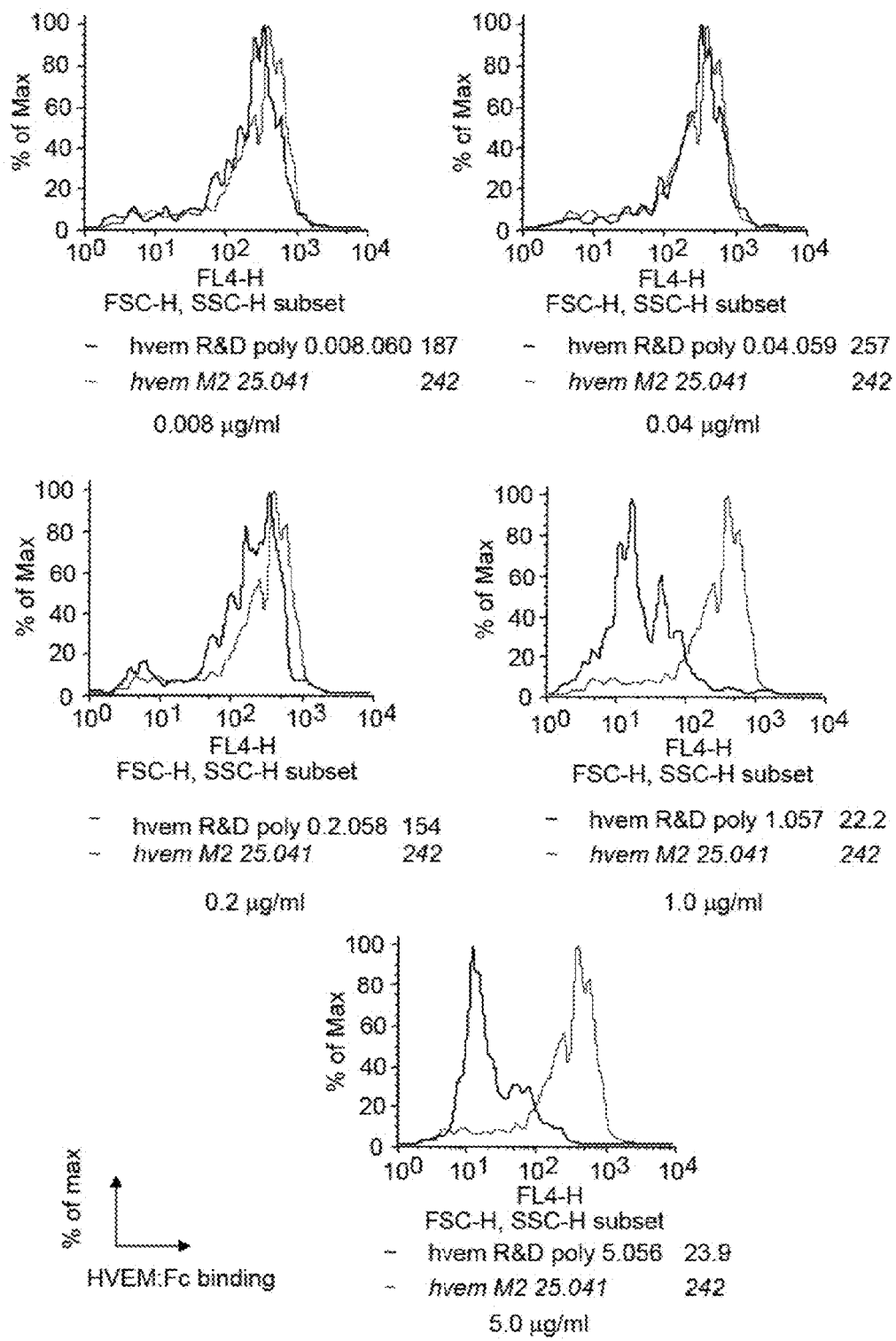

FIG. 13A
Monoclonal Abs - E1
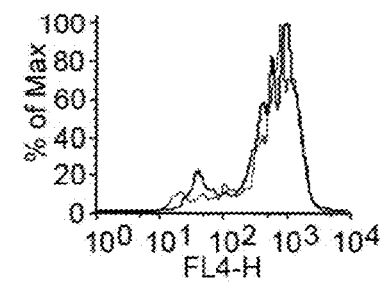
FSC-H, SSC-H subset
- ltbr E1 0.008.037  534
- ltbr M2 25.001    548
0.008 (µg/ml Ab)
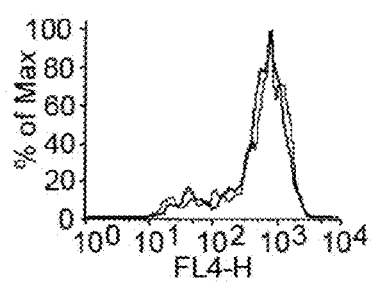
FSC-H, SSC-H subset
- ltbr E1 0.04.036  522
- ltbr M2 25.001    548
0.04 (µg/ml Ab)
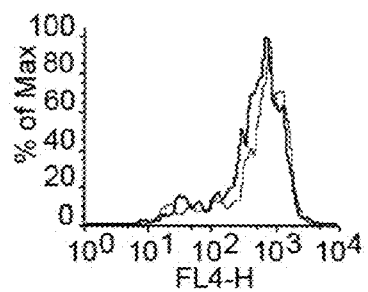
FSC-H, SSC-H subset
- ltbr E1 0.2.035  472
- ltbr M2 25.001   548
0.2 (µg/ml Ab)
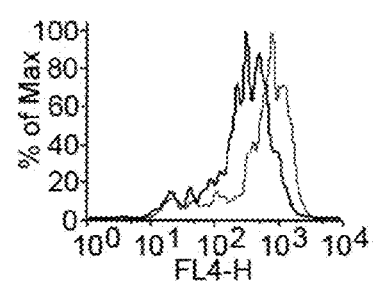
FSC-H, SSC-H subset
- ltbr E1 1.034      287
- ltbr M2 25.001     548
1.0 (µg/ml Ab)
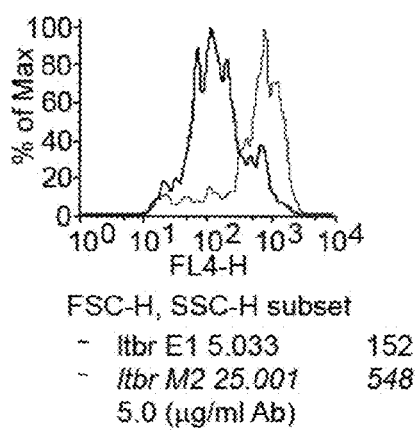
FSC-H, SSC-H subset
- ltbr E1 5.033     152
- ltbr M2 25.001    548
5.0 (µg/ml Ab)
% of max
LTBR:Fc binding Monoclonal Abs - E13

FIG. 13C
Monoclonal Abs - R&D
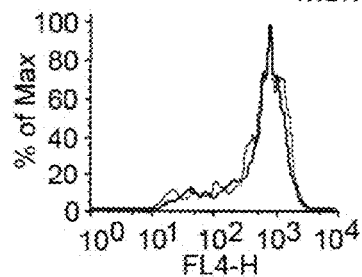
- ltbr R&D mono 0.008.025  539
- ltbr M2 25.001  548
0.008 (μg/ml Ab)
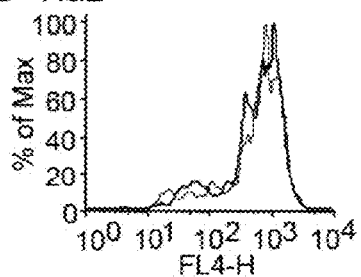
- ltbr R&D mono 0.04.024  535
- ltbr M2 25.001  548
0.04 (μg/ml Ab)
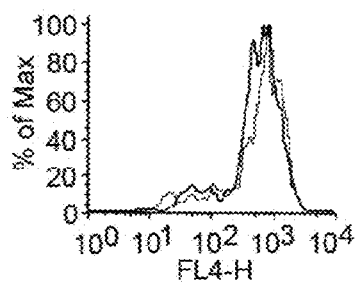
- ltbr R&D mono 0.2.023  528
- ltbr M2 25.001  548
0.2 (μg/ml Ab)
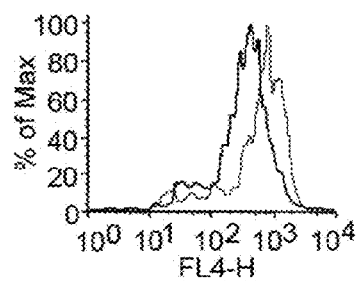
- ltbr R&D mono 1.022  323
- ltbr M2 25.001  548
1.0 (μg/ml Ab)
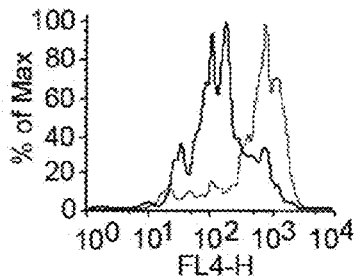
- ltbr R&D mono 5.021  155
- ltbr M2 25.001  548
5.0 (μg/ml Ab)
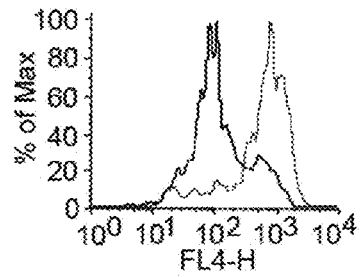
- ltbr R&D mono 25.020  128
- ltbr M2 25.001  548
25.0 (μg/ml Ab)
% of max ↑
LTBR.Fc binding →

Polyclonal Abs - eBioscience

FIG. 13E
Polyclonal Abs - R&D
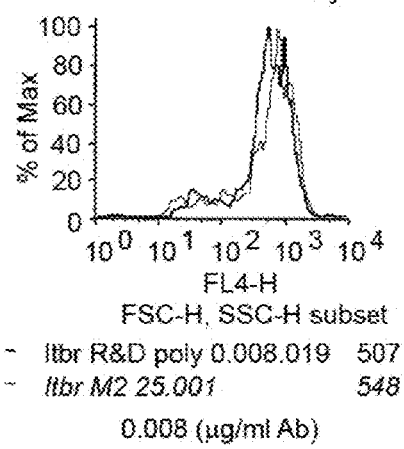
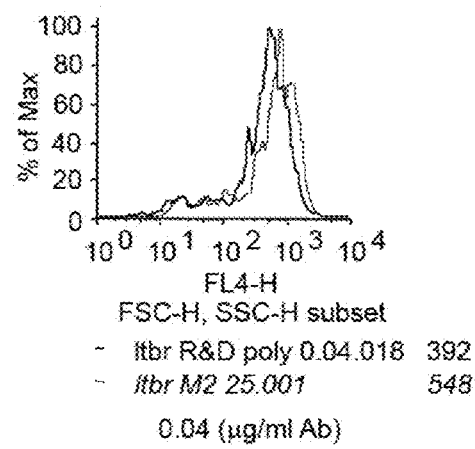
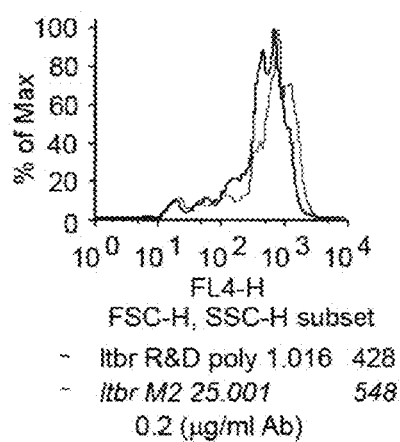
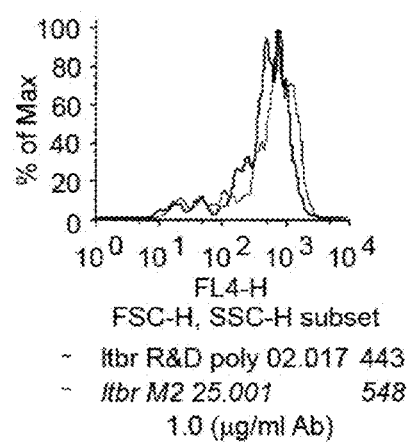
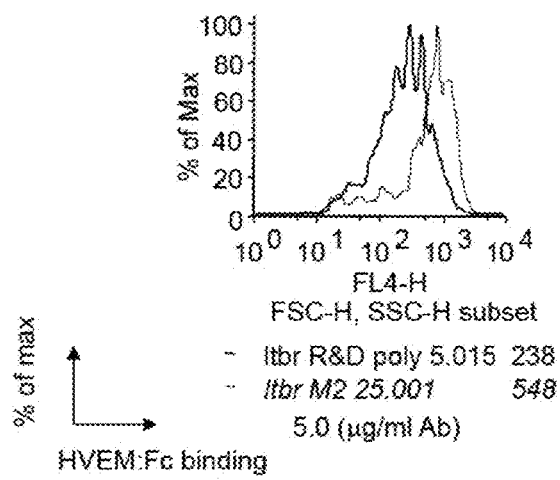
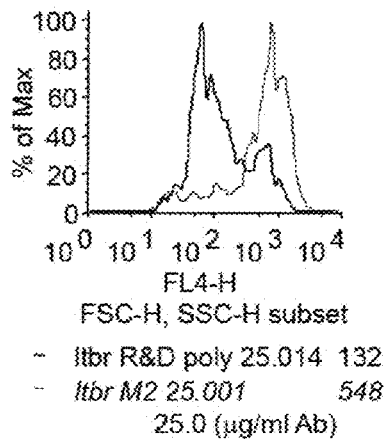

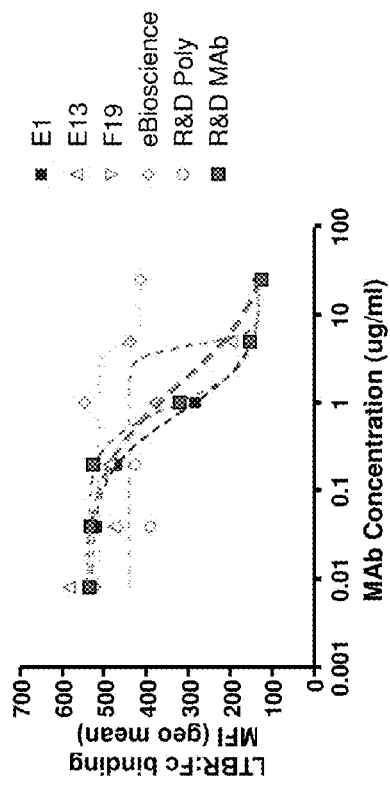
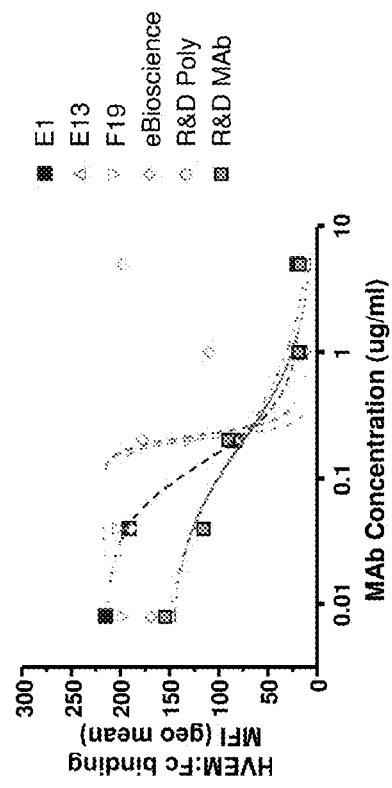
FIG. 14A
FIG. 14B

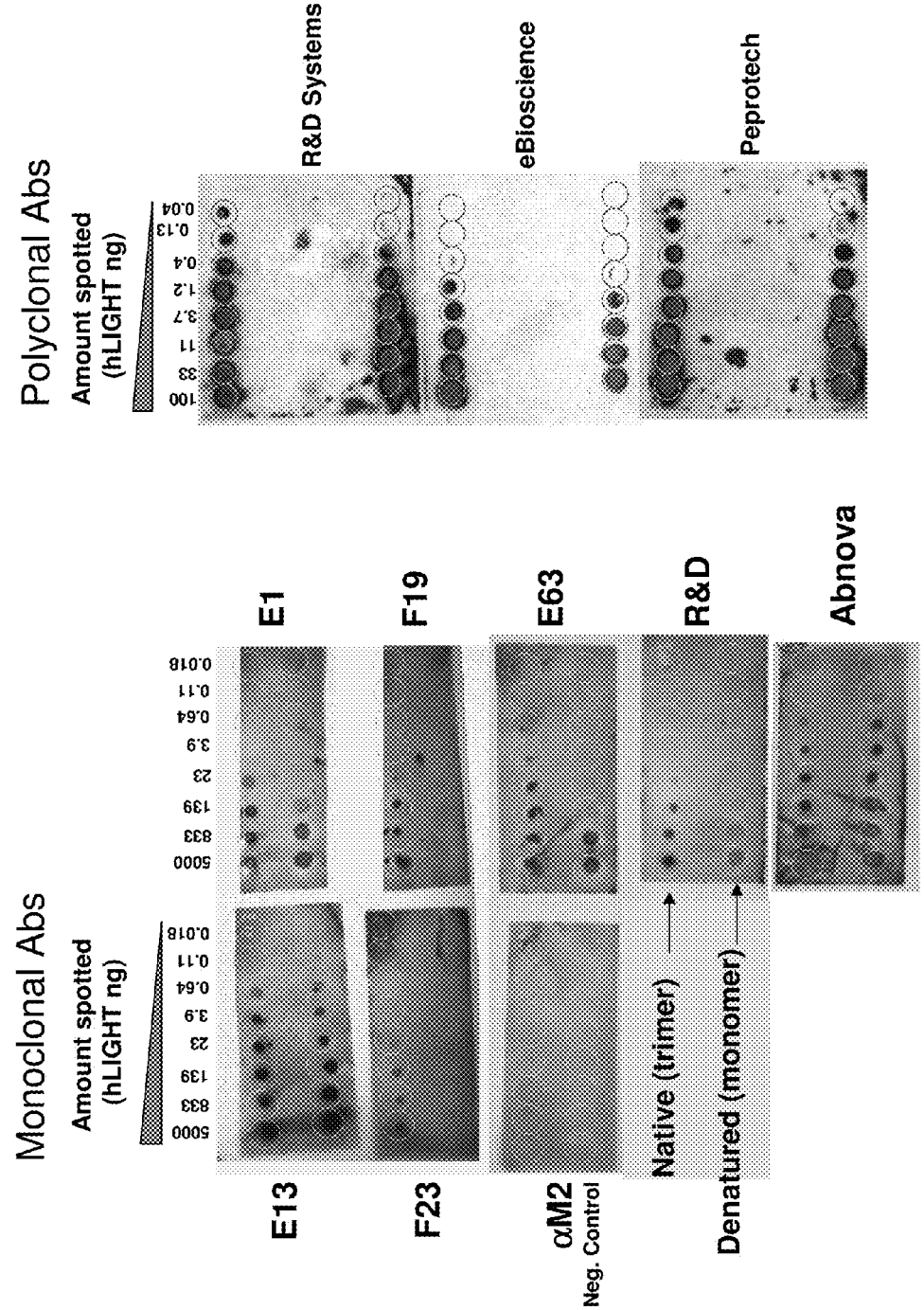

FIG. 16

| Antibody | Native-trimer* | Denatured-monomer* |
|---|---|---|
| E1 (human mAb) | 23 | 139 |
| E13 (human mAb) | 0.64 | 0.64 |
| E63 (human mAb) | 3.9 | 139 |
| F19 (human mAb) | 23 | >5000 |
| F23 (human mAb) | 23 | >5000 |
| Abnova (mouse mAb) | 0.64 | 0.64 |
| R&D systems (mouse mAb) | 23 | 139 |
| R&D systems (goat pAb) | 0.04 | 0.13 |
| eBiosciences (rabbit pAb) | 0.4 | 1.2 |
| Peprotech (rabbit pAb) | 0.04 | 0.13 |

Monoclonals: E1–R&D systems (mouse mAb)
Polyclonals: R&D systems (goat pAb)–Peprotech (rabbit pAb)

*Limit of detection (lowest amt of LIGHT detected (ng))

FIG. 20

| Soluble Ab | Coated Ab | | | | |
|---|---|---|---|---|---|
| | E1 | E1kappa(B) | F19 | F19kappa(B) | |
| E1 | 90 | 91 | 0 | 0 | |
| E1kappa(B) | 92 | 92 | 0 | 0 | |
| F19 | 0 | 0 | 98 | 98 | |
| F19kappa(B) | 0 | 24 | 98 | 98 | |
| AntiM2 | 0 | 0 | 0 | 0 | |

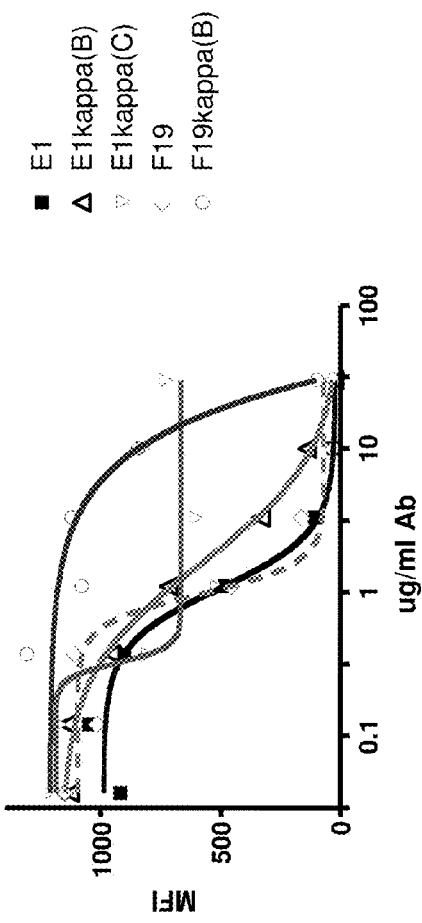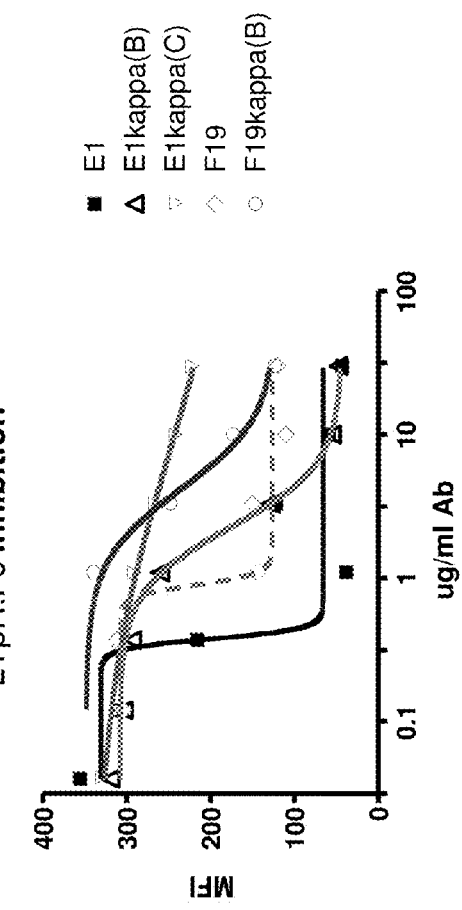
FIG. 21A
FIG. 21B

Extracellular: a.a. 214

Cytoplasmic: a.a. 32

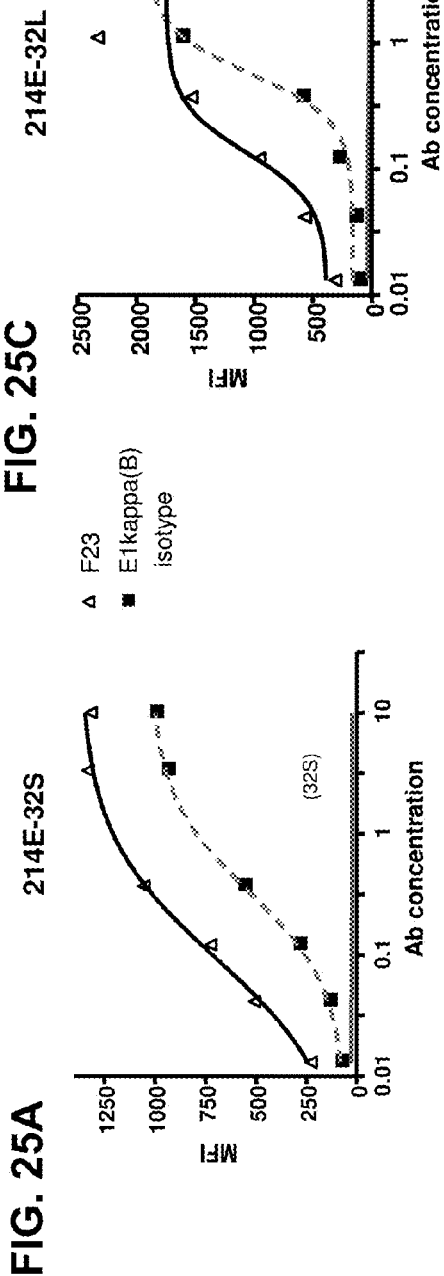
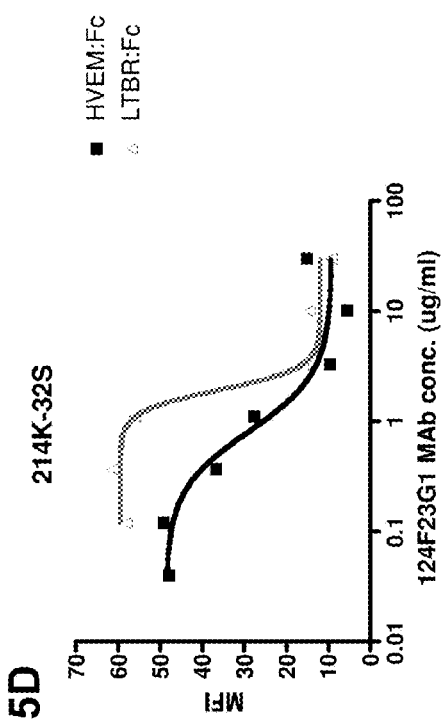
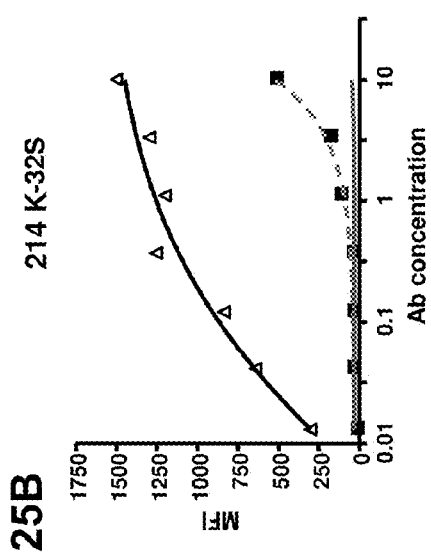
FIG. 25A  FIG. 25B  FIG. 25C  FIG. 25D

Control Ab

Anti-LIGHT Ab

ANTAGONISTIC HUMAN LIGHT-SPECIFIC HUMAN MONOCLONAL ANTIBODIES

CROSS-REFERENCE TO RELATED APPLICATIONS

This application is a continuation of U.S. patent application Ser. No. 13/889,608, filed May 8, 2013, which is a continuation of U.S. patent application Ser. No. 13/240,356, filed Sep. 22, 2011, which is a continuation of U.S. patent application Ser. No. 12/439,518, filed Mar. 6, 2009, now issued as U.S. Pat. No. 8,058,402, which is a U.S. national stage application and claims the benefit of PCT application Ser. No. PCT/US07/018832 filed Aug. 24, 2007, which claims priority to each of U.S. provisional application Ser. Nos. 60/897,875 filed Jan. 25, 2007 and 60/840,774 filed Aug. 28, 2006, each of which is herein incorporated by reference in its entirety.

INTRODUCTION

Provided herein are antibodies that immunospecifically bind to a human LIGHT (hLIGHT) (lymphotoxin-like, exhibits inducible expression and competes with HSV glycoprotein D for HVEM, a receptor expressed by T lymphocytes) polypeptide, a hLIGHT polypeptide fragment or other hLIGHT epitope. In some embodiments the antibodies are fully human antibodies, preferably fully human monoclonal antibodies, that immunospecifically bind to a hLIGHT polypeptide, hLIGHT polypeptide fragment or hLIGHT epitope. Also provided are isolated nucleic acids encoding antibodies that immunospecifically bind to a hLIGHT polypeptide, hLIGHT polypeptide fragment, or hLIGHT epitope. The invention further provides vectors and host cells comprising nucleic acids encoding antibodies that immunospecifically bind to a hLIGHT polypeptide, hLIGHT polypeptide fragment, or hLIGHT epitope, as well as methods of making antibodies that immunospecifically bind to a hLIGHT polypeptide, hLIGHT polypeptide fragment, or hLIGHT epitope. Also provided are methods of using the anti-hLIGHT antibodies provided herein to inhibit hLIGHT biological activity in vivo and/or to treat or otherwise manage a hLIGHT-mediated disease in a patient.

BACKGROUND

LIGHT, (lymphotoxin-like, exhibits inducible expression and competes with HSV glycoprotein D for HVEM, a receptor expressed by T lymphocytes) is one potential cytokine target that has been implicated in the processes of chronic inflammatory autoimmune diseases (Mauri et al. 1998 Immunity 8 21-30). As a member of the TNF superfamily (TNFSF) of ligands, LIGHT is also known as TNFSF14 or CD258. LIGHT is expressed on the surface of T cells upon activation in a tightly regulated manner appearing within 4 hours, peaking by 12-24 hours and disappearing by 48 hours (Castellano et al. 2002 J Biol Chem 277 42841-51). However, LIGHT is also present at detectable levels constitutively on the surface of immature dendritic cells (Tamada et al. 2000 J Immunol 164 4105-10) and on T cells and natural killer (NK) cells of the gut (Cohavy et al. 2005 J Immunol 174 646-53). LIGHT mediates its biologic effects by binding three TNF superfamily receptors including the lymphotoxin β receptor (LTβR) (Crowe et al. 1994 Science 264 707-10, Browning et al. 1997 J Immunol 159 3288-98), the herpes virus entry mediator (HVEM) (Montgomery et al. 1996 Cell 87(3) 427-36), and decoy receptor 3 (DcR3) (Yu et al. 1999 J Biol Chem 274 13733-6).

Mice treated with an inhibitory LTβR-Fc fusion protein reduced the inflammatory symptoms in the CD4+ CD45RB$^{high}$ T cell transfer model of colitis, a CD4+ T cell-mediated pathology (Mackay et al. 1998 Gastroenterology 115 1464-75). Constitutive transgenic T cell specific expression of LIGHT also has been shown to lead to severe intestinal inflammation with autoimmune-like pathology resembling human inflammatory bowel disease (IBD) (Wang et al. 2005 J Immunol 174 8173-82, Shaikh et al. 2001 J Immunol 167 6330-7, Wang et al. 2001 J Immunol 167 5099-105, Wang et al. 2004 J Clin Invest 113 826-35). LIGHT-expressing lymphocytes can induce IBD-like symptoms (e.g., cytokine profiles of human Crohn's disease, fissuring ulcers, ileitis, and increases in colonic IFN-γ and TNF) when mesenteric lymph node cells from LIGHT transgenic animals are transferred to RAG−/− (Wang et al. 2005 J Immunol 174 8173-82). In human disease, increases of LIGHT expression were observed in patients with active Crohn's disease (Cohavy et al. 2005 J Immunol 174 646-53, Wang et al. 2005 J Immunol 174 8173-82, Wang et al. 2004 J Clin Invest 113 826-35, Cohavy et al. 2004 J Immunol 173 251-8). LIGHT has also been demonstrated to be elevated in gut T cells of IBD patients (Cohavy et al. 2004 J Immunol 173 251-8). Genetic evidence also supports a role for LIGHT in IBD (Granger et al. 2001 J Immunol 167 5122-8); (Rioux et al. 2000 Am J Hum Genet 66 1863-70; Low et al. 2004 Inflamm Bowel Dis 10 173-81; Bonen and Cho 2003 Gastroenterology 124 521-36).

Moreover, CCL20-CCR6 signaling has been shown to be involved in IBD, and LIGHT induces CCL20 secretion from the human colonic epithelial cell line HT29.14s. In human studies, epithelial cells of the colon have been found to be a major source of CCL20 in IBD patients and CCL20 expression is increased in human IBD patients (Kwon et al. 2002 Gut 51 818-26; (Kaser et al. 2004 J Clin Immunol 24 74-85).

hLIGHT has also been implicated in graft-versus-host disease (GVHD). For example, LIGHT has been shown to provide potent costimulatory activity for T cells, enhancing proliferation an the production of Th1 cytokines independent of the B7-CD28 pathway (see, e.g., Tamada et al. 2000 J. Immunol. 164 4105-4110). Blocking of LIGHT-HVEM costimulation by either anti-HVEM monoclonal antibodies, HVEM-Ig, or LTβR fusion protein inhibits allogeneic T cell responses (see, e.g., Tamada et al. 2000 J. Immunol. 164 4105-4110, Harrop et al. 19998 J. Immunol. 161 1786). Furthermore, in vivo administration of LTβR-Ig or murine anti-LIGHT antibodies inhibits anti-host cytotoxic T lymphocyte (CTL) responses in a murine acute GVHD model (Tamada et al. 2000 Nat. Med. 6 283-289).

Although observations such as those discussed above indicate a role for LIGHT in inflammatory disorders, such as IBD or GVHD, to date no human anti-human LIGHT antibodies have been produced, nor have any human anti-hLIGHT antibodies or monoclonal anti-hLIGHT antibodies been shown to be antagonistic to hLIGHT biological activity. As such, a need continues to exist for identification of therapies, such as anti-LIGHT therapies, useful for treatment of inflammatory disorders in humans. Citation or discussion of a reference herein shall not be construed as an admission that such is prior art to the present invention.

SUMMARY

Provided herein are antibodies, such as fully human antibodies, that immunospecifically bind to a hLIGHT polypeptide, a hLIGHT polypeptide fragment, or a hLIGHT epitope. Also provided are isolated nucleic acids encoding antibodies, such as fully human antibodies, that immunospecifically bind to a hLIGHT polypeptide, a hLIGHT polypeptide fragment, or a hLIGHT epitope. Further provided are vectors and host cells comprising nucleic acids encoding antibodies, such as fully human antibodies, that immunospecifically bind to a hLIGHT polypeptide, a hLIGHT polypeptide fragment, or a hLIGHT epitope. Also provided are methods of making antibodies, such as fully human antibodies, that immunospecifically bind to a hLIGHT polypeptide, a hLIGHT polypeptide fragment, or a hLIGHT epitope. Also provided herein is a method of treating a hLIGHT-mediated disease comprising administering an antibody, such as a fully human antibody, that immunospecifically binds to a hLIGHT polypeptide, a hLIGHT polypeptide fragment, or a hLIGHT epitope. In preferred embodiments, anti-hLIGHT antibodies provided herein are antagonist antibodies that ameliorate, neutralize or otherwise inhibit hLIGHT biological activity in vivo (e.g., the hLIGHT-mediated production or secretion of CCL20, IL-8 or RANTES from cells expressing a hLIGHT ligand, such as a hLIGHT receptor, (e.g., HVEM, LTβR and/or DcR3)). An antibody of the invention can be a full-length antibody or an antigen-binding antibody fragment. The antibodies of the invention are also useful for detecting hLIGHT, as well as for ameliorating, neutralizing or otherwise inhibiting hLIGHT activity, e.g., in a human subject suffering from a disorder in which hLIGHT activity is detrimental.

Thus, in one aspect, provided herein is an isolated antibody that immunospecifically binds to a hLIGHT polypeptide (e.g., a cell surface-expressed or soluble hLIGHT), a hLIGHT polypeptide fragment, or a hLIGHT epitope. In some embodiments, the antibody immunospecifically binds to (a) a trimeric (or native) hLIGHT epitope, (b) a monomeric (or denatured) hLIGHT epitope, (c) both a trimeric hLIGHT epitope and a monomeric hLIGHT epitope, (d) a trimeric hLIGHT epitope but not a monomeric hLIGHT epitope, or (e) a monomeric hLIGHT epitope but not a trimeric hLIGHT epitope. In preferred embodiments, the antibody immunospecifically binds a trimeric hLIGHT epitope but not a human monomeric hLIGHT epitope. In preferred embodiments, the antibody is an E1 antibody, E13 antibody, E63 antibody, F19 antibody, or F23 antibody.

Hybridomas that produce each of the E1, E13, E63, F19 and F23 antibodies were deposited under provisions of the Budapest Treaty with the American Type Culture Collection (ATCC, 10801 University Blvd., Manassas, Va. 20110-2209) on Jul. 12, 2006 (ATCC Accession Nos. PTA-7729 (hybridoma 124 E1) and PTA-7728 (hybridoma 124 F23), respectively), Aug. 17, 2006 (ATCC Accession Nos. PTA-7818 (hybridoma 124 E63) and PTA-7819 (hybridoma 124 F19) and Aug. 23, 2006 (ATCC Accession No. PTA-7842 (hybridoma 124 E13), and are herein incorporated by reference. Antibodies produced by each of hybridomas 124 E1, 124 E13, 124 E63, 124 F19 and 124 F23 may also be referred to herein as E1, E13, E63, F19, F23, respectively, and/or by the ATCC Accession Numbers. PTA-7729, PTA-7842, PTA-7818, PTA-7819, and PTA-7728, respectively.

These antibodies, hybridomas, methods of making these antibodies, and methods of using these antibodies are all included in the invention.

In specific embodiments, an antibody of the invention is one that is competitively blocked (e.g., in a dose-dependent manner) by an E1 antibody, an E13 antibody, and/or an E63 antibody for binding to a hLIGHT polypeptide (e.g., a cell surface-expressed or soluble hLIGHT), a hLIGHT fragment, or a hLIGHT epitope. In other embodiments, the antibody is competitively blocked (e.g., in a dose-dependent manner) by an F19 antibody and/or an F23 antibody for binding to a hLIGHT polypeptide (e.g., a cell surface-expressed or soluble hLIGHT), a hLIGHT fragment, or a hLIGHT epitope. In specific embodiments, the antibody is competitively blocked (e.g., in a dose-dependent manner) by an E1 antibody, an E13 antibody and/or an E63 antibody, but is not competitively blocked (e.g., in a dose-dependent manner) by an F19 antibody and/or an F23 antibody, for binding to a hLIGHT polypeptide (e.g., a cell surface-expressed or soluble hLIGHT), a hLIGHT fragment, or a hLIGHT epitope. In other embodiments, the antibody is competitively blocked (e.g., in a dose-dependent manner) by an F19 antibody and/or an F23 antibody, but is not competitively blocked (e.g., in a dose-dependent manner) by an E1 antibody, an E13 antibody and/or an E63 antibody, for binding to a hLIGHT polypeptide (e.g., a cell surface-expressed or soluble hLIGHT), a hLIGHT fragment, or a hLIGHT epitope. Exemplary competitive blocking tests are provided in the Examples herein.

Also provided herein are antibodies, or antigen binding antibody fragments thereof that immunospecifically bind to a hLIGHT polypeptide (e.g., a cell surface-expressed or soluble hLIGHT), a hLIGHT polypeptide fragment, or a hLIGHT epitope. In certain embodiments, the antibody or antigen-binding fragment comprises a VH chain, VL chain, VH domain, VL domain, VH CDR1, VH CDR2, VH CDR3, VL CDR1, VL CDR2, and/or VL CDR3 of E1, E13, E63, F19 or F23.

In certain embodiments, the antibody or antigen binding fragment thereof comprises less than six CDRs. In some embodiments, the antibody or antigen binding fragment thereof comprises or consists of one, two, three, four, or five CDRs selected from the group consisting of VH CDR1, VH CDR2, VH CDR3, VL CDR1, VL CDR2, and/or VL CDR3. In specific embodiments, the antibody or antigen binding fragment thereof comprises or consists of one, two, three, four, or five CDRs selected from the group consisting of VH CDR1, VH CDR2, VH CDR3, VL CDR1, VL CDR2, and/or VL CDR3 of E1, E13, E63, F19 or F23.

Also provided herein are pharmaceutical compositions comprising an anti-hLIGHT antibody of the invention, such as E1, E13, E63, F19 or F23.

In specific embodiments, an antibody of the invention is a fully human antibody, a monoclonal antibody, a recombinant antibody, an antagonist antibody, or any combination thereof. In particular embodiments, the antibody is a fully human antibody, such as a fully human monoclonal antibody, or antigen binding fragment thereof, that immunospecifically binds to hLIGHT. In preferred embodiments, the antibody is an antagonist antibody.

In certain embodiments, the antibody competes (e.g., in a dose dependent manner) with HVEM, LTβR, DcR3, or fusion proteins thereof (e.g., Fc:HVEM, Fc: LTβR or Fc:DcR3), for binding to a hLIGHT polypeptide, such as a cell surface-expressed hLIGHT polypeptide or soluble hLIGHT polypeptide, a hLIGHT polypeptide fragment, or a hLIGHT epitope. Exemplary competitive blocking tests are provided in the Examples herein.

In a second aspect, provided herein are isolated nucleic acids encoding antibodies that immunospecifically bind to a hLIGHT polypeptide (e.g., a cell surface-expressed or soluble hLIGHT), a hLIGHT polypeptide fragment, or a hLIGHT epitope. In certain embodiments, the nucleic acid encodes a VH chain, VL chain, VH domain, VL domain, VH CDR1, VH CDR2, VH CDR3, VL CDR1, VL CDR2, and/or VL CDR3 of E1, E13, E63, F19 or F23.

In a third aspect, provided herein are vectors and host cells comprising nucleic acids encoding antibodies that immunospecifically bind to a hLIGHT polypeptide, a hLIGHT polypeptide fragment, or a hLIGHT epitope.

In a fourth aspect, provided herein are methods of making antibodies that immunospecifically bind to a hLIGHT polypeptide, a hLIGHT polypeptide fragment, or a hLIGHT epitope. In certain embodiments, the antibody immunospecifically binds to a single nucleotide polymorphism (SNP) variant of a hLIGHT polypeptide, such as 214E-32S, 214K-32S, 214E-32L and/or 214K-32L. Also provided herein are hybridomas that produce antibodies that immunospecifically bind to a hLIGHT polypeptide, or SNP variant thereof. In preferred embodiments, the hybridoma is the hybridoma that produces E1, E13, E63, F19 or F23.

In a fifth aspect, provided herein are methods of treating or otherwise alleviating one or more symptoms of a hLIGHT-mediated disease in a subject (e.g., a human subject), comprising administering to the subject an effective amount of an antibody that immunospecifically binds to a hLIGHT polypeptide (e.g., a cell surface-expressed or soluble hLIGHT), wherein hLIGHT activity is inhibited by the antibody. In certain embodiments, the hLIGHT-mediated disease is an IBD, such as Crohn's disease or ulcerative colitis. In other embodiments, the hLIGHT mediated disease is GVHD.

In a sixth aspect, provided herein are methods for decreasing or inhibiting binding of hLIGHT to HVEM, LTβR and/or DcR3 in a subject (e.g., a human subject), comprising administering to the subject an effective amount of an antibody that immunospecifically binds to a hLIGHT polypeptide (e.g., a cell surface-expressed or soluble hLIGHT).

In a seventh aspect, provided herein are methods for decreasing or inhibiting a hLIGHT biological activity, such as secretion of CCL20, IL8 and/or RANTES, in a subject (e.g., a human subject), comprising administering to the subject an effective amount of an antibody that immunospecifically binds to a hLIGHT polypeptide (e.g., a cell surface-expressed hLIGHT), wherein hLIGHT biological activity is decreased or inhibited by the antibody.

In an eighth aspect, provided herein are methods for decreasing or inhibiting binding of hLIGHT to HVEM, LTβR and/or DcR3 in a cell having cell surface-expressed hLIGHT, contacting the cell with an effective amount of an antibody that immunospecifically binds to a hLIGHT polypeptide (e.g., a cell surface-expressed or soluble hLIGHT), such as a hLIGHT polypeptide, a hLIGHT polypeptide fragment, or a hLIGHT epitope.

In a ninth aspect, provided herein are methods for decreasing or inhibiting a hLIGHT biological activity, such as secretion of CCL20, IL8 and/or RANTES, in a cell having a cell surface-expressed hLIGHT receptor (such as, HVEM, LTβR and/or Dc3R), contacting the cell with an effective amount of an antibody that immunospecifically binds to a hLIGHT polypeptide (e.g., a cell surface-expressed or soluble hLIGHT, or SNP variant thereof), wherein hLIGHT biological activity is decreased or inhibited by the antibody.

In a tenth aspect, provided herein is an antibody that immunospecifically binds to a hLIGHT polypeptide, a hLIGHT polypeptide fragment, or a hLIGHT epitope, wherein said antibody further comprises a detectable tag. In certain embodiments, anti-hLIGHT antibodies that comprise a detectable tag are used in a method for the detection of hLIGHT in a sample, said method comprising contacting the sample with the anti-hLIGHT antibody. In specific embodiments, the sample comprises a cell expressing hLIGHT on the surface of the cell.

In an eleventh aspect, provided herein are kits comprising an antibody that immunospecifically binds to a hLIGHT polypeptide, a hLIGHT polypeptide fragment, or a hLIGHT epitope.

TERMINOLOGY

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The term "about" or "approximately" means within 20%, preferably within 10%, and more preferably within 5% (or 1% or less) of a given value or range.

As used herein, "administer" or "administration" refers to the act of injecting or otherwise physically delivering a substance as it exists outside the body (e.g., an anti-hLIGHT antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

In the context of a polypeptide, the term "analog" as used herein refers to a polypeptide that possesses a similar or identical function as a hLIGHT polypeptide, a fragment of a hLIGHT polypeptide, or an anti-hLIGHT antibody but does not necessarily comprise a similar or identical amino acid sequence of a hLIGHT polypeptide, a fragment of a hLIGHT polypeptide, or an anti-hLIGHT antibody, or possess a similar or identical structure of a hLIGHT polypeptide, a fragment of a hLIGHT polypeptide, or an anti-hLIGHT antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, and preferably at least 90%, more preferably at least 95%, or most preferably at least 99% identical to the amino acid sequence of a hLIGHT polypeptide (e.g., SEQ ID NO:52), a fragment of a hLIGHT polypeptide, or an anti-hLIGHT antibody described herein; (b) a polypeptide encoded by a nucleotide sequence that hybridizes under stringent conditions to a nucleotide sequence encoding a hLIGHT polypeptide, a fragment of a hLIGHT polypeptide, or an anti-hLIGHT antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) *Molecular Cloning: A Laboratory Manual*, Cold Spring Harbor Laboratory Press, Cold Spring Harbor, N.Y.; Maniatis et al. (1982) *Molecular Cloning: A*

*Laboratory Manual*, Cold Spring Harbor Press, Cold Spring Harbor, N.Y.); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, and preferably at least 90%, more preferably at least 95%, or most preferably at least 99% identical to the nucleotide sequence encoding a hLIGHT polypeptide, a fragment of a hLIGHT polypeptide, or an anti-hLIGHT antibody (or VH or VL region thereof) described herein. A polypeptide with similar structure to a hLIGHT polypeptide, a fragment of a hLIGHT polypeptide, or an anti-hLIGHT antibody described herein refers to a polypeptide that has a similar secondary, tertiary or quaternary structure of a hLIGHT polypeptide, a fragment of a hLIGHT, or a hLIGHT antibody described herein. The structure of a polypeptide can determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions ×100%). In one embodiment, the two sequences are the same length.

The determination of percent identity between two sequences (e.g., amino acid sequences or nucleic acid sequences) can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score 50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm nih gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, an "antagonist" or "inhibitor" of hLIGHT refers to a molecule that is capable of inhibiting or otherwise decreasing one or more of the biological activities of hLIGHT, such as in a cell expressing hLIGHT or in a cell expressing a hLIGHT ligand, such as a hLIGHT receptor. For example, in certain embodiments, antibodies of the invention are antagonist antibodies that inhibit or otherwise decrease secretion of CCL20, IL-8 and/or RANTES from a cell having a cell surface-expressed hLIGHT receptor (e.g., HVEM, LTβR and/or DcR3) when said antibody is contacted with said cell. In some embodiments, an antagonist of hLIGHT (e.g., an antagonistic antibody of the invention) may, for example, act by inhibiting or otherwise decreasing the activation and/or cell signaling pathways of the cell expressing a hLIGHT receptor, thereby inhibiting a hLIGHT-mediated biological activity of the cell the relative to the hLIGHT-mediated biological activity in the absence of antagonist. In certain embodiments the antibodies provided herein are fully human, antagonistic anti-hLIGHT antibodies, preferably fully human, monoclonal, antagonistic anti-hLIGHT antibodies.

The term "antibody" and "immunoglobulin" or "Ig" may be used interchangeably herein. The terms "antibodies that immunospecifically bind to a hLIGHT antigen," "antibodies that immunospecifically bind to a hLIGHT epitope," "anti-hLIGHT antibodies" and analogous terms are also used interchangeably herein and refer to antibodies and fragments thereof, that specifically bind to a hLIGHT polypeptide, such as a hLIGHT antigen or epitope. An antibody or a fragment thereof that immunospecifically binds to a hLIGHT antigen may be cross-reactive with related antigens. Preferably, an antibody or a fragment thereof that immunospecifically binds to a hLIGHT antigen does not cross-react with other antigens. An antibody or a fragment thereof that immunospecifically binds to a hLIGHT antigen can be identified, for example, by immunoassays, BIAcore, or other techniques known to those of skill in the art. An antibody or a fragment thereof binds specifically to a hLIGHT antigen when it binds to a hLIGHT antigen with higher affinity than to any cross-reactive antigen as determined using experimental techniques, such as radioimmunoassays (RIA) and enzyme-linked immunosorbent assays (ELISAs). Typically a specific or selective reaction will be at least twice background signal or noise and more typically more than 10 times background. See, e.g., Paul, ed., 1989, *Fundamental Immunology Second Edition*, Raven Press, New York at pages 332-336 for a discussion regarding antibody specificity.

Antibodies of the invention include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies of the present invention include immunoglobulin molecules and immunologically active portions of immunoglobulin molecules, i.e., antigen binding domains or molecules that contain an antigen-binding site that immunospecifically binds to a hLIGHT antigen (e.g., one or more complementarity determining regions (CDRs) of an anti-hLIGHT antibody). The antibodies of the invention can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In preferred embodiments, the hLIGHT antibodies are fully human, such as fully human monoclonal hLIGHT antibodies. In certain embodiments, antibodies of the invention are IgG antibodies, or a class (e.g., human IgG1 or IgG4) or subclass thereof.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the complementarity determining regions (CDR)). The antigen binding region can be derived from any animal species, such as rodents (e.g., rabbit, rat or hamster) and humans. Preferably, the antigen binding region will be of human origin.

As used herein, the term "composition" is intended to encompass a product containing the specified ingredients (e.g., an antibody of the invention) in, optionally, the specified amounts, as well as any product which results, directly or indirectly, from combination of the specified ingredients in, optionally, the specified amounts.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

In the context of a polypeptide, the term "derivative" as used herein refers to a polypeptide that comprises an amino acid sequence of a hLIGHT polypeptide, a fragment of a hLIGHT polypeptide, or an antibody that immunospecifically binds to a hLIGHT polypeptide which has been altered by the introduction of amino acid residue substitutions, deletions or additions. The term "derivative" as used herein also refers to a hLIGHT polypeptide, a fragment of a hLIGHT polypeptide, or an antibody that immunospecifically binds to a hLIGHT polypeptide which has been chemically modified, e.g., by the covalent attachment of any type of molecule to the polypeptide. For example, but not by way of limitation, a hLIGHT polypeptide, a fragment of a hLIGHT polypeptide, or a hLIGHT antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hLIGHT polypeptide, a fragment of a hLIGHT polypeptide, or a hLIGHT antibody may be chemically modified by chemical modifications using techniques known to those of skill in the art, including, but not limited to specific chemical cleavage, acetylation, formulation, metabolic synthesis of tunicamycin, etc. Further, a derivative of a hLIGHT polypeptide, a fragment of a hLIGHT polypeptide, or a hLIGHT antibody may contain one or more non-classical amino acids. A polypeptide derivative possesses a similar or identical function as a hLIGHT polypeptide, a fragment of a hLIGHT polypeptide, or a hLIGHT antibody described herein.

The term "effective amount" as used herein refers to the amount of a therapy (e.g., an antibody or pharmaceutical composition provided herein) which is sufficient to reduce and/or ameliorate the severity and/or duration of a given disease and/or a symptom related thereto. This term also encompasses an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than anti-hLIGHT antibody provided herein). In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g., inhibition of a hLIGHT biological activity of a cell, such as inhibition of secretion of CCL20, IL-8 or RANTES from the cell).

The term "epitope" as used herein refers to a localized region on the surface of an antigen, such as hLIGHT polypeptide or hLIGHT polypeptide fragment, that is capable of being bound to one or more antigen binding regions of an antibody, and that has antigenic or immunogenic activity in an animal, preferably a mammal, and most preferably in a human, that is capable of eliciting an immune response. An epitope having immunogenic activity is a portion of a polypeptide that elicits a antibody response in an animal. An epitope having antigenic activity is a portion of a polypeptide to which an antibody immunospecifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide The epitope may or may not be a three-dimensional surface feature of the antigen. In certain embodiments, a hLIGHT epitope is a three-dimensional surface feature of a hLIGHT polypeptide (e.g., in a trimeric form of a hLIGHT polypeptide). In other embodiments, a hLIGHT epitope is linear feature of a hLIGHT polypeptide (e.g., in a trimeric form or monomeric form of the hLIGHT polypeptide). Antibodies provided herein may immunospecifically bind to an epitope of the monomeric (denatured) form of hLIGHT, an epitope of the trimeric (native) form of hLIGHT, or both the monomeric (denatured) form and the trimeric (native) form of hLIGHT. In specific embodiments, the antibodies provided herein immunospecifically bind to an epitope of the trimeric form of hLIGHT but do not immunospecifically bind the monomeric form of hLIGHT.

The term "excipients" as used herein refers to inert substances which are commonly used as a diluent, vehicle, preservatives, binders, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, *Remington's Pharmaceutical Sciences* (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, hLIGHT fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hLIGHT polypeptide or an antibody that immunospecifically binds to a hLIGHT polypeptide. In a specific embodiment, a fragment of a hLIGHT polypeptide or an antibody that immunospecifically binds to a hLIGHT antigen retains at least 1, at least 2, or at least 3 functions of the polypeptide or antibody.

The terms "fully human antibody" or "human antibody" are used interchangeably herein and refer to an antibody that comprises a human variable region and, most preferably a human constant region. In specific embodiments, the terms refer to an antibody that comprises a variable region and constant region of human origin. "Fully human" anti-hLIGHT antibodies, in certain embodiments, can also encompass antibodies which bind hLIGHT polypeptides and are encoded by nucleic acid sequences which are naturally occurring somatic variants of human germline immunoglobulin nucleic acid sequence. In a specific embodiment, the anti-hLIGHT antibodies provided herein are fully human antibodies. The term "fully human antibody" includes antibodies having variable and constant regions corresponding to human germline immunoglobulin sequences as described by Kabat et al. (See Kabat et al. (1991) *Sequences of Proteins of Immunological Interest*, Fifth Edition, U.S. Department of Health and Human Services, NIH Publication No. 91-3242). Exemplary methods of producing fully human antibodies are provided, e.g., in the Examples herein, but any method known in the art may be used.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "fusion protein" as used herein refers to a polypeptide that comprises an amino acid sequence of an antibody and an amino acid sequence of a heterologous polypeptide or protein (i.e., a polypeptide or protein not normally a part of the antibody (e.g., a non-anti-hLIGHT antigen antibody)). The term "fusion" when used in relation to hLIGHT or to a anti-hLIGHT antibody refers to the joining of a peptide or polypeptide, or fragment, variant and/or derivative thereof, with a heterologous peptide or polypeptide. Preferably, the fusion protein retains the biological activity of the hLIGHT or anti-hLIGHT antibody. In certain embodiments, the fusion protein comprises a hLIGHT antibody VH domain, VL domain, VH CDR (one, two or three VH CDRs), and/or VL CDR (one, two or three VL CDRs), wherein the fusion protein immunospecifically binds to a hLIGHT epitope.

The term "heavy chain" when used in reference to an antibody refers to five distinct types, called alpha (α), delta (δ), epsilon (ε), gamma (γ) and mu (μ), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. Preferably the heavy chain is a human heavy chain.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "immunomodulatory agent" and variations thereof including, but not limited to, immunomodulatory agents, as used herein refer to an agent that modulates a host's immune system. In certain embodiments, an immunomodulatory agent is an immunosuppressant agent. In certain other embodiments, an immunomodulatory agent is an immunostimulatory agent. In accordance with the invention, an immunomodulatory agent used in the combination therapies of the invention does not include an anti-hLIGHT antibody or antigen-binding fragment Immunomodulatory agents include, but are not limited to, small molecules, peptides, polypeptides, proteins, fusion proteins, antibodies, inorganic molecules, mimetic agents, and organic molecules.

As used herein, the term "in combination" in the context of the administration of other therapies refers to the use of more than one therapy. The use of the term "in combination" does not restrict the order in which therapies are administered to a subject with an infection. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a hLIGHT-mediated disease. Any additional therapy can be administered in any order with the other additional therapies. In certain embodiments, the antibodies of the invention can be administered in combination with one or more therapies (e.g., therapies that are not the antibodies of the invention that are currently administered to prevent, treat, manage, and/or ameliorate a hLIGHT-mediated disease. Non-limiting examples of therapies that can be administered in combination with an antibody of the invention include analgesic agents, anesthetic agents, antibiotics, or immunomodulatory agents or any other agent listed in the *U.S. Pharmacopoeia* and/or *Physician's Desk Reference*.

The term "inorganic salt" as used herein refers to any compounds containing no carbon that result from replacement of part or all of the acid hydrogen or an acid by a metal or a group acting like a metal and are often used as a tonicity adjusting compound in pharmaceutical compositions and preparations of biological materials. The most common inorganic salts are NaCl, KCl, $NaH_2PO_4$, etc.

An "isolated" or "purified" antibody is substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e., culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. In a preferred embodiment, antibodies of the invention are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody of the invention is isolated or purified.

The term "human LIGHT," "hLIGHT" or "hLIGHT polypeptide" and similar terms refers to the polypeptides ("polypeptides," "peptides" and "proteins" are used interchangeably herein) comprising the amino acid sequence of SEQ ID NO:52 and related polypeptides, including SNP variants thereof. Related polypeptides include allelic variants (e.g., SNP variants); splice variants; fragments; derivatives; substitution, deletion, and insertion variants; fusion polypeptides; and interspecies homologs, preferably, which retain hLIGHT activity and/or are sufficient to generate an anti-hLIGHT immune response. Exemplary non-synonymous SNP variants include, but are not limited to, hLIGHT polypeptides comprising 214E-325 (a glutamic acid at position 214 and serine at position 32 of a hLIGHT polypeptide (e.g., the hLIGHT polypeptide depicted in SEQ ID NO:52)), 214K-32S, 214E-32L and 214E-32L. Also encompassed are soluble forms of hLIGHT which are sufficient to generate an anti-hLIGHT immunological response (see, e.g., SEQ ID NO:53 and SEQ ID NO:54). As those skilled in the art will appreciate, an anti-hLIGHT antibody of the invention can bind to a hLIGHT polypeptide, polypeptide fragment, antigen, and/or epitope, as an epitope is part of the larger antigen, which is part of the larger polypeptide fragment, which, in turn, is part of the larger polypeptide hLIGHT can exist in a trimeric (native) or monomeric (denatured) form.

The terms "Kabat numbering," and like terms are recognized in the art and refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3.

The term "light chain" when used in reference to an antibody refers to two distinct types, called kappa (κ) of lambda (λ) based on the amino acid sequence of the constant domains. Light chain amino acid sequences are well known in the art. In preferred embodiments, the light chain is a human light chain.

As used herein, the terms "manage," "managing," and "management" refer to the beneficial effects that a subject derives from a therapy (e.g., a prophylactic or therapeutic agent), which does not result in a cure of the infection. In certain embodiments, a subject is administered one or more therapies (e.g., prophylactic or therapeutic agents, such as an antibody of the invention) to "manage" a hLIGHT-mediated disease (e.g., IBD or GVHD), one or more symptoms thereof, so as to prevent the progression or worsening of the disease.

The term "monoclonal antibody" refers to an antibody obtained from a population of homogenous or substantially homogeneous antibodies, and each monoclonal antibody will typically recognize a single epitope on the antigen. In preferred embodiments, a "monoclonal antibody," as used herein, is an antibody produced by a single hybridoma or other cell, wherein the antibody immunospecifically binds to only a hLIGHT epitope as determined, e.g., by ELISA or other antigen-binding or competitive binding assay known in the art or in the Examples provided herein. The term "monoclonal" is not limited to any particular method for making the antibody. For example, monoclonal antibodies of the invention may be made by the hybridoma method as described in Kohler et al.; Nature, 256:495 (1975) or may be isolated from phage libraries using the techniques as described herein, for example. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York). Other exemplary methods of producing other monoclonal antibodies are provided in the Examples herein.

The term "naturally occurring" or "native" when used in connection with biological materials such as nucleic acid molecules, polypeptides, host cells, and the like, refers to those which are found in nature and not manipulated by a human being.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., see, for example, Chapter 11 in: *Short Protocols in Molecular Biology*, (2002) 5th Ed., Ausubel et al., eds., John Wiley and Sons, New York).

As used herein, the term "polynucleotide," "nucleotide," nucleic acid" "nucleic acid molecule" and other similar terms are used interchangeable and include DNA, RNA, mRNA and the like.

As used herein, the terms "prevent," "preventing," and "prevention" refer to the total or partial inhibition of the development, recurrence, onset or spread of a hLIGHT-mediated disease and/or symptom related thereto, resulting from the administration of a therapy or combination of therapies provided herein (e.g., a combination of prophylactic or therapeutic agents, such as an antibody of the invention).

As used herein, the term "prophylactic agent" refers to any agent that can totally or partially inhibit the development, recurrence, onset or spread of a hLIGHT-mediated disease and/or symptom related thereto in a subject. In certain embodiments, the term "prophylactic agent" refers to an antibody of the invention. In certain other embodiments, the term "prophylactic agent" refers to an agent other than an antibody of the invention. Preferably, a prophylactic agent is an agent which is known to be useful to or has been or is currently being used to prevent a hLIGHT-mediated disease and/or a symptom related thereto or impede the onset, development, progression and/or severity of a hLIGHT-mediated disease and/or a symptom related thereto. In specific embodiments, the prophylactic agent is a fully human anti-hLIGHT antibody, such as a fully human anti-hLIGHT monoclonal antibody.

In certain embodiments of the invention, a "prophylactically effective serum titer" is the serum titer in a subject, preferably a human, that totally or partially inhibits the development, recurrence, onset or spread of a hLIGHT-mediated disease and/or symptom related thereto in said subject.

The term "hLIGHT antigen" refers to that portion of a hLIGHT polypeptide to which an antibody immunospecifically binds. A hLIGHT antigen also refers to an analog or derivative of a hLIGHT polypeptide or fragment thereof to which an antibody immunospecifically binds. In some embodiments, a hLIGHT antigen is a monomeric hLIGHT antigen or a trimeric hLIGHT antigen. A region of a hLIGHT polypeptide contributing to an epitope may be contiguous amino acids of the polypeptide or the epitope may come together from two or more non-contiguous regions of the polypeptide The epitope may or may not be a three-dimensional surface feature of the antigen. A localized region on the surface of a hLIGHT antigen that is capable of eliciting an immune response is a hLIGHT epitope. The epitope may or may not be a three-dimensional surface feature of the antigen.

A "hLIGHT-mediated disease" and "hLIGHT-mediated disorder" are used interchangeably and refer to any disease that is completely or partially caused by or is the result of hLIGHT. In certain embodiments, hLIGHT is aberrantly (e.g., highly) expressed on the surface of a cell. In some embodiments, hLIGHT may be aberrantly upregulated on a particular cell type. In other embodiments, normal, aberrant or excessive cell signaling is caused by binding of hLIGHT to a hLIGHT ligand. In certain embodiments, the hLIGHT ligand is a hLIGHT receptor (e.g., HVEM, LTβR, or DCR3), for example, that is expressed on the surface of a cell, such as a colonic epithelial cell. In certain embodiments, the hLIGHT-mediated disease is an inflammatory bowel disease (IBD), such as Crohn's disease (CD) or ulcerative colitis (UC). In other embodiments, the hLIGHT-mediated disease is graft-versus-host disease (GVHD).

A "hLIGHT ligand" refers to a molecule which binds or otherwise interacts with hLIGHT. In preferred embodiments, the hLIGHT ligand is a hLIGHT receptor.

The terms "hLIGHT receptor" or "hLIGHT binding receptor" are used interchangeably herein and refer to a receptor polypeptide that binds to hLIGHT. In specific embodiments, the hLIGHT receptor is HVEM, FcβR or DcR3. In some embodiments, the hLIGHT receptor is expressed on the surface of a cell, such as a colonic epithelial cell.

The term "saccharide" as used herein refers to a class of molecules that are derivatives of polyhydric alcohols. Saccharides are commonly referred to as carbohydrates and may contain different amounts of sugar (saccharide) units, e.g., monosaccharides, disaccharides and polysaccharides.

The term "serum titer" as used herein refers to an average serum titer in a population of least 10, preferably at least 20, and most preferably at least 40 subjects up to about 100, 1000 or more.

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) might be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (60$^{th}$ ed., 2006).

The term "small molecule" and analogous terms include, but are not limited to, peptides, peptidomimetics, amino acids, amino acid analogues, polynucleotides, polynucleotide analogues, nucleotides, nucleotide analogues, organic or inorganic compounds (i.e., including heterorganic and/or ganometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The terms "stability" and "stable" as used herein in the context of a liquid formulation comprising an antibody that immunospecifically binds to a hLIGHT antigen refer to the resistance of the antibody in the formulation to thermal and chemical unfolding, aggregation, degradation or fragmentation under given manufacture, preparation, transportation and storage conditions. The "stable" formulations of the invention retain biological activity equal to or more than 80%, 85%, 90%, 95%, 98%, 99%, or 99.5% under given manufacture, preparation, transportation and storage conditions. The stability of the antibody can be assessed by degrees of aggregation, degradation or fragmentation by methods known to those skilled in the art, including but not limited to reduced Capillary Gel Electrophoresis (rCGE), Sodium Dodecyl Sulfate Polyacrylamide Gel Electrophoresis (SDS-PAGE) and HPSEC, compared to a reference antibody. The overall stability of a formulation comprising an antibody that immunospecifically binds to a hLIGHT antigen can be assessed by various immunological assays including, for example, ELISA and radioimmunoassay using the specific epitope of hLIGHT.

As used herein, the terms "subject" and "patient" are used interchangeably. As used herein, a subject is preferably a mammal such as a non-primate (e.g., cows, pigs, horses, cats, dogs, rats, etc.) or a primate (e.g., monkey and human), most preferably a human. In one embodiment, the subject is a mammal, preferably a human, having a hLIGHT-mediated disease. In another embodiment, the subject is a mammal, preferably a human, at risk of developing a hLIGHT-mediated disease.

As used herein "substantially all" refers to refers to at least about 60%, at least about 70%, at least about 75%, at least about 80%, at least about 85%, at least about 90%, at least about 95%, at least about 98%, at least about 99%, or about 100%.

The term "substantially free of surfactant" as used herein refers to a formulation of an antibody that immunospecifically binds to a hLIGHT antigen, said formulation containing less than 0.0005%, less than 0.0003%, or less than 0.0001% of surfactants and/or less than 0.0005%, less than 0.0003%, or less than 0.0001% of surfactants.

The term "substantially free of salt" as used herein refers to a formulation of an antibody that immunospecifically binds to a hLIGHT antigen, said formulation containing less than 0.0005%, less than 0.0003%, or less than 0.0001% of inorganic salts.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials.

As used herein, the term "tag" refers to any type of moiety that is attached to, e.g., a polypeptide and/or a polynucleotide that encodes a hLIGHT or hLIGHT antibody or antigen binding fragment thereof. For example, a polynucleotide that encodes a hLIGHT, hLIGHT antibody or antigen binding fragment thereof can contain one or more additional tag-encoding nucleotide sequences that encode a, e.g., a detectable moiety or a moiety that aids in affinity purification. When translated, the tag and the antibody can be in the form of a fusion protein. The term "detectable" or "detection" with reference to a tag refers to any tag that is capable of being visualized or wherein the presence of the tag is otherwise able to be determined and/or measured (e.g., by quantitation). A non-limiting example of a detectable tag is a fluorescent tag.

As used herein, the term "therapeutic agent" refers to any agent that can be used in the treatment, management or amelioration of a hLIGHT-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a hLIGHT-mediated disease or one or more symptoms related thereto. In specific embodiments, the therapeutic agent is a fully human anti-hLIGHT antibody, such as a fully human anti-hLIGHT monoclonal antibody.

The combination of therapies (e.g., use of prophylactic or therapeutic agents) which is more effective than the additive effects of any two or more single therapy. For example, a synergistic effect of a combination of prophylactic and/or therapeutic agents permits the use of lower dosages of one or more of the agents and/or less frequent administration of said agents to a subject with a hLIGHT-mediated disease. The ability to utilize lower dosages of prophylactic or therapeutic therapies and/or to administer said therapies less frequently reduces the toxicity associated with the administration of said therapies to a subject without reducing the efficacy of said therapies in the prevention, management, treatment or amelioration of a hLIGHT-mediated disease. In addition, a synergistic effect can result in improved efficacy of therapies in the prevention, or in the management, treatment or amelioration of a hLIGHT-mediated disease. Finally, synergistic effect of a combination of therapies (e.g., prophylactic or therapeutic agents) may avoid or reduce adverse or unwanted side effects associated with the use of any single therapy.

In certain embodiments of the invention, a "therapeutically effective serum titer" is the serum titer in a subject, preferably a human, that reduces the severity, the duration and/or the symptoms associated with a hLIGHT-mediated disease in said subject.

As used herein, the term "therapy" refers to any protocol, method and/or agent that can be used in the prevention, management, treatment and/or amelioration of a hLIGHT-mediated disease (e.g., IBD or GVHD). In certain embodiments, the terms "therapies" and "therapy" refer to a biological therapy, supportive therapy, and/or other therapies useful in the prevention, management, treatment and/or amelioration of a hLIGHT-mediated disease known to one of skill in the art such as medical personnel.

As used herein, the terms "treat," "treatment" and "treating" refer to the reduction or amelioration of the progression, severity, and/or duration of a hLIGHT-mediated disease (e.g., IBD or GVHD) resulting from the administration of one or more therapies (including, but not limited to, the administration of one or more prophylactic or therapeutic agents, such as an antibody of the invention). In specific embodiments, such terms refer to the reduction or inhibition of the binding of hLIGHT to HVEM, the reduction or inhibition of the binding of hLIGHT to LTβR, the reduction or inhibition of the binding of hLIGHT to DcR3, the reduction or inhibition of the production or secretion of CCL20 from a cell expressing a hLIGHT receptor of a subject, the reduction or inhibition of the production or secretion of IL-8 from a cell expressing a hLIGHT receptor of a subject, the reduction or inhibition of the production or secretion of RANTES from a cell expressing a hLIGHT receptor of a subject, and/or the inhibition or reduction of one or more symptoms associated with a hLIGHT-mediated disease, such as an IBD or GVHD. In specific embodiments, a prophylactic agent is a fully human anti-hLIGHT antibody, such as a fully human anti-hLIGHT monoclonal antibody.

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the light and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) 5$^{th}$ ed. ("Kabat et al."). In preferred embodiments, the variable region is a human variable region.

The term "variant" when used in relation to hLIGHT or to a hLIGHT antibody refers to a peptide or polypeptide comprising one or more (such as, for example, about 1 to about 25, about 1 to about 20, and preferably about 1 to about 15, more preferably about 1 to about 10, and most preferably about 1 to about 5) amino acid sequence substitutions, deletions, and/or additions as compared to a native or unmodified sequence. For example, a hLIGHT variant may result from one or more (such as, for example, about 1 to about 25, about 1 to about 20, and preferably about 1 to about 15, more preferably about 1 to about 10, and most preferably about 1 to about 5) changes to an amino acid sequence of native hLIGHT. Also by way of example, a variant of an anti-hLIGHT antibody may result from one or more (such as, for example, about 1 to about 25, about 1 to about 20, and preferably about 1 to about 15, more preferably about 1 to about 10, and most preferably about 1 to about 5) changes to an amino acid sequence of a native or previously unmodified anti-hLIGHT antibody. Variants may be naturally occurring, such as allelic or splice variants, or may be artificially constructed. Polypeptide variants may be prepared from the corresponding nucleic acid molecules encoding said variants. In preferred embodiments, the hLIGHT variant or hLIGHT antibody variant retains hLIGHT or hLIGHT antibody functional activity, respectively. In specific embodiments, a hLIGHT antibody variant immunospecifically binds hLIGHT and/or is antagonistic to hLIGHT activity. In certain embodiments, the variant is encoded by a single nucleotide polymorphism (SNP) variant of hLIGHT. An exemplary SNP variant of hLIGHT encodes either a glutamic acid (E) or an lysine (K) at amino acid position 214. Another exemplary SNP variant of hLIGHT encodes either a serine (S) or a leucine (L) at amino acid position 32.

BRIEF DESCRIPTION OF THE DRAWINGS

FIG. 1A—The human T cell line II23.D7 was activated with PMA and inonomycin overnight and stained for the activation marker CD69 in combination with various anti-hLIGHT antibodies. CD69 positive cells were gated and analyzed for hLIGHT staining (bold line) compared to control human anti-influenza IgG1 (dotted line) or staining of non-activated II23.D7 cells with anti-hLIGHT antibodies (grey line). Binding was detected with goat anti-human IgG-APC secondary antibody. FIG. 1B—The staining of activated the human T cell line II-23.D7 with human anti-hLIGHT antibodies is saturable. Activated II-23.D7 cells were labeled with human anti-hLIGHT antibodies at various concentrations and detected with anti-human IgG-APC. Plots of the geometric mean fluorescence intensity data are shown along with non-linear regression.

In FIG. 2A and FIG. 2B, graded amounts of anti-hLIGHT antibodies were used to stain EL4-hLIGHT cells, detected with anti-human IgG-APC and analyzed by flow cytometry. The geometric mean fluorescence intensity (MFI) was determined and non-linear regression analysis applied. In all experiments human anti-influenza protein M2 was used as a negative control. Data obtained from this analysis is represented in FIG. 3.

FIG. 3 depicts characteristics of human anti-hLIGHT monoclonal antibodies.

FIG. 4 depicts antibody cross-blocking by ELISA. This analysis defines two groups based on competition for binding to hLIGHT by ELISA. The individual antibodies were coated in the wells of a 96 well plate. Soluble FLAG-hLIGHT was pre-incubated with soluble anti-hLIGHT antibodies and then added to the coated wells. Binding of FLAG-hLIGHT to the coated antibody was detected with anti-FLAG IgG-HRP. The percent inhibition was determined using the OD of each sample in the following formula: % inhibition=(max−sample/max)×100.

In FIG. 5A and FIG. 5B, graded amounts of antibodies were incubated with EL4-hLIGHT cells, biotinylated human HVEM:Fc was added at a sub-saturating concentration and detected with SA-APC. As shown in (A), the human anti-influenza M2 antibody was used as a control.

In FIG. 6A and FIG. 6B, graded amounts of antibodies were incubated with EL4-hLIGHT cells, polyHis tagged human LTβR:Fc was added at a sub-saturating concentration and detected with anti-His-APC. As shown in FIG. 6A, the human anti-influenza M2 antibody was used as a control.

FIG. 9A—Recombinant soluble hLIGHT (1 μg/ml) was pre-incubated with anti-hLIGHT antibodies and added to the growth medium of HT29.14s cells. Growth media was harvested from two wells from each treatment at day 3. Levels of CCL20 were determined by ELISA. Media alone, soluble hLIGHT alone, soluble hLIGHT incubated with anti-influenza M2 antibody and each anti-hLIGHT antibody alone were included as controls. FIG. 9B—Nonlinear regression analysis of data represented in panel A.

FIGS. 10A-10B shows human anti-hLIGHT antibodies inhibit cell surface expressed hLIGHT-mediated RANTES secretion from human colonic epithelial cells. In FIG. 10A fixed EL4-hLIGHT cells were pre-incubated with anti-hLIGHT antibodies and added to the growth medium of HT29.14s cells. Growth media was harvested from two wells for each treatment at day 3. Levels of RANTES were determined by ELISA. Media alone, EL4-hLIGHT cells alone, soluble hLIGHT alone, and each anti-hLIGHT antibody alone were included as controls. FIG. 10B—Plot of data represented in FIG. 10A.

FIG. 11 depicts the results of a competitive blocking experiment for binding to hLIGHT.

FIGS. 12A-12F depicts the blocking activity of antibodies for HVEM:Fc binding to 293 hLIGHT cells. E1, E13 F19 human anti-hLIGHT monoclonal antibodies, the R&D mAb, and commercially available goat anti-hLIGHT polyclonal antibodies (R&D Systems), and rabbit anti-hLIGHT polyclonal antibodies (eBioscience) were tested for their ability to block binding of HVEM:Fc to 293 cells expressing hLIGHT.

FIGS. 13A-13E depicts the blocking activity of antibodies for LTβR:Fc binding to 293 hLIGHT cells. E1 and E13 human anti-hLIGHT monoclonal antibodies, the R&D mAb, and commercially available goat anti-hLIGHT polyclonal antibodies (R&D Systems), and rabbit anti-hLIGHT polyclonal antibodies (eBioscience) were tested for their ability to block binding of LTβR:Fc to 293 cells expressing hLIGHT.

FIG. 14 depicts the blocking activity of antibodies for (FIG. 14A) LTβR:Fc and (FIG. 14B) HVEM:Fc binding to 293 hLIGHT cells and is a graphical representation of the data shown in FIGS. 12 and 13.

FIGS. 15A-15B depicts the binding of various anti-hLIGHT antibodies to native or denatured soluble hLIGHT. Five micrograms of soluble human LIGHT was either boiled in 2×SDS sample buffer (denatured) or untreated (native), and then both were serially diluted in 6× increments. 5 μl of each hLIGHT dilution was spotted simultaneously onto hydrated 0.2 μm PVDF membranes (Invitrogen, Carlsbad, Calif.) using an 8 multi-channel pipette. The blots were allowed to air dry then re-hydrated, blocked (1×TBST (Tris-buffered saline Tween-20) +2.5% skim milk+0.02% sodium azide). Each blot was probed with 5 μg/ml of each primary antibody. The blots were washed 3×in 1×TBST followed by biotinylated secondary Abs (Biotin-Goat aHuman (Vector Labs, Burlingame, Calif.), Biotin-Goat a mouse (Jackson labs, Bar Harbor, Me.), Biotin-Mouse α goat (Sigma-Aldrich corp., St. Louis, Mo.)) at 5 μg/ml. The blots were washed 3× in 1×TBST followed by super SA-HRP (Amersham Biosciences, Piscataway, N.J.). Chemiluminescence was used for detection using the ECL detection kit (Amersham Biosciences, Piscataway, N.J.) and signal was visualized by exposure to X-OMAT AR imaging film (Kodak, Rochester, N.Y.). FIG. 15A—Dot blot results using E1, E13, E63, F19, F23 human anti-hLIGHT mAb, or two murine anti-hLIGHT monoclonal antibodies commercially available from R&D Systems ("R&D mouse mAb") and Abnova ("Abnova mouse mAb"). An anti-M2 (irrelevant antigen) antibody was used as a negative control. FIG. 15B—Dot blot results using a commercial goat anti-hLIGHT polyclonal antibody preparation (R&D Systems "R&D goat pAb") or two commercial rabbit anti-hLIGHT polyclonal antibody preparations (eBioscience ("eBioscience rabbit pAb") and Peprotech ("Peprotech rabbit pAb")).

FIG. 16 depicts the binding of various anti-hLIGHT antibodies to native or denatured soluble hLIGHT and summarizes the data presented in FIG. 15 in tabular form.

FIG. 20 depicts antibody cross-blocking by ELISA comparing single kappa chain antibodies to their parental counterparts. This analysis defines two groups based on competition for binding to hLIGHT by ELISA. The individual antibodies were coated in the wells of a 96 well plate. Soluble FLAG-hLIGHT was pre-incubated with soluble anti-hLIGHT antibodies and then added to the coated wells. Binding of FLAG-hLIGHT to the coated antibody was detected with anti-FLAG IgG-HRP. The percent inhibition was determined using the OD of each sample in the following formula: % inhibition=(max−sample/max)×100.

FIGS. 21A-21B depicts the blockade of (FIG. 21A) human HVEM:Fc or (FIG. 21B) human LTβR:Fc binding to native hLIGHT on the cell surface by human anti-hLIGHT monoclonal antibodies and their single kappa chain recombinant counterparts. Graded amounts of antibodies were incubated with EL4-hLIGHT cells, biotinylated human HVEM:Fc or polyHis labeled human LTβR:Fc added at a sub-saturating concentration, and then detected with SA-APC or anti-His-APC. Antibodies were purified from either hybridoma cultures or 293F cells transiently transfected with mammalian expression vectors encoding the different kappa chain cDNAs paired with the heavy chain gene.

(FIG. 24B) encoding a leucine (L) or serine (S) at amino acid position 32) across various ethnic populations.

FIGS. 25A-25D. FIGS. 25A-25C depict a dose titration of the staining of cell lines expressing non-synonymous SNP variants of human LIGHT with the human anti-hLIGHT antibodies 124F23 and 124E1kappa((B). Graded amounts of anti-hLIGHT antibodies were used to stain EL4-hLIGHT cells expressing either the SNP variant (FIG. 25A) 214E-32S (FIG. 25B) 214K-32S, or (FIG. 25C) 214E-32L, detected with anti-human IgG-APC and analyzed by flow cytometry. FIG. 25D depicts a dose titration of human anti-LIGHT antibody-mediated blockade of human HVEM:Fc (squares) or LTBR:Fc (triangles) binding to cell surface expressed 214K-32S LIGHT SNP variant performed as in FIG. 5. For FIG. 25A-25D, the geometric mean fluorescence intensity (MFI) was determined and non-linear regression analysis applied.

FIG. 26A—The EL4-LIGHT SNP 214E cell line and (FIG. 26B) the EL4 SNP 214K cell line were stained with one concentration (10 μg/ml) of each anti-hLIGHT antibody. Binding was detected with goat anti-human IgG-APC secondary antibody. Isotype control human IgG was used as a negative control.

(FIG. 31A) Anti-LIGHT MAb treated mouse cecum section and (FIG. 31B) control human IgG treated mouse. Involution of the sub-mucosa indicates ascites, dashed arrows indicate regions of blood and the solid arrow indicates a region of lymphocyte infiltrate.

DETAILED DESCRIPTION

Figure 1A:
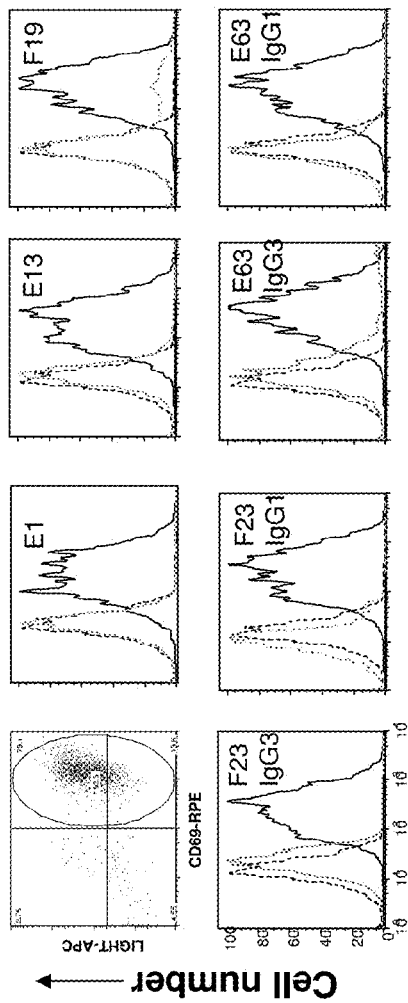
FIGS. 1A-1B depicts a cytometric analysis of endogenously expressed hLIGHT with human anti-hLIGHT antibodies.

Provided herein are antibodies that immunospecifically bind to a hLIGHT polypeptide, a hLIGHT polypeptide fragment, or a hLIGHT epitope. Also provided are isolated nucleic acids encoding antibodies that immunospecifically bind to a hLIGHT polypeptide, a hLIGHT polypeptide fragment, or a hLIGHT epitope. Further provided are vectors and host cells comprising nucleic acids encoding antibodies that immunospecifically bind to a hLIGHT polypeptide, a hLIGHT polypeptide fragment, or a hLIGHT epitope. Also provided are methods of making antibodies that that immunospecifically bind to a hLIGHT polypeptide, a hLIGHT polypeptide fragment, or a hLIGHT epitope. Also provided herein is a method of treating or managing a hLIGHT-mediated disease comprising administering an antibody that immunospecifically binds to a hLIGHT polypeptide, a hLIGHT polypeptide fragment, or a hLIGHT epitope.

Antibodies

Antibodies of the invention include, but are not limited to, synthetic antibodies, monoclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In particular, antibodies provided herein include immunoglobulin molecules and immunologically active portions of immunoglobulin molecules, i.e., molecules that contain an antigen binding site that immunospecifically binds to a hLIGHT antigen. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, preferably an IgG1 or IgG4.

Variants and derivatives of antibodies include antibody fragments that retain the ability to specifically bind to an epitope. Preferred fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')$_2$ (two Fab' molecules joined by inter-chain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody to be used with the invention comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in *The Pharmacology of Monoclonal Antibodies*, vol. 113, Rosenburg and Moore eds. Springer-Verlag, New York, pp. 269-315 (1994).

The antibodies of the invention may be from any animal origin including birds and mammals (e.g., human, murine, donkey, sheep, rabbit, goat, guinea pig, camel, horse, or chicken). In certain embodiments, the antibodies of the invention are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In preferred embodiments, the antibodies of the invention are fully human antibodies, such as fully human antibodies that immunospecifically bind a hLIGHT polypeptide, a hLIGHT polypeptide fragment, or a hLIGHT epitope. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies (e.g., anti-hLIGHT antibodies derived from other species) when administered to the subject.

The antibodies of the present invention may be monospecific, bispecific, trispecific or of greater multispecificity. Multispecific antibodies may be specific for different epitopes of a hLIGHT polypeptide or may be specific for both a hLIGHT polypeptide as well as for a heterologous epitope, such as a heterologous polypeptide or solid support material. In preferred embodiments, the antibodies provided herein are monospecific for a given epitope of a hLIGHT polypeptide and do not immunospecifically bind to other epitopes.

In preferred embodiments, antibodies of the compositions comprising the antibodies and methods of using the antibodies of the present invention include an E1, E13, E63, F19 or F23 antibody (ATCC Accession Nos. PTA-7729, PTA-7842, PTA-7818, PTA-7819, or PTA-7728, respectively). Also provided herein are hybridomas that produce E1, E13, E63, F19 or F23 antibody (ATCC Accession Nos. PTA-7729, PTA-7842, PTA-7818, PTA-7819, or PTA-7728, respectively) and/or other anti-hLIGHT monoclonal antibodies described herein.

In certain embodiments, an isolated antibody is provided herein that immunospecifically binds to a hLIGHT epitope wherein the binding to the hLIGHT epitope by the antibody is competitively blocked (e.g., in a dose-dependent manner) by: (a) an E1 antibody, E13 antibody, or E63 antibody, or (b) an F19 antibody or F23 antibody; with the proviso that the binding to the hLIGHT epitope is not blocked by both of: (a) the E1 antibody and the F19 antibody, (b) the E1 antibody and the F23 antibody, (c) the E13 antibody and the F19 antibody, (d) the E13 antibody and the F23 antibody, (e) the E63 antibody and the F19 antibody, or (f) the E63 antibody and the F23 antibody. The antibody may or may not be a fully human antibody. In preferred embodiments, the antibody is a fully human monoclonal anti-hLIGHT antibody, and even more preferably a fully human, monoclonal, antagonist anti-hLIGHT antibody. Exemplary competitive blocking tests that can be used are provided in the Examples herein.

In other embodiments, an isolated antibody, preferably a fully human antibody, is provided herein that immunospecifically binds to a hLIGHT epitope, wherein the binding to the hLIGHT epitope by the antibody is competitively blocked (e.g., in a dose-dependent manner) by: (a) an E1 antibody, E13 antibody, or E63 antibody, or (b) an F19 antibody or F23 antibody. The antibody may or may not be a fully human antibody. In preferred embodiments, the antibody is a fully human monoclonal anti-hLIGHT antibody, and even more preferably a fully human, monoclonal, antagonist anti-hLIGHT antibody. Exemplary competitive blocking tests that can be used are provided in the Examples herein.

In some embodiments, the antibodies provided herein compete (e.g., in a dose-dependent manner) with HVEM, LTβR and/or DcR3 (or fusion protein(s) thereof) for binding to cell surface-expressed hLIGHT. In other embodiments, the antibodies provided herein compete (e.g., in a dose-dependent manner) with HVEM, LTβR and/or DcR3 (or fusion protein(s) thereof) for binding to soluble hLIGHT. Exemplary competitive binding assays that can be used are provided in the Examples herein. In one embodiment, the antibody partially or completely inhibits binding of HVEM, LTβR and/or DcR3 to cell surface-expressed hLIGHT, such as hLIGHT. In another embodiment, the antibody partially or completely inhibits binding of HVEM, LTβR and/or DcR3 to soluble hLIGHT. In some embodiments, the antibodies provided herein partially or completely inhibits the secretion of CCL20, IL-8, and/or RANTES from a cell having cell surface-expressed hLIGHT ligand, such as a hLIGHT receptor (e.g., HVEM, LTβR and/or DcR3). In certain embodiments, the cell expressing the hLIGHT receptor is a colonic epithelial cell.

The antibodies of the present invention include those antibodies and antigen-binding fragments of the following antibodies: an E1 antibody (ATCC Accession No. PTA-7729), E13 antibody (ATCC Accession No. PTA-7842), or E63 antibody (ATCC Accession No. PTA-7818), an F19 antibody (ATCC Accession No. PTA-7819) or F23 antibody (ATCC Accession No. PTA-7728) antibody, the Examples Section, and elsewhere in the application. In a specific embodiment, an antibody of the present invention is E1, E13, E63, F19, or F23 antibody. In another embodiment, an antibody of the invention comprises an antigen-binding fragment (e.g., a Fab fragment) of E1, E13, E63, F19, or F23.

Preferably, the antibodies of the invention are fully human, monoclonal antibodies, such as fully human, monoclonal antagonist antibodies, that immunospecifically bind to hLIGHT.

In some embodiments, the antibodies provided herein bind to a hLIGHT epitope that is a three-dimensional surface feature of a hLIGHT polypeptide (e.g., in a trimeric form of a hLIGHT polypeptide). A region of a hLIGHT polypeptide contributing to an epitope may be contiguous amino acids of the polypeptide or the epitope may come together from two or more non-contiguous regions of the polypeptide A hLIGHT epitope may be present in (a) the trimeric form ("a trimeric hLIGHT epitope") of hLIGHT, (b) the monomeric form ("a monomeric hLIGHT epitope") of hLIGHT, (c) both the trimeric and monomeric form of hLIGHT, (d) the trimeric form, but not the monomeric form of hLIGHT, or (e) the monomeric form, but not the trimeric form of hLIGHT.

For example, in some embodiments, the epitope is only present or available for binding in the trimeric (native) form, but is not present or available for binding in the monomeric (denatured) form by an anti-hLIGHT antibody. In other embodiments, the hLIGHT epitope is linear feature of the hLIGHT polypeptide (e.g., in a trimeric form or monomeric form of the hLIGHT polypeptide). Antibodies provided herein may immunospecifically bind to (a) an epitope of the monomeric form of hLIGHT, (b) an epitope of the trimeric form of hLIGHT, (c) an epitope of the monomeric but not the trimeric form of hLIGHT, (d) an epitope of the trimeric but not the monomeric form of hLIGHT, or (e) both the monomeric form and the trimeric form of hLIGHT. In preferred embodiments, the antibodies provided herein immunospecifically bind to an epitope of the trimeric form of hLIGHT but do not immunospecifically bind to an epitope the monomeric form of hLIGHT.

In a specific embodiment, the present invention provides for one or more antibodies that immunospecifically bind to a hLIGHT epitope, said antibodies comprising a VH chain and/or VL chain having the amino acid sequence of a VH chain and/or VL chain of an E1, E13, E63, F19, and/or F23 antibody; or of an antibody produced by a hybridoma having ATCC Accession Nos. PTA-7729, PTA-7842, PTA-7818, PTA-7819, or PTA-7728.

In another embodiment, the present invention provides for one or more antibodies that immunospecifically bind to a hLIGHT epitope, said antibodies comprising a VH domain and/or VL domain having the amino acid sequence of a VH domain and/or VL domain of E1, E13, E63, F19, and/or F23 antibody; or of an antibody produced by a hybridoma having ATCC Accession Nos. PTA-7729, PTA-7842, PTA-7818, PTA-7819, or PTA-7728.

In another embodiment, the present invention provides for antibodies that immunospecifically bind to a hLIGHT epitope, said antibodies comprising one, two, three, or more CDRs having the amino acid sequence of one, two, three, or more CDRs of E1, E13, E63, F19, and/or F23 antibody; or of an antibody produced by a hybridoma having ATCC Accession Nos. PTA-7729, PTA-7842, PTA-7818, PTA-7819, or PTA-7728.

In one embodiment, the present invention provides for one or more antibodies that immunospecifically bind to a hLIGHT epitope, said antibodies comprising a combination of VH CDRs and/or VL CDRs having the amino acid sequence of VH CDRs and/or VL CDRs of E1, E13, E63, F19, and/or F23; or of an antibody produced by a hybridoma having ATCC Accession Nos. PTA-7729, PTA-7842, PTA-7818, PTA-7819, or PTA-7728.

The present invention provides antibodies that immunospecifically bind to a hLIGHT epitope, said antibodies comprising a VH chain and/or VL chain having an amino acid sequence of a VH chain and/or VL chain, respectively, of an antibody that immunospecifically binds to a hLIGHT epitope wherein the binding to the hLIGHT epitope by the antibody is competitively blocked in a dose-dependent manner by: (a) an E1, E13, or E63 antibody, or (b) an F19 or F23 antibody; with the proviso that the binding to the hLIGHT epitope is not blocked by both of: (a) the E1 and the F19 antibody, (b) the E1 and the F23 antibody, (c) the E13 and the F19 antibody, (d) the E13 and the F23 antibody, (e) the E63 and the F19 antibody, or (f) the E63 and the F23 antibody.

The present invention also provides fully human antibodies that immunospecifically bind to a hLIGHT epitope, said antibodies comprising a VH chain and/or VL chain having an amino acid sequence of a VH chain and/or VL chain, respectively, of an antibody that immunospecifically binds to a hLIGHT epitope, wherein the binding to the hLIGHT epitope by the antibody is competitively blocked in a dose-dependent manner by: (a) an E1 antibody, E13 antibody, or E63 antibody, or (b) an F19 antibody or F23 antibody. Preferably, the fully human antibody is a fully human monoclonal antibody and/or a hLIGHT antagonist antibody.

The present invention provides antibodies that immunospecifically bind to a hLIGHT epitope, said antibodies comprising a VH domain and/or VL domain having an amino acid sequence of a VH domain and/or VL domain, respectively, of an antibody that immunospecifically binds to a hLIGHT epitope wherein the binding to the hLIGHT epitope by the antibody is competitively blocked in a dose-dependent manner by: (a) an E1, E13, or E63 antibody, or (b) an F19 or F23 antibody; with the proviso that the binding to the hLIGHT epitope is not blocked by both of: (a) the E1 and the F19 antibody, (b) the E1 and the F23 antibody, (c) the E13 and the F19 antibody, (d) the E13 and the F23 antibody, (e) the E63 and the F19 antibody, or (f) the E63 and the F23 antibody.

The present invention also provides fully human antibodies that immunospecifically bind to a hLIGHT epitope, said antibodies comprising a VH domain and/or VL domain having an amino acid sequence of a VH domain and/or VL domain, respectively, of an antibody that immunospecifically binds to a hLIGHT epitope, wherein the binding to the hLIGHT epitope by the antibody is competitively blocked in a dose-dependent manner by: (a) an E1 antibody, E13 antibody, or E63 antibody, or (b) an F19 antibody or F23 antibody. Preferably, the fully human antibody is a fully human monoclonal antibody and/or a hLIGHT antagonist antibody.

The present invention provides antibodies that immunospecifically bind to a hLIGHT epitope, said antibodies comprising one, two or three VH CDRs (i.e., VH CDR1, VH CDR2, and/or VH CDR3) having an amino acid sequence one, two or three VH CDRs, respectively, of an antibody that immunospecifically binds to a hLIGHT epitope wherein the binding to the hLIGHT epitope by the antibody is competitively blocked in a dose-dependent manner by: (a) an E1, E13, or E63 antibody, or (b) an F19 or F23 antibody; with the proviso that the binding to the hLIGHT epitope is not blocked by both of: (a) the E1 and the F19 antibody, (b) the E1 and the F23 antibody, (c) the E13 and the F19 antibody, (d) the E13 and the F23 antibody, (e) the E63 and the F19 antibody, or (f) the E63 and the F23 antibody.

The present invention also provides fully human antibodies that immunospecifically bind to a hLIGHT epitope, said antibodies comprising one, two or three VH CDRs (i.e., VH CDR1, VH CDR2, and/or VH CDR3) having an amino acid sequence one, two or three VH CDRs, respectively, of an antibody that immunospecifically binds to a hLIGHT epitope, wherein the binding to the hLIGHT epitope by the antibody is competitively blocked in a dose-dependent manner by: (a) an E1 antibody, E13 antibody, or E63 antibody, or (b) an F19 antibody or F23 antibody. Preferably, the fully human antibody is a fully human monoclonal antibody and/or a hLIGHT antagonist antibody.

The present invention provides antibodies that immunospecifically bind to a hLIGHT epitope, said antibodies comprising one, two or three VL CDRs (i.e., VL CDR1, VL CDR2, and/or VL CDR3) having an amino acid sequence one, two or three VL CDRs, respectively, of an antibody that immunospecifically binds to a hLIGHT epitope wherein the binding to the hLIGHT epitope by the antibody is competitively blocked in a dose-dependent manner by: (a) an E1, E13, or E63 antibody, or (b) an F19 or F23 antibody; with the proviso that the binding to the hLIGHT epitope is not blocked by both of: (a) the E1 and the F19 antibody, (b) the E1 and the F23 antibody, (c) the E13 and the F19 antibody, (d) the E13 and the F23 antibody, (e) the E63 and the F19 antibody, or (f) the E63 and the F23 antibody.

The present invention also provides fully human antibodies that immunospecifically bind to a hLIGHT epitope, said antibodies comprising one, two or three VL CDRs (i.e., VL CDR1, VL CDR2, and/or VL CDR3) having an amino acid sequence one, two or three VL CDRs, respectively, of an antibody that immunospecifically binds to a hLIGHT epitope, wherein the binding to the hLIGHT epitope by the antibody is competitively blocked in a dose-dependent manner by: (a) an E1 antibody, E13 antibody, or E63 antibody, or (b) an F19 antibody or F23 antibody. Preferably, the fully human antibody is a fully human monoclonal antibody and/or a hLIGHT antagonist antibody.

The present invention also provides antibodies that immunospecifically bind to a hLIGHT epitope, said antibodies comprising one or more VH CDRs (i.e., VH CDR1, VH CDR2, and/or VH CDR3) having an amino acid sequence of any one of the VH CDRs (i.e., VH CDR1, VH CDR2, and/or VH CDR3) of E1, E13, E63, F19, and/or F23; or of an antibody produced by a hybridoma having ATCC Accession Nos. PTA-7729, PTA-7842, PTA-7818, PTA-7819, or PTA-7728; or any combination thereof.

In one embodiment, antibodies that immunospecifically bind to a hLIGHT epitope comprise a VH domain having the amino acid sequence of the VH domain depicted in any one of SEQ ID NOS:1, 2, 3, 4 or 5 and/or a VL domain having the amino acid sequence of the VL domain depicted in any one of SEQ ID NOS:82, 6, 83, 7, 8, 90, 9, 91, or 10.

In certain embodiments, an antibody that immunospecifically binds to a hLIGHT epitope comprises (a) a VH domain having the amino acid sequence depicted in SEQ ID NO:1 and a VL domain having the amino acid sequence depicted in any one of SEQ ID NOS:82, 6 or 83; (b) a VH domain having the amino acid sequence depicted in SEQ ID NO:2 and a VL domain having the amino acid sequence depicted in SEQ ID NO:7; (c) a VH domain having the amino acid sequence depicted in SEQ ID NO:3 and a VL domain having the amino acid sequence depicted in SEQ ID NO:8; (d) a VH domain having the amino acid sequence depicted in SEQ ID NO:4 and a VL domain having the amino acid sequence depicted in any one of SEQ ID NOS:90, 9, 91 or 92; or (e) a VH domain having the amino acid sequence depicted in SEQ ID NO:5 and a VL domain having the amino acid sequence depicted in SEQ ID NO:10. Preferably, the antibody is a fully human antibody, such as a fully human monoclonal antibody, and/or a hLIGHT antagonist antibody.

In another embodiment, antibodies that immunospecifically bind to a hLIGHT epitope comprise a VH domain having the amino acid sequence of the VH domain of an antibody having ATCC Accession Nos. PTA-7729, PTA-7842, PTA-7818, PTA-7819, or PTA-7728 (E1, E13, E63, F19 or F23, respectively) and/or a VL domain having the amino acid sequence of the VL domain of an antibody having ATCC Accession No. ATCC Accession Nos. PTA-7729, PTA-7842, PTA-7818, PTA-7819, or PTA-7728 (E1, E13, E63, F19 or F23, respectively).

In certain embodiments, an antibody that immunospecifically binds to a hLIGHT epitope comprises (a) a VH domain having the amino acid sequence of an antibody having ATCC Accession No. PTA-7729 (E1) and a VL domain having the amino acid sequence of an antibody having ATCC Accession No. PTA-7729 (E1); (b) a VH domain having the amino acid sequence of an antibody having ATCC Accession No. PTA-7842 (E13) and a VL domain having the amino acid sequence of an antibody having ATCC Accession No. PTA-7842 (E13); (c) a VH domain having the amino acid sequence of an antibody having ATCC Accession No. PTA-7818 (E63) and a VL domain having the amino acid sequence of an antibody having ATCC Accession No. PTA-7818 (E63); (d) a VH domain having the amino acid sequence of an antibody having ATCC Accession No. PTA-7819 (F19) and a VL domain having the amino acid sequence of an antibody having ATCC Accession No. PTA-7819 (F19); or (e) a VH domain having the amino acid sequence of an antibody having ATCC Accession No. PTA-7728 (F23) and a VL domain having the amino acid sequence of an antibody having ATCC Accession No. PTA-7728 (F23). Preferably, the antibody is a fully human antibody, such as a fully human monoclonal antibody, and/or a hLIGHT antagonist antibody.

In some embodiments, antibodies of the invention comprise a VH CDR1 having the amino acid sequence of the VH CDR1 of any one of the VH regions depicted in SEQ ID NOS:1, 2, 3, 4 or 5. In another embodiment, antibodies of the invention comprise a VH CDR2 having the amino acid sequence of the VH CDR2 of any one of the VH regions depicted in SEQ ID NOS:1, 2, 3, 4 or 5. In another embodiment, antibodies of the invention comprise a VH CDR3 having the amino acid sequence of the VH CDR3 of any one of the VH regions depicted in SEQ ID NOS:1, 2, 3, 4 or 5. In certain embodiments, antibodies of the invention comprise a VH CDR1 and/or a VH CDR2 and/or a VH CDR3 independently selected from a VH CDR1, VH CDR2, VH CDR3 as depicted in any one of the VH regions depicted in SEQ ID NOS:1, 2, 3, 4 or 5.

The present invention also provides antibodies that immunospecifically bind to a hLIGHT epitope, said antibodies comprising one or more VL CDRs (i.e., VL CDR1, VL CDR2, and/or VL CDR3) having an amino acid sequence of any one of the VL CDRs (i.e., VL CDR1, VL CDR2 and/or VL: CDR3) of E1, E13, E63, F19, and/or F23; or of an antibody produced by a hybridoma having ATCC Accession Nos. PTA-7729, PTA-7842, PTA-7818, PTA-7819, or PTA-7728 (E1, E13, E63, F19 or F23, respectively); or any combination thereof.

In certain embodiments, an antibody that immunospecifically binds to an hLIGHT epitope comprises (1) a VH domain having (a) a VH CDR1, VH CDR2, and/or VH CDR3 having the amino acid sequence depicted in SEQ ID NOS:11, 12 and/or 13, respectively, (b) a VH CDR1, VH CDR2, and/or VH CDR3 having the amino acid sequence depicted in SEQ ID NOS:14, 15 and/or 16, respectively, (c) a VH CDR1, VH CDR2, and/or VH CDR3 having the amino acid sequence depicted in SEQ ID NOS:17, 18, and/or 19, respectively, (d) a VH CDR1, VH CDR2, and/or VH CDR3 having the amino acid sequence depicted in SEQ ID NOS: 20, 21 and/or 22, respectively, or (e) a VH CDR1, VH CDR2, and/or VH CDR3 having the amino acid sequence depicted in SEQ ID NOS:23, 24 and/or 24, respectively, and/or (2) a VL domain having (a) a VL CDR1 having the amino acid sequence depicted in any one of SEQ ID NOS:84, 26 or 85; a VL CDR2 having the amino acid sequence depicted in any one of SEQ ID NOS:86, 27, or 87; and/or a VL CDR3 having the amino acid sequence depicted in any one of SEQ ID NOS:88, 28, or 89, (b) a VL CDR1, VL CDR2, and/or VL CDR3 having the amino acid sequence depicted in SEQ ID NOS:29, 30 and/or 31, respectively, (c) a VL CDR1, VL CDR2, and/or VL CDR3 having the amino acid sequence depicted in SEQ ID NOS:32, 33 and/or 34, respectively, (d) a VL CDR1 having the amino acid sequence depicted in any one of SEQ ID NOS:93, 35, 94, or 95; a VL CDR2 having the amino acid sequence depicted in any one of SEQ ID NOS:96, 36, 97, or 98; and/or a VL CDR3 having the amino acid sequence depicted in any one of SEQ ID NOS:99, 37, 100, or 101, or (e) a VL CDR1, VL CDR2, and/or VL CDR3 having the amino acid sequence depicted in SEQ ID NOS:38, 39 and/or 40, respectively. Preferably, the antibody is a fully human antibody, such as a fully human monoclonal antibody, and/or a hLIGHT antagonist antibody.

In some embodiments, an antibody that immunospecifically binds to an hLIGHT epitope comprises (1) a VH domain having (a) a VH CDR1, VH CDR2, and/or VH CDR3 having the amino acid sequence of a VH CDR1, VH CDR2, and/or VH CDR3 of an antibody having ATCC Accession No. PTA-7729 (E1), (b) a VH CDR1, VH CDR2, and/or VH CDR3 having the amino acid sequence of a VH CDR1, VH CDR2, and/or VH CDR3 of an antibody having ATCC Accession No. PTA-7842 (E13), (c) a VH CDR1, VH CDR2, and/or VH CDR3 having the amino acid sequence of a VH CDR1, VH CDR2, and/or VH CDR3 of an antibody having ATCC Accession No. PTA-7818 (E63), (d) a VH CDR1, VH CDR2, and/or VH CDR3 having the amino acid sequence of a VH CDR1, VH CDR2, and/or VH CDR3 of an antibody having ATCC Accession No. PTA-7819 (F19), or (e) a VH CDR1, VH CDR2, and/or VH CDR3 having the amino acid sequence of a VH CDR1, VH CDR2, and/or VH CDR3 of an antibody having ATCC Accession No. PTA-7728 (F23), and/or (2) a VL domain having (a) a VL CDR1, VL CDR2, and/or VL CDR3 having the amino acid sequence of a VL CDR1, VL CDR2, and/or VL CDR3 of an antibody having ATCC Accession No. PTA-7729 (E1), (b) a VL CDR1, VL CDR2, and/or VL CDR3 having the amino acid sequence of a VL CDR1, VL CDR2, and/or VL CDR3 of an antibody having ATCC Accession No. PTA-7842 (E13), (c) a VL CDR1, VL CDR2, and/or VL CDR3 having the amino acid sequence of a VL CDR1, VL CDR2, and/or VL CDR3 of an antibody having ATCC Accession No. PTA-7818 (E63), (d) a VL CDR1, VL CDR2, and/or VL CDR3 having the amino acid sequence of a VL CDR1, VL CDR2, and/or VL CDR3 of an antibody having ATCC Accession No. PTA-7819 (F19), or (e) a VL CDR1, VL CDR2, and/or VL CDR3 having the amino acid sequence of a VL CDR1, VL CDR2, and/or VL CDR3 of an antibody having ATCC Accession No. PTA-7728 (F23). Preferably, the antibody is a fully human antibody, such as a fully human monoclonal antibody, and/or a hLIGHT antagonist antibody.

In certain embodiments, an antibody that immunospecifically binds to an hLIGHT epitope comprises (1) (a) a VH domain having a VH CDR1, VH CDR2, and/or VH CDR3 having the amino acid sequence depicted in SEQ ID NOS: 11, 12 and/or 13, respectively, and (b) a VL domain having a VL CDR1 having the amino acid sequence depicted in any one of SEQ ID NOS:84, 26 or 85; a VL CDR2 having the amino acid sequence depicted in any one of SEQ ID NOS:86, 27, or 87; and/or a VL CDR3 having the amino acid sequence depicted in any one of SEQ ID NOS:88, 28, or 89; (2) (a) a VH domain having a VH CDR1, VH CDR2, and/or VH CDR3 having the amino acid sequence depicted in SEQ ID NOS:14, 15 and/or 16, respectively, and (b) a VL CDR1, VL CDR2, and/or VL CDR3 having the amino acid sequence depicted in SEQ ID NOS:29, 30 and/or 31, respectively; (3) (a) a VH domain having a VH CDR1, VH CDR2, and/or VH CDR3 having the amino acid sequence depicted in SEQ ID NOS:17, 18, and/or 19, respectively, and (b) a VL domain having a VL CDR1, VL CDR2, and/or VL CDR3 having the amino acid sequence depicted in SEQ ID NOS: 32, 33 and/or 34, respectively; (4) (a) a VH domain having a VH CDR1, VH CDR2, and/or VH CDR3 having the amino acid sequence depicted in SEQ ID NOS:20, 21 and/or 22, respectively, and (b) a VL domain having a VL CDR1 having the amino acid sequence depicted in any one of SEQ ID NOS:93, 35, 94, or 95; a VL CDR2 having the amino acid sequence depicted in any one of SEQ ID NOS:96, 36, 97, or 98; and/or a VL CDR3 having the amino acid sequence depicted in any one of SEQ ID NOS: 99, 37, 100, or 101; or (5) (a) a VH domain having a VH CDR1, VH CDR2, and/or VH CDR3 having the amino acid sequence depicted in SEQ ID NOS:23, 24 and/or 24, respectively, and (b) a VL domain having a VL CDR1, VL CDR2, and/or VL CDR3 having the amino acid sequence depicted in SEQ ID NOS:38, 39 and/or 40, respectively. Preferably, the antibody is a fully human antibody, such as a fully human monoclonal antibody, and/or a hLIGHT antagonist antibody.

In some embodiments, an antibody that immunospecifically binds to an hLIGHT epitope comprises (1) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7729 (E1), and (b) a VL domain having a VL CDR1, VL CDR2, and/or VL CDR3 having the amino acid sequence of a VL CDR1, VL CDR2, and/or VL CDR3 of an antibody having ATCC Accession No. PTA-7729 (E1); (2) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7842 (E13) and (b) a VL domain having a VL CDR1, VL CDR2, and/or VL CDR3 having the amino acid sequence of a VL CDR1, VL CDR2, and/or VL CDR3 of an antibody having ATCC Accession No. PTA-7842 (E13); (3) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7818 (E63) and (b) a VL domain having a VL CDR1, VL CDR2, and/or VL CDR3 having the amino acid sequence of a VL CDR1, VL CDR2, and/or VL CDR3 of an antibody having ATCC Accession No. PTA-7818 (E63); (4) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7819 (F19) and a VL CDR1, VL CDR2, and/or VL CDR3 having the amino acid sequence of a VL CDR1, VL CDR2, and/or VL CDR3 of an antibody having ATCC Accession No. PTA-7819 (F19); or (5) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7728 (F23) and (b) a VL domain having a VL CDR1, VL CDR2, and/or VL CDR3 having the amino acid sequence of a VL CDR1, VL CDR2, and/or VL CDR3 of an antibody having ATCC Accession No. PTA-7728 (F23). Preferably, the antibody is a fully human antibody, such as a fully human monoclonal antibody, and/or a hLIGHT antagonist antibody.

In some embodiments, antibodies of the invention comprise a VL CDR1 having the amino acid sequence of the VL CDR1 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively). In another embodiment, antibodies of the invention comprise a VL CDR2 having the amino acid sequence of the VL CDR2 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively). In another embodiment, antibodies of the invention comprise a VL CDR3 having the amino acid sequence of the VL CDR3 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively). In certain embodiments, antibodies of the invention comprise a VL CDR1 and/or a VL CDR2 and/or a VL CDR3 independently selected from the VL CDR1, VL CDR2, VL CDR3 as depicted in any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively).

In some embodiments, antibodies of the invention comprises a (1) VH domain or chain having one or more of (a) a VH CDR1 having the amino acid sequence of a VH CDR1 of any one of the VH regions depicted in SEQ ID NOS:1, 2, 3, 4 or 5; or of an antibody produced by a hybridoma having ATCC Accession No. PTA-7729, PTA-7842, PTA-7818, PTA-7819, or PTA-7728 (E1, E13, E63, F19 or F23, respectively), (b) a VH CDR2 having the amino acid sequence of a VH CDR2 of any one of the VH regions depicted in SEQ ID NOS:1, 2, 3, 4 or 5; or of an antibody produced by a hybridoma having ATCC Accession No. PTA-7729, PTA-7842, PTA-7818, PTA-7819, or PTA-7728 (E1, E13, E63, F19 or F23, respectively), or (c) a VH CDR3 having the amino acid sequence a VH CDR3 of any one of the VH regions depicted in SEQ ID NOS:1, 2, 3, 4 or 5; or of an antibody produced by a hybridoma having ATCC Accession No. PTA-7729, PTA-7842, PTA-7818, PTA-7819, or PTA- 7728 (E1, E13, E63, F19 or F23, respectively); and/or (2) a VL domain or chain having one of more of (a) a VL CDR1 having the amino acid sequence of the VL CDR1 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively), (b) a VL CDR2 having the amino acid sequence of a VL CDR2 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively), and/or (c) a VL CDR3 having the amino acid sequence of a VL CDR3 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively).

35 or 38); VH CDR2 (SEQ ID NOS:12, 15, 18, 21 or 24) and VL CDR2 (SEQ ID NOS:86, 27, 87, 30, 33, 96, 36, 97, 98, or 39); a VH CDR2 (SEQ ID NOS:12, 15, 18, 21 or 24) and a VL CDR3 (SEQ ID NOS:88, 28, 89, 31, 34, 99, 37, 100, 101 or 40); a VH CDR3 (SEQ ID NOS:13, 16, 19, 22 or 25) and a VH CDR1 (SEQ ID NOS:11, 14, 17, 20, or 23); a VH CDR3 (SEQ ID NOS:13, 16, 19, 22 or 25) and a VL CDR2 (SEQ ID NOS:86, 27, 87, 30, 33, 96, 36, 97, 98, or 39); a VH CDR3 (SEQ ID NOS:13, 16, 19, 22 or 25) and a VL CDR3 (SEQ ID NOS:88, 28, 89, 31, 34, 99, 37, 100, 101 or 40); a VH1 CDR1, a VH CDR2 (SEQ ID NOS:12, 15, 18, 21 or 24) and a VL CDR1 (SEQ ID NOS:84, 26, 85, 29, 32, 35 or 38); a VH CDR1 (SEQ ID NOS:11, 14, 17, 20, or 23), a VH CDR2 (SEQ ID NOS:12, 15, 18, 21 or 24) and a VL CDR2 (SEQ ID NOS:86, 27, 87, 30, 33, 96, 36, 97, 98, or 39); a VH CDR1 (SEQ ID NOS:11, 14, 17, 20, or 23), a VH CDR2 (SEQ ID NOS:12, 15, 18, 21 or 24) and a VL CDR3 (SEQ ID NOS:88, 28, 89, 31, 34, 99, 37, 100, 101 or 40); a VH CDR2 (SEQ ID NOS:12, 15, 18, 21 or 24), a VH CDR3 (SEQ ID NOS:13, 16, 19, 22 or 25) and a VL CDR1 (SEQ

TABLE 1

Sequences of CDR regions of antibodies E1, E13, E63, F19, and F23 (SEQ ID NOS).

| Ab | VH | VH CDR1 | VH CDR2 | VH CDR3 | VL | VL CDR1 | VL CDR2 | VL CDR3 |
|---|---|---|---|---|---|---|---|---|
| E1 | (SEQ ID NO: 1) | RFNMN (SEQ ID NO: 11) | YISSSSYTIYYADS VKG (SEQ ID NO: 12) | SIAAFDY (SEQ ID NO: 13) | (SEQ ID NO: 82, 6*, 83) | RASQGISSALA (SEQ ID NO: 84) RASQSVSSSYLT (SEQ ID NO: 26*) RASQSVSSSYLA (SEQ ID NO: 85) | DASSLES (SEQ ID NO: 86) GASSRAT (SEQ ID NO: 27*) GASNRAT (SEQ ID NO: 87) | QQFNSYRT (SEQ ID NO: 88) QQYGSSMYT (SEQ ID NO: 28*) QQYGSSPWT (SEQ ID NO: 89) |
| E13 | (SEQ ID NO: 2) | NAWMS (SEQ ID NO: 14) | RIKSKIDGGTTDYA APVKG (SEQ ID NO: 15) | AMAGAFGF (SEQ ID NO: 16) | (SEQ ID NO: 7) | RASQSVSSSYLA (SEQ ID NO: 29) | GASSRAT (SEQ ID NO: 30) | QQYGSSPMYT (SEQ ID NO: 31) |
| E63 | (SEQ ID NO: 3) | SGGYYWS (SEQ ID NO: 17) | YIYYSGSTNYNPSLKS (SEQ ID NO: 18) | WITMFRGVGFDP (SEQ ID NO: 19) | (SEQ ID NO: 8) | RASQSIGSSLH (SEQ ID NO: 32) | YASQSFS (SEQ ID NO: 33) | HQSSSLPLT (SEQ ID NO: 34) |
| F19 | (SEQ ID NO: 4) | GYNWH (SEQ ID NO: 20) | EITHSGSTNYNPSLKS (SEQ ID NO: 21) | EIAVAGTGYYGMDV (SEQ ID NO: 22) | (SEQ ID NO: 90, 9*, 91, 92) | RVSQGISSYLN (SEQ ID NO: 93) RASQGINSAFA (SEQ ID NO: 35*) RMSQGISSYLA (SEQ ID NO: 94) RASQGVSSYLA (SEQ ID NO: 95) | SASNLQS (SEQ ID NO: 96) DASSLES (SEQ ID NO: 36*) AASTLQS (SEQ ID NO: 97) DASNRAT (SEQ ID NO: 98) | QRTJNAPPT (SEQ ID NO: 99) QQFNSYPLT (SEQ ID NO: 37*) QQYYSFPYT (SEQ ID NO: 100) QQRSNWHP (SEQ ID NO: 101) |
| F23 | (SEQ ID NO: 5) | GYYWN (SEQ ID NO: 23) | EINQYNPSLKS (SEQ ID NO: 24) | EIATADKGYYGLDV (SEQ ID NO: 25) | (SEQ ID NO: 10) | RASQGISSALA (SEQ ID NO: 38) | DASSLES (SEQ ID NO: 39) | QQFNSYPLT SEQ ID NO: 40) |

*Preferred E1 and F19 VL and VL CDR1-3 sequences.

The present invention also provides antibodies comprising one or more VH CDRs and one or more VL CDRs listed in Table I. In particular, the invention provides for an antibody comprising a VH CDR1 (SEQ ID NOS:11, 14, 17, 20, or 23) and a VL CDR1 (SEQ ID NOS:84, 26, 85, 29, 32, 35 or 38); a VH CDR1 (SEQ ID NOS:11, 14, 17, 20, or 23) and a VL CDR2 (SEQ ID NOS:86, 27, 87, 30, 33, 96, 36, 97, 98, or 39); a VH CDR1 (SEQ ID NOS:11, 14, 17, 20, or 23) and a VL CDR3 (SEQ ID NOS:88, 28, 89, 31, 34, 99, 37, 100, 101 or 40); a VH CDR2 (SEQ ID NOS:12, 15, 18, 21 or 24) and a VL CDR1 (SEQ ID NOS:84, 26, 85, 29, 32, 35 or 38), a VH CDR2 (SEQ ID NOS:12, 15, 18, 21 or 24), a VH CDR3 (SEQ ID NOS:13, 16, 19, 22 or 25) and a VL CDR2 (SEQ ID NOS:86, 27, 87, 30, 33, 96, 36, 97, 98, or 39); a VH CDR2 (SEQ ID NOS:12, 15, 18, 21 or 24) and a VL CDR3 (SEQ ID NOS:88, 28, 89, 31, 34, 99, 37, 100, 101 or 40); a VH CDR1 (SEQ ID NOS:11, 14, 17, 20, or 23), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR1 (SEQ ID NOS:11, 14, 17, 20, or 23), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR2 (SEQ ID NOS:12, 15, 18, 21 or 24), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR2 (SEQ ID NOS:12, 15, 18, 21 or 24), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR3 (SEQ ID NOS:13, 16, 19, 22 or 25), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR3 (SEQ ID NOS:13, 16, 19, 22 or 25), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25) and a VL CDR1 (SEQ ID NOS:84, 26, 85, 29, 32, 35 or 38); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25) and a VL CDR2 (SEQ ID NOS:86, 27, 87, 30, 33, 96, 36, 97, 98, or 39); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25) and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR2 (SEQ ID NOS:12, 15, 18, 21 or 24), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR1 (SEQ ID NOS:11, 14, 17, 20, or 23), a VH CDR2 (SEQ ID NOS:12, 15, 18, 21 or 24), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR3 (SEQ ID NOS:13, 16, 19, 22 or 25), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR1 (SEQ ID NOS:11, 14, 17, 20, or 23), a VH CDR3 (SEQ ID NOS:13, 16, 19, 22 or 25), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR2 (SEQ ID NOS:12, 15, 18, 21 or 24), a VH CDR3 (SEQ ID NOS:13, 16, 19, 22 or 25), a VL CDR2 (SEQ ID NOS:86, 27, 87, 30, 33, 96, 36, 97, 98, or 39) and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38), a VL CDR2 (SEQ ID NOS:86, 27, 87, 30, 33, 96, 36, 97, 98, or 39), and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38), a VL CDR2 (SEQ ID NOS:86, 27, 87, 30, 33, 96, 36, 97, 98, or 39), and a VL CDR3 (SEQ ID NOS:88, 28, 89, 31, 34, 99, 37, 100, 101 or 40); or any combination thereof of the VH CDRs (SEQ ID NOS:11-25) and VL CDRs (SEQ ID NOS:26-40) listed in Table I. The corresponding VH CDRs and VL CDRs of ATCC Accession No. PTA-7729, PTA-7842, PTA-7818, PTA-7819, or PTA-7728 (E1, E13, E63, F19, or F23), may also be used in any of the combinations listed above. Preferably, the antibody is a fully human antibody, such as a fully human monoclonal antibody, and/or a hLIGHT antagonist antibody.

The present invention also provides antibodies that immunospecifically bind to a hLIGHT epitope, the antibodies comprising derivatives of the VH domains, VH CDRs, VL domains, and VL CDRs described herein that immunospecifically bind to a hLIGHT antigen. The present invention also provides antibodies comprising derivatives of E1, E13, E63, F19, and/or F23, wherein said antibodies immunospecifically bind to a hLIGHT epitope. Standard techniques known to those of skill in the art can be used to introduce mutations in the nucleotide sequence encoding a molecule of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In another embodiment, an antibody that immunospecifically binds to a hLIGHT epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of E1, E13, E63, F19, and/or F23, or an antigen-binding fragment thereof, such as a VH domain, VL domain, VH chain, or VL chain. In one embodiment, an antibody that immunospecifically binds to a hLIGHT epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in SEQ ID NOS:1, 2, 3, 4 or 5. In another embodiment, an antibody that immunospecifically binds to a hLIGHT epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in SEQ ID NOS:82, 6, 83, 7, 8, 90, 9, 91, 92, or 10. In yet another embodiment, an antibody that immunospecifically binds to a hLIGHT epitope comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence depicted in SEQ ID NOS:11, 12, 13, 14, 15, 16, 17, 18, 19, 20, 21, 22, 23, 24, or 25 (VH CDRs) and/or a VL CDR amino acid sequence depicted in SEQ ID NOS:84, 26, 85, 86, 27, 87, 88, 28, 89, 2, 30, 31, 32, 33, 34, 93, 35, 94, 95, 96, 36, 97, 98, 99, 37, 100, 101, 38, 39, or 40.

In specific embodiments, the antibody is a fully human anti-human antibody, such as a fully human monoclonal antibody. Fully human antibodies may be produced by any method known in the art. Exemplary methods include immunization with a hLIGHT antigen (any hLIGHT polypeptide capable of eliciting an immune response, and optionally conjugated to a carrier) of transgenic animals (e.g., mice) that are capable of producing a repertoire of human antibodies in the absence of endogenous immunoglobulin production; see, e.g., Jakobovits et al., (1993) Proc. Natl. Acad. Sci., 90:2551; Jakobovits et al., (1993) Nature, 362:255 258 (1993); Bruggermann et al., (1993) Year in Immunol., 7:33. Other methods of producing fully human anti-hLIGHT antibodies can be found in the Examples provided herein.

Alternatively, fully human antibodies may be generated through the in vitro screening of phage display antibody libraries; see e.g., Hoogenboom et al., J. Mol. Biol., 227:381 (1991); Marks et al., J. Mol. Biol., 222:581 (1991), incorporated herein by reference. Various antibody-containing phage display libraries have been described and may be readily prepared by one skilled in the art. Libraries may contain a diversity of human antibody sequences, such as human Fab, Fv, and scFv fragments, that may be screened against an appropriate target.

In preferred embodiments, the antibodies used in accordance with the methods of the invention have a high affinity for a hLIGHT polypeptide, or polypeptide fragment or epitope thereof. In one embodiment, the antibodies used in accordance with the methods of the invention have a higher affinity for a hLIGHT antibody than known antibodies (e.g., commercially available monoclonal antibodies discussed elsewhere herein). In a specific embodiment, the antibodies used in accordance with the methods of the invention have a 2- to 10-fold (or more) higher affinity for a hLIGHT antigen than a known anti-hLIGHT antibody as assessed by techniques described herein or known to one of skill in the art (e.g., a BIAcore assay). In accordance with these embodiments, the affinity of the antibodies are, in one embodiment, assessed by a BIAcore assay.

In a specific embodiment, an antibody that immunospecifically binds a hLIGHT antigen comprises an amino acid sequence of a VH domain and/or an amino acid sequence a VL domain encoded by a nucleotide sequence that hybridizes to (1) the complement of a nucleotide sequence encoding any one of the VH and/or VL domains depicted in SEQ ID NOS:41, 42, 43, 44 or 45 (VH) and/or SEQ ID NOS:102, 46, 103, 47, 48, 104, 49, 105, 106, or 50 (VL) or (2) the complement of a nucleotide sequence encoding any one of the VH or VL domains of an antibody produced by a hybridoma having ATCC Accession No. PTA-7729, PTA-7842, PTA-7818, PTA-7819, or PTA-7728 (E1, E13, E63, F19 or F23) under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

In another embodiment, an antibody that immunospecifically binds a hLIGHT antigen comprises an amino acid sequence of a VH CDR or an amino acid sequence of a VL CDRs encoded by a nucleotide sequence that hybridizes to the complement of a nucleotide sequence encoding any one of the VH CDRs and/or VL CDRs depicted in SEQ ID NOS:11, 12, 13, 14, 15, 16, 17, 18, 19, 20, 21, 22, 23, 24, or 25 (VH CDRs) and/or SEQ ID NOS:84, 26, 85, 86, 27, 87, 88, 28, 89, 2, 30, 31, 32, 33, 34, 93, 35, 94, 95, 96, 36, 97, 98, 99, 37, 100, 101, 38, 39, or 40 (VL CDRs) or (b) the complement of a nucleic acid sequence encoding any one of the VH CDRs and/or VL CDRs of an antibody produced by a hybridoma having ATCC Accession No. PTA-7729, PTA-7842, PTA-7818, PTA-7819, or PTA-7728 (E1, E13, E63, F19 or F23) under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3)

The antibodies of the invention include antibodies that are chemically modified, i.e., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

The present invention also provides antibodies that immunospecifically bind to a hLIGHT antigen which comprise a framework region known to those of skill in the art (e.g., a human or non-human fragment). The framework region may, for example, be naturally occurring or consensus framework regions. Most preferably, the framework region of an antibody of the invention is human (see, e.g., Chothia et al., 1998, *J. Mol. Biol.* 278:457-479 for a listing of human framework regions, which is incorporated by reference herein in its entirety). See also Kabat et al. (1991) *Sequences of Proteins of Immunological Interest* (U.S. Department of Health and Human Services, Washington, D.C.) 5th ed.

In a specific embodiment, the present invention provides for antibodies that immunospecifically bind to a hLIGHT antigen, said antibodies comprising the amino acid sequence of one or more of the CDRs of E1, E13, E63, F19, and/or F23 (i.e., SEQ ID NOS:11, 12, 13, 14, 15, 16, 17, 18, 19, 20, 21, 22, 23, 24, or 25 (VH CDRs) or SEQ ID NOS:84, 26, 85, 86, 27, 87, 88, 28, 89, 2, 30, 31, 32, 33, 34, 93, 35, 94, 95, 96, 36, 97, 98, 99, 37, 100, 101, 38, 39, or 40 (VL CDRs), or of an antibody produced by a hybridoma having ATCC Accession No. PTA-7729, PTA-7842, PTA-7818, PTA-7819, or PTA-7728, and human framework regions with one or more amino acid substitutions at one, two, three or more of the following residues: (a) rare framework residues that differ between the murine antibody framework (i.e., donor antibody framework) and the human antibody framework (i.e., acceptor antibody framework); (b) Venier zone residues when differing between donor antibody framework and acceptor antibody framework; (c) interchain packing residues at the VH/VL interface that differ between the donor antibody framework and the acceptor antibody framework; (d) canonical residues which differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the VH domain and the VL domain. In certain embodiments, antibodies that immunospecifically bind to a hLIGHT antigen comprising the human framework regions with one or more amino acid substitutions at one, two, three or more of the above-identified residues are antagonistic hLIGHT antibodies.

The present invention encompasses antibodies that immunospecifically bind to a hLIGHT antigen, said antibodies comprising the amino acid sequence of the VH domain and/or VL domain or an antigen-binding fragment thereof of an antibody produced by the hybridoma having ATCC Accession No. PTA-7729, PTA-7842, PTA-7818, PTA-7819, or PTA-7728), or of an E1, E13, E63, F19, and/or F23 antibody, having mutations (e.g., one or more amino acid substitutions) in the framework regions. In certain embodiments, antibodies that immunospecifically bind to a hLIGHT antigen comprise the amino acid sequence of the VH domain and/or VL domain or an antigen-binding fragment thereof of E1, E13, E63, F19, and/or F23 with one or more amino acid residue substitutions in the framework regions of the VH and/or VL domains.

The present invention also encompasses antibodies that immunospecifically bind to a hLIGHT antigen, said antibodies comprising the amino acid sequence of the VH domain and/or VL domain of an antibody produced by the hybridoma having ATCC Accession No. PTA-7729, PTA-7842, PTA-7818, PTA-7819, or PTA-7728, or of an E1, E13, E63, F19, and/or F23 antibody, having mutations (e.g., one or more amino acid residue substitutions) in the hypervariable and framework regions. Preferably, the amino acid substitutions in the hypervariable and framework regions improve binding of the antibody to a hLIGHT antigen.

In some embodiments, antibodies provided herein decrease or inhibit binding of hLIGHT to HVEM, LTβR and/or DcR3, and/or decrease or inhibit a hLIGHT biological activity, such as secretion of CCL20, IL8 and/or RANTES, in subject (e.g., a human subject). In certain embodiments, antibodies provided herein, such as a human monoclonal anti-hLIGHT antibody, decreases or inhibits binding of a soluble or cell-surface expressed hLIGHT to HVEM or LTβR, and/or decreases or inhibits secretion of CCL20 and/or RANTES after contact with a soluble or cell-surface expressed hLIGHT, in a subject. In some embodiments, the hLIGHT is a SNP variant of hLIGHT, such as 214E-32S, 214K-32S, 214E-32L or 214K-32L. Blocking activity of an antibody provided herein of hLIGHT binding to HVEM, LTβR and/or DCR3 can be detected using an assay as described in any one of Examples 1-4 Inhibition of biological activity of cells expressing a hLIGHT receptor by a hLIGHT antibody provided herein can be detected using an assay as described in any one of Examples 1-4.

In other embodiments, antibodies provided herein decrease or inhibit binding of hLIGHT to HVEM, LTβR and/or DcR3 and/or decrease or inhibit a hLIGHT biological activity, such as secretion of CCL20, IL8 and/or RANTES, in a cell having a cell surface-expressed hLIGHT receptor (such as, HVEM, LTβR and/or Dc3R). In certain embodiments, antibodies provided herein, such as a human monoclonal anti-hLIGHT antibody, decreases or inhibits binding of a soluble or cell-surface expressed hLIGHT to HVEM or LTβR, and/or decreases or inhibits secretion of CCL20 and/or RANTES, in a cell having a cell surface-expressed hLIGHT receptor after contact with a soluble or cell-surface expressed hLIGHT. In some embodiments, the hLIGHT is a SNP variant of hLIGHT, such as 214E-32S, 214K-32S, 214E-32L or 214K-32L. Blocking activity of an antibody provided herein of hLIGHT binding to HVEM, LTβR and/or DCR3 can be detected using an assay as described in any one of Examples 1-4 Inhibition of biological activity of cells expressing a hLIGHT receptor by a hLIGHT antibody provided herein can be detected using an assay as described in any one of Examples 1-4.

The present invention also provides for fusion proteins comprising an antibody provided herein that immunospecifically binds to a hLIGHT antigen and a heterologous polypeptide. In some embodiments, the heterologous polypeptide to which the antibody is fused is useful for targeting the antibody to cells having cell surface-expressed hLIGHT.

The present invention also provides for panels of antibodies that immunospecifically bind to a hLIGHT antigen. In specific embodiments, the invention provides for panels of antibodies having different association rate constants different dissociation rate constants, different affinities for hLIGHT antigen, and/or different specificities for a hLIGHT antigen. The invention provides panels of about 10, preferably about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96 well or 384 well plates, such as for assays such as ELISAs.

Antibody Conjugates and Fusion Proteins

In some embodiments, antibodies of the invention are conjugated or recombinantly fused to a diagnostic, detectable or therapeutic agent or any other molecule. The conjugated or recombinantly fused antibodies can be useful, e.g., for monitoring or prognosing the onset, development, progression and/or severity of a hLIGHT-mediated disease as part of a clinical testing procedure, such as determining the efficacy of a particular therapy.

Such diagnosis and detection can accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I and $^{121}$I), carbon ($^{14}$C), sulfur ($^{35}$S), tritium ($^{3}$H), indium ($^{115}$In, $^{113}$In, $^{112}$I, and $^{111}$In), technetium ($^{99}$Tc), thallium ($^{201}$Ti) gallium ($^{68}$Ga, $^{67}$Ga), palladium ($^{103}$Pd), molybdenum ($^{99}$Mo), xenon ($^{133}$Xe), fluorine ($^{18}$F), $^{153}$SM, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

The present invention further encompasses uses of the antibodies of the invention conjugated or recombinantly fused to a therapeutic moiety (or one or more therapeutic moieties). The antibody may be conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun 266: 76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7): 2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432, 959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; 1ST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618, 709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, an antibody of the invention may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (pro-thrombin), factor V, XIIa, VIII, XIIIa, XI, XIa, IX, IXa, X, phospholipid, and fibrin monomer).

The present invention encompasses antibodies of the invention recombinantly fused or chemically conjugated (covalent or non-covalent conjugations) to a heterologous protein or polypeptide (or fragment thereof, preferably to a polypeptide of about 10, about 20, about 30, about 40, about 50, about 60, about 70, about 80, about 90 or about 100 amino acids) to generate fusion proteins. In particular, the invention provides fusion proteins comprising an antigen-binding fragment of an antibody of the invention (e.g., a Fab fragment, Fd fragment, Fv fragment, F(ab)$_2$ fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses hLIGHT or an hLIGHT receptor. For example, an antibody that immunospecifically binds to a cell surface receptor expressed by a particular cell type (e.g., an immune cell) may be fused or conjugated to a modified antibody of the invention.

A conjugated or fusion protein of the invention comprises any antibody of the invention described herein and a heterologous polypeptide. In one embodiment, a conjugated or fusion protein of the invention comprises E1, E13, E63, F19, or F23 antibody, or an antibody produced by a hybridoma having ATCC Accession No. PTA-7729, PTA-7842, PTA-7818, PTA-7819, or PTA-7728 (E1, E13, E63, F19, or F23), and a heterologous polypeptide. In another embodiment, a conjugated or fusion protein of the invention comprises an antigen-binding fragment of E1, E13, E63, F19, or F23, or of an antibody produced by a hybridoma having ATCC Accession No. PTA-7729, PTA-7842, PTA-7818, PTA-7819, or PTA-7728 (E1, E13, E63, F19, or F23), and a heterologous polypeptide. In another embodiment, a conjugated or fusion protein of the invention comprises a VH domain having the amino acid sequence of any one of the VH domains depicted in SEQ ID NOS:1, 2, 3, 4 or 5, or of an antibody produced by a hybridoma having ATCC Accession No. PTA-7729, PTA-7842, PTA-7818, PTA-7819, or PTA-7728 (E1, E13, E63, F19, or F23), and/or a VL domain having the amino acid sequence of any one of the VL domains depicted in SEQ ID NOS:82, 6, 83, 7, 8, 90, 9, 91, 92, or 10, or of an antibody produced by a hybridoma having ATCC Accession No. PTA-7729, PTA-7842, PTA-7818, PTA-7819, or PTA-7728 (E1, E13, E63, F19, or F23), and a heterologous polypeptide. In another embodiment, a conjugated or fusion protein of the present invention comprises one or more VH CDRs having the amino acid sequence of any one of the VH CDRs depicted in SEQ ID NOS:11, 12, 13, 14, 15, 16, 17, 18, 19, 20, 21, 22, 23, 24, or 25, or of an antibody produced by a hybridoma having ATCC Accession No. PTA-7729, PTA-7842, PTA-7818, PTA-7819, or PTA-7728 (E1, E13, E63, F19, or F23), and a heterologous polypeptide. In another embodiment, a conjugated or fusion protein comprises one or more VL CDRs having the amino acid sequence of any one of the VL CDRs depicted in SEQ ID NOS:84, 26, 85, 86, 27, 87, 88, 28, 89, 2, 30, 31, 32, 33, 34, 93, 35, 94, 95, 96, 36, 97, 98, 99, 37, 100, 101, 38, 39, or 40, or of an antibody produced by a hybridoma having ATCC Accession No. PTA-7729, PTA-7842, PTA-7818, PTA-7819, or PTA-7728 (E1, E13, E63, F19, or F23), and a heterologous polypeptide. In another embodiment, a conjugated or fusion protein of the invention comprises at least one VH domain and at least one VL domain depicted in SEQ ID NOS:1, 2, 3, 4 or 5 and SEQ ID NOS:82, 6, 83, 7, 8, 90, 9, 91, 92, or 10, respectively, or of an antibody produced by a hybridoma having ATCC Accession No. PTA-7729, PTA-7842, PTA-7818, PTA-7819, or PTA-7728 (E1, E13, E63, F19, or F23), and a heterologous polypeptide. In yet another embodiment, a conjugated or fusion protein of the invention comprises at least one VH CDR and at least one VL CDR depicted in SEQ ID NOS:11, 12, 13, 14, 15, 16, 17, 18, 19, 20, 21, 22, 23, 24, or 25 and SEQ ID NOS:84, 26, 85, 86, 27, 87, 88, 28, 89, 2, 30, 31, 32, 33, 34, 93, 35, 94, 95, 96, 36, 97, 98, 99, 37, 100, 101, 38, 39, or 40, respectively, or of an antibody produced by a hybridoma having ATCC Accession No. PTA-7729, PTA-7842, PTA-7818, PTA-7819, or PTA-7728 (E1, E13, E63, F19, or F23), and a heterologous polypeptide.

In addition, an antibody of the invention can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7, 10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Moreover, antibodies of the invention can be fused to marker sequences, such as a peptide to facilitate purification. In preferred embodiments, the marker amino acid sequence is a hexa-histidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992, which are incorporated herein by reference in their entireties.

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of antibodies of the invention (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding an antibody of the invention may be recombined with one or more components, motifs, sections, parts, domains, fragments, etc. of one or more heterologous molecules.

An antibody of the invention can also be conjugated to a second antibody to form an antibody heteroconjugate as described in U.S. Pat. No. 4,676,980, which is incorporated herein by reference in its entirety.

The therapeutic moiety or drug conjugated or recombinantly fused to an antibody of the invention that immunospecifically binds to a hLIGHT antigen should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody of the invention: the nature of the disease, the severity of the disease, and the condition of the subject.

Antibodies of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Pharmaceutical Compositions

Therapeutic formulations containing one or more antibodies of the invention provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies of the invention provided herein can also, for example, be formulated in liposomes. Liposomes containing the molecule of interest are prepared by methods known in the art, such as described in Epstein et al. (1985) *Proc. Natl. Acad. Sci. USA* 82:3688; Hwang et al. (1980) *Proc. Natl. Acad. Sci. USA* 77:4030; and U.S. Pat. Nos. 4,485,045 and 4,544,545. Liposomes with enhanced circulation time are disclosed in U.S. Pat. No. 5,013,556.

Particularly useful immunoliposomes can be generated by the reverse phase evaporation method with a lipid composition containing phosphatidylcholine, cholesterol and PEG-derivatized phosphatidylethanolamine (PEG-PE). Liposomes are extruded through filters of defined pore size to yield liposomes with the desired diameter. Fab' fragments of an antibody provided herein can be conjugated to the liposomes as described in Martin et al. (1982) *J. Biol. Chem.* 257:286-288 via a disulfide interchange reaction. A chemotherapeutic agent (such as Doxorubicin) is optionally contained within the liposome; See Gabizon et al., (1989) *J. National Cancer Inst.* 81(19):1484.

Formulations, such as those described herein, can also contain more than one active compound as necessary for the particular indication being treated. In certain embodiments, formulations comprise an antibody of the invention and one or more active compounds with complementary activities that do not adversely affect each other. Such molecules are suitably present in combination in amounts that are effective for the purpose intended. For example, an antibody of the invention can be combined with one or more other therapeutic agents. Such combined therapy can be administered to the patient serially or simultaneously or in sequence.

An antibody of the invention can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* (1990) Mack Publishing Co., Easton, Pa.

The formulations to be used for in vivo administration can be sterile. This is readily accomplished by filtration through, e.g., sterile filtration membranes.

Sustained-release preparations can also be prepared. Suitable examples of sustained-release preparations include semipermeable matrices of solid hydrophobic polymers containing the antagonist, which matrices are in the form of shaped articles, e.g., films, or microcapsule. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The pharmaceutical compositions provided herein contain therapeutically effective amounts of one or more of the antibodies of the invention provided herein, and optionally one or more additional prophylactic of therapeutic agents, in a pharmaceutically acceptable carrier. Such pharmaceutical compositions are useful in the prevention, treatment, management or amelioration of a hLIGHT-mediated disease, such as an inflammatory bowel disease, or one or more of the symptoms thereof.

Pharmaceutical carriers suitable for administration of the compounds provided herein include any such carriers known to those skilled in the art to be suitable for the particular mode of administration.

In addition, the antibodies of the invention may be formulated as the sole pharmaceutically active ingredient in the composition or may be combined with other active ingredients (such as one or more other prophylactic or therapeutic agents).

The compositions can contain one or more antibodies of the invention. In one embodiment, the antibodies are formulated into suitable pharmaceutical preparations, such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the antibodies described above are formulated into pharmaceutical compositions using techniques and procedures well known in the art (see, e.g., Ansel (1985) *Introduction to Pharmaceutical Dosage Forms*, 4$^{th}$ Ed., p. 126).

In the compositions, effective concentrations of one or more antibodies or derivatives thereof is (are) mixed with a suitable pharmaceutical carrier. The concentrations of the compounds in the compositions are effective for delivery of an amount, upon administration, that treats, prevents, or ameliorates a hLIGHT-mediated disease or symptom thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

An antibody of the invention is included in the pharmaceutically acceptable carrier in an effective amount sufficient to exert a therapeutically useful effect in the absence of undesirable side effects on the patient treated. The therapeutically effective concentration can be determined empirically by testing the compounds in in vitro and in vivo systems using routine methods and then extrapolated therefrom for dosages for humans.

The concentration of antibody in the pharmaceutical composition will depend on, e.g., the physicochemical characteristics of the antibody, the dosage schedule, and amount administered as well as other factors known to those of skill in the art.

In one embodiment, a therapeutically effective dosage produces a serum concentration of antibody of from about 0.1 ng/ml to about 50-100 µg/ml. The pharmaceutical compositions, in another embodiment, provide a dosage of from about 0.001 mg to about 2000 mg of antibody per kilogram of body weight per day. Pharmaceutical dosage unit forms can be prepared to provide from about 0.01 mg, 0.1 mg or 1 mg to about 500 mg, 1000 mg or 2000 mg, and in one embodiment from about 10 mg to about 500 mg of the antibody and/or a combination of other optional essential ingredients per dosage unit form.

The antibody can be administered at once, or may be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The antibody is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In preferred embodiments, one or more anti-hLIGHT antibodies of the invention are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see *Remington's Pharmaceutical Sciences* (1990) Mack Publishing Co., Easton, Pa.

Dosage forms or compositions containing antibody in the range of 0.005% to 100% with the balance made up from non-toxic carrier can be prepared. Methods for preparation of these compositions are known to those skilled in the art.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms. In certain embodiments, the formulations are capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, *acacia* mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The antibodies of the invention can be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The antibody can also be mixed with other active materials which do not impair the desired action, or with materials that supplement the desired action, such as antacids, H2 blockers, and diuretics. The active ingredient is an antibody or pharmaceutically acceptable derivative thereof as described herein. Higher concentrations, up to about 98% by weight of the active ingredient may be included.

In all embodiments, tablets and capsules formulations can be coated as known by those of skill in the art in order to modify or sustain dissolution of the active ingredient. Thus, for example, they may be coated with a conventional enterically digestible coating, such as phenylsalicylate, waxes and cellulose acetate phthalate.

In preferred embodiments, the formulations are liquid dosage forms. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, *acacia*, tragacanth, bentonite, and surfactants such as polyoxyethylene sorbitan monooleate. Suspending agents include sodium carboxymethylcellulose, pectin, tragacanth, Veegum and *acacia*. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is, in one embodiment, encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The antibody diffuses through the outer polymeric membrane in a release rate controlling step. The amount of antibody contained in such parenteral compositions is highly dependent on the specific nature thereof, as well as the activity of the compound and the needs of the subject.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration can be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The antibody can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and may be empirically determined.

In other embodiments, the pharmaceutical formulations are lyophilized powders, which can be reconstituted for administration as solutions, emulsions and other mixtures. They may also be reconstituted and formulated as solids or gels.

The lyophilized powder is prepared by dissolving a antibody provided herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The antibodies of the invention can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration can be manufactured using the same pharmaceutically acceptable substance and by the same methods as for formulations for oral administration.

The antibodies and other compositions provided herein may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, the anti-hLIGHT antibodies of the invention are targeted (or otherwise administered) to the colon, such as in a patient having or at risk of having an IBD.

In one embodiment, liposomal suspensions, including tissue-targeted liposomes, such as tumor-targeted liposomes, may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Methods of Administration and Dosing

The present invention further provides for compositions comprising one or more antibodies of the invention for use in the prevention, management, treatment and/or amelioration of a hLIGHT-mediated disease (or symptom thereof).

In certain embodiments, provided herein are compositions comprising one or more antibodies of the invention for use in the prevention, management, treatment and/or amelioration of a hLIGHT-mediated disease, such as IBD (e.g., ulcerative colitis or Crohn's disease), or a symptom thereof. IBD symptoms may range from mild to severe and generally depend upon the part of the intestinal tract involved. Exemplary symptoms of IBD include abdominal cramps and pain, bloody diarrhea, severe urgency to have a bowel movement, fever, loss of appetite, weight loss, anemia, fatigue, and/or sores on lower legs, ankles, calves, thighs, and arms. Exemplary intestinal complications of IBD include profuse bleeding from the ulcers, perforation or rupture of the bowel, strictures and obstruction, fistulae (abnormal passage) and perianal disease, toxic megacolon (e.g., acute nonobstructive dilation of the colon), and/or malignancy (e.g., cancer of the colon or small intestine). Exemplary extraintestinal complications of IBD include arthritis, skin conditions, inflammation of the eye, liver and kidney disorders, and/or bone loss. Any combination of these symptoms may be prevented, managed, treated, and/or ameliorated using the compositions and methods provided herein.

In certain embodiments, provided herein are compositions comprising one or more antibodies of the invention for use in the prevention, management, treatment and/or amelioration of an hLIGHT-mediated disease, such as GVHD, or a symptom thereof. GVHD generally occurs following allogeneic or matched unrelated bone marrow transplants (BMT).

In some embodiments, the GVHD is acute GVHD. The symptoms of acute GVHD can happen quickly and can be mild or severe. In certain instances, acute GVHD develops within about three months after transplant, such as when blood counts recover after transplant. It certain instances, the acute GVHD affects the skin, gastrointestinal (GI) tract and/or liver. For example, in some patients, acute skin GVHD begins with a rash, for example, on the palms of the patient's hands, soles of the feet, or shoulders. However, the rash can become widespread, and may be itchy and painful and/or might blister and peel. Acute liver GVHD may affect normal functions of the liver, such as liver enzymes, and may in turn, cause jaundice. Acute liver GVHD may also cause the patient's abdomen to become swollen and painful if the liver becomes enlarged. Finally, symptoms of acute gut GVHD (or GVHD of the digestive system) can include diarrhea, mucus or blood in the stool, cramping or abdominal pain, indigestion, nausea and/or loss of appetite. Other general symptoms of acute GVHD can include anemia. low grade fever, and/or being more prone to infections. Any combination of these symptoms of acute GVHD may be prevented, managed, treated, and/or ameliorated using the compositions and methods provided herein.

In other embodiments, the GVHD is chronic GVHD. Chronic GVHD can occur from about three months to about a year or longer after transplant. Chronic GVHD can be mild or severe, and generally includes symptoms similar to those of acute GVHD. Chronic GVHD can affect the skin and digestive system, including the liver but can also involve other organs and the immune system (e.g., making the patient more prone to infections) and/or connective tissues. Symptoms of chronic skin GVHD include a rash, dry skin, tight skin, itchy skin, darkening of the color of the skin, thickening of the skin, and/or may affect hair (e.g., hair loss, turning gray) or nails (e.g., hard or brittle nails). Chronic gut GVHD can affect the digestive system, mouth, esophagus, lining of the stomach, and/or lining of the bowel, and symptoms can include diarrhea, dry or sore mouth, painful swallowing, low nutrient absorption by the stomach, bloating, stomach cramps. Chronic liver GVHD can cause damage and scarring of the liver (cirrhosis). Chronic GVHD of the eyes can affect the glands that make tears, causing eyes to become dry, burning and painful or difficult to tolerate bright light. Chronic lung GVHD can cause shortness of breath, wheezing, persistent cough, and/or being more prone to chest infections. Chronic GVHD affects tendons (e.g., inflammation) that connect muscle to bone causing difficulty straightening or bending your arms and legs. Any combination of these symptoms of chronic GVHD may be prevented, managed, treated, and/or ameliorated using the compositions and methods provided herein.

In a specific embodiment, a composition for use in the prevention, management, treatment and/or amelioration of a hLIGHT-mediated disease comprises an E1, E13, E63, F19, and/or F23 antibody. In one embodiment, a composition for use in the prevention, management, treatment and/or amelioration of a hLIGHT-mediated disease comprises an antibody produced by a hybridoma having ATCC Accession No. PTA-7729, PTA-7842, PTA-7818, PTA-7819, or PTA-7728 (E1, E13, E63, F19 or F23). In another specific embodiment, a composition for use in the prevention, management, treatment and/or amelioration of a hLIGHT-mediated disease comprises an antigen-binding fragment of an E1, E13, E63, F19, and/or F23 antibody. In another embodiment, a composition for use in the prevention, management, treatment and/or amelioration of a hLIGHT-mediated disease comprises an antigen-binding fragment of an antibody produced by a hybridoma having ATCC Accession No. PTA-7729, PTA-7842, PTA-7818, PTA-7819, or PTA-7728 (E1, E13, E63, F19 or F23).

In another embodiment, a composition for use in the prevention, management, treatment and/or amelioration of a hLIGHT-mediated disease comprises one or more antibodies comprising one or more VH domains having an amino acid sequence of any one of the VH domains depicted in SEQ ID NOS:1, 2, 3, 4 or 5, or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VH CDR1s having an amino acid sequence of any one of the VH CDR1s depicted in SEQ ID NOS:11, 14, 17, 20, or 23 (i.e., VH CDR1s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VH CDR2s having an amino acid sequence of any one of the VH CDR2s depicted in SEQ ID NOS:12, 15, 18, 21, or 24 (i.e., VH CDR2s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23). In a preferred embodiment, a composition for use in the prevention, management, treatment and/or amelioration of a hLIGHT-mediated disease comprises one or more antibodies comprising one or more VH CDR3s having an amino acid sequence of any one of the VH CDR3s depicted in SEQ ID NOS:13, 16, 19, 22, or 25 (i.e., VH CDR3s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23).

In another embodiment, a composition for use in the prevention, management, treatment and/or amelioration of a hLIGHT-mediated disease comprises one or more antibodies comprising one or more VL domains having an amino acid sequence of any one of the VL domains depicted in SEQ ID NOS:82, 6, 83, 7, 8, 90, 9, 91, 92, or 10, or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VL CDR1s having an amino acid sequence of any one of the VL CDR1s depicted in SEQ ID NOS:84, 26, 85, 29, 32, 93, 35, 94, 95, or 38 (i.e., VL CDR1s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VL CDR2s having an amino acid sequence of any one of the VL CDR2s depicted in SEQ ID NOS:86, 27, 87, 30, 33, 96, 36, 97, 98, or 39 (i.e., VL CDR2s of the VL depicted in SEQ ID NOS:82, 6, 83, 7, 8, 90, 9, 91, 92, or 10, respectively); or of an antibody produced by a hybridoma having ATCC Accession No. PTA-7729, PTA-7842, PTA-7818, PTA-7819, or PTA-7728 (E1, E13, E63, F19 or F23). In a preferred embodiment, a composition for use in the prevention, management, treatment and/or amelioration of a hLIGHT-mediated disease comprises one or more antibodies comprising one or more VL CDR3s having an amino acid sequence of any one of the VL CDR3s depicted in SEQ ID NOS:88, 28, 89, 31, 34, 99, 37, 100, 101, or 40 (i.e., VL CDR3s of the VL depicted in SEQ ID NOS:82, 6, 83, 7, 8, 90, 9, 91, 92, or 10, respectively); or of an antibody produced by a hybridoma having ATCC Accession No. PTA-7729, PTA-7842, PTA-7818, PTA-7819, or PTA-7728 (E1, E13, E63, F19 or F23).

In another embodiment, a composition for use in the prevention, management, treatment and/or amelioration of a hLIGHT-mediated disease comprises one or more antibodies comprising one or more VH domains having an amino acid sequence of any one of the VH domains depicted in SEQ ID NOS:1, 2, 3, 4 or 5, or of an antibody produced by a hybridoma having ATCC Accession No. PTA-7729, PTA-7842, PTA-7818, PTA-7819, or PTA-7728 (E1, E13, E63, F19 or F23), and one or more VL domains having an amino acid sequence of any one of the VL domains depicted in SEQ ID NOS:82, 6, 83, 7, 8, 90, 9, 91, 92, or 10, or of an antibody produced by a hybridoma having ATCC Accession No. PTA-7729, PTA-7842, PTA-7818, PTA-7819, or PTA-7728 (E1, E13, E63, F19 or F23).

In another embodiment, a composition for use in the prevention, management, treatment and/or amelioration of a hLIGHT-mediated disease comprises one or more antibodies comprising one or more VH CDR1s having an amino acid sequence of any one of the VH CDR1s depicted in SEQ ID NOS:11, 14, 17, 20, or 23 (i.e., VH CDR1s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR1s having an amino acid sequence of any one of the VL CDR1s depicted in SEQ ID NOS:84, 26, 85, 29, 32, 93, 35, 94, 95, or 38 (i.e., VL CDR1s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VH CDR1s having an amino acid sequence of any one of the VH CDR1s depicted in SEQ ID NOS:11, 14, 17, 20, or 23 (i.e., VH CDR1s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR2s having an amino acid sequence of any one of the VL CDR2s depicted in SEQ ID NOS:86, 27, 87, 30, 33, 96, 36, 97, 98, or 39 (i.e., VL CDR2s of the VL depicted in SEQ ID NOS:82, 6, 83, 7, 8, 90, 9, 91, 92, or 10, respectively). In another embodiment, a composition for use in the prevention, management, treatment and/or amelioration of a hLIGHT-mediated disease comprises one or more antibodies comprising one or more VH CDR1s having an amino acid sequence of any one of the VH CDR1s depicted in SEQ ID NOS:11, 14, 17, 20, or 23 (i.e., VH CDR1s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR3s having an amino acid sequence of any one of the VL CDR3s depicted in SEQ ID NOS:88, 28, 89, 31, 34, 99, 37, 100, 101, or 40 (i.e., VL CDR3s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23).

In another embodiment, a composition for use in the prevention, management, treatment and/or amelioration of a hLIGHT-mediated disease comprises one or more antibodies comprising one or more VH CDR2s having an amino acid sequence of any one of the VH CDR2s depicted in SEQ ID NOS:12, 15, 18, 21, or 24 (i.e., VH CDR2s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR1s having an amino acid sequence of any one of the VL CDR1s depicted in SEQ ID NOS:84, 26, 85, 29, 32, 93, 35, 94, 95, or 38 (i.e., VL CDR1s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VH CDR2s having an amino acid sequence of any one of the VH CDR2s depicted in SEQ ID NOS:12, 15, 18, 21, or 24 (i.e., VH CDR2s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR2s having an amino acid sequence of any one of the VL CDR2s depicted in SEQ ID NOS:86, 27, 87, 30, 33, 96, 36, 97, 98, or 39 (i.e., VL CDR2s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VH CDR2s having an amino acid sequence of any one of the VH CDR2s depicted in SEQ ID NOS:12, 15, 18, 21, or 24 (i.e., VH CDR2s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR3s having an amino acid sequence of any one of the VL CDR3s having an amino acid sequence of any one of the VL CDR3s depicted in SEQ ID NOS:88, 28, 89, 31, 34, 99, 37, 100, 101, or 40 (i.e., VL CDR3s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23).

In another embodiment, a composition for use in the prevention, management, treatment and/or amelioration of a hLIGHT-mediated disease comprises one or more antibodies comprising one or more VH CDR3s having an amino acid sequence of any one of the VH CDR3s depicted in SEQ ID NOS:13, 16, 19, 22, or 25 (i.e., VH CDR3s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR1s having an amino acid sequence of any one of the VL CDR1s depicted in SEQ ID NOS:84, 26, 85, 29, 32, 93, 35, 94, 95, or 38 (i.e., VL CDR1s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VH CDR3s having an amino acid sequence of any one of the VH CDR3s depicted in SEQ ID NOS:13, 16, 19, 22, or 25 (i.e., VH CDR3s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR2s having an amino acid sequence of any one of the VL CDR2s depicted in SEQ ID NOS:86, 27, 87, 30, 33, 96, 36, 97, 98, or 39 (i.e., VL CDR2s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23). In another embodiment, a composition for use in the prevention, management, treatment and/or amelioration of a hLIGHT-mediated disease comprises one or more antibodies comprising one or more VH CDR3s having an amino acid sequence of any one of the VH CDR3s depicted in SEQ ID NOS:13, 16, 19, 22, or 25 (i.e., VH CDR3s of the VH depicted in SEQ ID NOS:1, 2, 3, 4 or 5, respectively), or of an antibody produced by a hybridoma having ATCC Accession No. PTA-7729, PTA-7842, PTA-7818, PTA-7819, or PTA-7728 (E1, E13, E63, F19 or F23), and one or more VL CDR3s having an amino acid sequence of any one of the VL CDR3s depicted in SEQ ID NOS:88, 28, 89, 31, 34, 99, 37, 100, 101, or 40 (i.e., VL CDR3s of the VL depicted in SEQ ID NOS:82, 6, 83, 7, 8, 90, 9, 91, 92, or 10, respectively), or of an antibody produced by a hybridoma having ATCC Accession No. PTA-7729, PTA-7842, PTA-7818, PTA-7819, or PTA-7728 (E1, E13, E63, F19 or F23).

In one embodiment, a composition for use in the prevention, management, treatment and/or amelioration of a hLIGHT-mediated disease comprises a VH domain having the amino acid sequence of the VH domain depicted in any one of SEQ ID NOS:1, 2, 3, 4 or 5 and/or a VL domain having the amino acid sequence of the VL domain depicted in any one of SEQ ID NOS:82, 6, 83, 7, 8, 90, 9, 91, or 10.

In certain embodiments, a composition for use in the prevention, management, treatment and/or amelioration of a hLIGHT-mediated disease comprises an antibody that immunospecifically binds to a hLIGHT epitope, wherein said antibody comprises (a) a VH domain having the amino acid sequence depicted in SEQ ID NO:1 and a VL domain having the amino acid sequence depicted in any one of SEQ ID NOS:82, 6 or 83; (b) a VH domain having the amino acid sequence depicted in SEQ ID NO:2 and a VL domain having the amino acid sequence depicted in SEQ ID NO:7; (c) a VH domain having the amino acid sequence depicted in SEQ ID NO:3 and a VL domain having the amino acid sequence depicted in SEQ ID NO:8; (d) a VH domain having the amino acid sequence depicted in SEQ ID NO:4 and a VL domain having the amino acid sequence depicted in any one of SEQ ID NOS:90, 9, 91 or 92; or (e) a VH domain having the amino acid sequence depicted in SEQ ID NO:5 and a VL domain having the amino acid sequence depicted in SEQ ID NO:10. Preferably, the antibody is a fully human antibody, such as a fully human monoclonal antibody, and/or a hLIGHT antagonist antibody.

In some embodiments, a composition for use in the prevention, management, treatment and/or amelioration of a hLIGHT-mediated disease comprises an antibody that immunospecifically binds to a hLIGHT epitope, wherein said antibody comprises a VH domain having the amino acid sequence of the VH domain of an antibody having ATCC Accession No. PTA-7729, PTA-7842, PTA-7818, PTA-7819, or PTA-7728 (E1, E13, E63, F19 or F23, respectively) and/or a VL domain having the amino acid sequence of the VL domain of an antibody having ATCC Accession No. PTA-7729, PTA-7842, PTA-7818, PTA-7819, or PTA-7728 (E1, E13, E63, F19 or F23, respectively).

In certain embodiments, a composition for use in the prevention, management, treatment and/or amelioration of a hLIGHT-mediated disease comprises an antibody that immunospecifically binds to a hLIGHT epitope, wherein said antibody comprises (a) a VH domain having the amino acid sequence of an antibody having ATCC Accession No.

PTA-7729 (E1) and a VL domain having the amino acid sequence of an antibody having ATCC Accession No. PTA-7729 (E1); (b) a VH domain having the amino acid sequence of an antibody having ATCC Accession No. PTA-7842 (E13) and a VL domain having the amino acid sequence of an antibody having ATCC Accession No. PTA-7842 (E13); (c) a VH domain having the amino acid sequence of an antibody having ATCC Accession No. PTA-7818 (E63) and a VL domain having the amino acid sequence of an antibody having ATCC Accession No. PTA-7818 (E63); (d) a VH domain having the amino acid sequence of an antibody having ATCC Accession No. PTA-7819 (F19) and a VL domain having the amino acid sequence of an antibody having ATCC Accession No. PTA-7819 (F19); or (e) a VH domain having the amino acid sequence of an antibody having ATCC Accession No. PTA-7728 (F23) and a VL domain having the amino acid sequence of an antibody having ATCC Accession No. PTA-7728 (F23). Preferably, the antibody is a fully human antibody, such as a fully human monoclonal antibody, and/or a hLIGHT antagonist antibody.

In some embodiments, a composition for use in the prevention, management, treatment and/or amelioration of a hLIGHT-mediated disease comprises an antibody that immunospecifically binds to a hLIGHT epitope, wherein said antibody comprises a VH CDR1 having the amino acid sequence of the VH CDR1 of any one of the VH regions depicted in SEQ ID NOS:1, 2, 3, 4 or 5. In another embodiment, a composition for use in the prevention, management, treatment and/or amelioration of a hLIGHT-mediated disease comprises an antibody that immunospecifically binds to a hLIGHT epitope, wherein said antibody comprises a VH CDR2 having the amino acid sequence of the VH CDR2 of any one of the VH regions depicted in SEQ ID NOS:1, 2, 3, 4 or 5. In another embodiment, a composition for use in the prevention, management, treatment and/or amelioration of a hLIGHT-mediated disease comprises an antibody that immunospecifically binds to a hLIGHT epitope, wherein said antibody comprises a VH CDR3 having the amino acid sequence of the VH CDR3 of any one of the VH regions depicted in SEQ ID NOS:1, 2, 3, 4 or 5. In certain embodiments, a composition for use in the prevention, management, treatment and/or amelioration of a hLIGHT-mediated disease comprises an antibody that immunospecifically binds to a hLIGHT epitope, wherein said antibody comprises a VH CDR1 and/or a VH CDR2 and/or a VH CDR3 independently selected from a VH CDR1, VH CDR2, VH CDR3 as depicted in any one of the VH regions depicted in SEQ ID NOS:1, 2, 3, 4 or 5.

The present invention also provides a composition for use in the prevention, management, treatment and/or amelioration of a hLIGHT-mediated disease comprises an antibody that immunospecifically binds to a hLIGHT epitope, wherein said antibody comprises one or more VL CDRs (i.e., VL CDR1, VL CDR2, and/or VL CDR3) having an amino acid sequence of any one of the VL CDRs (i.e., VL CDR1, VL CDR2 and/or VL: CDR3) of E1, E13, E63, F19, and/or F23; or of an antibody produced by a hybridoma having ATCC Accession No. PTA-7729, PTA-7842, PTA-7818, PTA-7819, or PTA-7728 (E1, E13, E63, F19 or F23, respectively); or any combination thereof.

In certain embodiments, a composition for use in the prevention, management, treatment and/or amelioration of a hLIGHT-mediated disease comprises an antibody that immunospecifically binds to a hLIGHT epitope, wherein said antibody comprises (1) a VH domain having (a) a VH CDR1, VH CDR2, and/or VH CDR3 having the amino acid sequence depicted in SEQ ID NOS:11, 12 and/or 13, respectively, (b) a VH CDR1, VH CDR2, and/or VH CDR3 having the amino acid sequence depicted in SEQ ID NOS:14, 15 and/or 16, respectively, (c) a VH CDR1, VH CDR2, and/or VH CDR3 having the amino acid sequence depicted in SEQ ID NOS:17, 18, and/or 19, respectively, (d) a VH CDR1, VH CDR2, and/or VH CDR3 having the amino acid sequence depicted in SEQ ID NOS:20, 21 and/or 22, respectively, or (e) a VH CDR1, VH CDR2, and/or VH CDR3 having the amino acid sequence depicted in SEQ ID NOS:23, 24 and/or 24, respectively, and/or (2) a VL domain having (a) a VL CDR1 having the amino acid sequence depicted in any one of SEQ ID NOS:84, 26 or 85; a VL CDR2 having the amino acid sequence depicted in any one of SEQ ID NOS:86, 27, or 87; and/or a VL CDR3 having the amino acid sequence depicted in any one of SEQ ID NOS:88, 28, or 89, (b) a VL CDR1, VL CDR2, and/or VL CDR3 having the amino acid sequence depicted in SEQ ID NOS:29, 30 and/or 31, respectively, (c) a VL CDR1, VL CDR2, and/or VL CDR3 having the amino acid sequence depicted in SEQ ID NOS:32, 33 and/or 34, respectively, (d) a VL CDR1 having the amino acid sequence depicted in any one of SEQ ID NOS:93, 35, 94, or 95; a VL CDR2 having the amino acid sequence depicted in any one of SEQ ID NOS:96, 36, 97, or 98; and/or a VL CDR3 having the amino acid sequence depicted in any one of SEQ ID NOS: 99, 37, 100, or 101, or (e) a VL CDR1, VL CDR2, and/or VL CDR3 having the amino acid sequence depicted in SEQ ID NOS:38, 39 and/or 40, respectively. Preferably, the antibody is a fully human antibody, such as a fully human monoclonal antibody, and/or a hLIGHT antagonist antibody.

In some embodiments, a composition for use in the prevention, management, treatment and/or amelioration of a hLIGHT-mediated disease comprises an antibody that immunospecifically binds to a hLIGHT epitope, wherein said antibody comprises (1) a VH domain having (a) a VH CDR1, VH CDR2, and/or VH CDR3 having the amino acid sequence of a VH CDR1, VH CDR2, and/or VH CDR3 of an antibody having ATCC Accession No. PTA-7729 (E1), (b) a VH CDR1, VH CDR2, and/or VH CDR3 having the amino acid sequence of a VH CDR1, VH CDR2, and/or VH CDR3 of an antibody having ATCC Accession No. PTA-7842 (E13), (c) a VH CDR1, VH CDR2, and/or VH CDR3 having the amino acid sequence of a VH CDR1, VH CDR2, and/or VH CDR3 of an antibody having ATCC Accession No. PTA-7818 (E63), (d) a VH CDR1, VH CDR2, and/or VH CDR3 having the amino acid sequence of a VH CDR1, VH CDR2, and/or VH CDR3 of an antibody having ATCC Accession No. PTA-7819 (F19), or (e) a VH CDR1, VH CDR2, and/or VH CDR3 having the amino acid sequence of a VH CDR1, VH CDR2, and/or VH CDR3 of an antibody having ATCC Accession No. PTA-7728 (F23), and/or (2) a VL domain having (a) a VL CDR1, VL CDR2, and/or VL CDR3 having the amino acid sequence of a VL CDR1, VL CDR2, and/or VL CDR3 of an antibody having ATCC Accession No. PTA-7729 (E1), (b) a VL CDR1, VL CDR2, and/or VL CDR3 having the amino acid sequence of a VL CDR1, VL CDR2, and/or VL CDR3 of an antibody having ATCC Accession No. PTA-7842 (E13), (c) a VL CDR1, VL CDR2, and/or VL CDR3 having the amino acid sequence of a VL CDR1, VL CDR2, and/or VL CDR3 of an antibody having ATCC Accession No. PTA-7818 (E63), (d) a VL CDR1, VL CDR2, and/or VL CDR3 having the amino acid sequence of a VL CDR1, VL CDR2, and/or VL CDR3 of an antibody having ATCC Accession No. PTA-7819 (F19), or (e) a VL CDR1, VL CDR2, and/or VL CDR3 having the amino acid sequence of a VL CDR1, VL CDR2, and/or VL CDR3 of an antibody having ATCC Accession No. PTA-7728 (F23). Preferably, the antibody is a fully human antibody, such as a fully human monoclonal antibody, and/or a hLIGHT antagonist antibody.

In certain embodiments, a composition for use in the prevention, management, treatment and/or amelioration of a hLIGHT-mediated disease comprises an antibody that immunospecifically binds to a hLIGHT epitope, wherein said antibody comprises (1) (a) a VH domain having a VH CDR1, VH CDR2, and/or VH CDR3 having the amino acid sequence depicted in SEQ ID NOS:11, 12 and/or 13, respectively, and (b) a VL domain having a VL CDR1 having the amino acid sequence depicted in any one of SEQ ID NOS:84, 26 or 85; a VL CDR2 having the amino acid sequence depicted in any one of SEQ ID NOS:86, 27, or 87; and/or a VL CDR3 having the amino acid sequence depicted in any one of SEQ ID NOS:88, 28, or 89; (2) (a) a VH domain having a VH CDR1, VH CDR2, and/or VH CDR3 having the amino acid sequence depicted in SEQ ID NOS: 14, 15 and/or 16, respectively, and (b) a VL CDR1, VL CDR2, and/or VL CDR3 having the amino acid sequence depicted in SEQ ID NOS:29, 30 and/or 31, respectively; (3) (a) a VH domain having a VH CDR1, VH CDR2, and/or VH CDR3 having the amino acid sequence depicted in SEQ ID NOS:17, 18, and/or 19, respectively, and (b) a VL domain having a VL CDR1, VL CDR2, and/or VL CDR3 having the amino acid sequence depicted in SEQ ID NOS:32, 33 and/or 34, respectively; (4) (a) a VH domain having a VH CDR1, VH CDR2, and/or VH CDR3 having the amino acid sequence depicted in SEQ ID NOS:20, 21 and/or 22, respectively, and (b) a VL domain having a VL CDR1 having the amino acid sequence depicted in any one of SEQ ID NOS:93, 35, 94, or 95; a VL CDR2 having the amino acid sequence depicted in any one of SEQ ID NOS:96, 36, 97, or 98; and/or a VL CDR3 having the amino acid sequence depicted in any one of SEQ ID NOS: 99, 37, 100, or 101; or (5) (a) a VH domain having a VH CDR1, VH CDR2, and/or VH CDR3 having the amino acid sequence depicted in SEQ ID NOS:23, 24 and/or 24, respectively, and (b) a VL domain having a VL CDR1, VL CDR2, and/or VL CDR3 having the amino acid sequence depicted in SEQ ID NOS:38, 39 and/or 40, respectively. Preferably, the antibody is a fully human antibody, such as a fully human monoclonal antibody, and/or a hLIGHT antagonist antibody.

In some embodiments, a composition for use in the prevention, management, treatment and/or amelioration of a hLIGHT-mediated disease comprises an antibody that immunospecifically binds to a hLIGHT epitope, wherein said antibody comprises (1) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7729 (E1), and (b) a VL domain having a VL CDR1, VL CDR2, and/or VL CDR3 having the amino acid sequence of a VL CDR1, VL CDR2, and/or VL CDR3 of an antibody having ATCC Accession No. PTA-7729 (E1); (2) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7842 (E13) and (b) a VL domain having a VL CDR1, VL CDR2, and/or VL CDR3 having the amino acid sequence of a VL CDR1, VL CDR2, and/or VL CDR3 of an antibody having ATCC Accession No. PTA-7842 (E13); (3) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7818 (E63) and (b) a VL domain having a VL CDR1, VL CDR2, and/or VL CDR3 having the amino acid sequence of a VL CDR1, VL CDR2, and/or VL CDR3 of an antibody having ATCC Accession No. PTA-7818 (E63); (4) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7819 (F19) and a VL CDR1, VL CDR2, and/or VL CDR3 having the amino acid sequence of a VL CDR1, VL CDR2, and/or VL CDR3 of an antibody having ATCC Accession No. PTA-7819 (F19); or (5) (a) a VH domain having a VH CDR1, VH CDR2, and/or VH CDR3 having the amino acid sequence of a VH CDR1, VH CDR2, and/or VH CDR3 of an antibody having ATCC Accession No. PTA-7728 (F23) and (b) a VL domain having a VL CDR1, VL CDR2, and/or VL CDR3 having the amino acid sequence of a VL CDR1, VL CDR2, and/or VL CDR3 of an antibody having ATCC Accession No. PTA-7728 (F23). Preferably, the antibody is a fully human antibody, such as a fully human monoclonal antibody, and/or a hLIGHT antagonist antibody.

In some embodiments, a composition for use in the prevention, management, treatment and/or amelioration of a hLIGHT-mediated disease comprises an antibody that immunospecifically binds to a hLIGHT epitope, wherein said antibody comprises a VL CDR1 having the amino acid sequence of the VL CDR1 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively). In another embodiment, a composition for use in the prevention, management, treatment and/or amelioration of a hLIGHT-mediated disease comprises an antibody that immunospecifically binds to a hLIGHT epitope, wherein said antibody comprises a VL CDR2 having the amino acid sequence of the VL CDR2 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively). In another embodiment, a composition for use in the prevention, management, treatment and/or amelioration of a hLIGHT-mediated disease comprises an antibody that immunospecifically binds to a hLIGHT epitope, wherein said antibody comprises a VL CDR3 having the amino acid sequence of the VL CDR3 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively). In certain embodiments, a composition for use in the prevention, management, treatment and/or amelioration of a hLIGHT-mediated disease comprises an antibody that immunospecifically binds to a hLIGHT epitope, wherein said antibody comprises a VL CDR1 and/or a VL CDR2 and/or a VL CDR3 independently selected from the VL CDR1, VL CDR2, VL CDR3 as depicted in any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively).

In some embodiments, a composition for use in the prevention, management, treatment and/or amelioration of a hLIGHT-mediated disease comprises an antibody that immunospecifically binds to a hLIGHT epitope, wherein said antibody comprises a (1) VH domain or chain having one or more of (a) a VH CDR1 having the amino acid sequence of a VH CDR1 of any one of the VH regions depicted in SEQ ID NOS:1, 2, 3, 4 or 5; or of an antibody produced by a hybridoma having ATCC Accession No. PTA-7729, PTA-7842, PTA-7818, PTA-7819, or PTA-7728 (E1, E13, E63, F19 or F23, respectively), (b) a VH CDR2 having the amino acid sequence of a VH CDR2 of any one of the VH regions depicted in SEQ ID NOS:1, 2, 3, 4 or 5; or of an antibody produced by a hybridoma having ATCC Accession No. PTA-7729, PTA-7842, PTA-7818, PTA-7819, or PTA-7728 (E1, E13, E63, F19 or F23, respectively), or (c) a VH CDR3 having the amino acid sequence a VH CDR3 of any one of the VH regions depicted in SEQ ID NOS:1, 2, 3, 4 or 5; or of an antibody produced by a hybridoma having ATCC Accession No. PTA-7729, PTA-7842, PTA-7818, PTA-7819, or PTA-7728 (E1, E13, E63, F19 or F23, respectively); and/or (2) a VL domain or chain having one of more of (a) a VL CDR1 having the amino acid sequence of the VL CDR1 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively), (b) a VL CDR2 having the amino acid sequence of a VL CDR2 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively), and/or (c) a VL CDR3 having the amino acid sequence of a VL CDR3 of any one of the VL regions depicted in SEQ ID NOS:82, 6, 83, 7, 8, 90, 9, 91, 92, or 10; or of an antibody produced by a hybridoma having ATCC Accession No. PTA-7729, PTA-7842, PTA-7818, PTA-7819, or PTA-7728 (E1, E13, E63, F19 or F23, respectively).

The present invention also provides a composition for use in the prevention, management, treatment and/or amelioration of a hLIGHT-mediated disease comprises an antibody that immunospecifically binds to a hLIGHT epitope, wherein said antibody comprises one or more VH CDRs and one or more VL CDRs listed in Table I. In particular, the invention provides for a composition for use in the prevention, management, treatment and/or amelioration of a hLIGHT-mediated disease comprises an antibody that immunospecifically binds to a hLIGHT epitope, wherein said antibody comprises a VH CDR1 (SEQ ID NOS:11, 14, 17, 20, or 23) and a VL CDR1 (SEQ ID NOS:84, 26, 85, 29, 32, 35 or 38); a VH CDR1 (SEQ ID NOS:11, 14, 17, 20, or 23) and a VL CDR2 (SEQ ID NOS:86, 27, 87, 30, 33, 96, 36, 97, 98, or 39); a VH CDR1 (SEQ ID NOS:11, 14, 17, 20, or 23) and a VL CDR3 (SEQ ID NOS:88, 28, 89, 31, 34, 99, 37, 100, 101 or 40); a VH CDR2 (SEQ ID NOS:12, 15, 18, 21 or 24) and a VL CDR1 (SEQ ID NOS:84, 26, 85, 29, 32, 35 or 38); VH CDR2 (SEQ ID NOS:12, 15, 18, 21 or 24) and a VL CDR2 (SEQ ID NOS:86, 27, 87, 30, 33, 96, 36, 97, 98, or 39); a VH CDR2 (SEQ ID NOS:12, 15, 18, 21 or 24) and a VL CDR3 (SEQ ID NOS:88, 28, 89, 31, 34, 99, 37, 100, 101 or 40); a VH CDR3 (SEQ ID NOS:13, 16, 19, 22 or 25) and a VH CDR1 (SEQ ID NOS:11, 14, 17, 20, or 23); a VH CDR3 (SEQ ID NOS:13, 16, 19, 22 or 25) and a VL CDR2 (SEQ ID NOS:86, 27, 87, 30, 33, 96, 36, 97, 98, or 39); a VH CDR3 (SEQ ID NOS:13, 16, 19, 22 or 25) and a VL CDR3 (SEQ ID NOS:88, 28, 89, 31, 34, 99, 37, 100, 101 or 40); a VH1 CDR1, a VH CDR2 (SEQ ID NOS:12, 15, 18, 21 or 24) and a VL CDR1 (SEQ ID NOS:84, 26, 85, 29, 32, 35 or 38); a VH CDR1 (SEQ ID NOS:11, 14, 17, 20, or 23), a VH CDR2 (SEQ ID NOS:12, 15, 18, 21 or 24) and a VL CDR2 (SEQ ID NOS:86, 27, 87, 30, 33, 96, 36, 97, 98, or 39); a VH CDR1 (SEQ ID NOS:11, 14, 17, 20, or 23), a VH CDR2 (SEQ ID NOS:12, 15, 18, 21 or 24) and a VL CDR3 (SEQ ID NOS:88, 28, 89, 31, 34, 99, 37, 100, 101 or 40); a VH CDR2 (SEQ ID NOS:12, 15, 18, 21 or 24), a VH CDR3 (SEQ ID NOS:13, 16, 19, 22 or 25) and a VL CDR1 (SEQ ID NOS:84, 26, 85, 29, 32, 35 or 38), a VH CDR2 (SEQ ID NOS:12, 15, 18, 21 or 24), a VH CDR3 (SEQ ID NOS:13, 16, 19, 22 or 25) and a VL CDR2 (SEQ ID NOS:86, 27, 87, 30, 33, 96, 36, 97, 98, or 39); a VH CDR2 (SEQ ID NOS:12, 15, 18, 21 or 24), a VH CDR2 (SEQ ID NOS:12, 15, 18, 21 or 24) and a VL CDR3 (SEQ ID NOS:88, 28, 89, 31, 34, 99, 37, 100, 101 or 40); a VH CDR1 (SEQ ID NOS:11, 14, 17, 20, or 23), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR1 (SEQ ID NOS:11, 14, 17, 20, or 23), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR2 (SEQ ID NOS:12, 15, 18, 21 or 24), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR2 (SEQ ID NOS:12, 15, 18, 21 or 24), a VH CDR2 (SEQ ID NOS:12, 15, 18, 21 or 24) and a VL CDR3 (SEQ ID NOS:88, 28, 89, 31, 34, 99, 37, 100, 101 or 40); a VH CDR3 (SEQ ID NOS:13, 16, 19, 22 or 25), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR3 (SEQ ID NOS:13, 16, 19, 22 or 25), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR2 (SEQ ID NOS:12, 15, 18, 21 or 24), a VH CDR3 (SEQ ID NOS:13, 16, 19, 22 or 25), a VL CDR2 (SEQ ID NOS:86, 27, 87, 30, 33, 96, 36, 97, 98, or 39) and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38) and a VL CDR2 (SEQ ID NOS:86, 27, 87, 30, 33, 96, 36, 97, 98, or 39); a VH CDR1 (SEQ ID NOS:11, 14, 17, 20, or 23), a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38) and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR2 (SEQ ID NOS:12, 15, 18, 21 or 24), a VL CDR1 (SEQ ID NOS:84, 26, 85, 29, 32, 35 or 38), a VL CDR2 (SEQ ID NOS:86, 27, 87, 30, 33, 96, 36, 97, 98, or 39), and a VL CDR3 (SEQ ID NOS:88, 28, 89, 31, 34, 99, 37, 100, 101 or 40); a VH CDR1 (SEQ ID NOS:11, 14, 17, 20, or 23), a VH CDR3 (SEQ ID NOS:13, 16, 19, 22 or 25), a VL CDR1 (SEQ ID NOS:84, 26, 85, 29, 32, 35 or 38), a VL CDR2 (SEQ ID NOS:86, 27, 87, 30, 33, 96, 36, 97, 98, or 39), and a VL CDR3 (SEQ ID NOS:88, 28, 89, 31, 34, 99, 37, 100, 101 or 40); a VH CDR2 (SEQ ID NOS:12, 15, 18, 21 or 24), a VH CDR3 (SEQ ID NOS:13, 16, 19, 22 or 25), a VL CDR1 (SEQ ID NOS:84, 26, 85, 29, 32, 35 or 38), a VL CDR2 (SEQ ID NOS:86, 27, 87, 30, 33, 96, 36, 97, 98, or 39), and a VL CDR3 (SEQ ID NOS:88, 28, 89, 31, 34, 99, 37, 100, 101 or 40); or any combination thereof of the VH CDRs (SEQ ID NOS:11-25) and VL CDRs (SEQ ID NOS: 26-40) listed in Table I. The corresponding VH CDRs and VL CDRs of ATCC Accession No. PTA-7729, PTA-7842, PTA-7818, PTA-7819, or PTA-7728 (E1, E13, E63, F19, or F23), may also be used in any of the combinations listed above. Preferably, the antibody is a fully human antibody, such as a fully human monoclonal antibody, and/or a hLIGHT antagonist antibody.

As discussed in more detail elsewhere herein, a composition of the invention may be used either alone or in combination with other compounds or compositions. Moreover, the antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

In some embodiments, provided herein are methods for decreasing or inhibiting binding of hLIGHT to HVEM, LTβR and/or DcR3 in a subject (e.g., a human subject), comprising administering to the subject an effective amount of an antibody that immunospecifically binds to a hLIGHT polypeptide (e.g., a cell surface-expressed or soluble hLIGHT). In one embodiment, the hLIGHT is a SNP variant of hLIGHT, such as 214E-32S, 214K-32S, 214E-32L or 214K-32L. In some embodiments, a hLIGHT biological activity, such as secretion of CCL20, IL8 and/or RANTES, is also decreased or inhibited in the subject.

In certain embodiments, provided herein are methods for decreasing or inhibiting a hLIGHT biological activity, such as secretion of CCL20, IL8 and/or RANTES, in a subject (e.g., a human subject), comprising administering to the subject an effective amount of an antibody that immunospecifically binds to a hLIGHT polypeptide (e.g., a cell surface-expressed hLIGHT), wherein hLIGHT biological activity is decreased or inhibited by the antibody. In some embodiments, the hLIGHT is a SNP variant of hLIGHT, such as 214E-32S, 214K-32S, 214E-32L or 214K-32L.

In other embodiments, provided herein are methods for decreasing or inhibiting binding of hLIGHT to HVEM, LTβR and/or DcR3 in a cell having cell surface-expressed hLIGHT, contacting the cell with an effective amount of an antibody that immunospecifically binds to a hLIGHT polypeptide (e.g., a cell surface-expressed or soluble hLIGHT), such as a hLIGHT polypeptide, a hLIGHT polypeptide fragment, or a hLIGHT epitope. In certain embodiments, the hLIGHT is a SNP variant of hLIGHT, such as 214E-32S, 214K-32S, 214E-32L or 214K-32L. In some embodiments, a hLIGHT biological activity, such as secretion of CCL20, IL8 and/or RANTES, is also decreased or inhibited in the cell.

In certain embodiments, provided herein are methods for decreasing or inhibiting a hLIGHT biological activity, such as secretion of CCL20, IL8 and/or RANTES, in a cell having a cell surface-expressed hLIGHT receptor (such as, HVEM, LTβR and/or Dc3R), contacting the cell with an effective amount of an antibody that immunospecifically binds to a hLIGHT polypeptide (e.g., a cell surface-expressed or soluble hLIGHT) wherein hLIGHT biological activity is decreased or inhibited by the antibody. In some embodiments, the hLIGHT is a SNP variant of hLIGHT, such as 214E-32S, 214K-32S, 214E-32L or 214K-32L.

Antibodies of the present invention may be used, for example, to purify, detect, and target hLIGHT antigens, in both in vitro and in vivo diagnostic and therapeutic methods. For example, the modified antibodies have use in immunoassays for qualitatively and quantitatively measuring levels of hLIGHT in biological samples. See, e.g., Harlow et al., Antibodies: A Laboratory Manual, (Cold Spring Harbor Laboratory Press, 2nd ed. 1988) (incorporated by reference herein in its entirety).

The invention also provides methods of preventing, managing, treating and/or ameliorating a hLIGHT-mediated disease by administrating to a subject of an effective amount of an antibody, or pharmaceutical composition comprising an antibody of the invention. In one aspect, an antibody is substantially purified (i.e., substantially free from substances that limit its effect or produce undesired side-effects). In preferred embodiments, the antibody is a fully human monoclonal antibody, such as a fully human monoclonal antagonist antibody. The subject administered a therapy is preferably a mammal such as non-primate (e.g., cows, pigs, horses, cats, dogs, rats etc.) or a primate (e.g., a monkey, such as a cynomolgous monkey, or a human). In a preferred embodiment, the subject is a human. In another preferred embodiment, the subject is a human infant or a human infant born prematurely. In another embodiment, the subject is a human with a hLIGHT-mediated disease.

Various delivery systems are known and can be used to administer a prophylactic or therapeutic agent (e.g., an antibody of the invention), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., an antibody of the invention), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody of the present invention), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition of the invention locally to the area in need of treatment. This may be achieved by, for example, and not by way of limitation, local infusion, by topical administration (e.g., by intranasal spray), by injection, or by means of an implant, said implant being of a porous, non-porous, or gelatinous material, including membranes, such as sialastic membranes, or fibers. Preferably, when administering an antibody of the invention, care must be taken to use materials to which the antibody does not absorb.

In another embodiment, a prophylactic or therapeutic agent, or a composition of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a prophylactic or therapeutic agent, or a composition of the invention can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibodies of the invention) or a composition of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more antibodies of the invention. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment, where the composition of the invention is a nucleic acid encoding a prophylactic or therapeutic agent (e.g., an antibody of the invention), the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et cll., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition of the invention comprises one, two or more antibodies of the invention. In another embodiment, a composition of the invention comprises one, two or more antibodies of the invention and a prophylactic or therapeutic agent other than an antibody of the invention. Preferably, the agents are known to be useful for or have been or are currently used for the prevention, management, treatment and/or amelioration of a hLIGHT-mediated disease. In addition to prophylactic or therapeutic agents, the compositions of the invention may also comprise a carrier.

The compositions of the invention include bulk drug compositions useful in the manufacture of pharmaceutical compositions (e.g., compositions that are suitable for administration to a subject or patient) that can be used in the preparation of unit dosage forms. In a preferred embodiment, a composition of the invention is a pharmaceutical composition. Such compositions comprise a prophylactically or therapeutically effective amount of one or more prophylactic or therapeutic agents (e.g., an antibody of the invention or other prophylactic or therapeutic agent), and a pharmaceutically acceptable carrier. Preferably, the pharmaceutical compositions are formulated to be suitable for the route of administration to a subject.

In a specific embodiment, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990) Mack Publishing Co., Easton, Pa. Such compositions will contain a prophylactically or therapeutically effective amount of the antibody, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides that an antibody of the invention is packaged in a hermetically sealed container such as an ampoule or sachette indicating the quantity of antibody. In one embodiment, the antibody is supplied as a dry sterilized lyophilized powder or water free concentrate in a hermetically sealed container and can be reconstituted, e.g., with water or saline to the appropriate concentration for administration to a subject. Preferably, the antibody is supplied as a dry sterile lyophilized powder in a hermetically sealed container at a unit dosage of at least 0.1 mg, at least 0.5 mg, at least 1 mg, at least 2 mg, or at least 3 mg, and more preferably at least 5 mg, at least 10 mg, at least 15 mg, at least 25 mg, at least 30 mg, at least 35 mg, at least 45 mg, at least 50 mg, at least 60 mg, at least 75 mg, at least 80 mg, at least 85 mg, at least 90 mg, at least 95 mg, or at least 100 mg. The lyophilized antibody can be stored at between 2 and 8° C. in its original container and the antibody can be administered within 12 hours, preferably within 6 hours, within 5 hours, within 3 hours, or within 1 hour after being reconstituted. In an alternative embodiment, an antibody is supplied in liquid form in a hermetically sealed container indicating the quantity and concentration of the antibody. Preferably, the liquid form of the antibody is supplied in a hermetically sealed container at least 0.1 mg/ml, at least 0.5 mg/ml, or at least 1 mg/ml, and more preferably at least 5 mg/ml, at least 10 mg/ml, at least 15 mg/ml, at least 25 mg/ml, at least 30 mg/ml, at least 40 mg/ml, at least 50 mg/ml, at least 60 mg/ml, at least 70 mg/ml, at least 80 mg/ml, at least 90 mg/ml, or at least 100 mg/ml.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a prophylactic or therapeutic agent (e.g., an antibody of the invention), or a composition of the invention that will be effective in the prevention, management, treatment and/or amelioration of a hLIGHT-mediated disease can be determined by standard clinical techniques. Accordingly, a dosage of an antibody or a composition that results in a serum titer of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, and preferably at least 2 µg/ml, at least 5 µg/ml, at least 10 µg/ml, at least 15 µg/ml, at least 20 µg/ml, at least 25 µg/ml, at least 30 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the prevention, management, treatment and/or amelioration of a hLIGHT-mediated disease. In addition, in vitro assays may optionally be employed to help identify optimal dosage ranges. The precise dose to be employed in the formulation will also depend on the route of administration, and the seriousness of a hLIGHT-mediated disease, and should be decided according to the judgment of the practitioner and each patient's circumstances.

Effective doses may be extrapolated from dose-response curves derived from in vitro or animal model test systems.

For the antibodies of the invention, the dosage administered to a patient is typically 0.1 mg/kg to 100 mg/kg of the patient's body weight. In some embodiments, the dosage administered to the patient is about 1 mg/kg to about 75 mg/kg of the patient's body weight. Preferably, the dosage administered to a patient is between 1 mg/kg and 20 mg/kg of the patient's body weight, more preferably 1 mg/kg to 5 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies of the invention may be reduced by enhancing uptake and tissue penetration of the antibodies by modifications such as, for example, lipidation.

In one embodiment, approximately 100 mg/kg or less, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less of an antibody the invention is administered 5 times, 4 times, 3 times, 2 times or, preferably, 1 time to manage a hLIGHT-mediated disease. In some embodiments, an antibody of the invention is administered about 1-12 times, wherein the doses may be administered as necessary, e.g., weekly, biweekly, monthly, bimonthly, trimonthly, etc., as determined by a physician. In some embodiments, a lower dose (e.g., 1-15 mg/kg) can be administered more frequently (e.g., 3-6 times). In other embodiments, a higher dose (e.g., 25-100 mg/kg) can be administered less frequently (e.g., 1-3 times). However, as will be apparent to those in the art, other dosing amounts and schedules are easily determinable and within the scope of the invention.

In a specific embodiment, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, approximately 0.1 mg/kg or less of an antibody the invention in a sustained release formulation is administered to a subject, preferably a human, to prevent, manage, treat and/or ameliorate a hLIGHT-mediated disease. In another specific embodiment, an approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less bolus of an antibody the invention not in a sustained release formulation is administered to a subject, preferably a human, to prevent, manage, treat and/or ameliorate a hLIGHT-mediated disease, and after a certain period of time, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 5 mg/kg or less of an antibody of the invention in a sustained release is administered to said subject (e.g., intranasally or intramuscularly) two, three or four times (preferably one time). In accordance with this embodiment, a certain period of time can be 1 to 5 days, a week, two weeks, or a month.

In some embodiments, a single dose of an antibody of the invention is administered to a patient to prevent, manage, treat and/or ameliorate a hLIGHT-mediated disease two, three, four, five, six, seven, eight, nine, ten, eleven, twelve times, thirteen, fourteen, fifteen, sixteen, seventeen, eighteen, nineteen, twenty, twenty-one, twenty-two, twenty-three, twenty-four, twenty five, or twenty six at bi-weekly (e.g., about 14 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In another embodiment, a single dose of an antibody of the invention is administered to patient to prevent, manage, treat and/or ameliorate a hLIGHT-mediated disease two, three, four, five, six, seven, eight, nine, ten, eleven, or twelve times at about monthly (e.g., about 30 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In one embodiment, a single dose of an antibody of the invention is administered to a patient to prevent, manage, treat and/or ameliorate a hLIGHT-mediated disease two, three, four, five, or six times at about bi-monthly (e.g., about 60 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each bi-monthly dose may or may not be identical).

In some embodiments, a single dose of an antibody of the invention is administered to a patient to prevent, manage, treat and/or ameliorate a hLIGHT-mediated disease two, three, or four times at about tri-monthly (e.g., about 120 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each tri-monthly dose may or may not be identical).

In certain embodiments, the route of administration for a dose of an antibody of the invention to a patient is intranasal, intramuscular, intravenous, or a combination thereof, but other routes described herein are also acceptable. Each dose may or may not be administered by an identical route of administration. In some embodiments, an antibody of the invention may be administered via multiple routes of administration simultaneously or subsequently to other doses of the same or a different antibody of the invention.

In certain embodiments, antibodies of the invention are administered prophylactically or therapeutically to a subject. Antibodies of the invention can be prophylactically or therapeutically administered to a subject so as to prevent, lessen or ameliorate a hLIGHT-mediated disease or symptom thereof.

Gene Therapy

In a specific embodiment, nucleic acids comprising sequences encoding antibodies of the invention or functional derivatives thereof, are administered to prevent, manage, treat and/or ameliorate a hLIGHT-mediated disease by way of gene therapy. Gene therapy refers to therapy performed by the administration to a subject of an expressed or expressible nucleic acid. In an embodiment of the invention, the nucleic acids produce their encoded antibody, and the antibody mediates a prophylactic or therapeutic effect.

Any of the methods for gene therapy available in the art can be used according to the present invention. Exemplary methods are described below.

For general review of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann Rev. Biochem. 62:191-217; May, 1993, TIBTECH 11(5): 155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred embodiment, a composition of the invention comprises nucleic acids encoding an antibody of the invention, said nucleic acids being part of an expression vector that expresses the antibody or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, 1989, Proc. Natl. Acad. Sci. USA 86:8932-8935; Zijlstra et al., 1989, Nature 342:435-438). In some embodiments, the expressed antibody molecule is a single chain antibody; alternatively, the nucleic acid sequences include sequences encoding both the heavy and light chains, or fragments thereof, of the antibody.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where the sequences are expressed to produce the encoded product. This can be accomplished by any of numerous methods known in the art, e.g., by constructing them as part of an appropriate nucleic acid expression vector and administering the vector so that the sequences become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; W093/14188, WO 93/20221). Alternatively, the nucleic acid can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342:435-438).

In a specific embodiment, viral vectors that contains nucleic acid sequences encoding an antibody of the invention are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences encoding the antibody to be used in gene therapy can be cloned into one or more vectors, which facilitates delivery of the gene into a subject. More detail about retroviral vectors can be found in Boesen et al., 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication W094/12649; and Wang et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Clin. Pharma. Ther. 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding an antibody of the invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, 1992, Cell 7 1:973-985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Diagnostic Use of Antibodies

Labeled Antibodies of the Invention and Derivatives and Analogs Thereof, which immunospecifically bind to a hLIGHT antigen can be used for diagnostic purposes to detect, diagnose, or monitor a hLIGHT-mediated disease. The invention provides methods for the detection of a hLIGHT-mediated disease comprising: (a) assaying the expression of a hLIGHT antigen in cells or a tissue sample of a subject using one or more antibodies of the invention that immunospecifically bind to the hLIGHT antigen; and (b) comparing the level of the hLIGHT antigen with a control level, e.g., levels in normal tissue samples (e.g., from a patient not having a hLIGHT-mediated disease, or from the same patient before disease onset), whereby an increase in the assayed level of hLIGHT antigen compared to the control level of the hLIGHT antigen is indicative of a hLIGHT-mediated disease.

The invention provides a diagnostic assay for diagnosing a hLIGHT-mediated disease comprising: (a) assaying for the level of a hLIGHT antigen in cells or a tissue sample of an individual using one or more antibodies of the invention that immunospecifically bind to a hLIGHT antigen; and (b) comparing the level of the hLIGHT antigen with a control level, e.g., levels in normal tissue samples, whereby an increase in the assayed hLIGHT antigen level compared to the control level of the hLIGHT antigen is indicative of a hLIGHT-mediated disease. A more definitive diagnosis of a hLIGHT-mediated disease may allow health professionals to employ preventative measures or aggressive treatment earlier thereby preventing the development or further progression of the hLIGHT-mediated disease.

Antibodies of the invention can be used to assay hLIGHT antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

One aspect of the invention is the detection and diagnosis of a hLIGHT-mediated disease in a human. In one embodiment, diagnosis comprises: a) administering (for example, parenterally, subcutaneously, or intraperitoneally) to a subject an effective amount of a labeled antibody that immunospecifically binds to a hLIGHT antigen; b) waiting for a time interval following the administering for permitting the labeled antibody to preferentially concentrate at sites in the subject where the hLIGHT antigen is expressed (and for unbound labeled molecule to be cleared to background level); c) determining background level; and d) detecting the labeled antibody in the subject, such that detection of labeled antibody above the background level indicates that the subject has a hLIGHT-mediated disease. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

In one embodiment, monitoring of a hLIGHT-mediated disease is carried out by repeating the method for diagnosing the a hLIGHT-mediated disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Methods of Producing Antibodies

Antibodies of the invention that immunospecifically bind to an antigen can be produced by any method known in the art for the synthesis of antibodies, in particular, by chemical synthesis or preferably, by recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Polyclonal antibodies that immunospecifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981) (said references incorporated by reference in their entireties). The term "monoclonal antibody" as used herein is not limited to antibodies produced through hybridoma technology. Other exemplary methods of producing monoclonal antibodies are discussed elsewhere herein, such as e.g., use of the KM Mouse™. Additional exemplary methods of producing monoclonal antibodies are provided in the Examples herein.

Methods for producing and screening for specific antibodies using hybridoma technology are routine and well known in the art. Briefly, mice can be immunized with a hLIGHT antigen and once an immune response is detected, e.g., antibodies specific for hLIGHT antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilptrack et al., 1997 Hybridoma 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting a modified antibody of the invention wherein, preferably, the hybridoma is generated by fusing splenocytes isolated from a mouse immunized with a hLIGHT antigen with myeloma cells and then screening the hybridomas resulting from the fusion for hybridoma clones that secrete an antibody able to bind to a hLIGHT antigen.

Antibody fragments which recognize specific hLIGHT antigens may be generated by any technique known to those of skill in the art. For example, Fab and $F(ab')_2$ fragments of the invention may be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH1 domain of the heavy chain. Further, the antibodies of the present invention can also be generated using various phage display methods known in the art.

For example, antibodies can also be generated using various phage display methods. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J.

Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

In preferred embodiments, human antibodies are produced. Human antibodies and/or fully human antibodies can be produced using any method known in the art, including the Examples provided herein. For example, transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the J$_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. Other methods are detailed in the Examples herein. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fabc, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. Examples of VL and VH constant domains that can be used in certain embodiments of the invention include, but are not limited to, C-kappa and C-gamma-1 (nG1m) described in Johnson et al. (1997) J. Infect. Dis. 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%. Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that immunospecifically bind to a hLIGHT antigen can, in turn, be utilized to generate antiidiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

Polynucleotides Encoding an Antibody

The invention provides polynucleotides comprising a nucleotide sequence encoding an antibody of the invention that immunospecifically binds to a hLIGHT epitope. The invention also encompasses polynucleotides that hybridize under high stringency, intermediate or lower stringency hybridization conditions, e.g., as defined supra, to polynucleotides that encode a modified antibody of the invention.

The polynucleotides may be obtained, and the nucleotide sequence of the polynucleotides determined, by any method known in the art. Since the amino acid sequences of E1, E13, E63, F19 and F23 are known (see, e.g., SEQ ID NOS:41, 42, 43, 44, 45, 102, 46, 103, 47, 48, 104, 49, 105, 106, and 50; and ATCC Accession Nos. PTA-7729, PTA-7842, PTA-7818, PTA-7819, or PTA-7728, respectively, which are incorporated herein by reference), nucleotide sequences encoding these antibodies and modified versions of these antibodies can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

Alternatively, a polynucleotide encoding an antibody of the invention may be generated from nucleic acid from a suitable source (e.g., a hybridoma having an ATCC Accession No. PTA-7729, PTA-7842, PTA-7818, PTA-7819, or PTA-7728 (E1, E13, E63, F19 or F23). If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

In certain embodiments, nucleic acid molecules of the invention comprise or consist of a nucleic acid sequence as depicted in any one of SEQ ID NOS:41, 42, 43, 44, 45 (encoding a VH) and/or SEQ ID NOS:102, 46, 103, 47, 48, 104, 49, 105, 106, or 50 (encoding a VL), or any combination thereof (e.g., as a nucleotide sequence encoding an antibody of the invention, such as a full-length antibody, heavy and/or light chain of an antibody, or a single chain antibody of the invention).

Recombinant Expression of an Antibody

Recombinant expression of an antibody of the invention (e.g., a full-length antibody, heavy and/or light chain of an antibody, or a single chain antibody of the invention) that immunospecifically binds to a hLIGHT antigen requires construction of an expression vector containing a polynucleotide that encodes the antibody. Once a polynucleotide encoding an antibody molecule, heavy or light chain of an antibody, or fragment thereof (preferably, but not necessarily, containing the heavy and/or light chain variable domain) of the invention has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a fragment thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or fragment thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In preferred embodiments, antibodies of the invention are produced in CHO cells. In a specific embodiment, the expression of nucleotide sequences encoding antibodies of the invention which immunospecifically bind to a hLIGHT antigen is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells. In preferred embodiments, fully human, monoclonal anti-hLIGHT antibodies of the invention are produced in mammalian cells, such as CHO cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann Rev. Pharmacol. Toxicol. 32:573-596; Mulligan, 1993, Science 260:926-932; and Morgan and Anderson, 1993, Ann Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art to facilitate purification.

Kits

The invention also provides a pharmaceutical pack or kit comprising one or more containers filled with one or more of the ingredients of the pharmaceutical compositions of the invention, such as one or more antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In a specific embodiment, the kits of the present invention contain a substantially isolated hLIGHT antigen as a control. Preferably, the kits of the present invention further comprise a control antibody which does not react with the hLIGHT antigen. In another specific embodiment, the kits of the present invention contain a means for detecting the binding of a modified antibody to a hLIGHT antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized hLIGHT antigen. The hLIGHT antigen provided in the kit may also be attached to a solid support. In a more specific embodiment the detecting means of the above described kit includes a solid support to which hLIGHT antigen is attached. Such a kit may also include a non-attached reporter-labeled anti-human antibody. In this embodiment, binding of the antibody to the hLIGHT antigen can be detected by binding of the said reporter-labeled antibody.

The following examples are offered by way of illustration, and not by way of limitation.

EXAMPLES

Example 1

Generation of Human Anti-hLight Antibodies

In this example, the generation of human anti-hLIGHT monoclonal antibodies using transchromosomal mice (KM Mice™) (WO 02/43478, WO 02/092812, Ishida and Lonberg, IBC's 11$^{th}$ Antibody Engineering Meeting. Abstract (2000); and Kataoka, S. IBC's 13$^{th}$ Antibody Engineering Meeting. Abstract (2002)) immunized with soluble recombinant hLIGHT is described. The antibodies described here specifically stained hLIGHT stably transfected cell lines, (EL4-hLIGHT and HEK 293-hLIGHT) and not the parental cell lines. Likewise, they bind to endogenously expressed hLIGHT on the surface of the human T cell hybridoma (II-23.D7) (Ware et al. 1986 Lymphokine Res 5 313-24) upon activation. Together, these data indicate that the antibodies immunospecifically bind to hLIGHT. The isolated antibodies recognize one of two epitopes on hLIGHT as determined by cross-blocking experiments, as described below. Moreover, the antibodies were able to block cell surface-expressed hLIGHT binding to soluble receptor-Fc fusion forms of both human HVEM and the LTβR. Soluble hLIGHT induces the secretion of the chemokines CCL20 and RANTES from the human colonic epithelial cell line HT29.14s (ATCC HTB-38) in a dose dependent manor. Incubation of soluble hLIGHT with anti-hLIGHT antibodies blocks hLIGHT-mediated secretion of both CCL20 and RANTES from HT29.14s cells. In addition, pre-incubation of cell surface expressed hLIGHT (EL4-hLIGHT) with these anti-hLIGHT antibodies blocks membrane-bound hLIGHT-induced chemokine secretion from HT29 cells. Together, these results illustrate functional and structural characteristics of the fully human anti-hLIGHT monoclonal antibodies and provide evidence of their usefulness in the treatment of hLIGHT-mediated diseases.

Materials and Methods

Antigen Preparation: The antigen used for immunizations in the generation of fully human anti-hLIGHT antibodies was a soluble version of hLIGHT that is truncated to include only the extracellular region, starting from the glycine at amino acid position 66 to Valine 240, and contains a FLAG epitope tag at the amino-terminus of the protein (SEQ ID NO:54). The production of this molecule has been reported previously (Rooney et al. 2000 J Biol Chem 275 14307-15).

Nucleic acid (SEQ ID NO:51) encoding the full-length hLIGHT amino acid sequence (SEQ ID NO:52) has been cloned from activated II23.D7 T cell hybridoma cells by reverse transcriptase-PCR (Mauri et al. 1998 Immunity 8 21-30). The 11-23 cell line (a D7 subclone) is a human CD4+ T cell hybridoma (Ware et al. 1986 Lymphokine Res 5 313-24). The hLIGHT PCR product was subcloned into the mammalian expression vector pcDNA3.1 (+) to create pcDNA3.1-hLIGHT. The extracellular domain (encoding Gly66 to Val240) was amplified from pcDNA3-hLIGHT by PCR using the following primers with incorporated restriction sites:

```
                                      (SEQ ID NO: 80)
forward,
5'-GTAGGAGAGATGGTCACCCGCCT-3'.

(SEQ ID NO: 81)
reverse,
5'-GGAACGCGAATTCCCACGTGTCAGACCCATGTCCAAT-3'.
```

The amplified hLIGHT PCR product was digested with EcoRI and ligated into the SnaBI and EcoRI sites of pCDNA3.1-VCAM-FLAG, which encodes the VCAM1 leader sequence followed by the FLAG epitope for the production of secreted, N-terminally FLAG-tagged protein (SEQ ID NO:52).

To produce a stable cell line for the production of soluble hLIGHT, HEK293 cells were transfected using the calcium phosphate method, and stable clones were selected with G418 (Invitrogen, Corp.) and screened for hLIGHT production by ELISA. Soluble hLIGHT was purified from culture supernatants of cells grown in DMEM containing 1.0% defined fetal bovine serum (Hyclone Laboratories, Logan, Utah). Soluble hLIGHT was purified by affinity chromatography with anti-FLAG (M2) antibody coupled to agarose beads. Soluble hLIGHT was eluted from the column using 20 mM glycine, 150 mM NaCl, pH 3.0, and pH-neutralized immediately by collection into 50 mM Tris, pH 7.4. Protein concentration was determined by absorbency at 280 nm.

```
Nucleotide sequence of a hLIGHT from initiation codon (ATG) to stop (TGA)
(SEQ ID NO: 51):
ATGGAGGAGA GTGTCGTACG GCCCTCAGTG TTTGTGGTGG ATGGACAGAC CGACATCCCA   60

TTCACGAGGC TGGGACGAAG CCACCGGAGA CAGTCGTGCA GTGTGGCCCG GGTGGGTCTG  120

GGTCTCTTGC TGTTGCTGAT GGGGGCCGGG CTGGCCGTCC AAGGCTGGTT CCTCCTGCAG  180

CTGCACTGGC GTCTAGGAGA GATGGTCACC CGCCTGCCTG ACGGACCTGC AGGCTCCTGG  240

GAGCAGCTGA TACAAGAGCG AAGGTCTCAC GAGGTCAACC CAGCAGCGCA TCTCACAGGG  300

GCCAACTCCA GCTTGACCGG CAGCGGGGGG CCGCTGTTAT GGGAGACTCA GCTGGGCCTG  360

GCCTTCCTGA GGGGCCTCAG CTACCACGAT GGGGCCCTTG TGGTCACCAA AGCTGGCTAC  420
```

-continued

```
TACTACATCT ACTCCAAGGT GCAGCTGGGC GGTGTGGGCT GCCCGCTGGG CCTGGCCAGC 480

ACCATCACCC ACGGCCTCTA CAAGCGCACA CCCCGCTACC CCGAGGAGCT GGAGCTGTTG 540

GTCAGCCAGC AGTCACCCTG CGGACGGGCC ACCAGCAGCT CCCGGGTCTG GTGGGACAGC 600

AGCTTCCTGG GTGGTGTGGT ACACCTGGAG GCTGGGGAGG AGGTGGTCGT CCGTGTGCTG 660

GATGAACGCC TGGTTCGACT GCGTGATGGT ACCCGGTCTT ACTTCGGGGC TTTCATGGTG 720

TGA                                                                780
```

Amino acid sequence of a full length hLIGHT 240 aa (SEQ ID NO: 52):
MEESVVRPSV FVVDGQTDIP FTRLGRSHRR QSCSVARVGL GLLLLLMGAG LAVQGWFLLQ  60

LHWRLGEMVT RLPDGPAGSW EQLIQERRSH EVNPAAHLTG ANSSLTGSGG PLLWETQLGL 120

AFLRGLSYHD GALVVTKAGY YYIYSKVQLG GVGCPLGLAS TITHGLYKRT PRYPEELELL 180

VSQQSPCGRA TSSSRVWWDS SFLGGVVHLE AGEEVVVRVL DERLVRLRDG TRSYFGAFMV 240

Nucleotide sequence of a soluble FLAG-tagged hLIGHT (VCAM leader
sequences shown, followed by FLAG encoding sequence in bold)
(SEQ ID NO: 53)
ATGCCTGGGA AGATGGTCGT GATCCTTGGA GCCTCAAATA TACTTTGGAT AATGTTTGCA  60

GCTTCTCAAG CTGACTACAA GGACGACGAT GACAAGTACG TAGGAGAGAT GGTCACCCGC 120

CTGCCTGACG GACCTGCAGG CTCCTGGGAG CAGCTGATAC AAGAGCGAAG GTCTCACGAG 180

GTCAACCCAG CAGCGCATCT CACAGGGGCC AACTCCAGCT TGACCGGCAG CGGGGGGCCG 240

CTGTTATGGG AGACTCAGCT GGGCCTGGCC TTCCTGAGGG GCCTCAGCTA CCACGATGGG 300

GCCCTTGTGG TCACCAAAGC TGGCTACTAC TACATCTACT CCAAGGTGCA GCTGGGCGGT 360

GTGGGCTGCC CGCTGGGCCT GGCCAGCACC ATCACCCACG GCCTCTACAA GCGCACACCC 420

CGCTACCCCG AGGAGCTGGA GCTGTTGGTC AGCCAGCAGT CACCCTGCGG ACGGGCCACC 480

AGCAGCTCCC GGGTCTGGTG GGACAGCAGC TTCCTGGGTG GTGTGGTACA CCTGGAGGCT 540

GGGGAGGAGG TGGTCGTCCG TGTGCTGGAT GAACGCCTGG TTCGACTGCG TGATGGTACC 600

CGGTCTTACT TCGGGGCTTT CATGGTGTGA                                   660
```

Amino acid sequence of a soluble FLAG-tagged hLIGHT 183 aa (FLAG in bold)
(SEQ ID NO: 54):
DYKDDDDKGE MVTRLPDGPA GSWEQLIQER RSHEVNPAAH LTGANSSLTG SGGPLLWETQ  60

LGLAFLRGLS YHDGALVVTK AGYYYIYSKV QLGGVGCPLG LASTITHGLY KRTPRYPEEL 120

ELLVSQQSPC GRATSSSRVW WDSSFLGGVV HLEAGEEVVV RVLDERLVRL RDGTRSYFGA 180

FMV                                                                240

EL4 (ATCC TIB-39) cells were stably transduced with a retrovirus containing the cDNA encoding full-length hLIGHT for the generation of the EL4-hLIGHT cell line.

Fc Fusion Protein Preparation: Cloning, expression, and purification of the soluble receptor fusion proteins containing the Fc region of human IgG1 and the ligand-binding domains of human LTβR and human HVEM have been described previously (Rooney et al. 2000 Methods Enzymol 322 345-63). Briefly, the extracellular regions of HVEM and the LTβR were isolated by polymerase chain reactions using primers with incorporated restriction endonuclease sites and ligated in-frame into the baculovirus vector pVL1392 (Pharmingen) containing the human Fc IgG1. *Trichoplusia ni* High-Five BTI-TN-5b1-4 (Tn5) insect cells (Invitrogen Corp.) were infected with the LTβR:Fc or HVEM:Fc recombinant baculoviruses for protein production (see antibody and protein purification).

Mice: Human trans-chromosomic KM Mice™ (WO 02/43478, WO 02/092812, Ishida and Lonberg, IBC's 11[th] Antibody Engineering Meeting. Abstract (2000); and Kataoka, S. IBC's 13[th] Antibody Engineering Meeting. Abstract (2002)) harboring human chromosome fragments encoding the human immunoglobulin region were obtained from Kirin Brewery Co., Ltd., Japan, and were housed in the animal facility at Gemini Science (La Jolla, Calif.). An overview of the technology for producing human antibodies is described in Lonberg and Huszar 1995 Int Rev Immunol 13 65-93. Transgenic animals with one or more human immunoglobulin genes (kappa or lambda) that do not express endogenous immunoglobulins are described, for example in, U.S. Pat. No. 5,939,598. Additional methods for producing human antibodies and human monoclonal antibodies are described (see, e.g., WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). Development of bovine carrying human immunoglobulin genes, TC cows, is described in Ishida and Lonberg (see Ishida 2000 11th Antibody Engineering Meeting, Kuroiwa et al. 2004 Nat Genet 36 775-80, Kuroiwa et al. 2002 Nat Biotechnol 20 889-94).

Immunization: FLAG-tagged soluble hLIGHT recombinant protein was mixed with an equal volume of complete Freund's adjuvant (CFA, Sigma) and an emulsion was prepared. Mice were immunized with 10 to 50 µg of protein sub-cutaneously (s.c.) and were boosted s.c. with 10 to 20 µg of protein emulsified in incomplete Freund's adjuvant (IFA, Sigma) at 2-3 week intervals for 2 to 3 boosts. A final intravenous (i.v.) injection of 10 µg of FLAG-tagged soluble hLIGHT without adjuvant was given 3 days prior to fusion.

Hybridoma Production: The mice displaying the highest anti-hLIGHT IgG specific antibody titer in their serum, as determined by the hLIGHT ELISA and FACS using hLIGHT transduced EL4 cells versus EL4 parental cells, were selected for the production of monoclonal antibodies. The spleens were harvested and single cell suspensions were fused to the SP2/O-Ag14 myeloma cell line (ATCC, Manassas, Va.) at a ratio of 5:1 with 50% polyethylene glycol (Boehringer Mannheim, Indianapolis, Ind.). The fusions were plated into 96 well flat bottom plates at an optimal density (here $1 \times 10^6$/ml) in complete DMEM-10 medium (Dulbecco's Modified Engle's Medium with 10% fetal bovine serum (FBS, Invitrogen, Corp.), 1% non-essential amino acids, 2 mM L-glutamine, 100 U/ml penicillin, 100 µg/ml streptomycin sulfate (all from BioWhittaker, Walkersville, Md.), HAT supplement (Sigma), and 10% Hybridoma Cloning Factor (HCF, Biovaris, San Diego, Calif.)) and cultured at 37° C. in a 10% $CO_2$ incubator. Approximately 2800 wells from 2 fusions were screened by ELISA for human kappa containing hLIGHT specific antibodies. Human anti-hLIGHT IgG antibodies were confirmed by flow cytometric analysis using hLIGHT-EL4 cells versus EL4 parental cells. Positive wells were also tested for receptor blocking activity by pre-incubation of crude hybridoma extinction culture growth media with EL4-hLIGHT cells and staining with half-saturating HVEM:Fc or LTβR:Fc. Positive wells were expanded and subjected to 3-5 rounds of limiting dilution cloning to obtain monoclonal antibodies.

Antibody and Protein Purification: For antibody purification, hybridomas were cultured in 2 liter roller bottles at 350 milliliter to 1 liter/bottle or in a 1 liter Integra system (INTEGRA Bioscience, Inc., Ijamsville, Md.) with hybridoma-SFM medium (Invitrogen, Corp.) supplemented with ultra low IgG fetal bovine serum (Invitrogen, Corp.).

The production of human and mouse LTβR:Fc and HVEM:Fc recombinant proteins has been previously reported (Rooney et al. 2000 Meth. Enzymol. 322:345-63) and were generated by infecting 1 liter of suspension Tn5 cells for 4 days. Both the human monoclonal antibodies and Fc fusion proteins were purified from culture media using recombinant Protein A-Sepharose Fast Flow gel (Amersham Biosciences). Conditioned medium generated in roller bottles was first concentrated using an Ultrasette tangential flow system (Pall Corp., East Hills, N.Y.). The conditioned medium was filtered with a 0.22 µm vacuum filter unit (Millipore, Bedford, Mass.) and loaded onto a Protein A-Sepharose Fast Flow column (Amersham Biosciences) of appropriate size for the amount of human antibody in the medium. The column was washed thoroughly with 20 column volumes of PBS and the antibody was eluted with 0.1 M Gly-HCl, pH 3.6, 0.15 M NaCl and neutralized with 1 M Tris-HCl, pH 8.0. The fractions were analyzed by SDS-PAGE and the positive fractions were pooled and concentrated with a centrifugal concentrator (Vivaspin, 50,000 MWCO: Sartorius, Gettingen, Germany).

Sephadex G-25 desalting columns, (NAP, Amersham Biosciences), were used for buffer exchange to PBS, pH 7.4. Finally, the antibody was filter sterilized using syringe filters with 0.22 µm pore diameters and the antibody concentration was determined by the Lowry method. Pyrogen content was determined using a Limulus Amebocyte Lysate (LAL) assay (Associates of Cape Cod, Falmouth, Mass.). The limits of detection of this assay are 0.06 EU/mg. If the test was negative, the samples were considered endotoxin free.

Human IgG Quantitation ELISA: To determine the amount of human antibody present in supernatants and purified stocks the following protocol was used. Goat anti-human Fcγ specific antibody (Jackson Immunoresearch Laboratories, West Grove, Pa.) was coated to the 96 well plates (Nunc, Denmark) in carbonate buffer at 0.5 µg/well for 1 hour at 37° C. The plates were then blocked with Super block (Pierce, Rockford, Ill.) for 30 minutes followed by addition of the samples to the plates. Standard curves were generated using total human IgG (Sigma) or purified human IgG1 or IgG4 (Kirin Brewery Co., Ltd). The plates were incubated for 1 hour at 37° C., washed in PBS/1% BSA/0.1% Tween20 (Sigma), and the bound antibody was detected with goat anti-human Fcγ specific antibody conjugated to horseradish peroxidase (HRP, Jackson Immunoresearch Laboratorie, West Grove, Pa.) for 1 hour at 37° C. The TMB substrate (Sigma) was added for 10 minutes and the reaction was stopped with $H_2SO_4$ (LabChem, Pittsburgh, Pa.). The OD was measured at 450 nm on a microplate reader.

Mammalian Cell Culture: The human II-23 cell line (D7 subclone), a CD4+ T cell hybridoma line (Ware et al. 1986 Lymphokine Res 5 313-24), was maintained in RPMI 1640 containing 10% FBS (HyClone Laboratories, Logan, Utah) and 100 U/ml penicillin/100 µg/ml streptomycin (Life Technologies, Grand Island, N.Y.). The human HT29.14s cell line, the EL4-hLIGHT cell line and the 293-hLIGHT cell line were all maintained in DMEM containing 10% FBS (HyClone Laboratories, Logan, Utah). All mammalian cells were cultured in a 5% $CO_2$ humidified incubator at 37° C.

Anti-hLIGHT Antibody Detection ELISA: Antibody titers, specificity, and production by hybridomas were determined by ELISA. In brief, 96 well flat bottom plates were coated with 50 µl of FLAG tagged soluble hLIGHT at 5 µg/ml in carbonate buffer (pH 9.4) overnight at 4° C. or at 37° C. for 1 hour. After washing twice with PBS/0.1% Tween 20, plates were blocked with PBS/1% BSA/0.1% Tween20 at 37° C. for 1 hour. The serum, supernatant, or purified antibody was diluted in blocking buffer, added to the wells, and the plates were incubated for 1 hour at 37° C. The plates were washed 4 times with PBS/0.1% Tween 20 and the peroxidase conjugated sheep anti-human kappa detection antibody (The Binding Site, Birmingham, UK) was added at a dilution of 1:2000. Following a 1 hour incubation at 37° C., the plates were washed and the TMB (Sigma) substrate was added and incubated at room temperature for 10 to 30 minutes. The reaction was stopped with $H_2SO_4$ (LabChem) and a microplate reader measured the optical density at 450 nm.

Flow Cytometry: Antibody titers, specificity, and relative binding affinities were determined by flow cytometric analysis using hLIGHT stable EL4 transduced cell lines or a 6-15 hr PMA (40 ng/ml) +inonomycin (500 ng/ml) activated II23.D7 T cell line. The cells were washed once in staining buffer: PBS+2% FBS+0.01% $NaN_3$+10 mM EDTA, then resuspended in serum, supernatant, or purified antibodies in a volume of 50 µl. The cells were incubated with the antibodies on ice for 20 minutes, washed twice in staining buffer then resuspended in an goat anti-human IgG-APC labeled secondary antibody (Donkey anti-human-APC, Jackson Immunoresearch Laboratories, West Grove, Pa.). Following a 20 minute incubation on ice, the cells were washed once and fixed 10 minutes with 1% paraformaldehyde or subjected to a final wash, then the cells were resuspended in staining buffer and the samples acquired using FACScan or FACS Calibur flow cytometers (Becton Dickinson Biosciences, Palo Alto, Calif.). The data were analyzed using CELLQUEST (Becton Dickinson Biosciences) or FLOW JO (TreeStar, Inc., San Carlos, Calif.) software.

Anti-hLIGHT Antibody Cross-Blocking Assays: An ELISA protocol was used to determine if the antibodies bind the same hLIGHT epitope. NUNC 96 well flat bottom ELISA plates were coated with the human anti-hLIGHT antibodies in carbonate buffer at 2 µg/ml for 1 hour at 37° C. The plates were washed and then blocked with PBS/1% BSA/Tween 20. The human anti-hLIGHT antibodies were then pre-incubated with recombinant human FLAG-tagged soluble hLIGHT for 30 minutes at 4° C. The combinations of antibody-hLIGHT protein were added to the plate and incubated for 1 hour at 4° C. After 3 washes, bound hLIGHT was detected with peroxidase conjugated M2-mouse anti-FLAG epitope tag Ig (Sigma). The percent inhibition was determined using the OD of each sample in the following formula: % inhibition=(max−sample/max)*100.

Human Cytokine Analysis. A panel of 8 human cytokines in the growth media of treated HT29.14s cells was measured using multiplex technology and following the manufacturer's instructions (Bio-Rad Laboratories, Hercules, Calif.). The detection of CCL20 in the culture media of HT29.14s cells was performed by ELISA (R&D systems, Minneapolis, Minn.) using manufacturers instructions.

In Vitro Assay for Antibody Mediated Blockade of Cell Surface Expressed LIGHT Binding to Soluble Receptor Fc Fusion Proteins. 1e5 EL4 hLIGHT cells were incubated with graded concentrations of each antibody for 30 minutes at 4° C. Sub-saturating amounts of HVEM:Fc-biotin (3 µg/ml) or LTβR:Fc-His (3 µg/ml) (Alexis Biochemicals) were then added to the cells and incubated for 30 minutes at 4 degrees C. The cells were then washed 2× with 200 n1 FACS buffer (1×PBS 2% FBS+0.02% azide). HVEM:Fc-biotin or LTβR:Fc-His were detected by a 30 minute incubation with either SA-APC at 2.5 µg/ml or anti-His-HRP respectively. Cells were then analyzed on a FACScaliber (Becton Dickinson) flow cytometers. Dead cells were gated out from the forward scatter vs. side scatter plot and geometric means of each histogram were calculated using FLOWJO (TreeStar, San Carlos, Calif., USA).

Isolation of Human Anti-hLIGHT Antibody Genes. Cultured hybridoma cells (124E63, 124F23, 124E1, 124E13 and 124F19), which produce E63 (IgG3), F23 (IgG4), E1 (IgG1), E13 (IgG1) and F19 (IgG1) antibodies, respectively, were collected by centrifugation. Total RNA was purified from these cells using RNEASY kit (QIAGEN Inc., Valencia, Calif.) following the manufacturer's instructions. The SMART RACE cDNA Amplification Kit (Clontech Co., Ltd., Palo Alto, Calif.) was used for cloning of cDNA that encodes the variable region of the immunoglobulin genes from total hybridoma cell RNA. Briefly, first strand cDNA was prepared by reverse transcriptase from 2 microgram of RNA. This cDNA was used as a template for polymerase chain reaction (PCR) to amplify the variable region and a part of the constant region of heavy and light chains (VH and VL, respectively). The 3' primers used for amplification of the heavy and light chain genes in the 5' RACE reactions were HH-2 (SEQ ID NO:64) (H chain constant region) and HK-2 (SEQ ID NO:65) (light chain constant region), respectively. The amplified sequences also contained the leader sequences. The reaction was as follows: 2.5 units PFU ULTRA DNA polymerase (Stratagene, La Jolla, Calif.); 0.2 µM 3' Primer (for Heavy chain: IgG1p, for light chain: hk5, Table 2); 1× Universal Primer Mix A for the 5' end (UMP primer mix A included in the SMART RACE Kit); 200 µM dNTP mix; 1 mM MgCl$_2$; Puff Ultra Buffer (final concentration is 1×); and cDNA template.

The thermocycling program was 5 cycles of: 94° C.×30 sec, 72° C.×3 min. 5 cycles of: 94° C.×30 sec, 70° C.×30 sec, 72° C.×3 min. 25 cycles of: 94° C.×30 sec, 68° C.×30 sec, 72° C.×3 min. followed by an extension at 72° C.×7 min. Amplified DNA fragments were collected by agarose gel electrophoresis, and purified by QIAQUICK Gel Extraction Kit (Qiagen Co., Ltd., Germany). Purified DNA fragments of VH and LV were integrated into PCR 4 Blunt-TOPO vector using the Zero Blunt TOPO PCR Cloning Kit (Invitrogen, Carlsbad, Calif.), and each construct plasmid was transformed into E. coli, and then cloned. Nucleotide sequences of each insert (HV and LV) in the construct plasmids were analyzed using specific universal vector primers M13F (SEQ ID NO:58) and M13R (SEQ ID NO:59). Based on the sequence obtained from VH and VL, oligonucleotide primers were designed to amplify the respective VH and VL (see Table 2).

cDNAs encoding E63, F23, E1 and F19 VH and VL were PCR subcloned from the PCR4 Blunt-TOPO vectors into the IgG1 expression vector. Because E13 was an IgG1 subtype with a single kappa chain (see below) hybridoma, there was no need to subclone the E13 cDNA into an IgG1 vector for the further analyses.

First, oligonucleotide primers containing 5'-SalI and 3'-NheI restriction enzyme recognition sites were designed to amplify the variable region of the heavy chain (VH) by PCR. For example, in the case of E63VH, PCR was performed using pTopoE63VH mini-prep DNA as a template, E63HF85 (SEQ ID NO:60) and E63HR38 (SEQ ID NO:61) as primers (see Table 2) with PFU ULTRA DNA polymerase. After digestion with NheI and SalI, the PCR product was sub-cloned into the IgG1 expression vector (IDEC Pharmaceuticals, San Diego, Calif., N5KG1-Val Lark (a modified vector of N5KG1 (U.S. Pat. No. 6,001,358)) that was pre-digested with NheI and SalI (8.9 kilobases DNA fragment). The existence of VH was analyzed by restriction digest.

Next, oligonucleotide primers containing 5' BglII and 3' BsiWI restriction enzyme recognition sites were designed to amplify the variable region of the light chain (VL) by PCR. For example, following subcloning of the E63VH described above, the E63VL was inserted into the N5KG1-Val Lark-VH vector by digesting the DNA vector with BglII and BsiWI. The 9.1 kb DNA fragment was then isolated. Similar to the VH construct, a primer set for PCR of VL was designed to contain the recognition sites for 5'BglI and 3'BsiWI. These primers, E63LF84 (SEQ ID NO:62) and E63LR43 (SEQ ID NO:63), were used to amplify VL from the pTopoE63VL mini-prep plasmid DNA. The PCR product was digested with BglII and BsiWI and isolated by agarose gel electrophoresis and gel purification. This fragment, containing E63VL, was ligated to the prepared 9.1 kb vector with T4 DNA ligase and used to transform Top10 cells (Invitrogen). Positive E. coli transformants were selected. This expression vector, pG1K112E63, was purified, and the presence of both E63VL and E63VH regions were confirmed by restriction analysis.

Generation of vectors to produce recombinant F23G1, E1G1 and F19G1 antibodies was performed in essentially the same manner as E63G1. PCR amplification of the F23VH was performed using F23HF86 (SEQ ID NO:66) and F23HR55 (SEQ ID NO:67). The F23VL amplification primers were F23LF36 (SEQ ID NO:68) and F23LR43 (SEQ ID NO:69). PCR amplification of the E1VH was performed using E1HFSalI (SEQ ID NO:70) and E1 HRNheI (SEQ ID NO:71). PCR amplification of E1VL kappa(A), E1 VL kappa(B) and E1 VL kappa(C) was performed using E1 KF2+3BglII (SEQ ID NO:74) paired with either E1KR2BsiWI (SEQ ID NO:75) or E1 KR3BsiWI (SEQ ID NO:76). PCR amplification of F19VH was performed using F19HFSalI (SEQ ID NO:72) and F19HRNheI (SEQ ID NO:73). PCR amplification of F19L kappa(A) and F19L kappa(B) was performed using F19KR1+2BsiWI (SEQ ID NO:77) and F19KF1+2+3BglII (SEQ ID NO:79). PCR amplification of F19L kappa(C) was performed using F19KR3BsiWI (SEQ ID NO:78) and F19KF1+2+3BglII (SEQ ID NO:79). The resulting vectors, pKLG1/F23, pKLG1/E1 and pKLG1/F19 are also confirmed by restriction enzyme digest and sequencing. F19L kappa(D) was not PCR amplified due to a reading frameshift, which was detected by sequence analysis, that produced a C-terminal segment of the antibody.

```
Nucleotide sequence of cDNA of E63 heavy chain variable region (VH) (from
initiation codon (ATG) to the end of variable region) (SEQ ID NO: 43):
ATGAAACACC TGTGGTTCTT CCTCCTCCTG GTGGCAGCTC CCAGATGGGT CCTGTCCCAG   60

GTGCAGCTGC AGGAGTCGGG CCCAGGACTG GTGAAGCCTT CGGAGACCCT GTCCCTCACC  120

TGCATTGTCT CTGGTGGCTC CGTCAGCAGT GGTGGTTACT ACTGGAGCTG GATCCGGCAG  180

CCCCCAGGGA AGGGACTGGA GTGGATTGGG TATATCTATT ACAGTGGGAG CACCAACTAC  240

AACCCCTCCC TCAAGAGTCG AGTCACCATA TCAGTAGACA CGTCCAAGAA CCAGTTCTCC  300

CTGAAGCTGA GCTCTGTGAC CGCTGCGGAC ACGGCCGTGT ATTACTGTGC GAGATGGATT  360

ACTATGTTTC GGGGAGTTGG GTTCGACCCC TGGGGCCAGG GAACCCTGGT CACCGTCTCC  420

TCA                                                                480

Nucleotide sequence of cDNA of E63 kappa light chain variable region (VL)
(from initiation codon (ATG) to the end of variable region) (SEQ ID NO: 48):
ATGTCGCCAT CACAACTCAT TGGGTTTCTG CTGCTCTGGG TTCCAGCCTC CAGGGGTGAA   60

ATTGTGCTGA CTCAGTCTCC AGACTTTCAG TCTGTGACTC CAAAGGAGAA AGTCACCATC  120

ACCTGCCGGG CCAGTCAGAG CATTGGTAGT AGCTTACACT GGTACCAGCA GAAACCAGAT  180

CAGTCTCCAA AGCTCCTCAT CAAGTATGCT TCCCAGTCCT TCTCAGGGGT CCCCTCGAGG  240

TTCAGTGGCA GTGGATCTGG GACAGATTTC ACCCTCACCA TCAATAGCCT GGAAGCTGAA  300

GATGCTGCAG CATATTACTG TCATCAGAGT AGTAGTTTAC CTCTCACTTT CGGCGGAGGG  360

ACCAAGGTGG AGATCAAA                                                420

Nucleotide sequence of cDNA of F23 heavy chain variable region (from initiation
codon (ATG) to the end of variable region) (SEQ ID NO: 45):
ATGGACCTCC TGCACAAGAA CATGAAACAC CTGTGGTTCT TCCTCCTCCT GGTGGCAGCT   60

CCCAGATGGG TCCTGTCCCA GGTGCAGCTA CAGCAGTGGG GCGCAGGACT GTTGAAGCCT  120

TCGGAGACCC TGTCCCTCAC CTGCGCTGTC TATGGTGGGT CCTTCAGTGG TTACTACTGG  180

AACTGGATCC GCCAGCCCCC AGGGAAGGGG CTGGAGTGGA TTGGGGAAAT CAATCAGTAC  240

AACCCGTCCC TCAAGAGTCG AGTCACCATA TCAGTAGACA CGTCCAAGAA CCAGTTCTCC  300

CTGAAGCTGA GCTCTGTGAC CGCCGCGGAC ACGGCTGTGT ATTACTGTGC GAGAGAGATA  360

GCAACAGCTG ATAAAGGGTA CTACGGTTTG GACGTCTGGG GCCAAGGGAC CACGGTCACC  420

GTCTCCTCA                                                          480

Nucleotide sequence of cDNA of F23 kappa light chain variable region (from
initiation codon (ATG) to the end of variable region) (SEQ ID NO: 50):
ATGGACATGA GGGTCCCCGC TCAGCTCCTG GGGCTTCTGC TGCTCTGGCT CCCAGGTGCC   60

AGATGTGCCA TCCAGTTGAC CCAGTCTCCA TCCTCCCTGT CTGCATCTGT AGGAGACAGA  120

GTCACCATCA CTTGCCGGGC AAGTCAGGGC ATTAGCAGTG CTTTAGCCTG GTATCAGCAG  180

AAACCAGGGA AAGCTCCTAA GCTCCTGATC TATGATGCCT CCAGTTTGGA AAGTGGGGTC  240

CCATCAAGGT TCAGCGGCAG TGGATCTGGG ACAGATTTCA CTCTCACCAT CAGCAGCCTG  300
```

CAGCCTGAAG ATTTTGCAAC TTATTACTGT CAACAGTTTA ATAGTTACCC GCTCACTTTC 360

GGCGGAGGGA CCAAGGTGGA GATCAAA 420

Nucleotide sequence of cDNA of E1 heavy chain variable region (from initiation codon (ATG) to the end of variable region) (SEQ ID NO: 41):
ATGGAGTTGG GGCTGTGCTG GGTTTTCCTT GTTGCTATTT TAGAAGGTGT CCAGTGTGAG 60

GTGCAGCTGG TGGAGTCTGG GGGAGGCTTG GTACAGCCTG GGGGGTCCCT GAGACTCTCC 120

TGTGCAGCCT CTGGATTCAC CTTCAGTAGA TTTAACATGA ACTGGGTCCG CCAGGCTCCA 180

GGGAAGGGGC TGGAGTGGGT TTCATACATT AGTAGTAGTA GTTATACCAT ATACTACGCA 240

GACTCTGTGA AGGGCCGATT CACCATCTCC AGAGACAATG CCAAGAACTC ACTGGATCTG 300

CAAATGAACA GCCTGAGAGA CGAGGACACG GCTGTGTATT ACTGTGCGAG GAGTATAGCA 360

GCAGCTTTTG ACTACTGGGG CCAGGGAGCC CTGGTCACCG TCTCCTCA 420

Nucleotide sequence of cDNA of E1 kappa light chain variable region #1(from initiation codon (ATG) to the end of variable region) (SEQ ID NO: 102):
ATGGACATGA GGGTCCCCGC TCAGCTCCTG GGGCTTCTGC TGCTCTGGCT CCCAGGTGCC 60

AGATGTGCCA TCCAGTTGAC CCAGTCTCCA TCCTCCCTGT CTGCATCTGT AGGAGACAGA 120

GTCACCATCA CTTGCCGGGC AAGTCAGGGC ATTAGCAGTG CTTTAGCCTG GTATCAGCAG 180

AAACCAGGGA AAGCTCCTAA GCTCCTGATC TATGATGCCT CCAGTTTGGA AAGTGGGGTC 240

CCATCAAGGT TCAGCGGCAG TGGATCTGGG ACAGATTTCA CTCTCACCAT CAGCAGCCTG 300

CAGCCTGAAG ATTTTGCAAC TTATTACTGT CAACAGTTTA ATAGTTACCG TACACTTTTG 360

GCCAGGGGAC CAAGCTGGAG ATCAAA 420

Nucleotide sequence of cDNA of E1 kappa light chain variable region #2(from initiation codon (ATG) to the end of variable region) (SEQ ID NO: 46):
ATGGAAACCC CAGCGCAGCT TCTCTTCCTC CTGCTACTCT GGCTCCCAGA TACCACCGGA 60

GAAATTGTGT TGACGCAGTC TCCAGGCACC CTGTCTTTGT CTCCAGGGGA AAGAGCCACC 120

CTCTCCTGCA GGGCCAGTCA GAGTGTTAGC AGCAGCTACT TAACCTGGTA CCAGCAGAAA 180

CCTGGCCAGG CTCCCAGGCT CCTCATCTAT GGTGCATCCA GCAGGGCCAC TGGCATCCCA 240

GACAGGTTCA GTGGCAGTGG GTCTGGGACA GACTTCACTC TCACCATCAG CAGACTGGAG 300

CCTGAAGATT TTGCAGTGTA TTACTGTCAG CAGTATGGTA GCTCAATGTA CACTTTTGGC 360

CAGGGGACCA AGCTGGAGAT CAAA 420

Nucleotide sequence of cDNA of E1 kappa light chain variable region #3(from initiation codon (ATG) to the end of variable region) (SEQ ID NO: 103):
ATGGAAACCC CAGCGCAGCT TCTCTTCCTC CTGCTACTCT GGCTCCCAGA TACCACCGGA 60

GAAATTGTGT TGACGCAGTC TCCAGGCACC CTGTCTTTGT CTCCAGGGGA AAGAGCCACC 120

CTCTCCTACA GGGCCAGTCA GAGTGTTAGC AGCAGCTACT TAGCCTGGTA CCAGCAGAAA 180

CCTGGCCAGG CTCCCAGGCT CCTCATCTAT GGTGCATCCA ACAGGGCCAC TGGCATCCCA 240

GACAGGTTCA GTGGCAGTGG GTCTGGGACA GACTTCACTC TCACCATCAG CAGACTGGAG 300

CCTGAAGATT TTGCAGTGTA TTACTGTCAG CAGTATGGTA GCTCACCGTG ACGTTCGGC 360

CAAGGGACCA AGGTGGAAAT CAAA 420

Nucleotide sequence of cDNA of E13 heavy chain variable region (from initiation codon (ATG) to the end of variable region) (SEQ ID NO: 42):
ATGGAGTTTG GGCTGAGCTG GATTTTCCTT GCTGCGATTT TAAAAGGTGT CCAGTGTGAG 60

GTGCAGCTGG TGGAGTCTGG GGGAGGCCTG GTAAAGCCTG GGGGGTCCCT TAGACTCTCC 120

TGTGCAGCCT CTGGATTCAC TCTCAGTAAC GCCTGGATGA GCTGGGTCCG CCAGGCTCCA 180

GGGAAGGGGC TGGAGTGGGT TGGCCGTATT AAAAGCAAAA TAGATGGTGG GACAACAGAC 240

TACGCTGCAC CCGTGAAAGG CAGATTCACC ATCTCAAGAG ATGATTCAAA AACACGCTG 300

-continued

TTTCTGCAAA TGAACAGCCT GAAAACCGAG GACACAGCCG TGTATTACTG TACCACAGCA 360

ATGGCTGGTG CGTTTGGCTT TTGGGGCCAG GGAACCCTGG TCACCGTCTC CTCA         420

Nucleotide sequence of cDNA of E13 kappa light chain variable region (from
initiation codon (ATG) to the end of variable region) (SEQ ID NO: 47):
ATGGAAACCC CAGCGCAGCT TCTCTTCCTC CTGCTACTCT GGCTCCCAGA TACCACCGGA 60

GAAATTGTGT TGACGCAGTC TCCAGGCACC CTGTCTTTGT CTCCAGGGGA AAGAGCCACC 120

CTCTCCTGCA GGGCCAGTCA GAGTGTTAGC AGCAGCTACT TAGCCTGGTA CCAGCAGAAA 180

CCTGGCCAGG CTCCCAGGCT CCTCATCTAT GGTGCATCCA GCAGGGCCAC TGGCATCCCA 240

GACAGGTTCA GTGGCAGTGG GTCTGGGACA GACTTCACTC TCACCATCAG CAGACTGGAG 300

CCTGAAGATT TTGCAGTGTA TTACTGTCAG CAGTATGGTA GCTCACCCAT GTACACTTTT 360

GGCCAGGGGA CCAAGCTGGA GATCAAACGA                                   420

Nucleotide sequence of cDNA of F19 heavy chain variable region (from initiation
codon (ATG) to the end of variable region) (SEQ ID NO: 44):
ATGAAACACC TGTGGTTCTT CCTCCTCCTG GTGGCAGCTC CCAGATGGGT CCTGTCCCAG 60

GTGCAGCTAC AGCAGTGGGG CGCAGGACTG TTGAAGCCTT CGGAGACCCT GTCCCTCACC 120

TGCGCTGTCT ATGGTGGGTC CTTCAGTGGT TACAACTGGC ACTGGATCCG CCAGCCCCCA 180

GGGAAGGGGC TGGAGTGGAT TGGGGAAATC ACTCATAGTG GAAGCACCAA TTACAACCCG 240

TCCCTCAAGA GTCGAGTCAC CATATCAGTA GACACGTCCA AGAACCAGTT CTCCCTGAAG 300

CTGAGCTCTG TGACCGCCGC GGACACGGCT GTGTATTACT GTGTGCGAGA GATTGCAGTG 360

GCTGGTACGG GCTACTACGG TATGGACGTC TGGGGCCAAG GGACCACGGT CACCGTCTCC 420

TCA                                                                480

Nucleotide sequence of cDNA of F19 kappa light chain variable region #1(from
initiation codon (ATG) to the end of variable region) (SEQ ID NO: 104):
ATGGACATGA GGGTCCCCGC TCAGCTCCTG GGGCTCCTAC TGCTCTGGGT CCCAGGTGCC 60

AGATGTGACA TCCAGTTGAC CCAGTCTCCA TCCTCCCTGT CTGCATCTGT AGGAGACAGA 120

GTCACCATCA CTTGCCGGGT GAGTCAGGGC ATTAGCAGTT ATTTAAATTG GTATCGGCAG 180

AAACCAGGGA AAGTTCCTAA GCTCCTGATC TATAGTGCAT CCAATTTGCA ATCTGGAGTC 240

CCATCTCGGT TCAGTGGCAG TGGATCTGGG ACAGATTTCA CTCTCACTAT CAGCAGCCTG 300

CAGCCTGAAG ATGTTGCAAC TTATTACGGT CAACGGACTT ACAATGCCCC TCCCACTTTC 360

GGCGGAGGGA CCAAGGTGGA GATCAAA                                      420

Nucleotide sequence of cDNA of F19 kappa light chain variable region #2(from
initiation codon (ATG) to the end of variable region) (SEQ ID NO: 49):
ATGGACATGA GGGTCCCCGC TCAGCTCCTG GGGCTTCTGC TGCTCTGGCT CCCAGGTGCC 60

AGATGTGCCA TCCAGTTGAC CCAGTCTCCA TCCTCCCTGT CTGCATCTGT AGGAGACAGA 120

GTCACCATCA CTTGCCGGGC AAGTCAGGGC ATTAACAGTG CTTTTGCCTG GTATCAGCAG 180

AAACCAGGGA AAGCTCCTAA GCTCCTGATC TATGATGCCT CCAGTTTGGA AAGTGGGGTC 240

CCATCAAGGT TCAGCGGCAG TGGATCTGGG ACAGATTTCA CTCTCACCAT CAGCAGCCTG 300

CAGCCTGAAG ATTTTGCAAC TTATTACTGT CAACAGTTTA ATAGTTACCC TCTCACTTTC 360

GGCGGAGGGA CCAAGGTGGA GATCAAA                                      420

Nucleotide sequence of cDNA of F19 kappa chain variable region #3(from
initiation codon (ATG) to the end of variable region) (SEQ ID NO: 105):
ATGGACATGA GGGTCCCCGC TCAGCTCCTG GGGCTCCTGC TGCTCTGGCT CCCAGGTGCC 60

AGATGTGTCA TCTGGATGAC CCAGTCTCCA TCCTTACTCT CTGCATCTAC AGGAGACAGA 120

GTCACCATCA GTTGTCGGAT GAGTCAGGGC ATTAGCAGTT ATTTAGCCTG GTATCAGCAA 180

AAACCAGGGA AGCCCCTGA GCTCCTGATC TATGCTGCAT CCACTTTGCA AAGTGGGGTC 240

CCATCAAGGT TCAGTGGCAG TGGATCTGGG ACAGATTTCA CTCTCACCAT CAGCTGCCTG 300

```
CAGTCTGAAG ATTTTGCAAC TTATTACTGT CAACAGTATT ATAGTTTCCC GTACACTTTT  360

GGCCAGGGGA CCAAGCTGGA GATCAAA                                     420
```

Nucleotide sequence of cDNA of F19 kappa chain variable region #4 (from initiation codon (ATG) to the end of variable region) (SEQ ID NO: 106):

```
ATGGAAGCCC AGCGCAGCT TCTCTTCCTC CTGCTACTCT GGCTCCCAGA TACCACCGGA  60

GAAATTGTGT TGACACAGTC TCCAGCCACC CTGTCTTTGT CTCCAGGGGA AAGAGCCACC 120

CTCTCCTGCA GGGCCAGTCA GGGTGTTAGC AGCTACTTAG CCTGGTACCA GCAGAAACCT 180

GGCCAGGCTC CCAGGCTCCT CATCTATGAT GCATCCAACA GGGCCACTGG CATCCCAGCC 240

AGGTTCAGTG GCAGTGGGCC TGGGACAGAC TTCACTCTCA CCATCAGCAG CCTAGAGCCT 300

GAAGATTTTG CAGTTTATTA CTGTCAGCAG CGTAGCAACT GGCATCCCGT TCGGCCAAGG 360

GACCAAGGTG GAGATTCAAA                                            420
```

Amino acid sequence of E63 heavy chain variable region (leader sequence (bold) and variable region) (SEQ ID NO: 3):
```
MKHLWFFLLL VAAPRWVLSQ VQLQESGPGL VKPSETLSLT CIVSGGSVSS GGYYWSWIRQ  60

PPGKGLEWIG YIYYSGSTNY NPSLKSRVTI SVDTSKNQFS LKLSSVTAAD TAVYYCARWI 120

TMFRGVGFDP WGQGTLVTVS S                                          180
```

Amino acid sequence of E63 kappa light chain variable region (leader sequence (bold) and variable region) (SEQ ID NO: 8):
```
MSPSQLIGFL LLWVPASRGE IVLTQSPDFQ SVTPKEKVTI TCRASQSIGS SLHWYQQKPD  60

QSPKLLIKYA SQSFSGVPSR FSGSGSGTDF TLTINSLEAE DAAAYYCHQS SSLPLTFGGG 120

TKVEIK                                                           180
```

Amino acid sequence of F23 heavy chain variable region (leader sequence (bold) and variable region) (SEQ ID NO: 5):
```
MDLLHKNMKH LWFFLLLVAA PRWVLSQVQL QQWGAGLLKP SETLSLTCAV YGGSFSGYYW  60

NWIRQPPGKG LEWIGEINQY NPSLKSRVTI SVDTSKNQFS LKLSSVTAAD TAVYYCAREI 120

ATADKGYYGL DVWGQGTTVT VSS                                        180
```

Amino acid sequence of F23 kappa light chain variable region (leader sequence (bold) and variable region) (SEQ ID NO: 10):
```
MDMRVPAQLL GLLLLWLPGA RCAIQLTQSP SSLSASVGDR VTITCRASQG ISSALAWYQQ  60

KPGKAPKLLI YDASSLESGV PSRFSGSGSG TDFTLTISSL QPEDFATYYC QQFNSYPLTF 120

GGGTKVEIK                                                        180
```

Amino acid sequence of E1 heavy chain variable region (leader sequence (bold) and variable region) (SEQ ID NO: 1):
```
MELGLCWVFL VAILEGVQCE VQLVESGGGL VQPGGSLRLS CAASGFTFSR FNMNWVRQAP  60

GKGLEWVSYI SSSSYTIYYA DSVKGRFTIS RDNAKNSLDL QMNSLRDEDT AVYYCARSIA 120

AAFDYWGQGA LVTVSS                                                180
```

Amino acid sequence of E1 kappa light chain variable region #1 (Elkappa(A)) (leader sequence (bold) and variable region) (SEQ ID NO: 82):
```
MDMRVPAQLL GLLLLWLPGA RCAIQLTQSP SSLSASVGDR VTITCRASQG ISSALAWYQQ  60

KPGKAPKLLI YDASSLESGV PSRFSGSGSG TDFTLTISSL QPEDFATYYC QQFNSYRTLL 120

ARGPSWRS                                                         180
```

Amino acid sequence of cDNA of E1 kappa light chain variable region #2 (E1kappa(B)) (leader sequence (bold) and variable region) (SEQ ID NO: 6):
```
METPAQLLFL LLLWLPDTTG EIVLTQSPGT LSLSPGERAT LSCRASQSVS SSYLTWYQQK  60

PGQAPRLLIY GASSRATGIP DRFSGSGSGT DFTLTISRLE PEDFAVYYCQ QYGSSMYTFG 120

QGTKLEIK                                                         180
```

Amino acid sequence of cDNA of E1 kappa light chain variable region #3
(E1kappa(C)) (leader sequence (bold) and variable region) (SEQ ID NO: 83):
METPAQLLFL LLLWLPDTTG EIVLTQSPGT LSLSPGERAT LSYRASQSVS SSYLAWYQQK  60

PGQAPRLLIY GASNRATGIP DRFSGSGSGT DFTLTISRLE PEDFAVYYCQ QYGSSPWTFG 120

QGTKVEIK                                                         180

Amino acid sequence of E13 heavy chain variable region (leader sequence (bold)
and variable region) (SEQ ID NO: 2):
MEFGLSWIFL AAILKGVQCE VQLVESGGGL VKPGGSLRLS CAASGFTLSN AWMSWVRQAP  60

GKGLEWVGRI KSKIDGGTTD YAAPVKGRFT ISRDDSKNTL FLQMNSLKTE DTAVYYCTTA 120

MAGAFGFWGQ GTLVTVSS                                              180

Amino acid sequence of E13 kappa light chain variable region (leader sequence
(bold) and variable region) (SEQ ID NO: 7):
METPAQLLFL LLLWLPDTTG EIVLTQSPGT LSLSPGERAT LSCRASQSVS SSYLAWYQQK  60

PGQAPRLLIY GASSRATGIP DRFSGSGSGT DFTLTISRLE PEDFAVYYCQ QYGSSPMYTF 120

GQGTKLEIKR                                                       180

Amino acid sequence of F19 heavy chain variable region (leader sequence (bold)
and variable region) (SEQ ID NO: 4):
MKHLWFFLLL VAAPRWVLSQ VQLQQWGAGL LKPSETLSLT CAVYGGSFSG YNWHWIRQPP  60

GKGLEWIGEI THSGSTNYNP SLKSRVTISV DTSKNQFSLK LSSVTAADTA VYYCVREIAV 120

AGTGYYGMDV WGQGTTVTVS S                                          180

Amino acid sequence of cDNA of F19 kappa light chain variable region #1
(F19kappa(A)) (leader sequence (bold) and variable region) (SEQ ID NO: 90):
MDMRVPAQLL GLLLLWVPGA RCDIQLTQSP SSLSASVGDR VTITCRVSQG ISSYLNWYRQ  60

KPGKVPKLLI YSASNLQSGV PSRFSGSGSG TDFTLTISSL QPEDVATYYG QRTYNAPPTF 120

GGGTKVEIK                                                        180

Amino acid sequence of cDNA of F19 kappa light chain variable region #2
(F19kappa(B)) (leader sequence (bold) and variable region) (SEQ ID NO: 9):
MDMRVPAQLL GLLLLWLPGA RCAIQLTQSP SSLSASVGDR VTITCRASQG INSAFAWYQQ  60

KPGKAPKLLI YDASSLESGV PSRFSGSGSG TDFTLTISSL QPEDFATYYC QQFNSYPLTF 120

GGGTKVEIK                                                        180

Amino acid sequence of cDNA of F19 kappa light chain variable region #3
(F19kappa(C)) (leader sequence (bold) and variable region) (SEQ ID NO: 91):
MDMRVPAQLL GLLLLWLPGA RCAIQLTQSP SSLSASVGDR VTITCRASQG INSAFAWYQQ  60

KPGKAPELLI YAASTLQSGV PSRFSGSGSG TDFTLTISCL QSEDFATYYC QQYYSFPYTF 120

GQGTKLEIK                                                        180

Amino acid sequence of cDNA of F19 kappa light chain variable region #4
(F19kappa(D)) (leader sequence (bold) and variable region) (SEQ ID NO: 92):
MEAPAQLLFL LLLWLPDTTG EIVLTQSPAT LSLSPGERAT LSCRASQGVS SYLAWYQQKP  60

GQAPRLLIYD ASNRATGIPA RFSGSGPGTD FTLTISSLEP EDFAVYYCQQ RSNWHPVRPR 120

DQGGDS                                                           180

TABLE 2

| SEQ ID NO: | Name | Sequence 5' to 3' | Length |
|---|---|---|---|
| | | Synthesized DNA primers | |
| 55 | RACEUPS5' | CTAATACGACTCACTATAGGGC | 22-mer |
| 56 | IgG1p | TCTTGTCCACCTTGGTGTTGCTGGGCTTGTG | 31-mer |
| 57 | HK5 | AGGCACACAACAGAGGCAGTTCCAGATTTC | 30-mer |
| 58 | M13F | GTAAAACGACGGCCAGTG | 18-mer |

TABLE 2-continued

Synthesized DNA primers

| SEQ ID NO: | Name | Sequence 5' to 3' | Length |
|---|---|---|---|
| 59 | M13R | CAGGAAACAGCTATGAC | 17-mer |
| 60 | E63HF85 | AGAGAGAGAGGTCGACCACCATGAAACACCTGTGGTTCTTC | 41-mer |
| 61 | E63HR38 | GAGAGAGAGAGCTAGCTGAGGAGACGGTGACCAGGGT | 37-mer |
| 62 | E63LF84 | AGAGAGAGAGATCTCTCACCATGTCGCCATCACAACTCATTG | 42-mer |
| 63 | E63LR43 | AGAGAGAGAGCGTACGTTTGATCTCCACCTTGGTCCCTCC | 40-mer |
| 64 | HH-2 | GCTGGAGGGCACGGTCACCACGCTG | 25-mer |
| 65 | HK-2 | GTTGAAGCTCTTTGTGACGGGCGAGC | 26-mer |
| 66 | F23HF86 | AGAGAGAGAGGTCGACCACCATGGACCTCCTGCACAAGAAC | 41-mer |
| 67 | F23HR55 | AGAGAGAGAGGCTAGCTGAGGAGACGGTGACCGT | 34-mer |
| 68 | F23LF36 | AGAGAGAGAGATCTCTCACCATGGACATGAGGGTCCCCGCTC | 42-mer |
| 69 | F23LR43 | AGAGAGAGAGCGTACGTTTGATCTCCACCTTGGTCCCTCC | 40-mer |
| 70 | E1HFSalI | AGAGAGAGAGGTCGACCACCATGGAGTTGGGGCTGTGCTGG | 41-mer |
| 71 | E1HRNheI | AGAGAGAGAGGCTAGCTGAGGAGACGGTGACCAGGGC | 37-mer |
| 72 | F19HFSalI | AGAGAGAGAGGTCGACCACCATGAAACACCTGTGGTTCTTC | 41-mer |
| 73 | F19HRNheI | AGAGAGAGAGGCTAGCTGAGGAGACGGTGACCGTGGT | 37-mer |
| 74 | E1KF2+3BglII | AGAGAGAGAGATCTCTCACCATGGAAACCCCAGCGCAGCTTC | 42-mer |
| 75 | E1KR2BsiWI | AGAGAGAGAGCGTACGTTTGATCTCCAGCTTGGTCCCCTG | 40-mer |
| 76 | E1KR3BsiWI | AGAGAGAGAGCGTACGTTTGATTTCCACCTTGGTCCCTTG | 40-mer |
| 77 | F19KR1+2BsiWI | AGAGAGAGAGCGTACGTTTGATCTCCACCTTGGTCCCTCC | 40-mer |
| 78 | F19KR3BsiWI | AGAGAGAGAGCGTACGTTTGATCTCCAGCTTGGTCCCCTG | 40-mer |
| 79 | F19KF1+2+3BglII | AGAGAGAGAGATCTCTCACCATGGACATGAGGGTCCCCGCTC | 42-mer |

The KM Mouse™ is described in, e.g., Fishwild et al. 1996, Nat. Biotechnol. 14:845-51; Lonberg et al. 2005 Nat. Biotechnol. 9:1117-1125; Tomizuka et al. 2000 Proc. Natl. Acad. Sci. USA 97:722-7; Tomizuka 1997 Nat Genet. 16:133-43, each of which is incorporated herein by reference in its entirety. Due to the nature of the KM Mouse™ (e.g., more than one kappa chain gene was integrated into the murine genome upon generation of the kappa transgenic strain) it is possible to have more than one kappa light chain cDNA expressed from a clonal hybridoma. To determine if this is the case, a minimum of ten cDNA clones are sequenced. In cases where more than one kappa light chain antibody cDNA is isolated (e.g., E1 and F19), several constructs are generated containing the various pairs of heavy chain cDNA combined with each kappa cDNA. These expression constructs are transfected into 293F cells using 293FECTIN (Invitrogen, San Diego, Calif.). Seventy-two hour culture supernatants are then tested for antibody activity to identify the correct heavy and light chain pair(s) that immunospecifically binds to hLIGHT (e.g., by Western blot, ELISA or other similar method). Please refer to Example 3 below for an exemplary method of characterizing antibodies (e.g., E1 and F19) having with multiple kappa chains.

Production of Recombinant Human Anti-hLIGHT Antibody from 293F Cells: Suspension cultures of 293F cells were maintained in Freestyle 293 expression medium while shaking at ~120 rpm/min in an 8% $CO_2$ humidified incubator at 37° C. For transient expression of recombinant antibodies, $3 \times 10^7$ 293 F cells were transfected with 30 μg of each plasmid encoding the recombinant IgG1 versions of either the E63 or F23 anti-hLIGHT antibodies using 293-fectin (Invitrogen, Carlsbad, Calif.) following manufacturer's instructions. Transfectants were allowed to grow in suspension in 30 mls of FREESTYLE 293 expression medium for 5 days under normal growth conditions. Growth medium was harvested and cells removed by centrifugation at a speed of 300 g followed by filtration through a 0.22 μm filter. The antibody concentration present in this unpurified material is determined by hIgG ELISA and used for in vitro assays to assess the functional properties of the subclass switched antibodies.

Results

KM Mice™ were immunized with soluble recombinant FLAG-tagged hLIGHT in CFA/IFA. Several of the mice raised anti-hLIGHT specific antibodies, with a range in human IgG hLIGHT specific titers measured by ELISA and FACS analysis staining of hLIGHT-EL4 cells. Splenocytes from the highest responders were fused with myeloma cells to generate human anti-hLIGHT producing hybridomas. The production of anti-hLIGHT antibodies by the individual hybridomas was determined in the primary screen by anti-hLIGHT ELISA. In this screen the anti-FLAG antibody was coated on the plate to capture FLAG-tagged recombinant hLIGHT in a successful effort to mask the FLAG epitope and prevent isolation of anti-FLAG antibody producing hybridomas. Media from ELISA positive clones was used in a secondary screen by flow cytometry staining the hLIGHT-EL4 cell line to confirm the identification of antibodies that immunospecifically bind to the native form of hLIGHT.

The positive hybridomas were tested for antagonistic activity by ranking the capacity of the antibodies produced by the hybridoma to block HVEM:Fc and LTβR:Fc binding to hLIGHT-EL4 cells. This blocking activity was normalized to antibody concentration determined by human IgG ELISA. The top 15 candidates were cloned by limiting dilution to yield monoclonal hybridomas, while the rest were frozen. Small scale purifications were produced from extinction cultures (<1 mg) for these 15 antibodies for further characterization and ranking based on the following criteria: relative binding affinity for hLIGHT, the ability to block human HVEM:Fc and LTβR:Fc binding to hLIGHT-EL4 cells, cross-blocking each other, and the ability to block soluble and cell surface-expressed hLIGHT-mediated chemokine secretion from the colonic epithelial cell line HT29.14s. Based on these studies, properties of the top 5 selected candidates (E1, E13, E63, F23 and F19) are presented in FIG. 3.

Figure 1B:
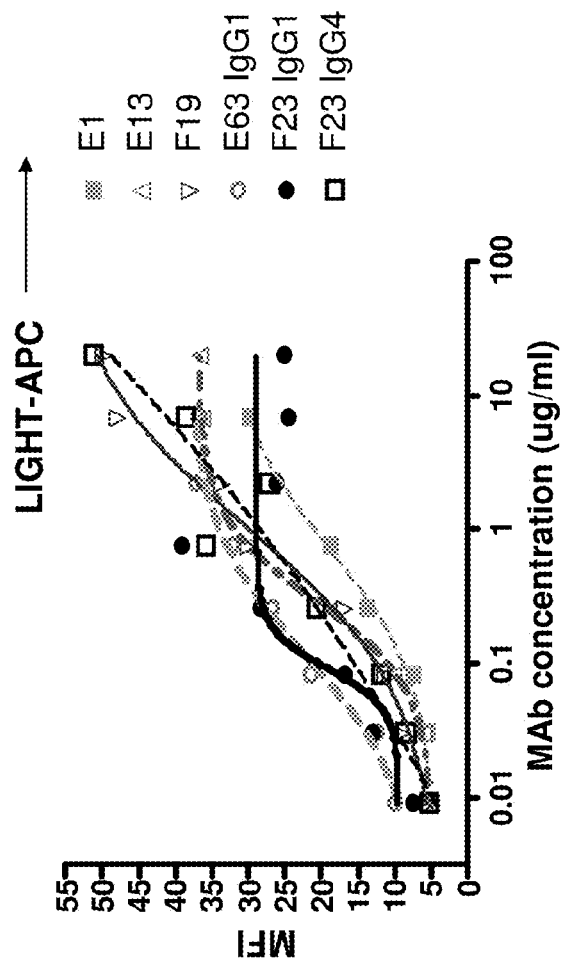
Figures 2A, 2B:
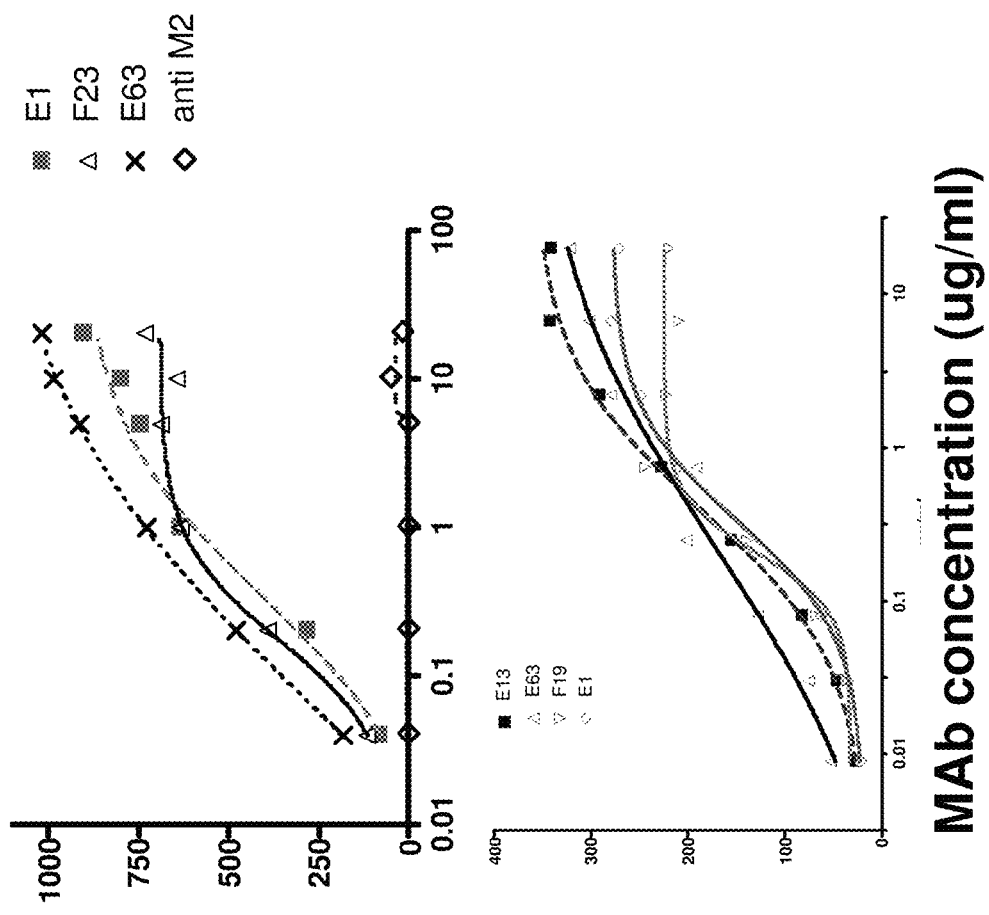
FIGS. 2A-2B depicts the staining of recombinant hLIGHT on EL4-hLIGHT cell line with human anti-hLIGHT antibodies.
Figures 5A, 5B:
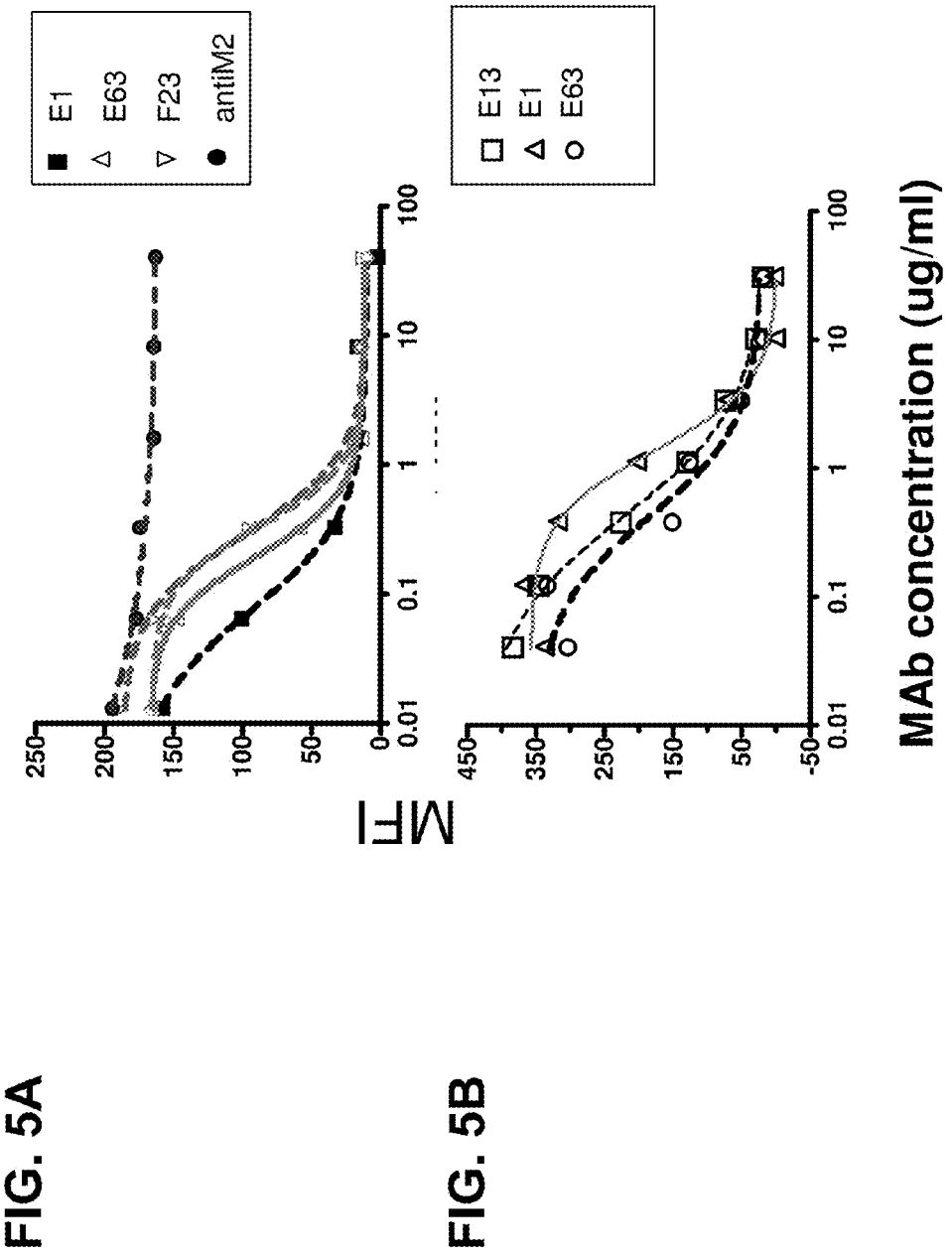
FIGS. 5A-5B depicts the blockade of human HVEM:Fc binding to native hLIGHT on the cell surface by human anti-hLIGHT monoclonal antibodies.
Figure 6A:
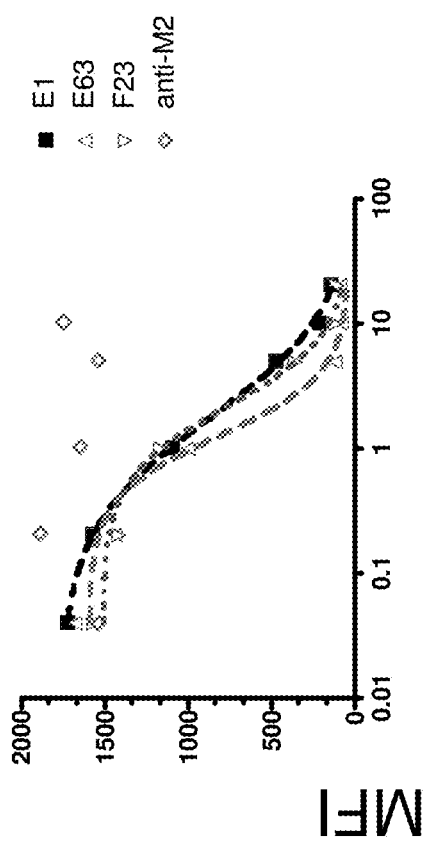
FIGS. 6A-6B depicts the blockade of human LTβR:Fc binding to native hLIGHT on the cell surface by human anti-hLIGHT monoclonal antibodies.
Figure 6B:
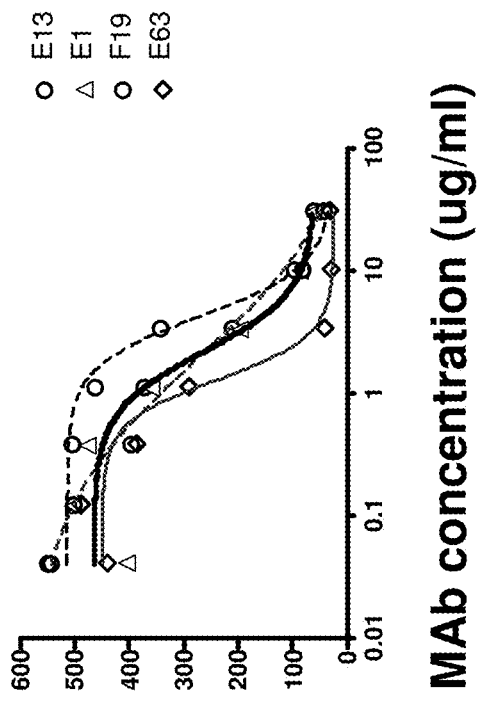

E1, E13, E63, F23 and F19 anti-hLIGHT monoclonal antibodies each bound specifically to the activated human T cell line (II23.D7) and the stable hLIGHT expressing cell line hLIGHT-EL4, but not to parental EL4 or resting II23.D7 cells (FIG. 1A). The binding of these human anti-hLIGHT antibodies reached saturation (FIG. 1B). The functional steady-state binding affinity of each antibody was determined by titrating the amount of antibody needed to label hLIGHT-EL4 cells (FIGS. 2A and 2B). Non-linear regression analysis was performed to determine the functional binding affinity measurement or EC50 for each candidate (FIG. 3). A range of functional affinities was observed. A low EC50 as well as a high level of staining (mean fluorescence intensity (MFI)) at saturation were both considered ideal during the ranking and selection process.

The antibodies were tested by ELISA to determine if they compete with one another for binding to soluble hLIGHT (FIG. 4). Two hLIGHT epitope groups were identified in this analysis. The "E antibodies" (E1, E13, and E63) crossblock each another, and the "F antibodies" (F19 and F23) cross-block each other. However, the "E antibodies" were not able to cross-block the "F antibodies" and vice versa. As expected, all antibodies blocked themselves in this assay.

The ability of E1, E13, E63, F23 and F19 to block the human HVEM:Fc and LTβR:Fc fusion proteins to cell surface expressed hLIGHT using a flow cytometric based assays is shown in FIGS. 5A and 5B, and FIGS. 6A and 6B respectively. In these experiments, graded amounts of each antibody were added to the EL4-hLIGHT cell line followed by the addition of a sub-saturating amount of the receptor fusion protein. The receptor fusion proteins were detected by either anti-His antibodies for His-tagged LTβR:Fc or streptavidin-PE for biotinylated HVEM:Fc. As shown, each of the antibodies blocked either receptor fusion protein from binding hLIGHT, in contrast to the fully human anti-influenza M2 antibody control which had no effect on either Fc-receptor binding. In each experiment, all antibodies blocked receptor binding in a dose dependent manner enabling analysis by non-linear regression to determine the IC$_{50}$ dose (FIG. 3). These values were taken into consideration when ranking the potential candidates.

Figure 7:
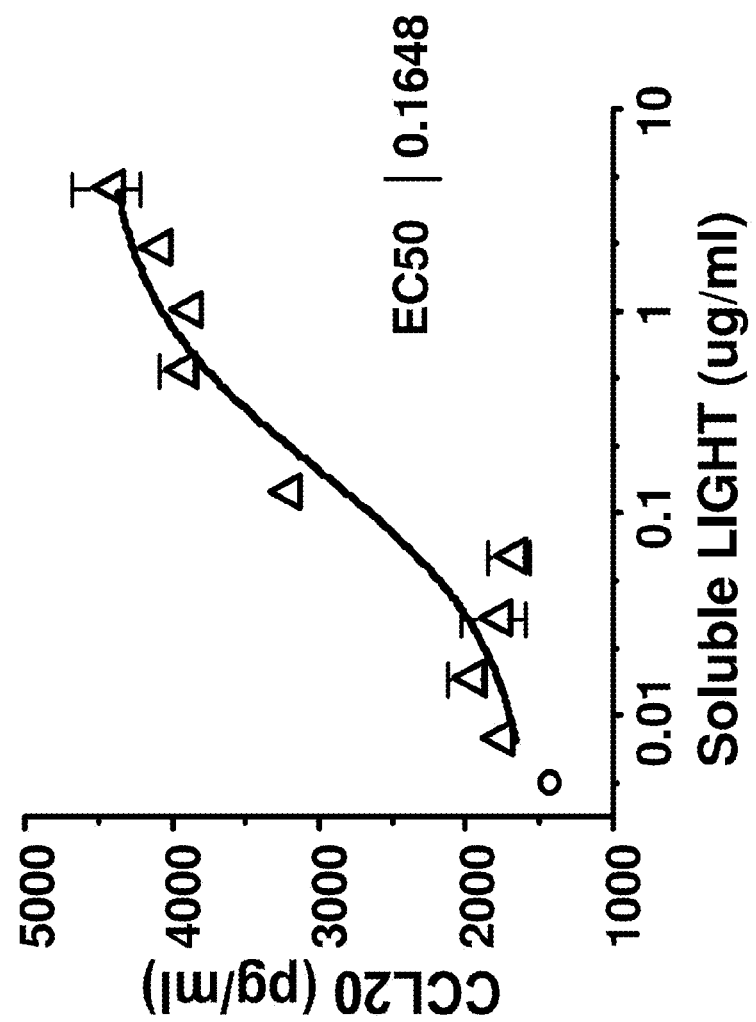
FIG. 7 depicts hLIGHT-mediated CCL20 secretion from human colonic epithelial cells. Recombinant soluble hLIGHT was added to the growth medium of HT29.14s cells at increasing concentrations. Growth media was harvested at day 3 post treatment and levels of CCL20 were determined by ELISA. Error bars indicate two independent treatments.
Figure 8A:
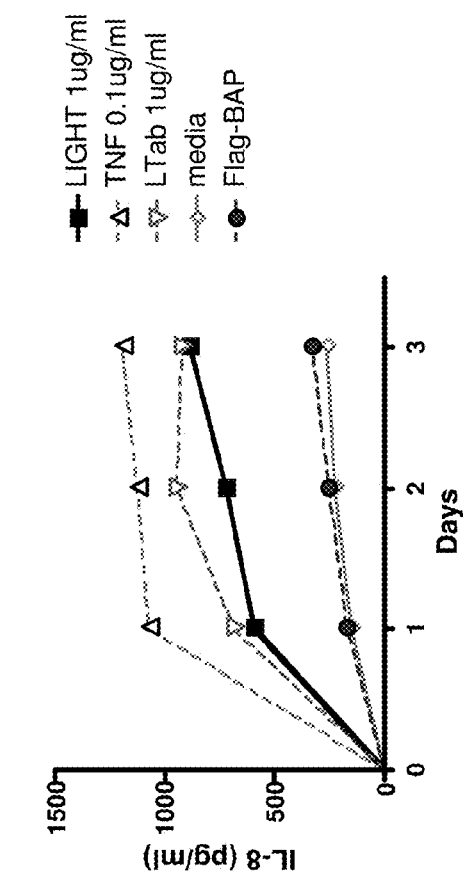
FIGS. 8A-8B depicts hLIGHT-mediated IL-8 and RANTES secretion from human colonic epithelial cells. Recombinant soluble hLIGHT, TNF, LTα$_1$β$_2$ and FLAG-BAP (as a negative control) were added to the growth medium of HT29.14s cells. Growth media was harvested from different wells at days 1, 2 and 3 post-treatment. Levels of IL-8 (FIG. 8A) and RANTES (FIG. 8B) were determined by ELISA. FLAG tagged bacterial alkaline phosphatase (FLAG-BAP) was used as a tagged irrelevant protein negative control.
Figure 8B:
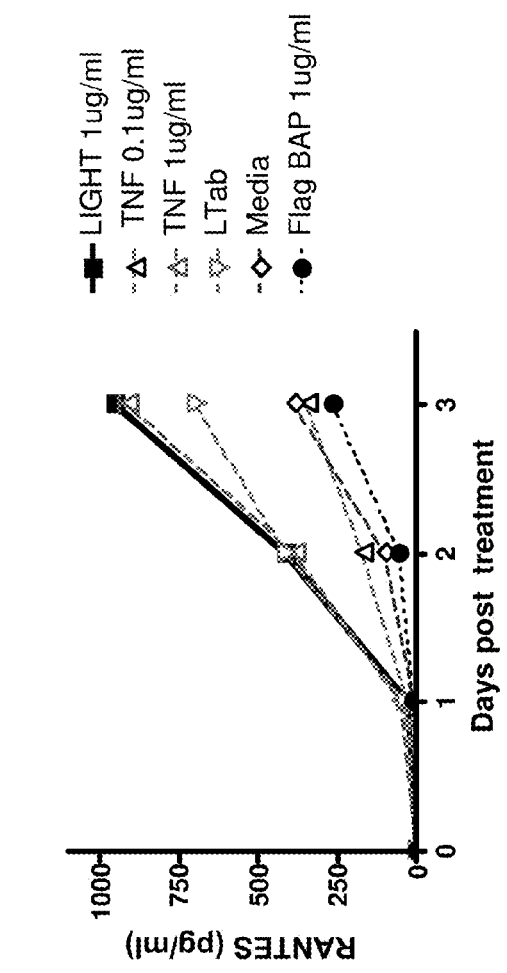

To directly prove the antagonistic antibodies of the invention block hLIGHT-mediated signaling, an assay to measure hLIGHT-mediated signaling in vitro was established. For this purpose, the colonic epithelial cell line HT29.14s, which expresses both LTβR and HVEM, was treated with graded amounts of soluble hLIGHT and growth media was analyzed for the presence of secreted cytokines over a several day time-course. Using standard ELISAs and suspension array multiplex analysis, it was determined that hLIGHT induces CCL20, IL-8 and RANTES in a dose dependent manner (FIG. 7 and FIGS. 8A and 8B). FIG. 7 represents a dose titration of soluble hLIGHT harvested at day 3. Recombinant TNF was used as a positive control for chemokine induction through the TNF receptors, while lymphotoxin (LT$\alpha_1\beta_2$) was used as a positive control for signaling through the LTβR. FLAG tagged bacterial alkaline phosphatase (FLAG-BAP) was used as a tagged irrelevant protein negative control. As expected, levels of chemokines produced by contacting the cells with hLIGHT were equivalent to those induced by LTαβ, whereas TNF was more effective at inducing CCL20 and IL-8, but induced similar levels of RANTES. This cellular response assay is used to measure hLIGHT signaling and assess the capacity of antibodies of the invention to block hLIGHT-mediated signaling events in vitro.

Figure 9A:
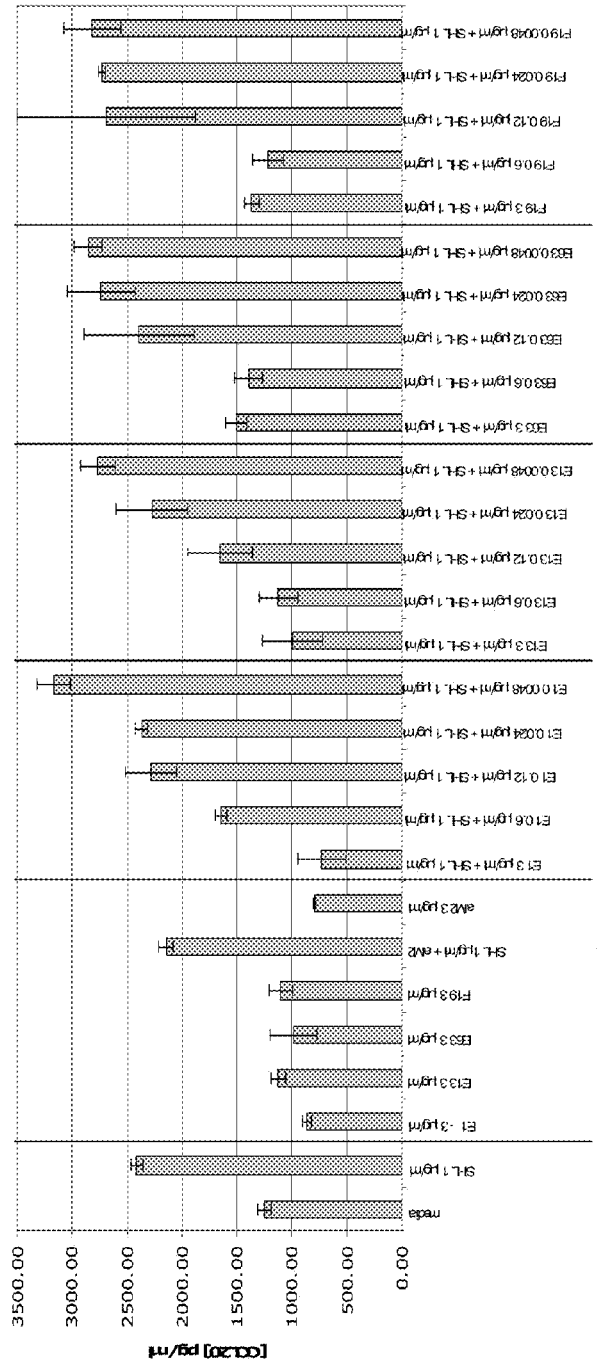
FIGS. 9A-9B shows human anti-hLIGHT antibodies inhibit hLIGHT-mediated CCL20 secretion from human colonic epithelial cells.
Figure 9B:
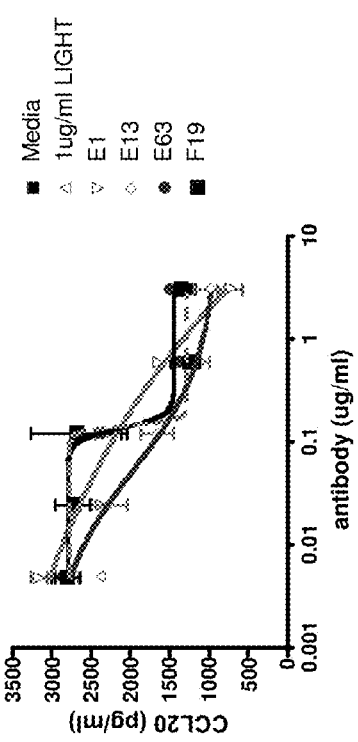

In the hLIGHT-mediated HT29.14s CCL20 induction assay, graded amounts of the anti-hLIGHT antibodies were pre-incubated with a constant amount of recombinant soluble hLIGHT, then added to HT29.14s cells (FIG. 9). Chemokine levels were assayed on day 3 or 4 post treatment and compared to levels induced by soluble hLIGHT alone or soluble hLIGHT pre-incubated with an irrelevant fully human anti-influenza M2 protein as an isotype control. In these assays, the antibodies of the invention tested herein blocked soluble hLIGHT-mediated CCL20 induction in a dose dependent manner. In some cases, non-linear regression analysis was able to produce IC50 values.

Without wishing to be bound by any particular mechanism or theory, it is believed that signaling initiated by cell surface hLIGHT binding to its cognate receptors on other cells may be critical for exerting observed T cell co-stimulatory activity through HVEM interactions or increased chemokine production through LTβR expressed on cells of stromal or epithelial origin in the gut, spleen or lymph nodes. Induction of CCL20 in the gut seems to be regulated more by the expression of LTβR ligands on cells that come in contact with epithelial cells than by soluble factors (Rumbo et al. 2004 Gastroenterology 127 213-23). Therefore, a cell surface hLIGHT signaling assay was developed to assess our antibodies ability to block cell surface hLIGHT. In this assay formalin fixed hLIGHT-EL4 cells were used to induce chemokines by incubating them with HT29.14s cells in a similar fashion to the soluble hLIGHT assay. These cells induced CCL20 and RANTES to equivalent levels as soluble hLIGHT. When graded amounts of anti-hLIGHT antibodies were pre-incubated with fixed hLIGHT-EL4 cells, the induction of RANTES was blocked to levels observed when no hLIGHT expressing cells were added (FIG. 10). In identical experiments CCL20 was likewise inhibited. Taken together, these data indicate that the antibodies of the invention can block both soluble and membrane bound hLIGHT signaling in vitro.

Example 2

Characterization of Commercially Available Mouse Anti-Human Monoclonal Antibodies Antibody Cross-Blocking. Cross-blocking experiments were conducted as described in Example 1 using mouse anti-hLIGHT monoclonal antibodies available from R&D Systems ("R&D mouse mAb") and Abnova ("Abnova mouse mAb"), as well as the human anti-hLIGHT monoclonal antibodies identified in Example 1, to assess which hLIGHT epitope that the antibodies bind. Results are presented in FIG. 11.

The results show that the R&D mouse mAb binds to the same epitope as the human E1, E13, and E63 monoclonal antibodies ("human E antibodies"), as well as the same epitope as the human F19 and F23 monoclonal antibodies ("human F antibodies"). Thus, in contrast to the human anti-hLIGHT E & F monoclonal antibodies identified in Example 1, which were found to immunospecifically bind to only one of two distinct epitopes, the R&D mouse mAb binds to both hLIGHT epitope groups. That is, the human E antibodies and the human F antibodies identified in Example 1 did not cross-block each other. Human E antibodies cross-blocked other human E antibodies, and human F antibodies cross-blocked other human F antibodies; whereas the human E antibodies and human F antibodies all were able to cross-block the R&D mouse mAb. Similarly, the R&D mouse mAb cross-blocked the human E antibodies as well as the human F antibodies.

The results also show that the Abnova mouse mAb does not bind either epitope that is bound by the human E antibodies and the human F antibodies. That is, the Abnova mouse mAb was not cross-blocked by any of human E1, E13, E63, F19 or F23 antibodies, nor was the Abnova mouse mAb able to cross-block any of the human E1, E13, E63, F19 or F23 antibodies.

Figure 12B:
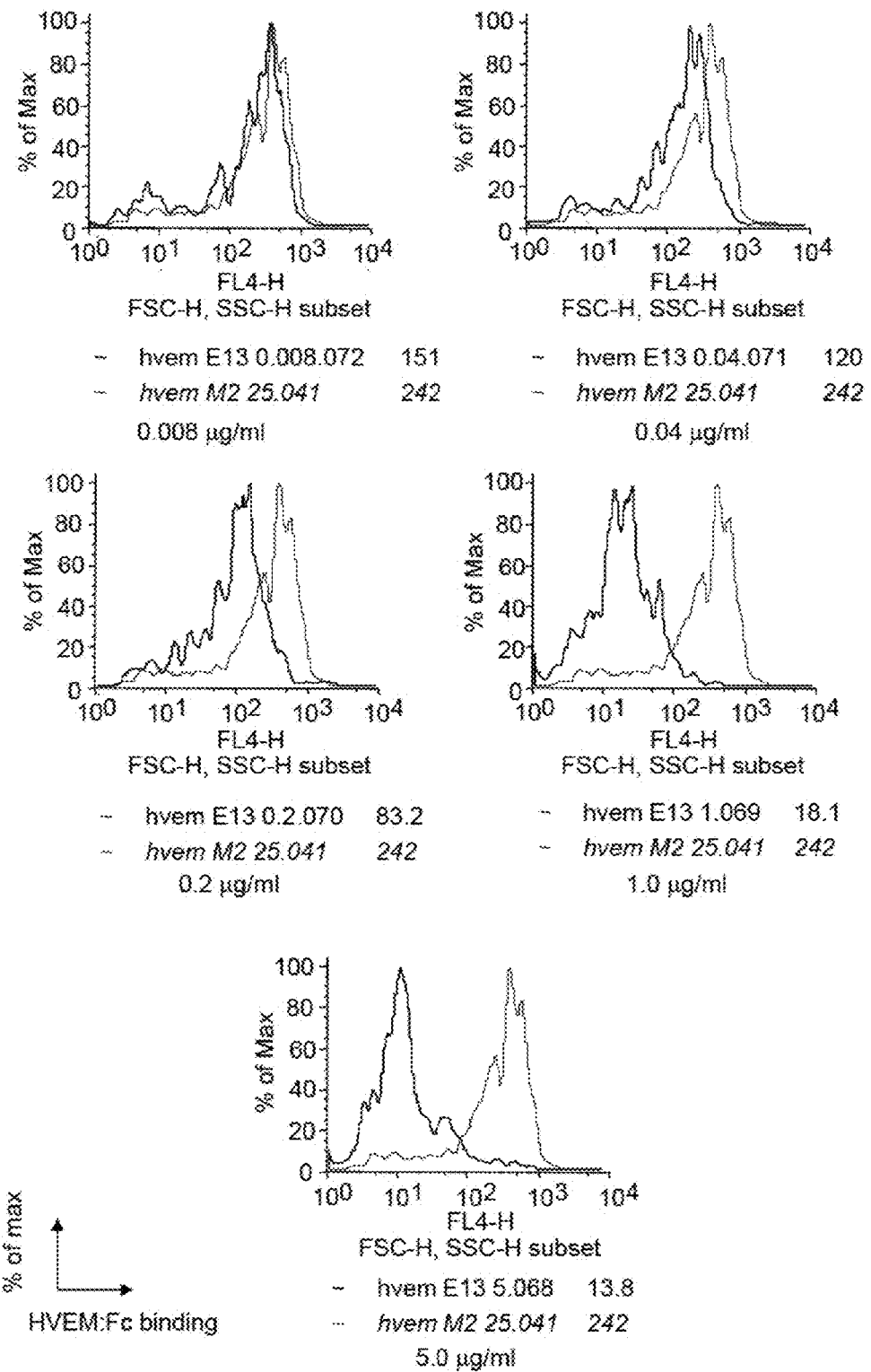
Figure 12C:
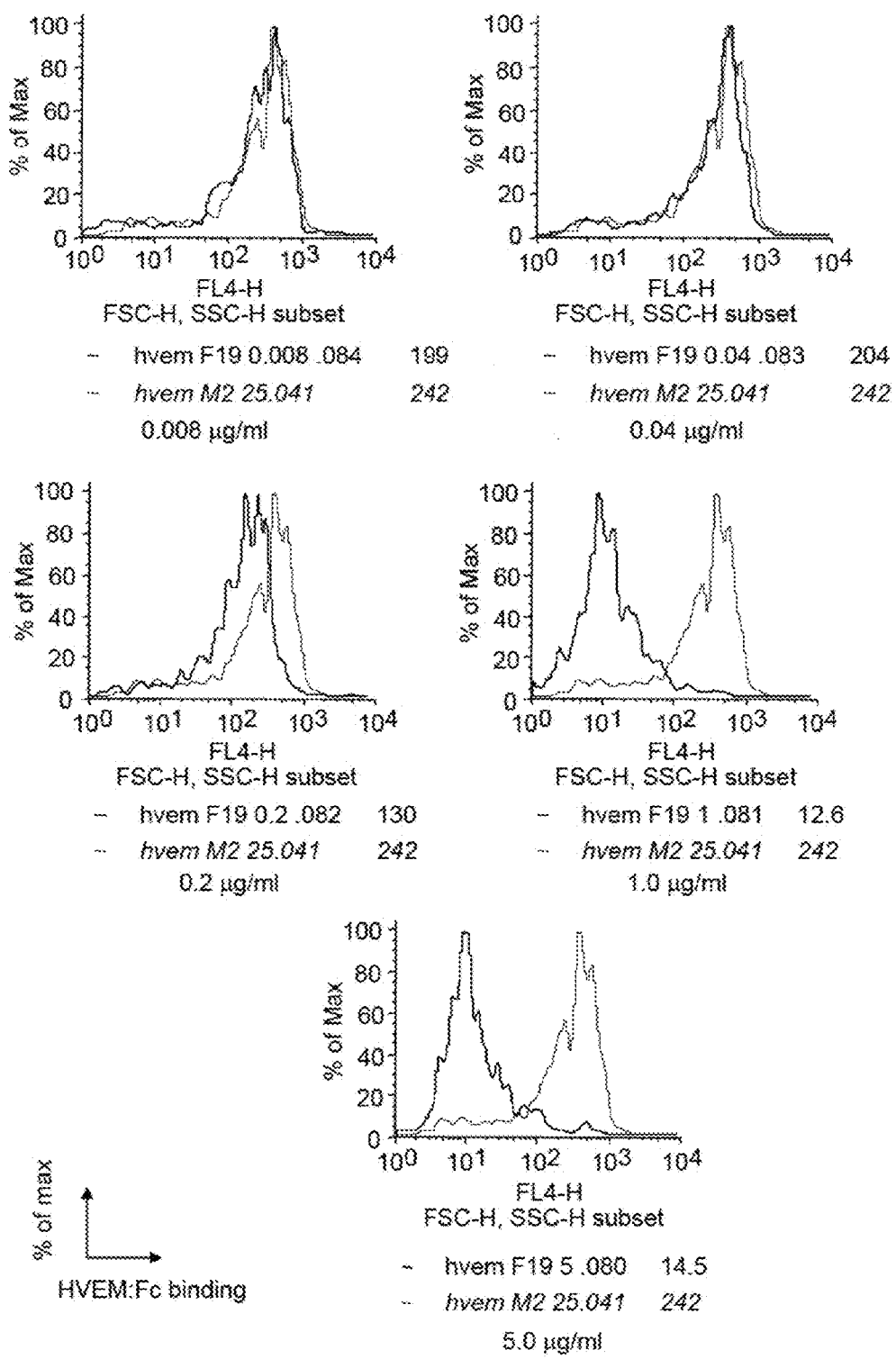
Figure 12E:
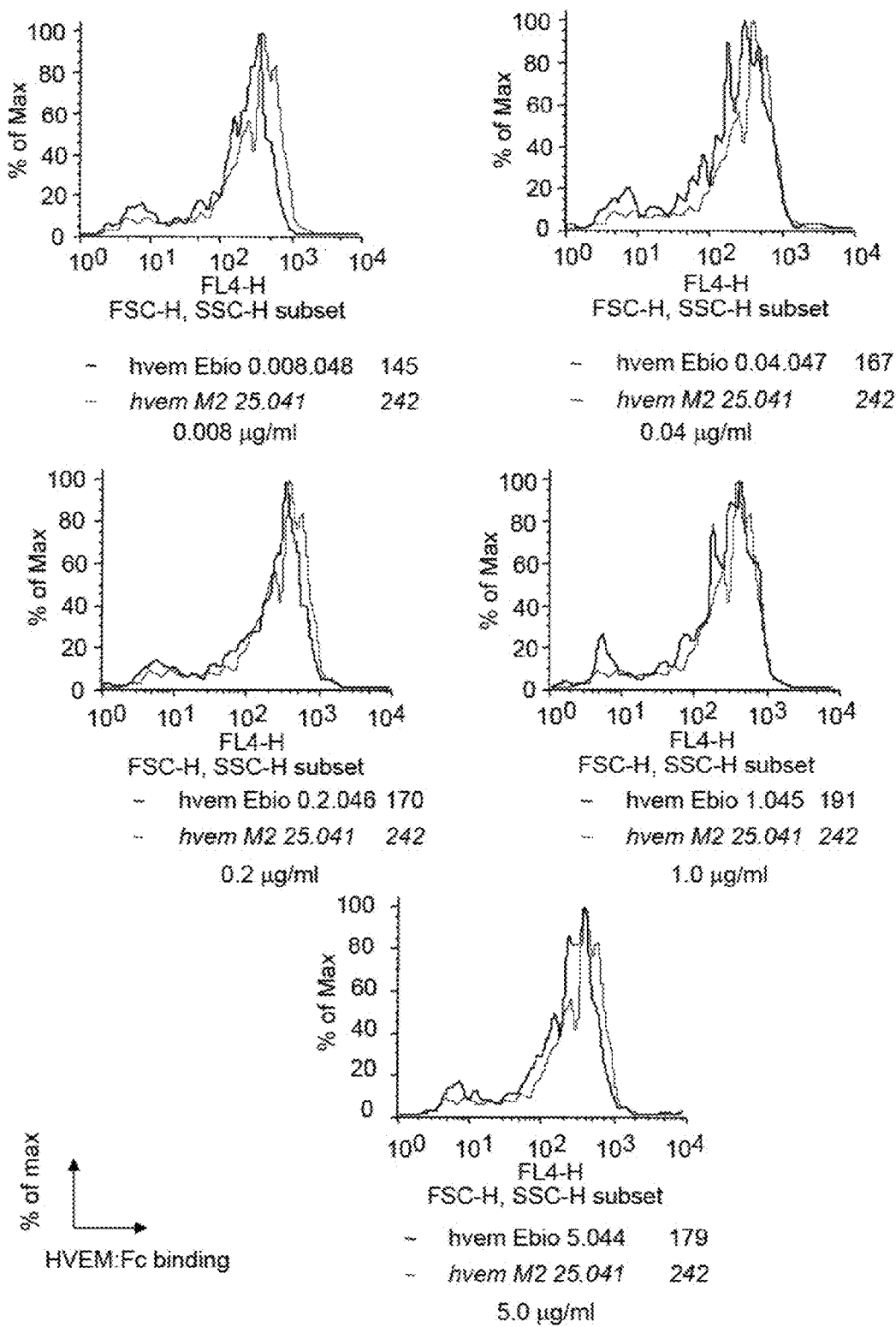

Blocking Activity of Antibodies for HVEM: Fc binding to 293 hLIGHT cells. E1, E13 and F19 human anti-hLIGHT monoclonal antibodies, the R&D mouse mAb, commercially available goat anti-hLIGHT polyclonal antibodies (R&D Systems), and rabbit anti-hLIGHT polyclonal antibodies (eBioscience) were tested for their ability to block binding of HVEM:Fc to 293 cells expressing hLIGHT as described in Example 1. The results are shown in FIG. 12 and FIG. 14B. All four monoclonal antibodies were able to inhibit binding in a dose-dependent manner, as determined by FACS analysis. The R&D goat polyclonal antibodies were also able to inhibit binding of the HVEM:Fc, whereas the eBioscience rabbit polyclonal antibody was not.

Figure 13B:
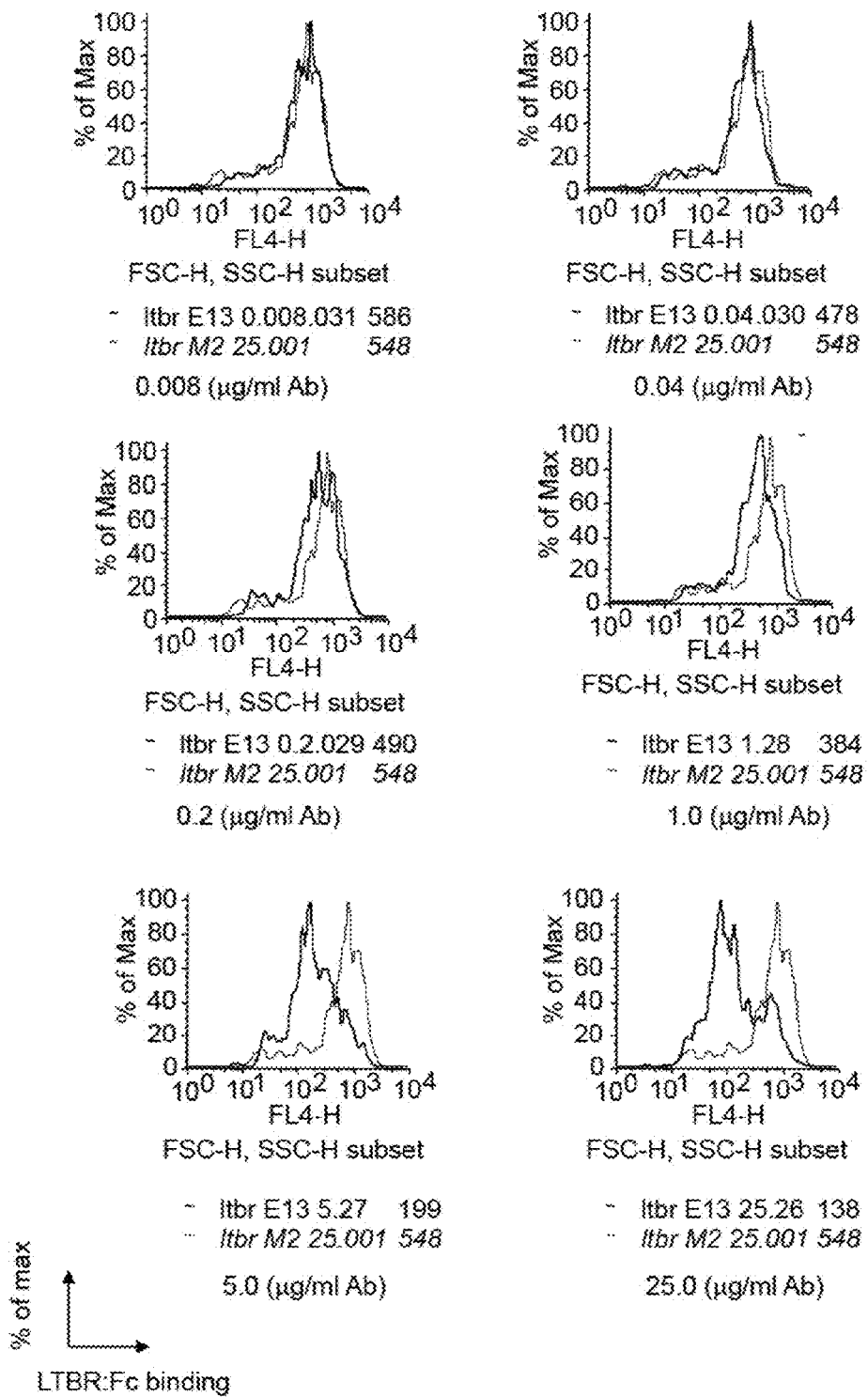
Figure 13D:
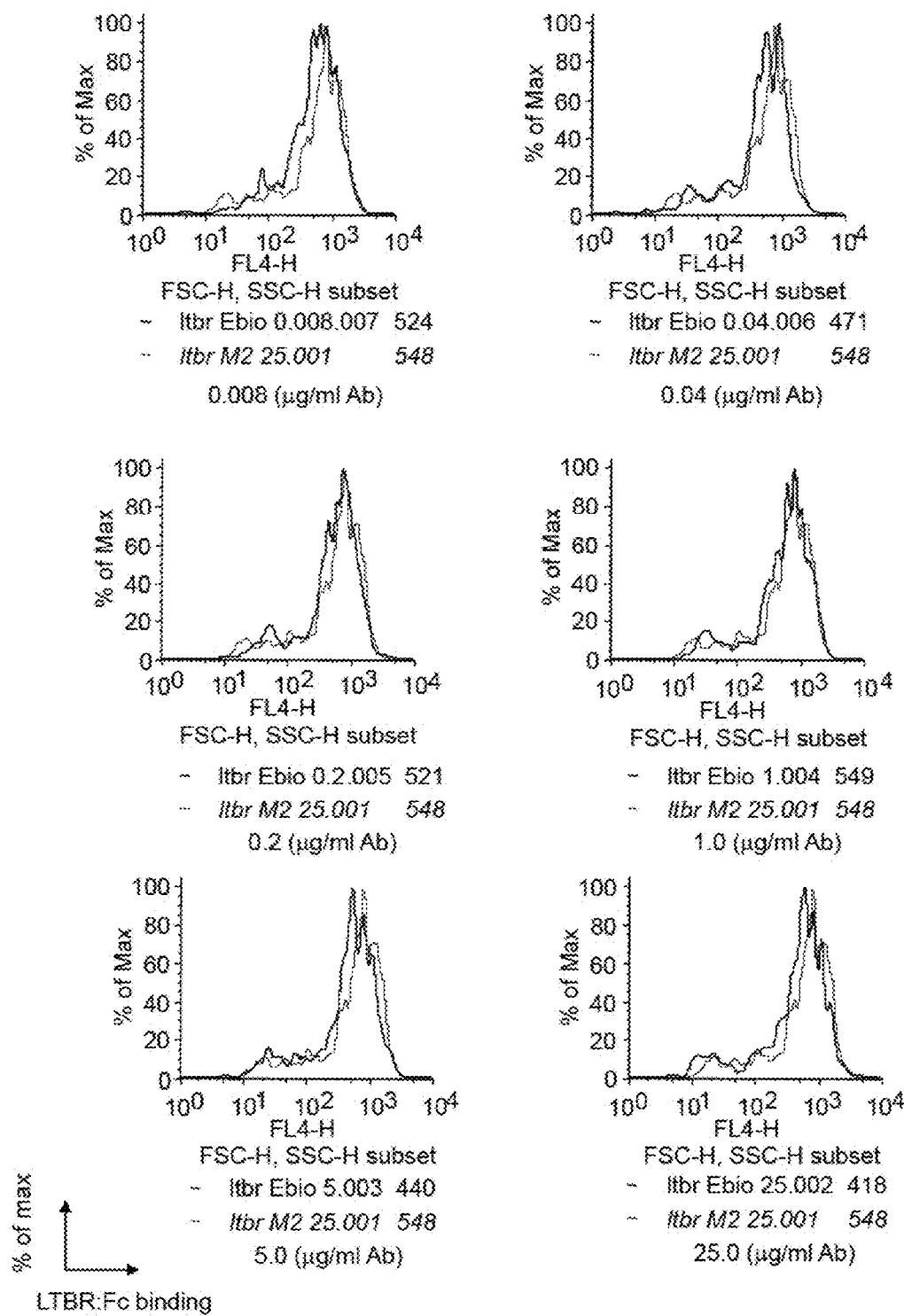

Blocking Activity of Antibodies for LTβR: Fc binding to 293 hLIGHT cells. E1 and E13 human anti-hLIGHT monoclonal antibodies, the R&D mouse mAb, commercially available goat anti-hLIGHT polyclonal antibodies (R&D Systems), and rabbit anti-hLIGHT polyclonal antibodies (eBioscience) were tested for their ability to block binding of LTβR:Fc to 293 cells expressing hLIGHT as described in Example 1. The results are shown in FIG. 13 and FIG. 14B. All four monoclonal antibodies were able to inhibit binding in a dose dependent manner, as determined by FACS analysis. The R&D goat polyclonal antibodies were also able to inhibit binding of the LTβR:Fc, whereas the rabbit eBioscience polyclonal antibody was not.

Binding to Native and Denatured hLIGHT. Five micrograms of soluble human LIGHT was either boiled in 2×SDS sample buffer (denatured) or untreated (native), and then both were serially diluted in 6× increments. 5 μl of each hLIGHT dilution was spotted simultaneously onto hydrated 0.2 μm PVDF membranes (Invitrogen, Carlsbad, Calif.) using an 8 multi-channel pipette. The blots were allowed to air dry then re-hydrated, blocked (1×TBST (Tris-buffered saline Tween-20) +2.5% skim milk+0.02% sodium azide). Each blot was probed with 5 μg/ml of each primary antibody (see below). The blots were washed 3× in 1×TBST followed by biotinylated secondary Abs (Biotin-Goat aHuman (Vector Labs, Burlingame, Calif.), Biotin-Goat a mouse (Jackson labs, Bar Harbor, Me.), Biotin-Mouse α goat (Sigma-Aldrich corp., St. Louis, Mo.)) at 5 μg/ml. The blots were washed 3×in 1×TBST followed by super SA-HRP (Amersham Biosciences, Piscataway, N.J.). Chemiluminescence was used for detection using the ECL detection kit (Amersham Biosciences, Piscataway, N.J.) and signal was visualized by exposure to X-OMAT AR imaging film (Kodak, Rochester, N.Y.)

The primary antibodies tested were the E1, E13, E63, F19, F23 human anti-hLIGHT mAb (see Example 1), murine anti-hLIGHT monoclonal antibodies commercially available from R&D Systems ("R&D mouse mAb") and Abnova ("Abnova mouse mAb"), a goat anti-hLIGHT polyclonal antibody preparation (R&D Systems "R&D goat pAb") and two rabbit anti-hLIGHT polyclonal antibody preparations (eBioscience ("eBioscience rabbit pAb") and Peprotech ("Peprotech rabbit pAb")).

The results are shown in FIG. 15 and FIG. 16. The human anti-hLIGHT monoclonal "E antibodies" of the invention (E1, E13 and E63) tested in this assay immunospecifically bind to both native and denatured forms of soluble hLIGHT (FIG. 15A and FIG. 16). Antibody E63 immunospecific ally binds to lower concentrations of native hLIGHT (lowest limit of detection is 3.9 ng native hLIGHT) than denatured hLIGHT (lowest limit of detection is 139 ng denatured hLIGHT). Antibody E1 also immunospecifically binds to lower concentrations of native hLIGHT (lowest limit of detection is 23 ng native hLIGHT) as compared to denatured hLIGHT (lowest limit of detection is 139 ng denatured hLIGHT). Antibody E13 immunospecifically binds to both native and denatured forms of hLIGHT with the lowest limit of detection of 0.64 ng for both forms of hLIGHT.

In contrast to the human anti-hLIGHT monoclonal "E antibodies," the human anti-hLIGHT monoclonal "F antibodies" of the invention (F19 and F23) tested in this assay immunospecifically bind to the native form of soluble hLIGHT (lowest limit of detection is 23 ng native hLIGHT), but not the denatured form, even at highest (>5000 ng) concentrations of denatured hLIGHT (FIG. 15A and FIG. 16).

Each of the commercially available mouse anti-hLIGHT monoclonal antibodies (R&D mouse mAb and Abnova mouse mAb) tested in this assay immunospecifically bind to both the native and denatured forms of soluble hLIGHT. The R&D mouse mAb immunospecifically binds to lower concentrations of native hLIGHT (lowest limit of detection is 23 ng native hLIGHT) as compared to denatured hLIGHT (lowest limit of detection is 139 ng denatured hLIGHT). The Abnova mouse mAb immunospecifically binds to about equal concentrations of both the native and denatured forms of soluble hLIGHT (lowest limit of detection is 0.64 ng native or denatured hLIGHT, respectively).

The three commercially available anti-hLIGHT polyclonal antibody preparations (R&D goat pAb, eBioscience rabbit pAb, and Peprotech rabbit pAb) each bound to both native and denatured forms of soluble hLIGHT. The R&D goat pAb immunospecifically binds to slightly lower concentrations of native hLIGHT (lowest limit of detection is 0.04 ng native hLIGHT) as compared to denatured hLIGHT (lowest limit of detection is 0.13 ng denatured hLIGHT). The eBioscience rabbit pAb also immunospecifically binds to slightly lower concentrations of native hLIGHT (lowest limit of detection is 0.4 ng native hLIGHT) as compared to denatured hLIGHT (lowest limit of detection is 1.2 ng denatured hLIGHT). Similarly, the Peprotech rabbit pAb also immunospecifically binds to slightly lower concentrations of native hLIGHT (lowest limit of detection is 0.04 ng native hLIGHT) as compared to denatured hLIGHT (lowest limit of detection is 0.13 ng denatured hLIGHT).

Figure 17:
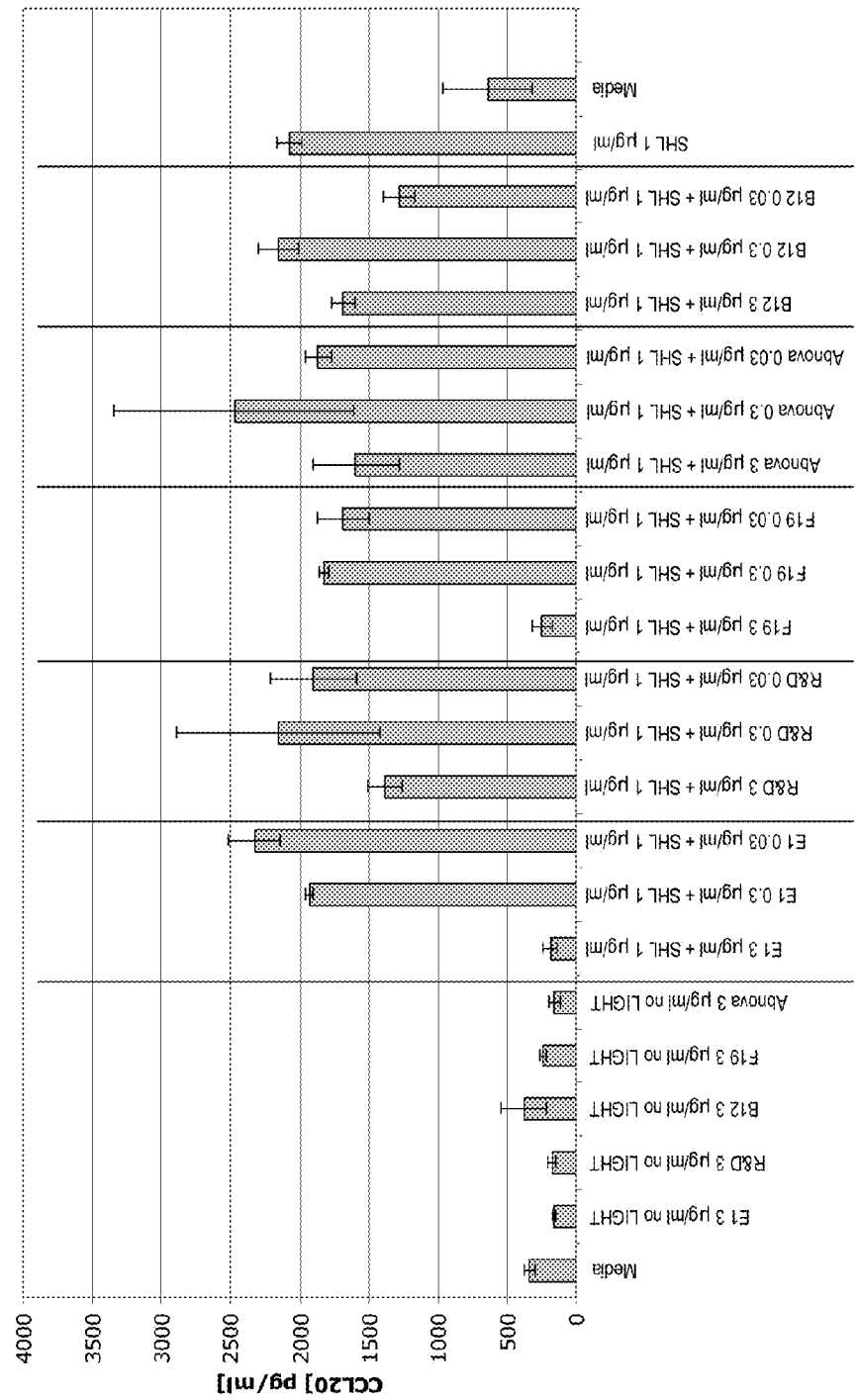
FIG. 17 shows that human anti-LIGHT antibodies of the invention inhibit LIGHT-mediated CCL20 secretion from human colonic epithelial cells, whereas commercially available mouse anti-hLIGHT antibodies do not. Recombinant soluble human LIGHT (1 μg/ml) was pre-incubated with anti-LIGHT antibodies and added to the growth medium of HT29.14s cells. Growth media was harvested from two wells from each treatment at day 3. Levels of CCL20 were determined by ELISA. Media alone, soluble LIGHT alone, soluble LIGHT incubated with anti-influenza M2 antibody, non-blocking anti-LIGHT Ab B12 and each anti-LIGHT antibody alone were included as controls. E1 and F19 are representatives of each cross-blocking epitope group.
Figure 18:
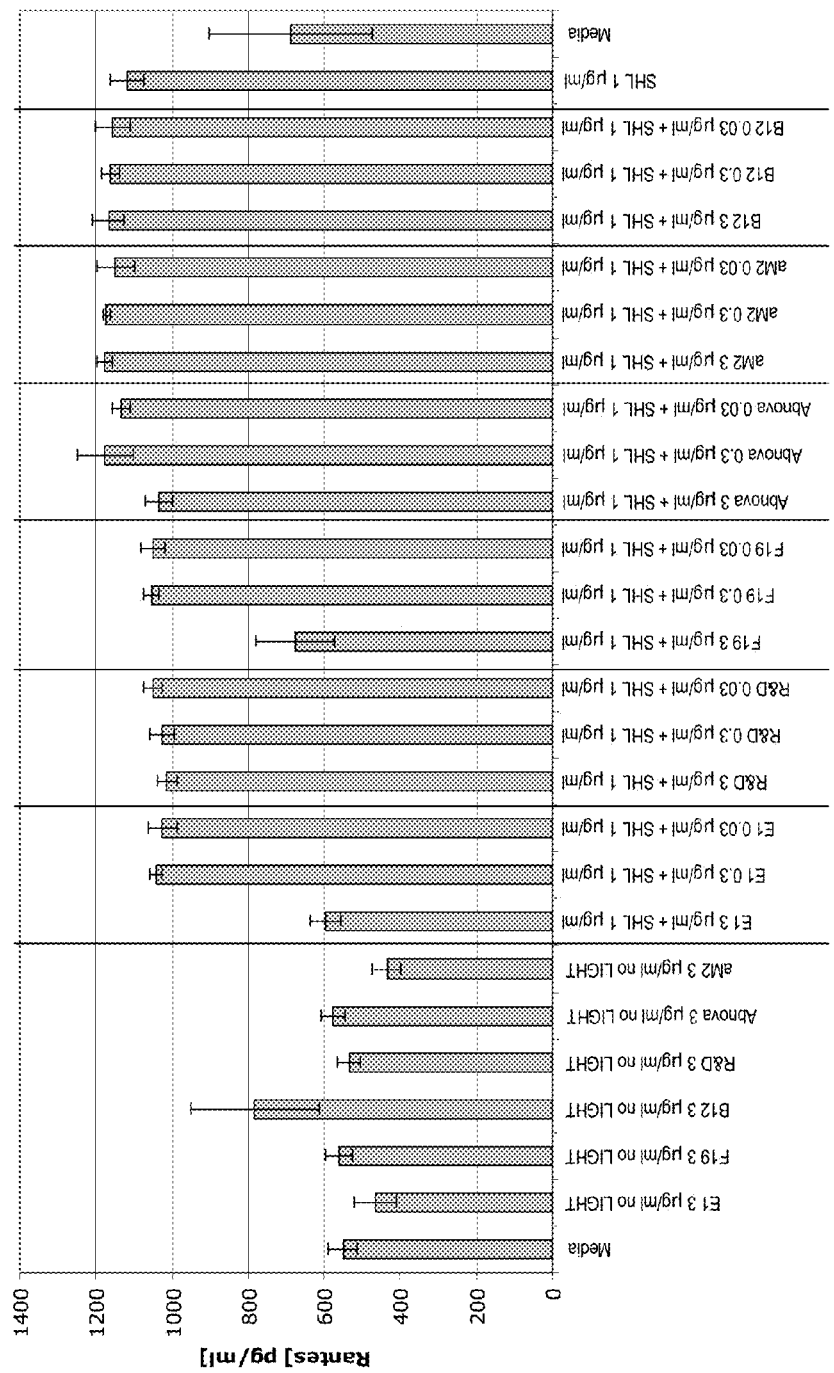
FIG. 18 shows that human anti-LIGHT antibodies of the invention inhibit LIGHT-mediated RANTES secretion from human colonic epithelial cells, whereas commercially available mouse anti-hLIGHT antibodies do not. Recombinant soluble human LIGHT (1 μg/ml) was pre-incubated with anti-LIGHT antibodies and added to the growth medium of HT29.14s cells. Growth media was harvested from two wells from each treatment at day 3. Levels of RANTES were determined by ELISA. Media alone, soluble LIGHT alone, soluble LIGHT incubated with anti-influenza M2 antibody, non-blocking anti-LIGHT Ab B12 and each anti-LIGHT antibody alone were included as controls. E1 and F19 are representatives of each cross-blocking epitope group

Inhibition of Biological Activity of Cells Expressing a hLIGHT Receptor. Experiments were also undertaken as described in Example 1 to determine whether the commercially available mouse anti-hLIGHT monoclonal antibodies were able to competitively block soluble hLIGHT from binding to cell surface-expressed LTBR and HVEM on HT29.14s cells. The results are presented in FIG. 17 (CCL20) and FIG. 18 (RANTES), and show that neither the R&D mouse mAb nor the Abnova mouse mAb was able to inhibit LIGHT-mediated CCL20 or RANTES chemokine production by these cells, whereas human E13 and human F23 mAbs were able to reduce chemokine secretion to background levels.

Example 3

Characterization of Kappa Chains of F19 and E1 Human Anti-hLIGHT Antibodies

The procedures discussed in Example 1 were used to find a preferred kappa chain—heavy chain pair of the antibodies produced by the E1 and F19 hybridomas. Based on the results of these experiments, it was shown that E1kappa(B) (SEQ NO:6) is the preferred kappa light chain of the hLIGHT antibodies produced by the E1 hybridoma, and F19kappa(B) (SEQ ID NO: 9) is the preferred kappa light chain of the hLIGHT antibodies produced by the F19 hybridoma.

Recombinant single kappa chain antibodies were generated by transient transfection of mammalian expression vectors containing the heavy chain genes paired with each of the individual kappa chain genes that existed in the parental hybridoma cells. This material was then tested in parallel with the purified antibodies generated from the respective parental hybridomas.

Figure 19A:
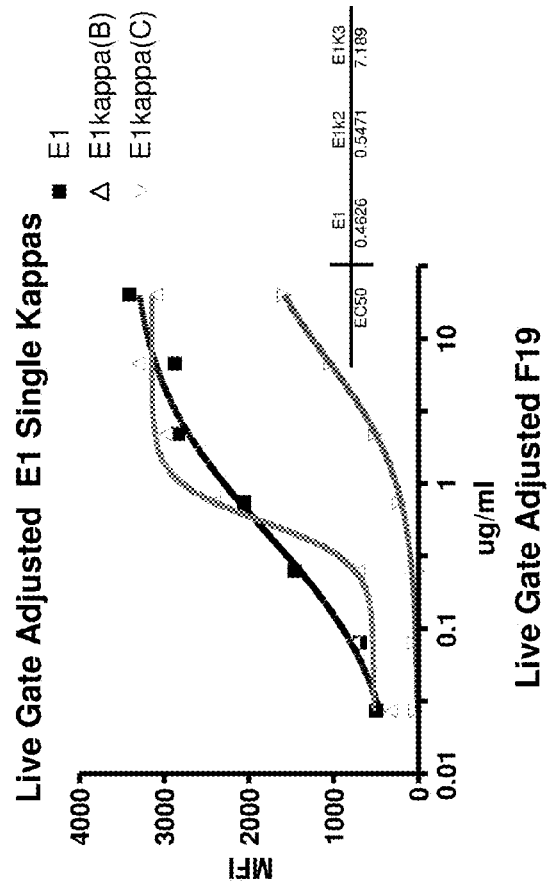
FIGS. 19A-19B depict a cytometric analysis of cell surface-expressed hLIGHT binding by human (FIG. 19A) E1 or (FIG. 19B) F19 anti-hLIGHT antibodies in comparison to their recombinant single kappa chain antibody counterparts. Stable hLIGHT expressing 293 cells were incubated with increasing amounts of anti-LIGHT antibodies indicated in the legend. Binding was detected with goat anti-human IgG-APC secondary antibody. Antibodies were purified from either hybridoma cultures or 293F cells transiently transfected with mammalian expression vectors encoding the different kappa chain cDNAs paired with the heavy chain gene. Plots of the geometric mean fluorescence intensity data are shown along with non-linear regression.
Figure 19B:
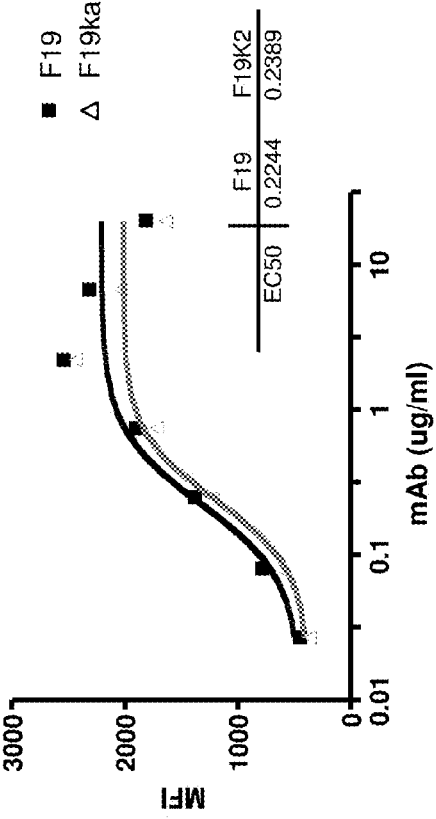

Antibody binding assays were performed as described in Example 1. The kappa chain—heavy chain pair comprising the E1kappa(B) or F19kappa(B) specifically stained hLIGHT stably transfected cell lines, (HEK 293-hLIGHT) to an equivalent degree compared to the respective parental hybridoma produced antibodies (FIG. 19).

Cross-blocking ELISA experiments were performed as indicated in Example 1, and the results indicated that these recombinant antibodies recognize the same epitopes on hLIGHT as their parental hybridoma Abs (FIG. 20).

The single kappa chain recombinant antibodies were further tested as described in Example 1 for their ability to block cell surface-expressed hLIGHT binding to soluble receptor-Fc fusion forms of both human HVEM and the LTβR (FIG. 21), Levels of blockade were not identical to the parental Abs.

Figure 22:
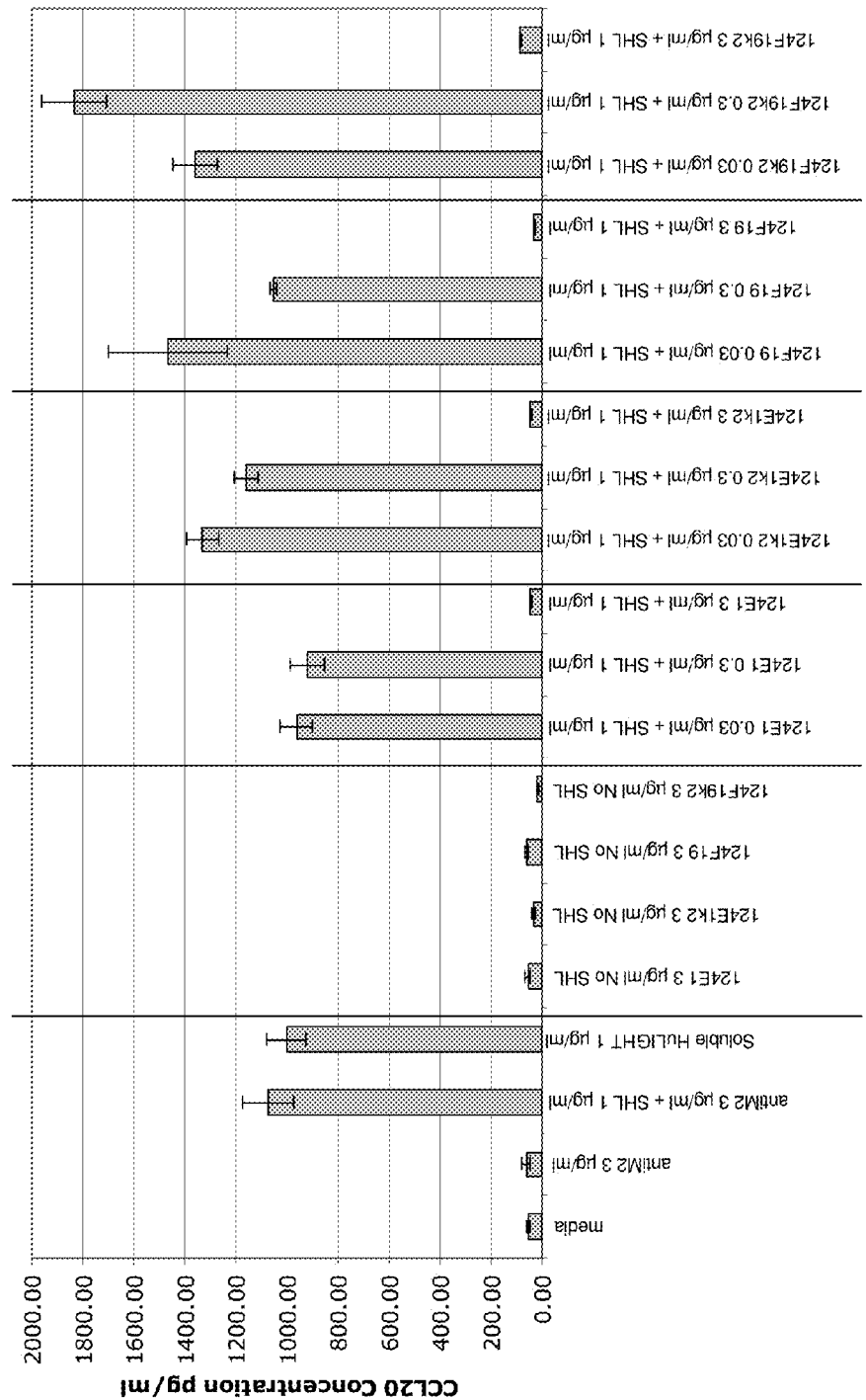
FIG. 22 depicts the inhibition of hLIGHT-mediated CCL20 secretion from human colonic epithelial cells by recombinant single kappa chain human anti-LIGHT antibodies compared to the parental hybridoma produced antibodies. Recombinant soluble human LIGHT (1 μg/ml) was pre-incubated with anti-LIGHT antibodies and added to the growth medium of HT29.14s cells. Growth media was harvested from two wells from each treatment at day 3. Levels of CCL20 were determined by ELISA. Media alone, soluble LIGHT alone (SHL), soluble LIGHT incubated with anti-influenza M2 antibody, or each antibody in the absence of soluble LIGHT were included as controls. Antibodies referred to as "E1k2" comprise E1kappa(B) and "F19k2" comprise F19kappa(B).
Figure 23:
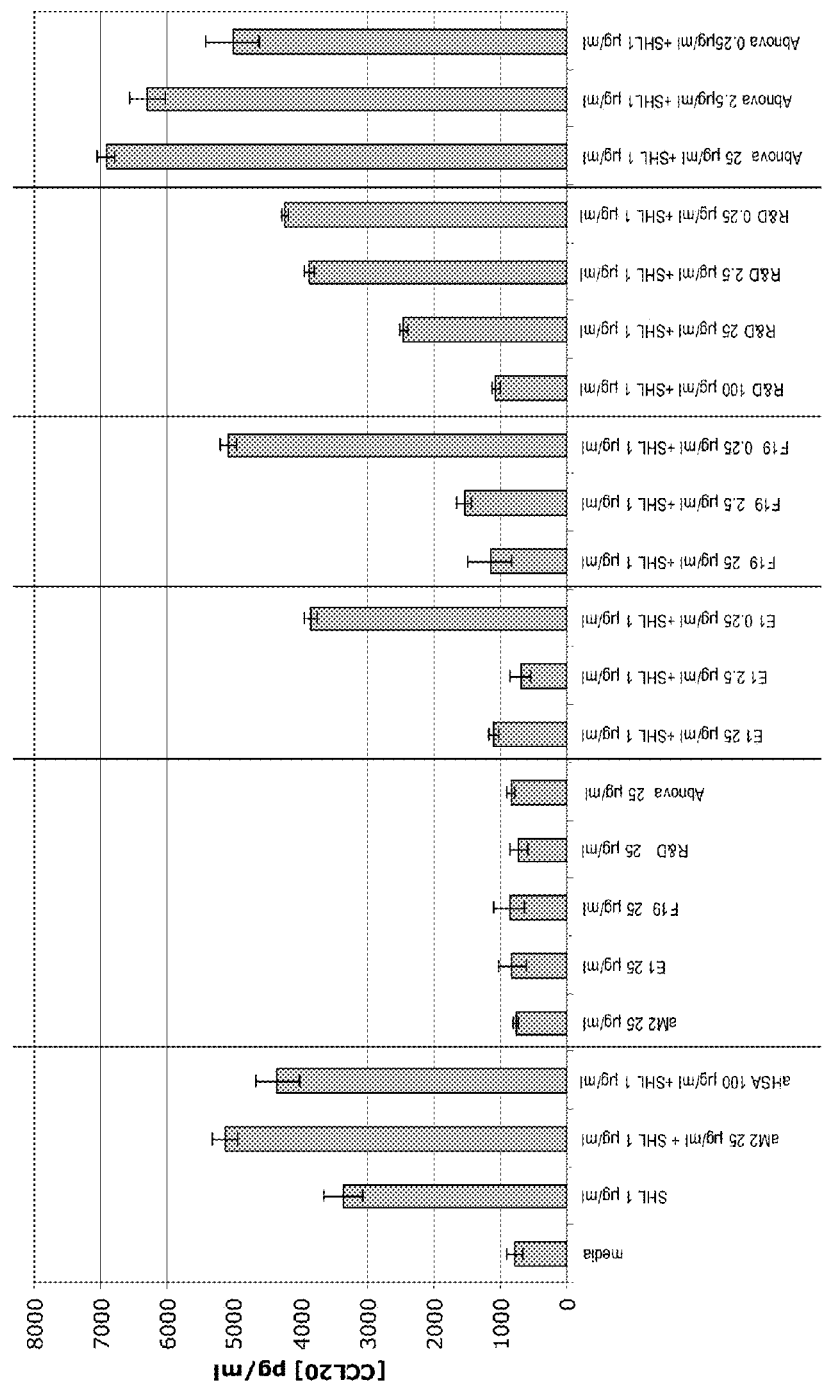
FIG. 23 shows that human anti-LIGHT antibodies of the invention inhibit LIGHT-mediated CCL20 secretion from human colonic epithelial cells, whereas commercially available mouse anti-hLIGHT antibodies either do not inhibit (Abnova) or inhibit only at exceedingly high concentrations (100 μg/ml) (R&D). Recombinant soluble human LIGHT (1 μg/ml) was pre-incubated with anti-LIGHT antibodies and added to the growth medium of HT29.14s cells. Growth media was harvested from two wells from each treatment at day 3. Levels of CCL20 were determined by ELISA. Media alone, soluble LIGHT alone (SHL), soluble LIGHT incubated with irrelevant anti-influenza M2 antibody, anti human serum albumin, or each antibody in the absence of soluble LIGHT were included as controls. E1 and F19 are representatives of each cross-blocking epitope group.

Finally, the recombinant single kappa antibodies were tested for their ability to inhibit LIGHT-mediated CCL20 secretion from HT29 colonic epithelial cells as described in Examples 1 and 2 (FIG. 22 and FIG. 23). In these experiments, incubation of soluble hLIGHT with anti-hLIGHT antibodies blocks hLIGHT-mediated secretion of CCL20 from HT29.14s cells similar to the parental hybridomas.

In addition, the single kappa chain recombinants also maintain the specificity of the parental hybridoma produced antibodies in the dot blot assessment of native vs. denatured LIGHT (data not shown).

Together, these results indicate that the E1kappa(B) (SEQ ID NO:6) is the preferred kappa light chain for use in combination with the E1 heavy chain (SEQ ID NO:1), and the F19kappa(B) (SEQ ID NO:9) is the preferred kappa light chain for use in combination with the F19 heavy chain (SEQ ID NO:4).

Example 4

Figures 24A, 24B:
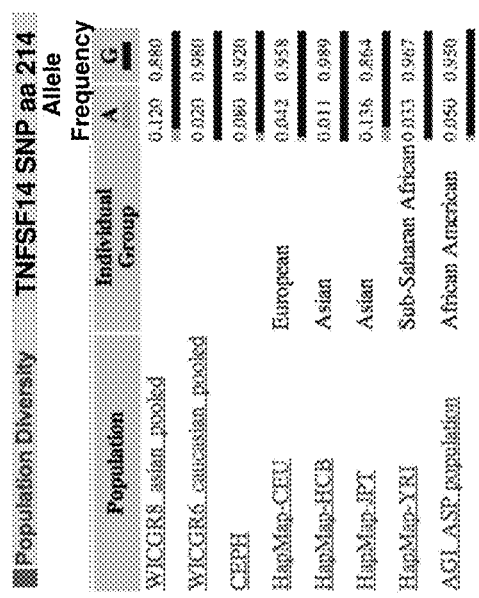
FIGS. 24A-24B depicts allelic frequency of certain non-synonymous single nucleotide polymorphism (SNP) hLIGHT variants (FIG. 24A) encoding a glutamic acid (E) or lysine (K) at amino acid position 214.

Antibody Binding and Antibody Mediated Blockade of Hvem:Fc and LtβR:Fc Binding to Single Nucleotide Polymorphism (Snp) Variants of Light At least two non-synonymous single nucleotide polymorphism (SNP) variants exist for human LIGHT (FIG. 24). One SNP variant encodes either a glutamic acid (E) or an lysine (K) at amino acid position 214, and the other SNP variant encodes either a serine (S) or a leucine (L) at amino acid position 32. As shown in FIGS. 24A-24B, the allelic frequency of each SNP variant across a variety of ethnic populations varies. Thus, hLIGHT antibodies that bind a given SNP variant may be more efficacious in the treatment or prevention of an hLIGHT-mediated disease, or symptom, thereof in those ethnic populations having a higher incidence of the given SNP variant.

In this example, hLIGHT antibodies provided herein were shown to bind non-synonymous hLIGHT SNP variants that are present in hLIGHT extracellular and cytoplasmic domains. The binding of these antibodies to SNP variants also correlated with the ability of the antibody to effectively block HVEM:Fc and LTβR:Fc to the hLIGHT SNP variant, and also effectively block biological activity of cells expressing a hLIGHT receptor.

Antibody Binding. Dose titrations of F23 and E1kappa(B) antibodies were performed as in Example 1 to determine if these antibodies bind cell surface-expressed hLIGHT SNP variants. An EL4 cell line was used in these experiments, which was prepared essentially as described in Example 1, and stably surface-expressed the respective hLIGHT SNP variant. As shown in FIGS. 25A and 25C, respectively, each of the F23 and E1kappa(B) antibodies bound both of the 214E-32S and 214E-32L SNP variants. However, as shown in FIG. 25B, only the F23, and not E1kappa(B) antibody, recognized the 214K-32S SNP variant.

Figure 26A:
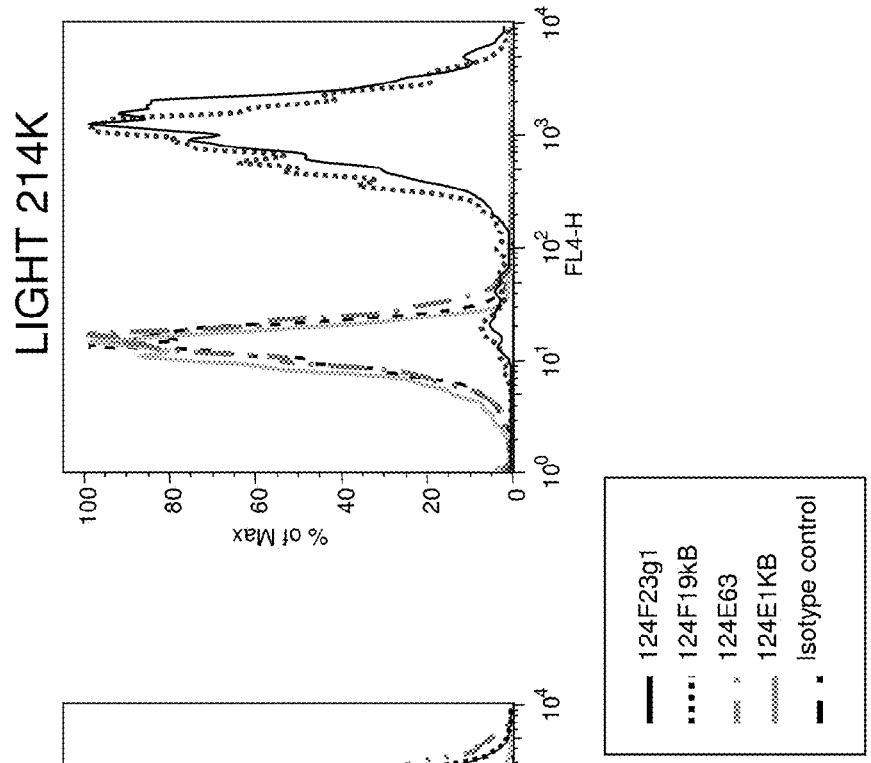
FIGS. 26A-26B depicts a flow cytometric analysis of cell lines expressing non-synonymous SNP variants with human anti-hLIGHT antibodies.
Figure 26B:
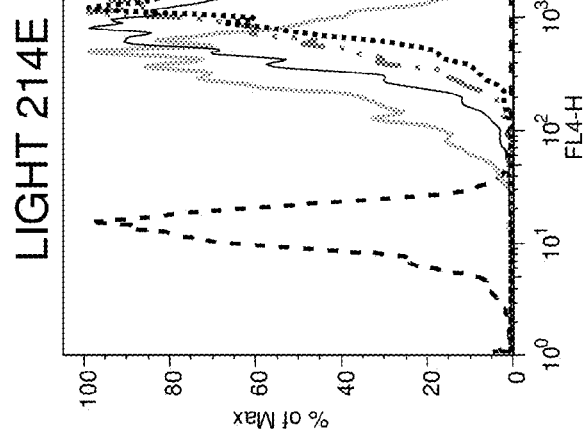

The F23 (an IgG1), F19, E63 and E1kappa(B) antibodies were also tested to determine if there was a difference between the ability of the "F antibodies" and the "E antibodies" to recognize either form of SNP variant. As shown in FIGS. 26A and 26B, the F23 and F19 antibodies bind both 214E and 214K SNP forms of hLIGHT. However, the E63 and E1kappa(B) antibodies bind only the predominant form of LIGHT 214E, and not 214K (FIGS. 26A and 26B).

Blocking Activity of Antibodies for HVEM:Fc and LTβR: Fc Binding to LIGHT SNP Variant 214K-32S. Since the F23 antibody bound both the predominant form (214E) and less predominant form (214K) of LIGHT variants, it was next determined whether the F23 antibody could block binding of HVEM:Fc or LTβR:Fc. Antibody-mediated blockade of the receptor fusion proteins was performed as in Example 1. In brief, the cell line EL4-214K-32S was incubated with increasing amounts of anti-LIGHT antibodies followed by the addition of either HVEM:Fc or LTβR:Fc. The effects of this preincubation on receptor binding was assessed by detection of either HVEM:Fc or LTβR:Fc as in Example 1. As shown in FIG. 25D, the F23 antibody effectively blocked both HVEM:Fc and LTβR:Fc binding to the LIGHT 214K-32S variant.

Inhibition of Cell Surface LIGHT SNP Variant-Mediated Biological Activity of Cells Expressing a LIGHT Receptor. This study was undertaken to determine if human anti-hLIGHT monoclonal antibodies previously shown to bind to both 214K and 214E hLIGHT SNP variants were also able to effecitvely block RANTES secretion in human colonic epithelial cells, HT29.14s, which express both LTβR and HVEM, by either cell-surface expressed hLIGHT 214E or 214K SNP variant, or soluble hLIGHT SNP variants thereof. In the cell surface expressed LIGHT-mediated HT29.14s RANTES induction assay, graded amounts of anti-hLIGHT antibodies were pre-incubated with a constant number of cells that express SNP variants of hLIGHT (214K or 214E). Chemokine levels were assayed on day 3 post-treatment and compared to levels induced by soluble hLIGHT alone, cells expressing hLIGHT alone or cells pre-incubated with an irrelevant human IgG as an isotype control protein.

In these assays, the antibodies provided herein (F19 and F23) blocked soluble hLIGHT and both cell surface expressed hLIGHT SNP variant (214E or 214K)-mediated RANTES induction in a dose dependent manner. The commercially available mouse anti-hLIGHT monoclonal antibody available from R&D systems (the R&D mouse mAb, as in Example 1) was not able to block either soluble or cell surface expressed hLIGHT-mediated chemokine secretion, regardless of SNP variant. Both the cell surface-expressed hLIGHT variants and soluble recombinant hLIGHT positive controls induced equivalent levels of RANTES, and pre-incubation of the negative control isotype hIgG with either the cell surface-expressed hLIGHT variants or soluble recombinant hLIGHT did not reduce the RANTES levels significantly.

Discussion. Of the thirty plus single nucleotide polymorphisms (SNPs) in the hLIGHT genomic locus, at least two non-synonymous hLIGHT exist with frequency data associated with them (FIG. 24). One encodes a glutamic acid (~0.9) or a lysine (0.1) at amino acid position 214 of hLIGHT and resides in the extracellular region of hLIGHT. The other encodes either a serine (0.99) or a leucine (0.011) at amino acid residue 32 and resides in the cytoplasmic region of hLIGHT. The hLIGHT genomic locus resides in a chromosomal region, ch19p13.3, that has contains a susceptibility locus for inflammatory bowel disease (Rioux et al. (2000) Am J Hum Genet. 66:1863-70), and thus suggests that a SNP may be a correlate of IBD disease frequency. Therefore, it was of interest to determine if the antagonistic anti-hLIGHT antibodies provided herein were able to recognize non-synonymous SNP variants of hLIGHT.

In this example, we tested the ability of the anti-hLIGHT antibodies to bind hLIGHT SNP variants stably expressed on the surface of EL4 cell lines. As shown in FIGS. 25A and 25B, F23 binds both SNP variants 214E and 214K, while E1kappa(B) binds only the predominant form 214E. F23 likewise blocks either HVEM:Fc or LTBR:Fc binding to these cells (FIG. 25D). As expected, the cytoplasmic SNP does not appear to affect binding of either antibody (FIG. 25C). When "E antibodies" and "F antibodies" were tested, only the F antibodies were able to bind to both 214K and 214E SNP variants (FIGS. 26A and 26B). The commercial R&D mouse mAb antibody was also able to bind both SNP variants (data not shown).

Figure 27:
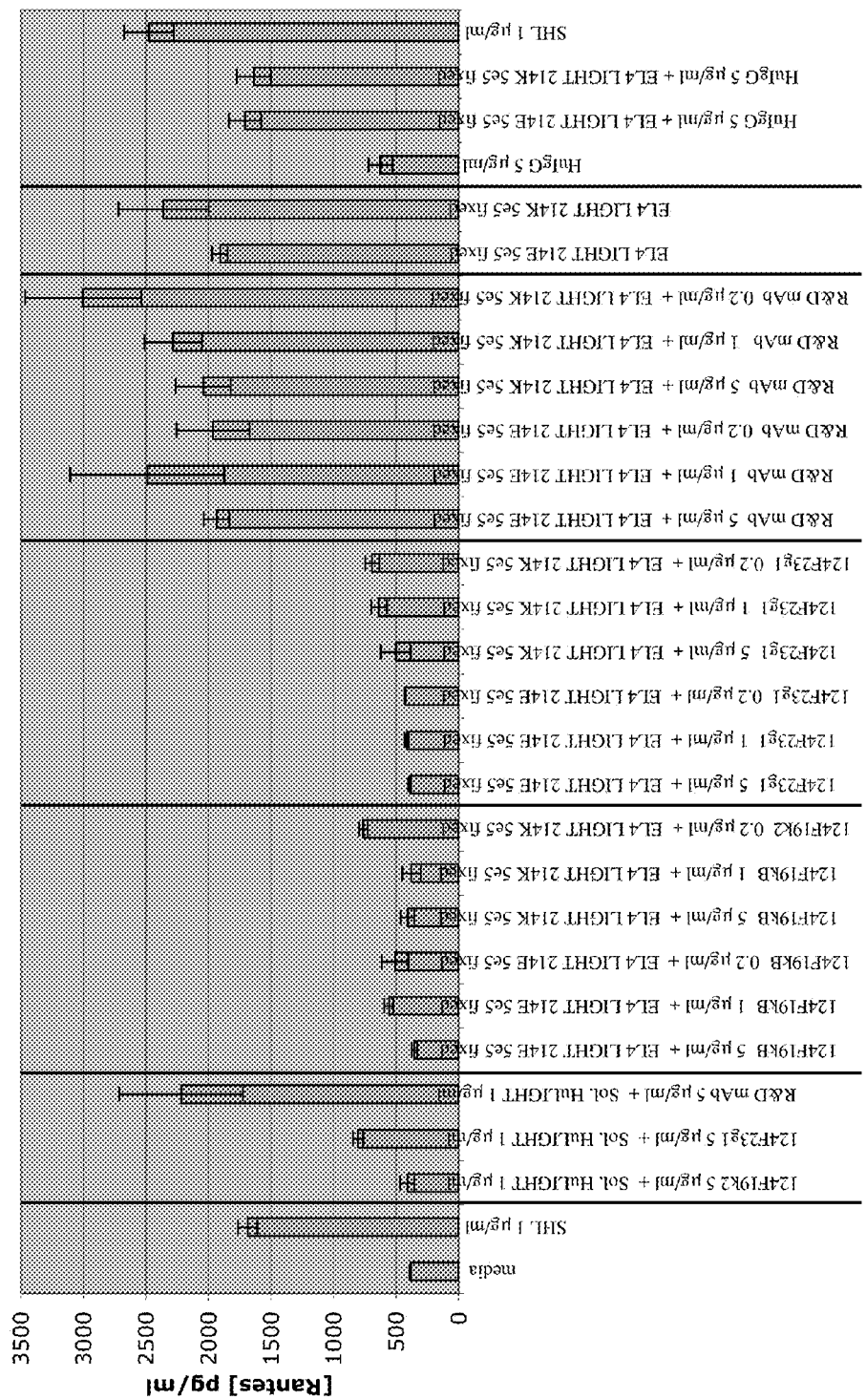
FIG. 27 depicts human anti-hLIGHT antibody inhibition of cell surface-expressed hLIGHT SNP variant-mediated RANTES secretion from human colonic epithelial cells. Recombinant soluble hLIGHT (SHL) (1 μg/ml) or $5 \times 10^5$ EL4-hLIGHT 214K or 214E SNP variant cells were preincubated with anti-hLIGHT antibodies and added to the growth medium of HT29.14s cells. Growth media was harvested from two wells from each treatment at day 3. Levels of RANTES were determined by ELISA. Media alone, EL4-hLIGHT cells alone, soluble hLIGHT alone and each anti-hLIGHT antibody alone were included as controls.

In addition to the anti-hLIGHT antibody blockade of soluble versions of the receptors to LIGHT SNP variants in vitro, cell surface hLIGHT SNP-mediated chemokine induction was also inhibited by anti-hLIGHT antibodies of this invention. In this assay, EL4 cell lines expressing either 214E or 214K hLIGHT SNP variants were fixed with formalin and used to treat the HT29 colonic epithelial cell line. As shown in FIG. 27, these cell lines alone induced similar levels of RANTES compared to 1 μg soluble LIGHT. Anti-hLIGHT "F antibodies" were tested by pre-incubating the hLIGHT-expressing cell lines with graded amounts of antibody and compared to isotype controls or the commercially available R&D mouse mAb. Both F23 and F19kappa (B) inhibited RANTES secretion mediated by either SNP variant expressing cell line. However, the R&D mouse mAb and the human isotype negative control did not inhibit RANTES secretion by either LIGHT SNP variant. This was despite the fact that the R&D mouse mAb was able to bind both SNP variants. These results not only demonstrate that the F23 and F19kappa(B) antibodies of this invention block either signaling by LIGHT SNP variant, but also display superiority to the commercial R&D mouse mAb.

Example 5

In Vivo Efficacy Study of 124F23 in Acute Xenogeneic Graft Versus Host Disease Model In this example, the in vivo efficacy of an anti-hLIGHT antibody provided herein was evaluated in a murine acute xenogeneic graft-versus-host disease model (GVHD). The F23 antibody was shown in this model to decrease overall gross pathology (diarrhea, peritoneal inflammation and ascites, and intestinal inflammation) and histopathology (inflammation severity, inflammation extent, villus damage/atrophy, and percent involvement), as well as a decrease in the number of T cells in the spleen.

Purification of Human PBMC from Whole Blood: Whole blood was collected from healthy donors between the ages of 18 and 50 by the normal blood donor program at Scripps Green Hospital (La Jolla, Calif.), and heparin was added to prevent clotting. No race, ethnicity, or gender was specified. The blood was diluted in PBS and then underlayed with FICOLL-PLAQUE Plus (Amersham Biosciences). The mononuclear cells were separated from the serum and platelets by centrifugation at 1800 RPM without the brake. The interface containing the PBMC was then collected and washed two times with PBS.

Acute Graft Versus Host Disease In Vivo Model: An acute xenogeneic graft versus host disease model was used to test the therapeutic potential of the F23 (124F23G1) human anti-human LIGHT antibody in vivo (Watanabe et al. 2006 1006. Clin Immunol. 120 247-59), essentially as outlined in FIG. 28. Briefly, severe combined immunodeficient (SCID) male mice aged 5-10 weeks were injected on day −2 with 20 μg rat anti-mouse IL2 receptor-beta (IL2Rβ) chain antibody (TMβ1, Tanaka et al. 1993 J Exp Med. 178 1103) to deplete endogenous murine natural killer cells. The following day (day −1), the mice received 2.5 Gy of sub-lethal irradiation using a cesium source to allow migration of the human cells to the intestinal tract. The next day (day 0) the mice received 10 million total human peripheral blood mononuclear cells in PBS by intraperitoneal injection followed immediately by intravenous injection of human anti-human LIGHT (124F23G1) or negative control hIgG1 (anti-dinitrophenol (anti-DNP), Kirin Brewery Co. Ltd.) antibodies at a dose of 100 µg in 100 µl PBS. The human T cells expand and induce a graft versus host like disease and symptoms thereof, resulting in, for example, weight loss, hematuria, hydroperitoneum, inflammatory cell infiltrates in the liver and intestinal tract, and eventually death. The disease is primarily mediated by human T cells as transfer of T cells alone induces similar symptoms. Body weight was determined every 3-4 days and mice received the anti-IL2Rβ antibody weekly. At day 12 the mice were sacrificed and analyzed for gross pathology and symptoms of disease, the spleens were collected for flow cytometric analysis and cecums for histology, and serum was collected for human cytokine and antibody analysis (Watanabe et al. 1006. Clin Immunol. 120 247-59).

Figure 29:
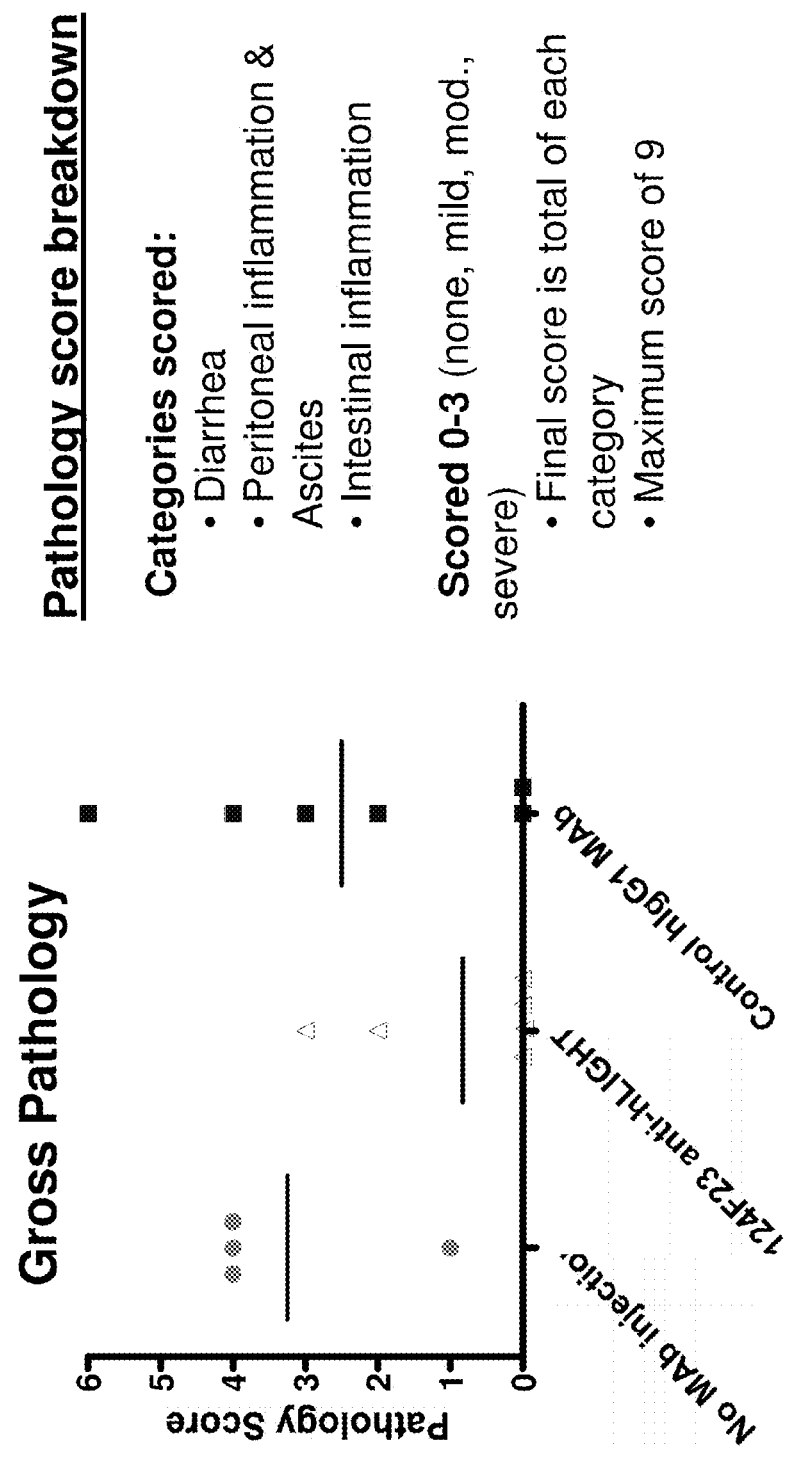
FIG. 29 depicts the gross pathology scores observed in the murine acute xenogeneic GVHD disease model. Pathology scores for no monoclonal antibody injection (circles), 124F23 anti-hLIGHT monoclonal antibody injection (triangles) and control human IgG1 monoclonal antibody (squares) are represented. Scores of 0, 1, 2, or 3 (none, mild, moderate, or severe, respectively) are assigned for each of three categories: diarrhea, peritoneal inflammation/ascites, and intestinal inflammation (maximum total score of 9).

In Vivo Functional Analysis of Human Anti-Human LIGHT Monoclonal Antibodies. The gross pathology observed at day 12 was scored as follows: diarrhea (0 or 1), hemorrhaging in the intestine and peritoneal cavity, and peritonitis (each ranked 0, 1, 2 or 3 as none, mild, moderate, or severe, respectively). The sum of all disease symptoms was used to determine the total gross pathology score. As shown in FIG. 29, mice that received the control antibody or PBMCs alone (no antibody injection) all displayed symptoms of GVHD, with higher pathology scores than mice that received 124F23G1 anti-LIGHT antibody.

Figure 30:
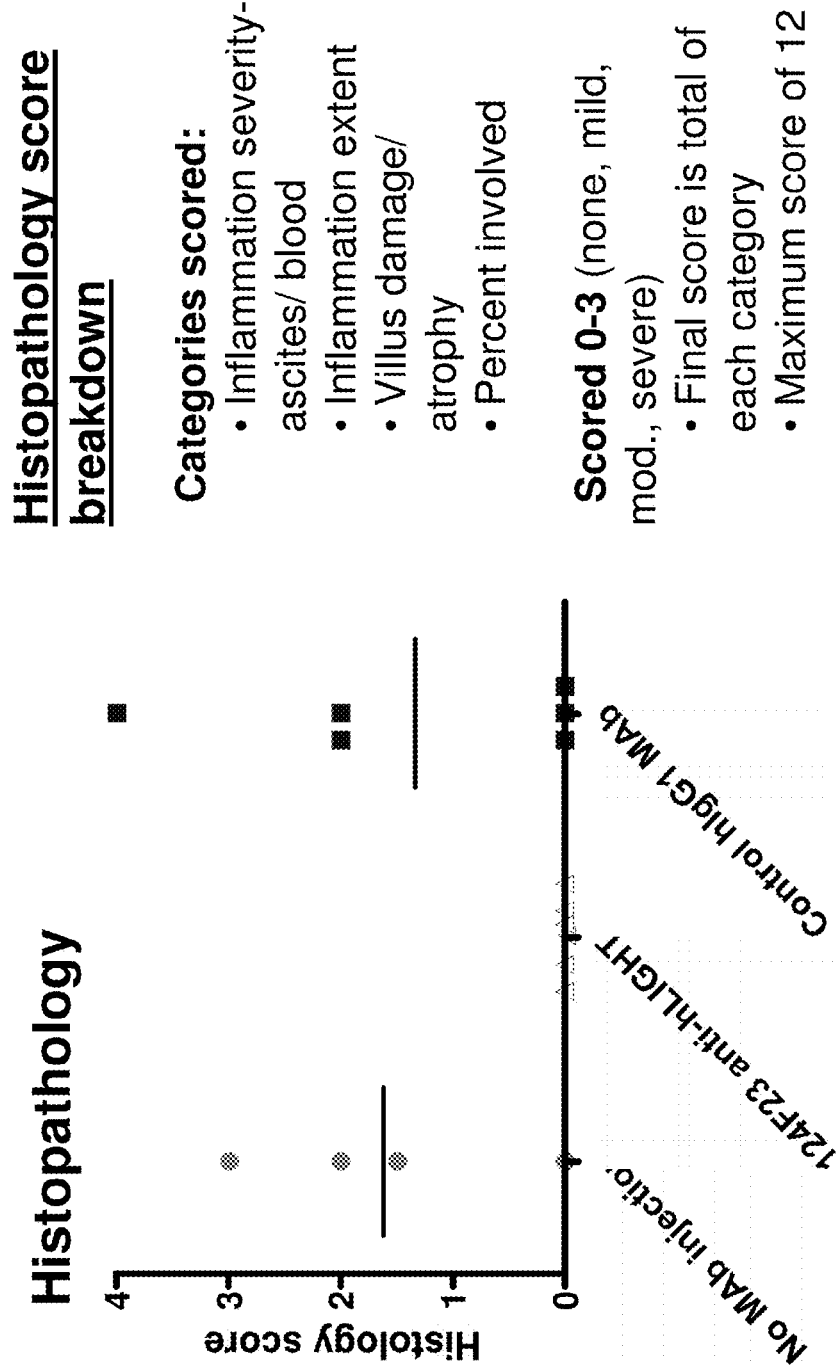
FIG. 30 depicts the histopathology scores observed in the murine acute xenogeneic GVHD disease model. Pathology scores for no MAb injection (circles), 124F23 anti-hLIGHT MAb injection (triangles) and control hIgG1 MAb (squares) are represented. Scores of 0, 1, 2, or 3 (none, mild, moderate, or severe, respectively) are assigned for each of four categories: inflammation severity, inflammation extent, villus damage/atrophy, and percent involvement (maximum total score of 12).
Figure 31B:
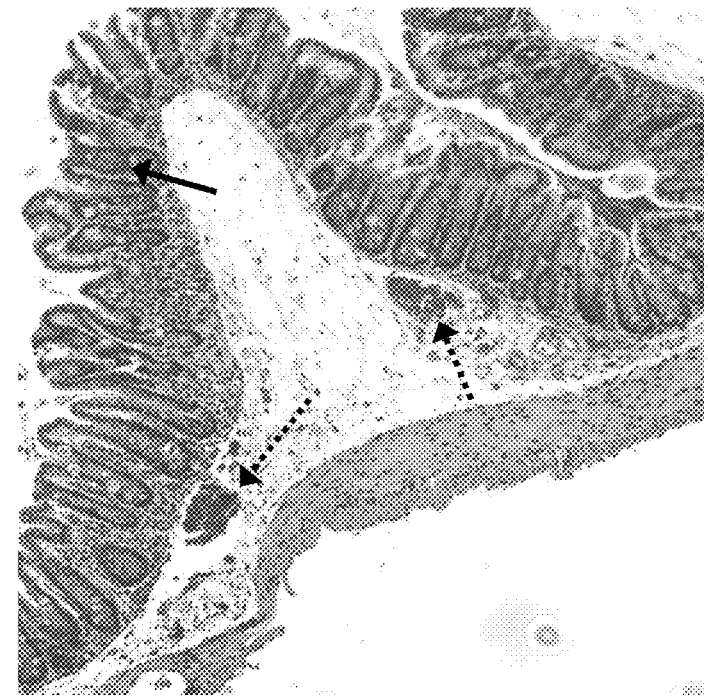
FIGS. 31A-31B depict representative histological hematoxylin and eosin (H&E) stained sections of the mouse cecum in the GVHD study.
Figure 31A:
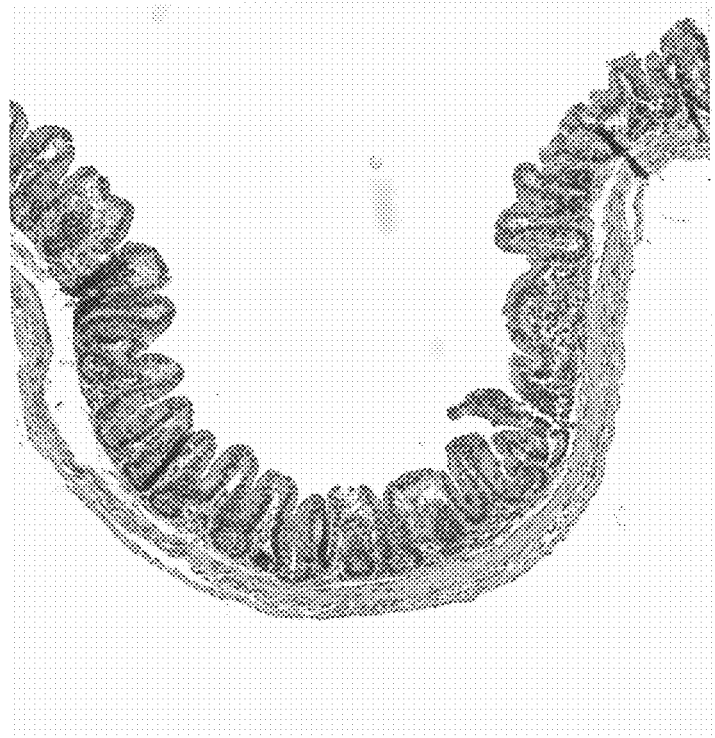

Histopathological analysis was performed on H&E sections of the cecum and scored as follows: inflammation severity, inflammation extent, villus damage/atrophy and percent involvement (each ranked 0, 1, 2 or 3 as none, mild, moderate, or severe, respectively). The final score was a sum of each category, with a maximum score of 12 for each mouse. As shown in FIG. 30, mice that received either the control antibody or PBMCs alone (no antibody injection) had similar histopathology, whereas the mice injected with 124F23G1 had no histological signs of disease. An example of the histology of the cecum observed in the anti-LIGHT treated animals is illustrated in FIG. 31A, which shows a uniform villus structure, sub-mucosa and muscle layer, as well as a lack of ascites or blood. In contrast, histology the cecum from a control antibody treated animal has prominent hallmarks of disease, including sub-mucosa filled with ascites, signs of intestinal bleeding indicated by clusters of erythrocytes and prominent lymphocyte infiltrates (FIG. 31B).

Figure 32:
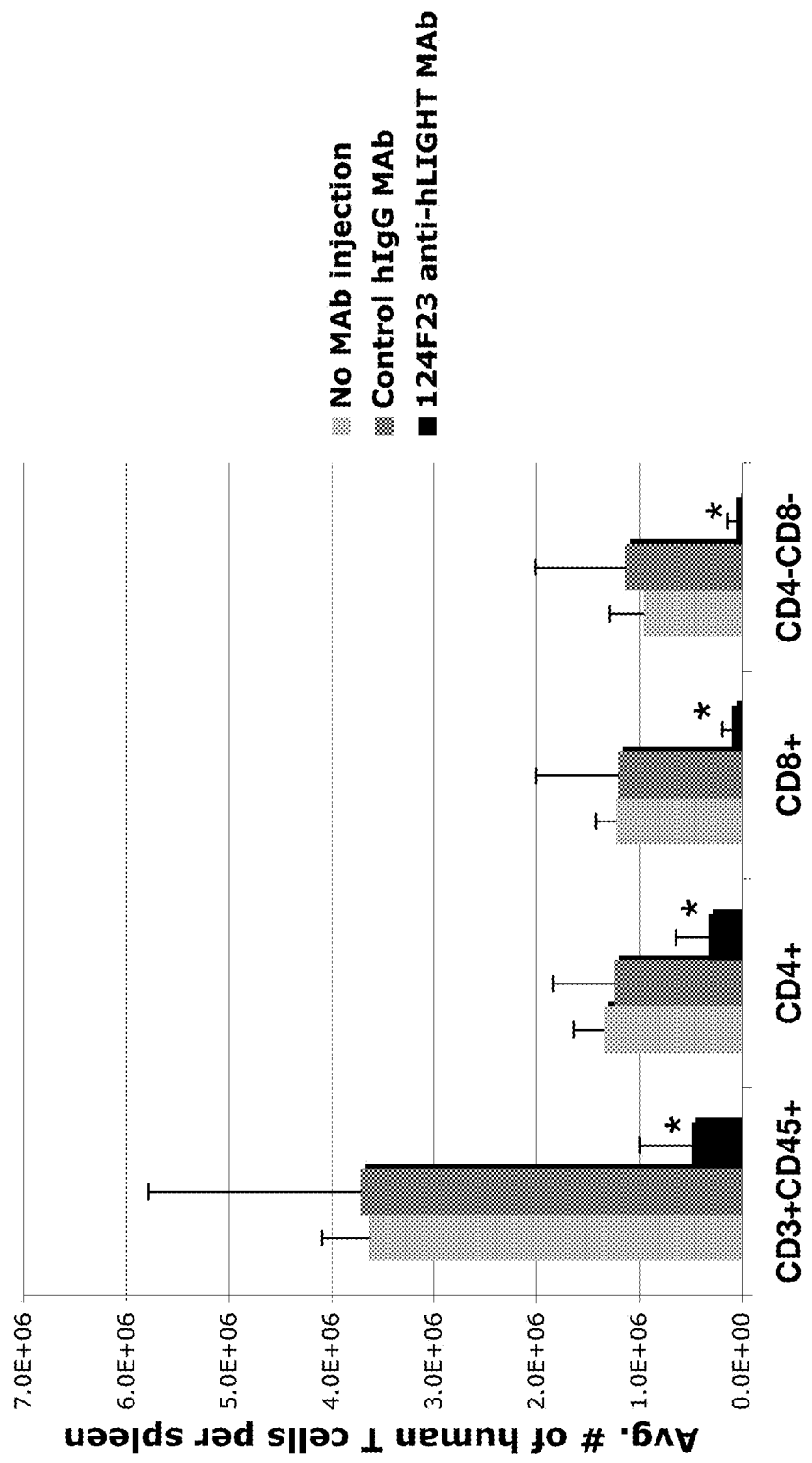
FIG. 32 depicts total T cell numbers in the spleen of mice in the xenogeneic GVHD study. Asterisks indicate student t-test values of less than 0.05 for the comparisons between anti-LIGHT MAb treated animals and controls.

Analyses of the spleens were in agreement with the gross pathology and histopathology. Human T cells were present in the spleens of mice treated with the control antibodies, but the number of human T cells in 124F23G1 treated animals were significantly lower than the number of T cells in the control animals (FIG. 32).

In follow-up studies, both T cell depleting (IgG1) and/or non-depleting (IgG4PE) versions of the anti-hLIGHT antibodies can be used to assess the mechanism of disease amelioration, such as whether T cells are being blocked by the antibody or instead undergo apoptosis.

Discussion: Acute Graft-versus-host disease (GVHD) is a major complication associated with allogeneic hematopoietic stem cell transplantation. GVHD is generally defined as the broad attack against host tissues by donor T cells. Following transplantation, systemic immunosuppression is the current method for preventing GVHD, however this can lead to opportunistic pathogen infections and relapse of leukemia. Therefore, blockade of T cell co-stimulatory signals is one of the more promising alternatives to immunosuppressants. Recent reports indicate that LIGHT-HVEM costimulation of T cells plays a critical pathogenic role in GVHD (Xu et al. (2007) 109:4097-4104). Thus, antagonistic anti-LIGHT antibodies may have therapeutic efficacy for GVHD. The in vivo efficacy demonstrated in the acute xenogeneic GVHD model demonstrates this potential.

Figure 28:
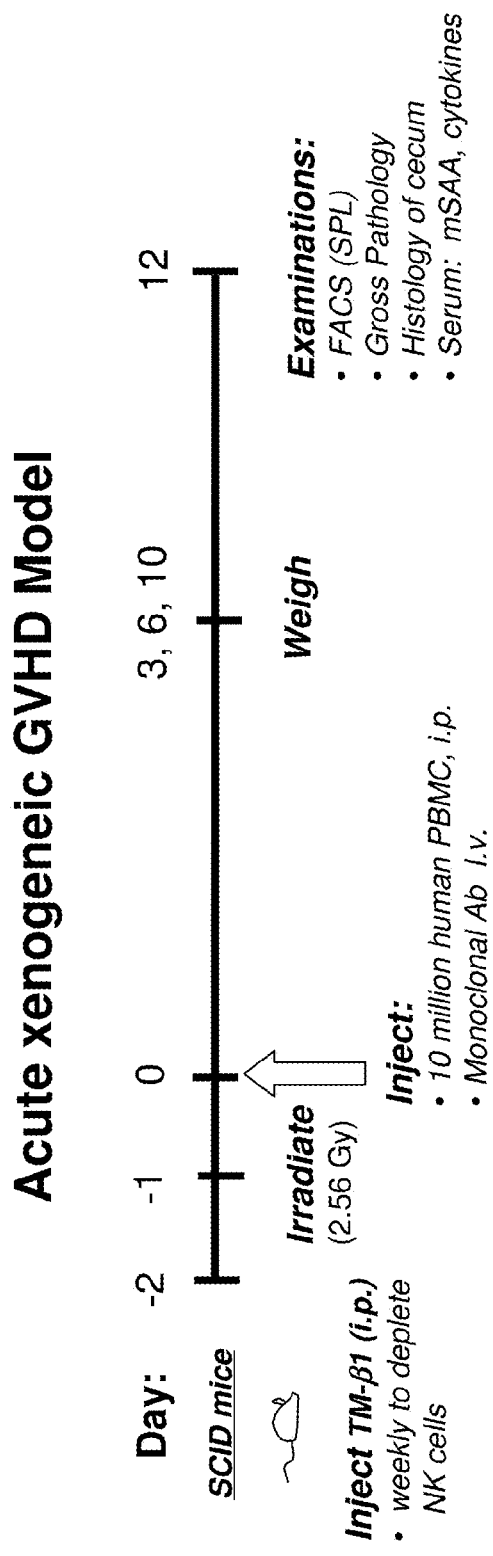
FIG. 28 depicts a schematic representation of the acute xenogeneic GVHD model. SCID mice are injected with an IL2Rβ antibody (TM-β1) on day −2 to deplete NK cells. On day −1, the mice receive 2.5 Gy of sublethal irradiation. On day 0, the mice receive 10 million human PBMC by intraperitoneal injection followed immediately by intravenous injection of a human anti-human LIGHT or negative control antibody. Mice are weighed at 3-4 day intervals, and at day 12, the mice are sacrificed and assessed for gross pathology. Spleens are removed for flow cytometric analysis, cecums are removed for histology, and serum is collected for cytokine and antibody analyses.

An acute xenogeneic model of GVHD where human PBMCs are injected into sub-lethally irradiated SCID mice depleted of NK cells (FIG. 28). In this model, irradiation initiates intestinal damage and T cells mediate to the intestinal inflammation of the disease. Animals show severe signs of disease within approximately 12 days post PBMC injection. Disease hallmarks include intestinal inflammation manifested in hemorrhaging, ascites and villus atrophy. In an initial study, treatment of mice with 100 micrograms of anti-LIGHT antibody (124F23G1) reduced the observed gross pathology in the intestine (FIG. 29). Likewise this reduction was corroborated by a more refined analysis by histopathology of the cecum, where anti-LIGHT antibody treatment lead to no detectable disease (FIG. 30). FIG. 31A shows representative H&E stained section of the cecum from an anti-LIGHT treated animal. In contrast, the cecum of a control antibody treated animal displays hallmarks of severe inflammation in the intestine, including red patches of cells indicative of hemorrhaging, the grossly involuted fluid filled sub-mucosa, and lymphocyte infiltrate (FIG. 31B). In this model, the transferred human T cells are primarily responsible for disease induction and splenic T cell numbers tend to correlate with disease severity. Anti-LIGHT antibody treatment significantly reduced total human T cell numbers in the spleen (FIG. 32). Thus, taken together, these data indicate that anti-LIGHT antibodies showed in vivo efficacy in this model, significantly reducing signs of disease relative to the negative control.

Example 6

X-Ray Crystallographic Analysis of a Human Light/Anti-Human Light Antibody (F23) Interaction The F23G1 antibody (or Fab fragment thereof) is used to assess the nature of preferential recognition of native trimeric hLIGHT. Structural analysis enables the identification of specific contact amino acid residues between the anti-hLIGHT antibody and the hLIGHT molecule to further define the conformational epitope recognized by the antibody. Crystallization of LIGHT-anti-LIGHT Fab complexes is performed by standard methods of sitting drop vapor diffusion (see, e.g., McRee 1993 In: *Practical Protein Crystallography* (Academic Press, San Diego, Calif.) at pp. 1-23; Rhodes 1993 In: *Crystallography Made Crystal Clear* (Academic Press, San Diego, Calif.) at pp. 8-10, 29-38. The crystals are analyzed using a SYNCHROTRON, and the data analyzed using the CCP4 software suite (Science & Technology Facilities Council, Computational Science and Engineering Department), which is a collection of disparate programs covering most of the computations required for macromolecular crystallography. As those skilled in the art will appreciate, other hLIGHT antibodies provided herein can be similarly used to determine hLIGHT epitope binding and amino acid contact residues.

Example 7

In Vivo Efficacy Study of 124F23 in Colitis Disease Model

Human T Cell Transfer Model of Colitis. Analogous to the CD4+/CD45Rbhi transfer model of mouse colitis described in Morrissey et al. (1993) J Exp Med. 178 237, RAG-/- mice are injected with human naïve T cells (CD45RA+ CD45RO-). In this model, an HLA transgenic strain (C57BL/6NTac-[KO]Abb-[Tg]DR-4) matched to the HLA type of a human donor is backcrossed onto a RAG-/- (B6.129S6-Rag2$^{tm1Fwa}$N12) background to enable antigen presentation between mouse recipient APCs and the human donor T cells. This interaction is necessary for T cell recognition of gut microflora, which is thought to be responsible for activation and homing of T cells to the gut. Animals experience weight loss and wasting disease, along with intestinal inflammation not seen in the RAG-/- mice.

In certain groups, a human-anti-hLIGHT antibody (e.g., F23) is administered at a dose of 100 μg (or, e.g., ranging from 2 μg-500 μg) per animal by intravenous injection simultaneously with human donor T cell administration. In certain groups, the anti-hLIGHT antibody is administered at various time intervals before and/or after human donor T cell administration. Because the anti-LIGHT antibodies bind LIGHT expressed on the surface of activated T cells, symptoms of disease are prevented and/or treated. In follow-up studies, both T cell depleting (IgG1) and/or non-depleting (IgG4PE) versions of the anti-hLIGHT antibodies can be used to assess the mechanism of disease amelioration. For example, IgG4 anti-LIGHT antibodies are able to block T cell co-stimulation and survival.

Example 8

IBD Model of Human Disease in Human Light Knock-in Mice

As discussed elsewhere herein, LIGHT has previously been implicated in IBD disease pathology (see, e.g., Wang et al. 2005 J. Immunol. 174:8173-82; Wang et al. 2004 J. Clin. Invest. 113:826-35; Cohavy et al. 2005 J. Immunol. 174: 646-53). In this example, a hLIGHT knock-in mouse model of IBD is created, and human anti-hLIGHT monoclonal antibodies of the invention are administered to the animal to assess the in vivo efficacy of these antibodies in the treatment of IBD. Because these antibodies have previously been shown to block hLIGHT receptor binding, blocking hLIGHT biological activity (see, e.g., Examples 1-4), and treating GVHD (Example 5), it is expected that hLIGHT antibodies of the invention are also effective in treating IBD.

LIGHT Knock-in Generation. Mice disrupted for the mouse LIGHT gene that also have a targeted insertion of the human LIGHT gene are generated using standard methods of gene targeting by homologous recombination. In brief, gene-targeted mouse ES cells are produced by electroporation of a gene-targeting construct into wild-type ES cells. Homologous recombination between the genome of the ES cell and two regions of homology in the targeting vector that flank the human LIGHT gene result in the replacement of the mouse LIGHT gene with the human LIGHT gene. A blastocyst is then implanted into pseudo-pregnant females leading to chimeric mouse generation. Breeding produces the homologous LIGHT knock-in animals.

IBD Models of Human Disease. The hLIGHT knock-in animals are used in established models of IBD. One established model of IBD includes the administration of dextran sodium sulfate (DSS) in drinking water (see, e.g., Mähler et al. 1998 Am J Physiol. 274G544-51). Briefly, experimental colitis is induced by giving 3.5% (w/v) DDS (mol. wt. 36,100-45,000; TbD Consultancy, Uppsala, Sweden) in acidified drinking water ad libitum for 5 days. DDS administration is then stopped, and mice receive acidified drinking water alone for 16 days until necropsy on day 21. This dose induces moderate to sever colitis while minimizing the mortality, though other doses may be used. The large intestine is then collected, and the cecum is separated from the colon. Standard tissue fixation and H&E staining is then performed to determine severity of inflammation and lesions. The mice are assessed for pathology, histopathology, wasting syndrome and/or death.

A second established model of IBD includes rectal administration of trinitrobenzene sulfonic acid (TNBS) (see, e.g., Neurath, et al. 1995 J Exp Med. 182 1281-90). Briefly, to induce colitis, mice are briefly anesthetized with metofane, and a 3.5 F catheter is then carefully inserted into the solon, such that the time is about 4 cm. proximal to the anus. To induce colitis, 0.5 mg of hapten reagent TNBS (Sigma, St. Louis, Mo.) in 50% ethanol (to break the instestinal barrier) is inserted into the lumen of the colon via the catheter fitted onto a 1 ml syringe. In control experiments, mice receive 50% ethanol alone. The total injection volume is 100 μl in both groups allowing TNBS or ethanol to reach the entire colon, including the cecum and appendix. Animals are then kept in a vertical position for 30 seconds and returned to their cages, or the CD4+/CD45Rbhi transfer model of mouse colitis (see, e.g., Morrissey, et al. 1993 J Exp Med. 178 237-44). Anti-LIGHT antibodies can then be used for treatment and prevention of established disease, such as in doses of 2-500 μg per animal, essentially as described above. The large instestine is then collected, and the cecum is separated from the colon. At various time points thereafter, the intestine is removed, and standard tissue fixation and H&E staining is then performed to determine severity of inflammation and lesions. The mice are assessed for pathology, histopathology, wasting syndrome and/or death.

A third established model of IBD is the CD4+/CD45RBhi transfer model of mouse colitis (see, e.g., Morrissey, et al. 1993 J Exp Med. 178 237-44). Briefly, purified CD4+ lymph node T cells are sorted according to their expression of CD45RB and injected into the hLIGHT knock-in mice. Standard tissue fixation and H&E staining is then performed to determine severity of inflammation and lesions. The mice are assessed for pathology, histopathology, wasting syndrome and/or death.

Anti-LIGHT antibodies (e.g., doses of 2-500 μg per animal) can be used with any IBD model, such as those described above, to assess the efficacy in the treatment and prevention of IBD, essentially as described above. Because these antibodies have previously been shown to block hLIGHT receptor binding, blocking hLIGHT biological activity (see, e.g., Examples 1-4), and treating GVHD (Example 5), it is expected that hLIGHT antibodies of the invention are also effective in treating IBD.

The present specification is being electronically filed with a computer readable form (CRF) copy of the Sequence Listing. The CRF entitled 7505_049_999_SEQLIST_2. TXT, which was created on Oct. 24, 2009 and is 48,257 bytes in size, is identical to the paper copy of the Substitute Sequence Listing and is incorporated herein by reference in its entirety.

The embodiments of the present invention described above are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims. Furthermore, as used in this specification and claims, the singular forms "a," "an" and "the" include plural forms unless the content clearly dictates otherwise. Thus, for example, reference to "an antibody" includes a mixture of two or more such antibodies, and the like. Additionally, ordinarily skilled artisans will recognize that operational sequences must be set forth in some specific order for the purpose of explanation and claiming, but the present invention contemplates various changes beyond such specific order.

The contents of all references described herein are hereby incorporated by reference.

Other embodiments are within the following claims.

```

What is claimed is:

1. An isolated antibody,
   (a) characterized by having six complementarity determining regions (CDRs) of antibody F19 or antibody F23 and a framework region having an amino acid sequence of at least 85% sequence identity to the framework region of the variable region of antibody F19 or antibody F23; and
   (b1) characterized by exhibiting binding specificity for an epitope of hLIGHT, wherein said binding is blocked by:
      (i) an antibody produced by hybridoma ATCC Accession No. PTA-7819, or
      (ii) an antibody produced by hybridoma ATCC Accession No. PTA-7728, with the proviso that the binding to the epitope of hLIGHT is not blocked by both of:
      (iii) an antibody produced by hybridoma ATCC Accession No. PTA-7729 and an antibody produced by hybridoma ATCC Accession No. PTA-7842,
      (iv) an antibody produced by hybridoma ATCC Accession No. PTA-7729 and an antibody produced by hybridoma ATCC Accession No. PTA-7818, or
      (v) an antibody produced by hybridoma ATCC Accession No. PTA-7842 and an antibody produced by hybridoma ATCC Accession No. PTA-7818; or
   (b2) characterized by being fully human and exhibiting binding specificity for an epitope of hLIGHT, wherein said binding is blocked by:
      (i) an antibody produced by hybridoma ATCC Accession No. PTA-7819, or
      (ii) an antibody produced by hybridoma ATCC Accession No. PTA-7728.

2. The isolated antibody of claim 1, wherein the binding is blocked in a dose-dependent manner.

3. The isolated antibody of claim 1, wherein the antibody is an antagonist antibody.

4. The isolated antibody of claim 3, wherein
(a) the antibody competes with HVEM, LTβR, or a fusion protein thereof, for binding to cell surface-expressed hLIGHT or soluble hLIGHT;
(b) the antibody partially or completely inhibits binding of HVEM, LTβR, DcR3, or any combination thereof, to cell surface-expressed hLIGHT or soluble hLIGHT; or
(c) the antibody partially or completely inhibits hLIGHT-mediated secretion of CCL20, IL-8, RANTES, or any combination thereof, from a cell having a cell surface-expressed hLIGHT receptor.

5. The isolated antibody of claim 1, wherein the antibody comprises:
(a) a heavy chain variable region (VH) of an antibody produced by hybridoma ATCC Accession No. PTA-7819 or hybridoma ATCC Accession No. PTA-7728;
(b) a light chain variable region (VL) of an antibody produced by hybridoma ATCC Accession No. PTA-7819 or hybridoma ATCC Accession No. PTA-7728; or
(c) a VH of an antibody produced by hybridoma ATCC Accession No. PTA-7819 or hybridoma ATCC Accession No. PTA-7728, and a VL of an antibody produced by hybridoma ATCC Accession No. PTA-7819 or hybridoma ATCC Accession No. PTA-7728.

6. The isolated antibody of claim 1, wherein the isolated antibody is an antibody produced by hybridoma ATCC Accession No. PTA-7819 or an antibody produced by hybridoma ATCC Accession No. PTA-7728.

7. The isolated antibody of claim 1, wherein the antibody comprises:
(a) a VH selected from (i) amino acids 20-141 of SEQ ID NO:4 and (ii) amino acids 27-143 of SEQ ID NO:5;
(b) a VL selected from (i) amino acids 23-129 of SEQ ID NO:90, (ii) amino acids 23-129 of SEQ ID NO:91, (iii) amino acids 21-126 of SEQ ID NO:92, (iv) amino acids 23-129 of SEQ ID NO:9, and (v) amino acids 23-129 of SEQ ID NO:10; or
(c) a VH selected from (i) amino acids 20-141 of SEQ ID NO:4 and (ii) amino acids 27-143 of SEQ ID NO:5; and a VL selected from (i) amino acids 23-129 of SEQ ID NO:90, (ii) amino acids 23-129 of SEQ ID NO:91, (iii) amino acids 21-126 of SEQ ID NO:92, (iv) amino acids 23-129 of SEQ ID NO:9, and (v) amino acids 23-129 of SEQ ID NO:10.

8. The isolated antibody of claim 1, wherein the antibody comprises:
(a) a VH comprising:
(i) a VH CDR1 as set forth in SEQ ID NO:20,
(ii) a VH CDR2 as set forth in SEQ ID NO:21, and
(iii) a VH CDR3 as set forth in SEQ ID NO:22;
and a VL comprising:
(i) a VL CDR1 selected from the group consisting of SEQ ID NOs:93, 35, 94, and 95,
(ii) a VL CDR2 selected from the group consisting of SEQ ID NOs:96, 36, 97, and 98, and
(iii) a VL CDR3 selected from the group consisting of SEQ ID NOs:99, 37, 100, and 101; or (b) a VH comprising:
(i) a VH CDR1 as set forth in SEQ ID NO:23,
(ii) a VH CDR2 as set forth in SEQ ID NO:24, and
(iii) a VH CDR3 as set forth in SEQ ID NO:25,
and a VL comprising:
(i) a VL CDR1 as set forth in SEQ ID NO:38,
(ii) a VL CDR2 as set forth in SEQ ID NO:39, and
(iii) a VL CDR3 as set forth in SEQ ID NO:40.

9. The isolated antibody of claim 1, wherein the antibody comprises:
(a) a VH encoded by a nucleotide sequence that hybridizes under stringent conditions to the complement of a nucleotide sequence set forth in any one of SEQ ID NOs:44 and 45;
(b) a VL encoded by a nucleotide sequence that hybridizes under stringent conditions to the complement of a nucleotide sequence set forth in any one of SEQ ID NOs:104, 49, 105, 106 and 50; or
(c) a VH encoded by a nucleotide sequence that hybridizes under stringent conditions to the complement of a nucleotide sequence set forth in any one of SEQ ID NOs:44 and 45, and a VL encoded by a nucleotide sequence that hybridizes under stringent conditions to the complement of a nucleotide sequence set forth in any one of SEQ ID NOs:104, 49, 105, 106 and 50, wherein said stringent conditions comprise hybridizing in 6x sodium chloride/sodium citrate (SSC) at about 45° C., and washing in 0.2xSSC/0.1% SDS at about 50-65° C.

10. The isolated antibody of claim 1, wherein the antibody is an IgG antibody.

11. The isolated antibody of claim 10, wherein the antibody is an IgG1 antibody or an IgG4 antibody.

12. The isolated antibody of claim 1, wherein the antibody is selected from the group consisting a fully human antibody, a chimeric or humanized antibody, an antigen binding fragment, a Fab fragment, a F(ab')2 fragment, a single chain Fv (sFv) antibody, a diabody, or a triabody.

13. The isolated antibody of claim 1, wherein the antibody is a monoclonal antibody or a recombinant antibody.

14. A pharmaceutical composition comprising an antibody of claim 1.

15. A hybridoma that produces an antibody as recited in claim 1.

16. The hybridoma of claim 15, wherein the hybridoma is hybridoma ATCC Accession No. PTA-7819 or hybridoma ATCC Accession No. PTA-7728.

17. A kit comprising an antibody of claim 1.

18. The isolated antibody of claim 1, wherein the variable region of antibody F19 comprises amino acids 20-141 of the amino acid sequence set forth in SEQ ID NO:4 and amino acids 23-129 of the amino acid sequence set forth in SEQ ID NO:9, and wherein the variable region of antibody F23 comprises amino acids 27-143 of the amino acid sequence set forth in SEQ ID NO:5 and amino acids 23-129 of the amino acid sequence set forth in SEQ ID NO:10.

* * * * *

                            SEQUENCE LISTING

<160> NUMBER OF SEQ ID NOS: 106

<210> SEQ ID NO 1
<211> LENGTH: 136
<212> TYPE: PRT
<213> ORGANISM: Homo sapiens
<220> FEATURE:
<223> OTHER INFORMATION: E1 heavy chain variable region

<400> SEQUENCE: 1

Met Glu Leu Gly Leu Cys Trp Val Phe Leu Val Ala Ile Leu Glu Gly
 1               5                  10                  15

Val Gln Cys Glu Val Gln Leu Val Glu Ser Gly Gly Leu Val Gln
            20                  25                  30

Pro Gly Gly Ser Leu Arg Leu Ser Cys Ala Ala Ser Gly Phe Thr Phe
            35                  40                  45

Ser Arg Phe Asn Met Asn Trp Val Arg Gln Ala Pro Gly Lys Gly Leu
        50                  55                  60

Glu Trp Val Ser Tyr Ile Ser Ser Ser Tyr Thr Ile Tyr Tyr Ala
 65                  70                  75                  80

Asp Ser Val Lys Gly Arg Phe Thr Ile Ser Arg Asp Asn Ala Lys Asn
                85                  90                  95

Ser Leu Asp Leu Gln Met Asn Ser Leu Arg Asp Glu Asp Thr Ala Val
            100                 105                 110

Tyr Tyr Cys Ala Arg Ser Ile Ala Ala Phe Asp Tyr Trp Gly Gln
        115                 120                 125

Gly Ala Leu Val Thr Val Ser Ser
        130                 135

<210> SEQ ID NO 2
<211> LENGTH: 138
<212> TYPE: PRT
<213> ORGANISM: Homo sapiens
<220> FEATURE:
<223> OTHER INFORMATION: E13 heavy chain variable region

<400> SEQUENCE: 2

Met Glu Phe Gly Leu Ser Trp Ile Phe Leu Ala Ala Ile Leu Lys Gly
 1               5                  10                  15

Val Gln Cys Glu Val Gln Leu Val Glu Ser Gly Gly Leu Val Lys
            20                  25                  30

Pro Gly Gly Ser Leu Arg Leu Ser Cys Ala Ala Ser Gly Phe Thr Leu
            35                  40                  45

Ser Asn Ala Trp Met Ser Trp Val Arg Gln Ala Pro Gly Lys Gly Leu
        50                  55                  60

Glu Trp Val Gly Arg Ile Lys Ser Lys Ile Asp Gly Thr Thr Asp
 65                  70                  75                  80

Tyr Ala Ala Pro Val Lys Gly Arg Phe Thr Ile Ser Arg Asp Asp Ser
                85                  90                  95

Lys Asn Thr Leu Phe Leu Gln Met Asn Ser Leu Lys Thr Glu Asp Thr
            100                 105                 110

Ala Val Tyr Tyr Cys Thr Thr Ala Met Ala Gly Ala Phe Gly Phe Trp
        115                 120                 125
```

```
Gly Gln Gly Thr Leu Val Thr Val Ser Ser
        130                 135

<210> SEQ ID NO 3
<211> LENGTH: 141
<212> TYPE: PRT
<213> ORGANISM: Homo sapiens
<220> FEATURE:
<223> OTHER INFORMATION: E63 heavy chain variable region

<400> SEQUENCE: 3

Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Ile Val Ser Gly Gly Ser Val
         35                  40                  45

Ser Ser Gly Gly Tyr Tyr Trp Ser Trp Ile Arg Gln Pro Pro Gly Lys
     50                  55                  60

Gly Leu Glu Trp Ile Gly Tyr Ile Tyr Tyr Ser Gly Ser Thr Asn Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Val Thr Ala Ala Asp Thr Ala
            100                 105                 110

Val Tyr Tyr Cys Ala Arg Trp Ile Thr Met Phe Arg Gly Val Gly Phe
        115                 120                 125

Asp Pro Trp Gly Gln Gly Thr Leu Val Thr Val Ser Ser
        130                 135                 140

<210> SEQ ID NO 4
<211> LENGTH: 141
<212> TYPE: PRT
<213> ORGANISM: Homo sapiens
<220> FEATURE:
<223> OTHER INFORMATION: F19 heavy chain variable region

<400> SEQUENCE: 4

Met Lys His Leu Trp Phe Phe Leu Leu Leu Val Ala Ala Pro Arg Trp
  1               5                  10                  15

Val Leu Ser Gln Val Gln Leu Gln Gln Trp Gly Ala Gly Leu Leu Lys
             20                  25                  30

Pro Ser Glu Thr Leu Ser Leu Thr Cys Ala Val Tyr Gly Gly Ser Phe
         35                  40                  45

Ser Gly Tyr Asn Trp His Trp Ile Arg Gln Pro Pro Gly Lys Gly Leu
     50                  55                  60

Glu Trp Ile Gly Glu Ile Thr His Ser Gly Ser Thr Asn Tyr Asn Pro
 65                  70                  75                  80

Ser Leu Lys Ser Arg Val Thr Ile Ser Val Asp Thr Ser Lys Asn Gln
                 85                  90                  95

Phe Ser Leu Lys Leu Ser Ser Val Thr Ala Ala Asp Thr Ala Val Tyr
            100                 105                 110

Tyr Cys Val Arg Glu Ile Ala Val Ala Gly Thr Gly Tyr Tyr Gly Met
        115                 120                 125

Asp Val Trp Gly Gln Gly Thr Thr Val Thr Val Ser Ser
        130                 135                 140
```

```
<210> SEQ ID NO 5
<211> LENGTH: 143
<212> TYPE: PRT
<213> ORGANISM: Homo sapiens
<220> FEATURE:
<223> OTHER INFORMATION: F23 heavy chain variable region

<400> SEQUENCE: 5

Met Asp Leu Leu His Lys Asn Met Lys His Leu Trp Phe Phe Leu Leu
 1               5                  10                  15

Leu Val Ala Ala Pro Arg Trp Val Leu Ser Gln Val Gln Leu Gln Gln
             20                  25                  30

Trp Gly Ala Gly Leu Leu Lys Pro Ser Glu Thr Leu Ser Leu Thr Cys
         35                  40                  45

Ala Val Tyr Gly Gly Ser Phe Ser Gly Tyr Tyr Trp Asn Trp Ile Arg
     50                  55                  60

Gln Pro Pro Gly Lys Gly Leu Glu Trp Ile Gly Glu Ile Asn Gln Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
            100                 105                 110

Val Tyr Tyr Cys Ala Arg Glu Ile Ala Thr Ala Asp Lys Gly Tyr Tyr
        115                 120                 125

Gly Leu Asp Val Trp Gly Gln Gly Thr Thr Val Thr Val Ser Ser
    130                 135                 140

<210> SEQ ID NO 6
<211> LENGTH: 128
<212> TYPE: PRT
<213> ORGANISM: Homo sapiens
<220> FEATURE:
<223> OTHER INFORMATION: E1 kappa light chain variable region #2
      (E1 kappa(B))

<400> SEQUENCE: 6

Met Glu Thr Pro Ala Gln Leu Leu Phe Leu Leu Leu Trp Leu Pro
 1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Val Ser Ser Ser Tyr Leu Thr Trp Tyr Gln Gln Lys Pro Gly Gln Ala
     50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
            100                 105                 110

Gly Ser Ser Met Tyr Thr Phe Gly Gln Gly Thr Lys Leu Glu Ile Lys
        115                 120                 125

<210> SEQ ID NO 7
<211> LENGTH: 130
<212> TYPE: PRT
<213> ORGANISM: Homo sapiens
<220> FEATURE:
<223> OTHER INFORMATION: E13 kappa light chain variable region
```

-continued

<400> SEQUENCE: 7

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Met Tyr Thr Phe Gly Gln Gly Thr Lys Leu Glu Ile
        115                 120                 125

Lys Arg
    130

<210> SEQ ID NO 8
<211> LENGTH: 126
<212> TYPE: PRT
<213> ORGANISM: Homo sapiens
<220> FEATURE:
<223> OTHER INFORMATION: E63 kappa light chain variable region

<400> SEQUENCE: 8

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Leu Thr Phe Gly Gly Gly Thr Lys Val Glu Ile Lys
        115                 120                 125

<210> SEQ ID NO 9
<211> LENGTH: 129
<212> TYPE: PRT
<213> ORGANISM: Homo sapiens
<220> FEATURE:
<223> OTHER INFORMATION: F19 kappa light chain variable region #2

<400> SEQUENCE: 9

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
            35                  40                  45

Gln Gly Ile Asn Ser Ala Phe Ala Trp Tyr Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Leu Thr Phe Gly Gly Gly Thr Lys Val Glu Ile
            115                 120                 125

Lys

<210> SEQ ID NO 10
<211> LENGTH: 129
<212> TYPE: PRT
<213> ORGANISM: Homo sapiens
<220> FEATURE:
<223> OTHER INFORMATION: F23 kappa light chain variable region

<400> SEQUENCE: 10

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
            35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Leu Thr Phe Gly Gly Gly Thr Lys Val Glu Ile
            115                 120                 125

Lys

<210> SEQ ID NO 11
<211> LENGTH: 5
<212> TYPE: PRT
<213> ORGANISM: Homo sapiens
<220> FEATURE:
<223> OTHER INFORMATION: CDR1 of E1 heavy chain variable region

<400> SEQUENCE: 11

Arg Phe Asn Met Asn
1               5

<210> SEQ ID NO 12
<211> LENGTH: 17
<212> TYPE: PRT
<213> ORGANISM: Homo sapiens
<220> FEATURE:
<223> OTHER INFORMATION: CDR2 of E1 heavy chain variable region

<400> SEQUENCE: 12

```
Tyr Ile Ser Ser Ser Ser Tyr Thr Ile Tyr Tyr Ala Asp Ser Val Lys
 1               5                  10                  15
Gly

<210> SEQ ID NO 13
<211> LENGTH: 7
<212> TYPE: PRT
<213> ORGANISM: Homo sapiens
<220> FEATURE:
<223> OTHER INFORMATION: CDR3 of E1 heavy chain variable region

<400> SEQUENCE: 13

Ser Ile Ala Ala Phe Asp Tyr
 1               5

<210> SEQ ID NO 14
<211> LENGTH: 5
<212> TYPE: PRT
<213> ORGANISM: Homo sapiens
<220> FEATURE:
<223> OTHER INFORMATION: CDR1 of E13 heavy chain variable region

<400> SEQUENCE: 14

Asn Ala Trp Met Ser
 1               5

<210> SEQ ID NO 15
<211> LENGTH: 19
<212> TYPE: PRT
<213> ORGANISM: Homo sapiens
<220> FEATURE:
<223> OTHER INFORMATION: CDR2 of E13 heavy chain variable region

<400> SEQUENCE: 15

Arg Ile Lys Ser Lys Ile Asp Gly Gly Thr Thr Asp Tyr Ala Ala Pro
 1               5                  10                  15
Val Lys Gly

<210> SEQ ID NO 16
<211> LENGTH: 8
<212> TYPE: PRT
<213> ORGANISM: Homo sapiens
<220> FEATURE:
<223> OTHER INFORMATION: CDR3 of E13 heavy chain variable region

<400> SEQUENCE: 16

Ala Met Ala Gly Ala Phe Gly Phe
 1               5

<210> SEQ ID NO 17
<211> LENGTH: 7
<212> TYPE: PRT
<213> ORGANISM: Homo sapiens
<220> FEATURE:
<223> OTHER INFORMATION: CDR1 of E63 heavy chain variable region

<400> SEQUENCE: 17

Ser Gly Gly Tyr Tyr Trp Ser
 1               5

<210> SEQ ID NO 18
<211> LENGTH: 16
<212> TYPE: PRT
<213> ORGANISM: Homo sapiens
<220> FEATURE:
<223> OTHER INFORMATION: CDR2 of E63 heavy chain variable region
```

```
<400> SEQUENCE: 18

Tyr Ile Tyr Tyr Ser Gly Ser Thr Asn Tyr Asn Pro Ser Leu Lys Ser
1               5                   10                  15

<210> SEQ ID NO 19
<211> LENGTH: 12
<212> TYPE: PRT
<213> ORGANISM: Homo sapiens
<220> FEATURE:
<223> OTHER INFORMATION: CDR3 of E63 heavy chain variable region

<400> SEQUENCE: 19

Trp Ile Thr Met Phe Arg Gly Val Gly Phe Asp Pro
1               5                   10

<210> SEQ ID NO 20
<211> LENGTH: 5
<212> TYPE: PRT
<213> ORGANISM: Homo sapiens
<220> FEATURE:
<223> OTHER INFORMATION: CDR1 of F19 heavy chain variable region #2
      (F19 kappa(B))

<400> SEQUENCE: 20

Gly Tyr Asn Trp His
1               5

<210> SEQ ID NO 21
<211> LENGTH: 16
<212> TYPE: PRT
<213> ORGANISM: Homo sapiens
<220> FEATURE:
<223> OTHER INFORMATION: CDR2 of F19 heavy chain variable region #2
      (F19 kappa(B))

<400> SEQUENCE: 21

Glu Ile Thr His Ser Gly Ser Thr Asn Tyr Asn Pro Ser Leu Lys Ser
1               5                   10                  15

<210> SEQ ID NO 22
<211> LENGTH: 14
<212> TYPE: PRT
<213> ORGANISM: Homo sapiens
<220> FEATURE:
<223> OTHER INFORMATION: CDR3 of F19 heavy chain variable region #2
      (F19 kappa(B))

<400> SEQUENCE: 22

Glu Ile Ala Val Ala Gly Thr Gly Tyr Tyr Gly Met Asp Val
1               5                   10

<210> SEQ ID NO 23
<211> LENGTH: 5
<212> TYPE: PRT
<213> ORGANISM: Homo sapiens
<220> FEATURE:
<223> OTHER INFORMATION: CDR1 of F23 heavy chain variable region

<400> SEQUENCE: 23

Gly Tyr Tyr Trp Asn
1               5

<210> SEQ ID NO 24
<211> LENGTH: 11
<212> TYPE: PRT
<213> ORGANISM: Homo sapiens
```

-continued

```
<220> FEATURE:
<223> OTHER INFORMATION: CDR2 of F23 heavy chain variable region

<400> SEQUENCE: 24

Glu Ile Asn Gln Tyr Asn Pro Ser Leu Lys Ser
1               5                   10

<210> SEQ ID NO 25
<211> LENGTH: 14
<212> TYPE: PRT
<213> ORGANISM: Homo sapiens
<220> FEATURE:
<223> OTHER INFORMATION: CDR3 of F23 heavy chain variable region

<400> SEQUENCE: 25

Glu Ile Ala Thr Ala Asp Lys Gly Tyr Tyr Gly Leu Asp Val
1               5                   10

<210> SEQ ID NO 26
<211> LENGTH: 12
<212> TYPE: PRT
<213> ORGANISM: Homo sapiens
<220> FEATURE:
<223> OTHER INFORMATION: CDR1 of E1 light chain variable region #2
      (E1 kappa(B))

<400> SEQUENCE: 26

Arg Ala Ser Gln Ser Val Ser Ser Ser Tyr Leu Thr
1               5                   10

<210> SEQ ID NO 27
<211> LENGTH: 7
<212> TYPE: PRT
<213> ORGANISM: Homo sapiens
<220> FEATURE:
<223> OTHER INFORMATION: CDR2 of E1 light chain variable region #2
      (E1 kappa(B))

<400> SEQUENCE: 27

Gly Ala Ser Ser Arg Ala Thr
1               5

<210> SEQ ID NO 28
<211> LENGTH: 9
<212> TYPE: PRT
<213> ORGANISM: Homo sapiens
<220> FEATURE:
<223> OTHER INFORMATION: CDR3 of E1 light chain variable region #2
      (E1 kappa(B))

<400> SEQUENCE: 28

Gln Gln Tyr Gly Ser Ser Met Tyr Thr
1               5

<210> SEQ ID NO 29
<211> LENGTH: 12
<212> TYPE: PRT
<213> ORGANISM: Homo sapiens
<220> FEATURE:
<223> OTHER INFORMATION: CDR1 of E13 light chain variable region

<400> SEQUENCE: 29

Arg Ala Ser Gln Ser Val Ser Ser Ser Tyr Leu Ala
1               5                   10

<210> SEQ ID NO 30
<211> LENGTH: 7
```

```
<212> TYPE: PRT
<213> ORGANISM: Homo sapiens
<220> FEATURE:
<223> OTHER INFORMATION: CDR2 of E13 light chain variable region

<400> SEQUENCE: 30

Gly Ala Ser Ser Arg Ala Thr
 1               5

<210> SEQ ID NO 31
<211> LENGTH: 10
<212> TYPE: PRT
<213> ORGANISM: Homo sapiens
<220> FEATURE:
<223> OTHER INFORMATION: CDR3 of E13 light chain variable region

<400> SEQUENCE: 31

Gln Gln Tyr Gly Ser Ser Pro Met Tyr Thr
 1               5                  10

<210> SEQ ID NO 32
<211> LENGTH: 11
<212> TYPE: PRT
<213> ORGANISM: Homo sapiens
<220> FEATURE:
<223> OTHER INFORMATION: CDR1 of E63 light chain variable region

<400> SEQUENCE: 32

Arg Ala Ser Gln Ser Ile Gly Ser Ser Leu His
 1               5                  10

<210> SEQ ID NO 33
<211> LENGTH: 7
<212> TYPE: PRT
<213> ORGANISM: Homo sapiens
<220> FEATURE:
<223> OTHER INFORMATION: CDR2 of E63 light chain variable region

<400> SEQUENCE: 33

Tyr Ala Ser Gln Ser Phe Ser
 1               5

<210> SEQ ID NO 34
<211> LENGTH: 9
<212> TYPE: PRT
<213> ORGANISM: Homo sapiens
<220> FEATURE:
<223> OTHER INFORMATION: CDR3 of E63 light chain variable region

<400> SEQUENCE: 34

His Gln Ser Ser Ser Leu Pro Leu Thr
 1               5

<210> SEQ ID NO 35
<211> LENGTH: 11
<212> TYPE: PRT
<213> ORGANISM: Homo sapiens
<220> FEATURE:
<223> OTHER INFORMATION: CDR1 of F19 light chain variable region #2
      (F19 kappa(B))

<400> SEQUENCE: 35

Arg Ala Ser Gln Gly Ile Asn Ser Ala Phe Ala
 1               5                  10

<210> SEQ ID NO 36
<211> LENGTH: 7
```

```
<212> TYPE: PRT
<213> ORGANISM: Homo sapiens
<220> FEATURE:
<223> OTHER INFORMATION: CDR2 of F19 light chain variable region #2
      (F19 kappa(B))

<400> SEQUENCE: 36

Asp Ala Ser Ser Leu Glu Ser
 1               5

<210> SEQ ID NO 37
<211> LENGTH: 9
<212> TYPE: PRT
<213> ORGANISM: Homo sapiens
<220> FEATURE:
<223> OTHER INFORMATION: CDR3 of F19 light chain variable region #2
      (F19 kappa(B))

<400> SEQUENCE: 37

Gln Gln Phe Asn Ser Tyr Pro Leu Thr
 1               5

<210> SEQ ID NO 38
<211> LENGTH: 11
<212> TYPE: PRT
<213> ORGANISM: Homo sapiens
<220> FEATURE:
<223> OTHER INFORMATION: CDR1 of F23 light chain variable region

<400> SEQUENCE: 38

Arg Ala Ser Gln Gly Ile Ser Ser Ala Leu Ala
 1               5                  10

<210> SEQ ID NO 39
<211> LENGTH: 7
<212> TYPE: PRT
<213> ORGANISM: Homo sapiens
<220> FEATURE:
<223> OTHER INFORMATION: CDR2 of F23 light chain variable region

<400> SEQUENCE: 39

Asp Ala Ser Ser Leu Glu Ser
 1               5

<210> SEQ ID NO 40
<211> LENGTH: 9
<212> TYPE: PRT
<213> ORGANISM: Homo sapiens
<220> FEATURE:
<223> OTHER INFORMATION: CDR3 of F23 light chain variable region

<400> SEQUENCE: 40

Gln Gln Phe Asn Ser Tyr Pro Leu Thr
 1               5

<210> SEQ ID NO 41
<211> LENGTH: 408
<212> TYPE: DNA
<213> ORGANISM: Homo sapiens
<220> FEATURE:
<223> OTHER INFORMATION: cDNA of E1 heavy chain variable region

<400> SEQUENCE: 41
atggagttgg ggctgtgctg ggttttcctt gttgctattt tagaaggtgt ccagtgtgag    60
gtgcagctgg tggagtctgg gggaggcttg gtacagcctg gggggtccct gagactctcc   120
tgtgcagcct ctggattcac cttcagtaga tttaacatga actgggtccg ccaggctcca   180
```

```
gggaagggc  tggagtgggt  ttcatacatt  agtagtagta  gttataccat  atactacgca      240
gactctgtga  agggccgatt  caccatctcc  agagacaatg  ccaagaactc  actggatctg      300
caaatgaaca  gcctgagaga  cgaggacacg  gctgtgtatt  actgtgcgag  gagtatagca      360
gcagcttttg  actactgggg  ccagggagcc  ctggtcaccg  tctcctca                   408

<210> SEQ ID NO 42
<211> LENGTH: 414
<212> TYPE: DNA
<213> ORGANISM: Homo sapiens
<220> FEATURE:
<223> OTHER INFORMATION: cDNA of E13 heavy chain variable region

<400> SEQUENCE: 42
atggagtttg  ggctgagctg  gattttcctt  gctgcgattt  taaaaggtgt  ccagtgtgag       60
gtgcagctgg  tggagtctgg  gggaggcctg  gtaaagcctg  ggggtccct   tagactctcc     120 tgtgcagcct  ctggattcac  tctcagtaac  gcctggatga  gctgggtccg  ccaggctcca     180 gggaagggc   tggagtgggt  tggccgtatt  aaaagcaaaa  tagatggtgg  gacaacagac     240
tacgctgcac  ccgtgaaagg  cagattcacc  atctcaagag  atgattcaaa  aaacacgctg     300
tttctgcaaa  tgaacagcct  gaaaaccgag  gacacagccg  tgtattactg  taccacagca     360
atggctggtg  cgtttggctt  ttggggccag  ggaaccctgg  tcaccgtctc  ctca           414

<210> SEQ ID NO 43
<211> LENGTH: 423
<212> TYPE: DNA
<213> ORGANISM: Homo sapiens
<220> FEATURE:
<223> OTHER INFORMATION: cDNA of E63 heavy chain variable region

<400> SEQUENCE: 43
atgaaacacc  tgtggttctt  cctcctcctg  gtggcagctc  ccagatgggt  cctgtcccag       60
gtgcagctgc  aggagtcggg  cccaggactg  gtgaagcctt  cggagaccct  gtccctcacc     120
tgcattgtct  ctggtggctc  cgtcagcagt  ggtggttact  actggagctg  gatccggcag     180
cccccaggga  agggactgga  gtggattggg  tatatctatt  acagtgggag  caccaactac     240 aaccctctc   tcaagagtcg  agtcaccata  tcagtagaca  cgtccaagaa  ccagttctcc     300
ctgaagctga  gctctgtgac  cgctgcggac  acggccgtgt  attactgtgc  gagatggatt     360
actatgtttc  ggggagttgg  gttcgacccc  tggggccagg  gaaccctggt  caccgtctcc     420
tca                                                                       423

<210> SEQ ID NO 44
<211> LENGTH: 423
<212> TYPE: DNA
<213> ORGANISM: Homo sapiens
<220> FEATURE:
<223> OTHER INFORMATION: cDNA of F19 heavy chain variable region

<400> SEQUENCE: 44
atgaaacacc  tgtggttctt  cctcctcctg  gtggcagctc  ccagatgggt  cctgtcccag       60
gtgcagctac  agcagtgggg  cgcaggactg  ttgaagcctt  cggagaccct  gtccctcacc     120
tgcgctgtct  atggtgggtc  cttcagtggt  tacaactggc  actggatccg  ccagccccca     180 gggaagggc   tggagtggat  tgggaaatc   actcatagtg  aagcaccaa   ttacaacccg     240 tccctcaaga  gtcgagtcac  catatcagta  gacacgtcca  agaaccagtt  ctccctgaag     300
```

```
ctgagctctg tgaccgccgc ggacacggct gtgtattact gtgtgcgaga gattgcagtg      360
gctggtacgg gctactacgg tatggacgtc tggggccaag ggaccacggt caccgtctcc      420
tca                                                                    423

<210> SEQ ID NO 45
<211> LENGTH: 429
<212> TYPE: DNA
<213> ORGANISM: Homo sapiens
<220> FEATURE:
<223> OTHER INFORMATION: cDNA of F23 heavy chain variable region

<400> SEQUENCE: 45
atggacctcc tgcacaagaa catgaaacac ctgtggttct cctcctcct ggtggcagct       60 cccagatggg tcctgtccca ggtgcagcta cagcagtggg cgcaggact gttgaagcct      120 tcggagaccc tgtccctcac ctgcgctgtc tatggtgggt ccttcagtgg ttactactgg     180
aactggatcc gccagccccc agggaagggg ctggagtgga ttggggaaat caatcagtac     240
aacccgtccc tcaagagtcg agtcaccata tcagtagaca cgtccaagaa ccagttctcc     300
ctgaagctga gctctgtgac cgccgcggac acggctgtgt attactgtgc gagagagata     360
gcaacagctg ataaagggta ctacggtttg gacgtctggg gccaagggac cacggtcacc     420
gtctcctca                                                            429

<210> SEQ ID NO 46
<211> LENGTH: 384
<212> TYPE: DNA
<213> ORGANISM: Homo sapiens
<220> FEATURE:
<223> OTHER INFORMATION: cDNA of E1 kappa light chain variable region #2
      (E1 kappa(B))

<400> SEQUENCE: 46
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact taacctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggta gctcaatgta cacttttggc     360
caggggacca agctggagat caaa                                            384

<210> SEQ ID NO 47
<211> LENGTH: 390
<212> TYPE: DNA
<213> ORGANISM: Homo sapiens
<220> FEATURE:
<223> OTHER INFORMATION: cDNA of E13 kappa light chain variable region

<400> SEQUENCE: 47
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggta gctcacccat gtacactttt     360
```

```
ggccagggga ccaagctgga gatcaaacga                                    390
```

```
<210> SEQ ID NO 48
<211> LENGTH: 378
<212> TYPE: DNA
<213> ORGANISM: Homo sapiens
<220> FEATURE:
<223> OTHER INFORMATION: cDNA of E63 kappa light chain variable region

<400> SEQUENCE: 48
atgtcgccat cacaactcat tgggtttctg ctgctctggg ttccagcctc caggggtgaa    60
attgtgctga ctcagtctcc agactttcag tctgtgactc caaaggagaa agtcaccatc   120
acctgccggg ccagtcagag cattggtagt agcttacact ggtaccagca gaaaccagat   180
cagtctccaa agctcctcat caagtatgct cccagtcct tctcaggggt ccctcgagg     240 ttcagtggca gtggatctgg gacagatttc accctcacca tcaatagcct ggaagctgaa   300
gatgctgcag catattactg tcatcagagt agtagtttac ctctcacttt cggcggaggg   360
accaaggtgg agatcaaa                                                 378
```

```
<210> SEQ ID NO 49
<211> LENGTH: 387
<212> TYPE: DNA
<213> ORGANISM: Homo sapiens
<220> FEATURE:
<223> OTHER INFORMATION: cDNA of F19 kappa light chain variable region
      #2 (F19 kappa(B))

<400> SEQUENCE: 49
atggacatga gggtccccgc tcagctcctg gggcttctgc tgctctggct cccaggtgcc    60
agatgtgcca tccagttgac ccagtctcca tcctccctgt ctgcatctgt aggagacaga   120
gtcaccatca cttgccgggc aagtcagggc attaacagtg cttttgcctg gtatcagcag   180
aaaccaggga agctcctaa gctcctgatc tatgatgcct ccagtttgga aagtggggtc    240
ccatcaaggt tcagcggcag tggatctggg acagatttca ctctcaccat cagcagcctg   300
cagcctgaag attttgcaac ttattactgt caacagttta atagttaccc tctcactttc   360
ggcggaggga ccaaggtgga gatcaaa                                       387
```

```
<210> SEQ ID NO 50
<211> LENGTH: 387
<212> TYPE: DNA
<213> ORGANISM: Homo sapiens
<220> FEATURE:
<223> OTHER INFORMATION: cDNA of F23 kappa light chain variable region

<400> SEQUENCE: 50
atggacatga gggtccccgc tcagctcctg gggcttctgc tgctctggct cccaggtgcc    60
agatgtgcca tccagttgac ccagtctcca tcctccctgt ctgcatctgt aggagacaga   120
gtcaccatca cttgccgggc aagtcagggc attagcagtg ctttagcctg gtatcagcag   180
aaaccaggga agctcctaa gctcctgatc tatgatgcct ccagtttgga aagtggggtc    240
ccatcaaggt tcagcggcag tggatctggg acagatttca ctctcaccat cagcagcctg   300
cagcctgaag attttgcaac ttattactgt caacagttta atagttaccc gctcactttc   360
ggcggaggga ccaaggtgga gatcaaa                                       387
```

```
<210> SEQ ID NO 51
<211> LENGTH: 723
<212> TYPE: DNA
```

<213> ORGANISM: Homo sapiens
<220> FEATURE:
<223> OTHER INFORMATION: Nucleotide sequence of a hLIGHT

<400> SEQUENCE: 51

```
atggaggaga gtgtcgtacg gccctcagtg tttgtggtgg atggacagac cgacatccca      60
ttcacgaggc tgggacgaag ccaccggaga cagtcgtgca gtgtggcccg ggtgggtctg     120
ggtctcttgc tgttgctgat gggggccggg ctggccgtcc aaggctggtt cctcctgcag     180
ctgcactggc gtctaggaga gatggtcacc cgcctgcctg acggacctgc aggctcctgg     240
gagcagctga tacaagagcg aaggtctcac gaggtcaacc cagcagcgca tctcacaggg     300
gccaactcca gcttgaccgg cagcgggggg ccgctgttat gggagactca gctgggcctg     360
gccttcctga ggggcctcag ctaccacgat ggggcccttg tggtcaccaa agctggctac     420
tactacatct actccaaggt gcagctgggc ggtgtgggct gcccgctggg cctggccagc     480
accatcaccc acggcctcta caagcgcaca ccccgctacc ccgaggagct ggagctgttg     540
gtcagccagc agtcaccctg cggacgggcc accagcagct cccgggtctg gtgggacagc     600
agcttcctgg gtggtgtggt acacctggag gctggggagg aggtggtcgt ccgtgtgctg     660
gatgaacgcc tggttcgact gcgtgatggt acccggtctt acttcggggc tttcatggtg     720
tga                                                                   723
```

<210> SEQ ID NO 52
<211> LENGTH: 240
<212> TYPE: PRT
<213> ORGANISM: Homo sapiens
<220> FEATURE:
<223> OTHER INFORMATION: a full length hLIGHT

<400> SEQUENCE: 52

```
Met Glu Glu Ser Val Val Arg Pro Ser Val Phe Val Val Asp Gly Gln
  1               5                  10                  15

Thr Asp Ile Pro Phe Thr Arg Leu Gly Arg Ser His Arg Arg Gln Ser
             20                  25                  30

Cys Ser Val Ala Arg Val Gly Leu Gly Leu Leu Leu Leu Leu Met Gly
         35                  40                  45

Ala Gly Leu Ala Val Gln Gly Trp Phe Leu Leu Gln Leu His Trp Arg
     50                  55                  60

Leu Gly Glu Met Val Thr Arg Leu Pro Asp Gly Pro Ala Gly Ser Trp
 65                  70                  75                  80

Glu Gln Leu Ile Gln Glu Arg Arg Ser His Glu Val Asn Pro Ala Ala
                 85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
```

```
                195                 200                 205
Leu Glu Ala Gly Glu Glu Val Val Arg Val Leu Asp Glu Arg Leu
        210                 215                 220

Val Arg Leu Arg Asp Gly Thr Arg Ser Tyr Phe Gly Ala Phe Met Val
225                 230                 235                 240

<210> SEQ ID NO 53
<211> LENGTH: 630
<212> TYPE: DNA
<213> ORGANISM: Homo sapiens
<220> FEATURE:
<223> OTHER INFORMATION: a soluble FLAG-tagged hLIGHT (240 aa)

<400> SEQUENCE: 53
atgcctggga agatggtcgt gatccttgga gcctcaaata tactttggat aatgtttgca      60
gcttctcaag ctgactacaa ggacgacgat gacaagtacg taggagagat ggtcacccgc     120
ctgcctgacg gacctgcagg ctcctgggag cagctgatac aagagcgaag gtctcacgag     180
gtcaacccag cagcgcatct cacagggggcc aactccagct tgaccggcag cgggggggccg   240 ctgttatggg agactcagct gggcctggcc ttcctgaggg gcctcagcta ccacgatggg     300
gcccttgtgg tcaccaaagc tggctactac tacatctact ccaaggtgca gctgggcggt     360
gtgggctgcc cgctgggcct ggccagcacc atcacccacg gcctctacaa gcgcacaccc     420 cgctacccccg aggagctgga gctgttggtc agccagcagt cacccctgcgg acgggccacc   480 agcagctccc gggtctggtg gacagcagc ttcctgggtg gtgtggtaca cctggaggct     540
ggggaggagg tggtcgtccg tgtgctggat aacgcctgg ttcgactgcg tgatggtacc      600
cggtcttact cgggggctttt catggtgtga                                    630

<210> SEQ ID NO 54
<211> LENGTH: 183
<212> TYPE: PRT
<213> ORGANISM: Homo sapiens
<220> FEATURE:
<223> OTHER INFORMATION: a soluble FLAG-tagged hLIGHT (183 aa)

<400> SEQUENCE: 54

Asp Tyr Lys Asp Asp Asp Lys Gly Glu Met Val Thr Arg Leu Pro
  1               5                  10                  15

Asp Gly Pro Ala Gly Ser Trp Glu Gln Leu Ile Gln Glu Arg Arg Ser
            20                  25                  30

His Glu Val Asn Pro Ala Ala His Leu Thr Gly Ala Asn Ser Ser Leu
        35                  40                  45

Thr Gly Ser Gly Gly Pro Leu Leu Trp Glu Thr Gln Leu Gly Leu Ala
 50                  55                  60

Phe Leu Arg Gly Leu Ser Tyr His Asp Gly Ala Leu Val Val Thr Lys
65                  70                  75                  80

Ala Gly Tyr Tyr Tyr Ile Tyr Ser Lys Val Gln Leu Gly Gly Val Gly
                    85                  90                  95

Cys Pro Leu Gly Leu Ala Ser Thr Ile Thr His Gly Leu Tyr Lys Arg
            100                 105                 110

Thr Pro Arg Tyr Pro Glu Glu Leu Glu Leu Leu Val Ser Gln Gln Ser
        115                 120                 125

Pro Cys Gly Arg Ala Thr Ser Ser Ser Arg Val Trp Trp Asp Ser Ser
    130                 135                 140

Phe Leu Gly Gly Val Val His Leu Glu Ala Gly Glu Glu Val Val Val
145                 150                 155                 160
```

Arg Val Leu Asp Glu Arg Leu Val Arg Leu Arg Asp Gly Thr Arg Ser
                165                 170                 175

Tyr Phe Gly Ala Phe Met Val
            180

<210> SEQ ID NO 55
<211> LENGTH: 22
<212> TYPE: DNA
<213> ORGANISM: Artificial Sequence
<220> FEATURE:
<223> OTHER INFORMATION: primer RACEUPS5'

<400> SEQUENCE: 55
ctaatacgac tcactatagg gc                                            22

<210> SEQ ID NO 56
<211> LENGTH: 31
<212> TYPE: DNA
<213> ORGANISM: Artificial Sequence
<220> FEATURE:
<223> OTHER INFORMATION: primer IgG1p

<400> SEQUENCE: 56
tcttgtccac cttggtgttg ctgggcttgt g                                  31

<210> SEQ ID NO 57
<211> LENGTH: 30
<212> TYPE: DNA
<213> ORGANISM: Artificial Sequence
<220> FEATURE:
<223> OTHER INFORMATION: primer HK5

<400> SEQUENCE: 57
aggcacacaa cagaggcagt tccagatttc                                    30

<210> SEQ ID NO 58
<211> LENGTH: 18
<212> TYPE: DNA
<213> ORGANISM: Artificial Sequence
<220> FEATURE:
<223> OTHER INFORMATION: primer M13F

<400> SEQUENCE: 58
gtaaaacgac ggccagtg                                                 18

<210> SEQ ID NO 59
<211> LENGTH: 17
<212> TYPE: DNA
<213> ORGANISM: Artificial Sequence
<220> FEATURE:
<223> OTHER INFORMATION: primer M13R

<400> SEQUENCE: 59
caggaaacag ctatgac                                                  17

<210> SEQ ID NO 60
<211> LENGTH: 41
<212> TYPE: DNA
<213> ORGANISM: Artificial Sequence
<220> FEATURE:
<223> OTHER INFORMATION: primer E63HF85

<400> SEQUENCE: 60
agagagagag gtcgaccacc atgaaacacc tgtggttctt c                       41

<210> SEQ ID NO 61
<211> LENGTH: 37
<212> TYPE: DNA
<213> ORGANISM: Artificial Sequence
<220> FEATURE:
<223> OTHER INFORMATION: primer E63HR38

<400> SEQUENCE: 61
gagagagaga gctagctgag gagacggtga ccagggt       37

<210> SEQ ID NO 62
<211> LENGTH: 42
<212> TYPE: DNA
<213> ORGANISM: Artificial Sequence
<220> FEATURE:
<223> OTHER INFORMATION: primer E63LF84

<400> SEQUENCE: 62
agagagagag atctctcacc atgtcgccat cacaactcat tg       42

<210> SEQ ID NO 63
<211> LENGTH: 40
<212> TYPE: DNA
<213> ORGANISM: Artificial Sequence
<220> FEATURE:
<223> OTHER INFORMATION: primer E63LR43

<400> SEQUENCE: 63
agagagagag cgtacgtttg atctccacct tggtccctcc       40

<210> SEQ ID NO 64
<211> LENGTH: 25
<212> TYPE: DNA
<213> ORGANISM: Artificial Sequence
<220> FEATURE:
<223> OTHER INFORMATION: primer HH-2

<400> SEQUENCE: 64
gctggagggc acggtcacca cgctg       25

<210> SEQ ID NO 65
<211> LENGTH: 26
<212> TYPE: DNA
<213> ORGANISM: Artificial Sequence
<220> FEATURE:
<223> OTHER INFORMATION: primer HK-2

<400> SEQUENCE: 65
gttgaagctc tttgtgacgg gcgagc       26

<210> SEQ ID NO 66
<211> LENGTH: 41
<212> TYPE: DNA
<213> ORGANISM: Artificial Sequence
<220> FEATURE:
<223> OTHER INFORMATION: primer F23HF86

<400> SEQUENCE: 66
agagagagag gtcgaccacc atggacctcc tgcacaagaa c       41

<210> SEQ ID NO 67
<211> LENGTH: 34
<212> TYPE: DNA
<213> ORGANISM: Artificial Sequence
<220> FEATURE:
<223> OTHER INFORMATION: primer F23HR55

<400> SEQUENCE: 67
agagagagag gctagctgag gagacggtga ccgt                                34

<210> SEQ ID NO 68
<211> LENGTH: 42
<212> TYPE: DNA
<213> ORGANISM: Artificial Sequence
<220> FEATURE:
<223> OTHER INFORMATION: primer F23LF36

<400> SEQUENCE: 68
agagagagag atctctcacc atggacatga gggtccccgc tc                       42

<210> SEQ ID NO 69
<211> LENGTH: 40
<212> TYPE: DNA
<213> ORGANISM: Artificial Sequence
<220> FEATURE:
<223> OTHER INFORMATION: primer F23LR43

<400> SEQUENCE: 69
agagagagag cgtacgtttg atctccacct tggtccctcc                          40

<210> SEQ ID NO 70
<211> LENGTH: 41
<212> TYPE: DNA
<213> ORGANISM: Artificial Sequence
<220> FEATURE:
<223> OTHER INFORMATION: primer E1HFSalI

<400> SEQUENCE: 70
agagagagag gtcgaccacc atggagttgg ggctgtgctg g                        41

<210> SEQ ID NO 71
<211> LENGTH: 37
<212> TYPE: DNA
<213> ORGANISM: Artificial Sequence
<220> FEATURE:
<223> OTHER INFORMATION: primer E1HRNheI

<400> SEQUENCE: 71
agagagagag gctagctgag gagacggtga ccagggc                             37

<210> SEQ ID NO 72
<211> LENGTH: 41
<212> TYPE: DNA
<213> ORGANISM: Artificial Sequence
<220> FEATURE:
<223> OTHER INFORMATION: primer F19HFSalI

<400> SEQUENCE: 72
agagagagag gtcgaccacc atgaaacacc tgtggttctt c                        41

<210> SEQ ID NO 73
<211> LENGTH: 37
<212> TYPE: DNA
<213> ORGANISM: Artificial Sequence
<220> FEATURE:
<223> OTHER INFORMATION: primer F19HRNheI

<400> SEQUENCE: 73
agagagagag gctagctgag gagacggtga ccgtggt                             37

<210> SEQ ID NO 74

```
<211> LENGTH: 42
<212> TYPE: DNA
<213> ORGANISM: Artificial Sequence
<220> FEATURE:
<223> OTHER INFORMATION: primer E1KF2+3BglII

<400> SEQUENCE: 74
agagagagag atctctcacc atggaaaccc cagcgcagct tc                              42

<210> SEQ ID NO 75
<211> LENGTH: 40
<212> TYPE: DNA
<213> ORGANISM: Artificial Sequence
<220> FEATURE:
<223> OTHER INFORMATION: primer E1KR2BsiWI

<400> SEQUENCE: 75
agagagagag cgtacgtttg atctccagct tggtcccctg                                40

<210> SEQ ID NO 76
<211> LENGTH: 40
<212> TYPE: DNA
<213> ORGANISM: Artificial Sequence
<220> FEATURE:
<223> OTHER INFORMATION: primer E1KR3BsiWI

<400> SEQUENCE: 76
agagagagag cgtacgtttg atttccacct tggtcccttg                                40

<210> SEQ ID NO 77
<211> LENGTH: 40
<212> TYPE: DNA
<213> ORGANISM: Artificial Sequence
<220> FEATURE:
<223> OTHER INFORMATION: primer F19KR1+2BsiWI

<400> SEQUENCE: 77
agagagagag cgtacgtttg atctccacct tggtccctcc                                40

<210> SEQ ID NO 78
<211> LENGTH: 40
<212> TYPE: DNA
<213> ORGANISM: Artificial Sequence
<220> FEATURE:
<223> OTHER INFORMATION: primer F19KR3BsiWI

<400> SEQUENCE: 78
agagagagag cgtacgtttg atctccagct tggtcccctg                                40

<210> SEQ ID NO 79
<211> LENGTH: 42
<212> TYPE: DNA
<213> ORGANISM: Artificial Sequence
<220> FEATURE:
<223> OTHER INFORMATION: primer F19KF1+2+3BglII

<400> SEQUENCE: 79
agagagagag atctctcacc atggacatga gggtccccgc tc                             42

<210> SEQ ID NO 80
<211> LENGTH: 23
<212> TYPE: DNA
<213> ORGANISM: Artificial Sequence
<220> FEATURE:
<223> OTHER INFORMATION: forward primer

<400> SEQUENCE: 80
```

```
gtaggagaga tggtcacccg cct                                              23
```

```
<210> SEQ ID NO 81
<211> LENGTH: 37
<212> TYPE: DNA
<213> ORGANISM: Artificial Sequence
<220> FEATURE:
<223> OTHER INFORMATION: reverse primer

<400> SEQUENCE: 81
ggaacgcgaa ttcccacgtg tcagacccat gtccaat                               37
```

```
<210> SEQ ID NO 82
<211> LENGTH: 128
<212> TYPE: PRT
<213> ORGANISM: Homo sapiens
<220> FEATURE:
<223> OTHER INFORMATION: E1 kappa light chain variable region #1
      (E1 kappa(A))

<400> SEQUENCE: 82
```

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Arg Thr Leu Leu Ala Arg Gly Pro Ser Trp Arg Ser
        115                 120                 125

```
<210> SEQ ID NO 83
<211> LENGTH: 128
<212> TYPE: PRT
<213> ORGANISM: Homo sapiens
<220> FEATURE:
<223> OTHER INFORMATION: Amino acid sequence of cDNA of E1 kappa light
      chain variable region #3 (E1 kappa(C))

<400> SEQUENCE: 83
```

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Tyr Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Asn Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Trp Thr Phe Gly Gln Gly Thr Lys Val Glu Ile Lys
        115                 120                 125

<210> SEQ ID NO 84
<211> LENGTH: 11
<212> TYPE: PRT
<213> ORGANISM: Homo sapiens
<220> FEATURE:
<223> OTHER INFORMATION: CDR1 of E1 light chain variable region #1
      (E1 kappa(A))

<400> SEQUENCE: 84

Arg Ala Ser Gln Gly Ile Ser Ser Ala Leu Ala
1               5                   10

<210> SEQ ID NO 85
<211> LENGTH: 12
<212> TYPE: PRT
<213> ORGANISM: Homo sapiens
<220> FEATURE:
<223> OTHER INFORMATION: CDR1 of E1 light chain variable region #3
      (E1 kappa(C))

<400> SEQUENCE: 85

Arg Ala Ser Gln Ser Val Ser Ser Ser Tyr Leu Ala
1               5                   10

<210> SEQ ID NO 86
<211> LENGTH: 7
<212> TYPE: PRT
<213> ORGANISM: Homo sapiens
<220> FEATURE:
<223> OTHER INFORMATION: CDR2 of E1 light chain variable region #1
      (E1 kappa(A))

<400> SEQUENCE: 86

Asp Ala Ser Ser Leu Glu Ser
1               5

<210> SEQ ID NO 87
<211> LENGTH: 7
<212> TYPE: PRT
<213> ORGANISM: Homo sapiens
<220> FEATURE:
<223> OTHER INFORMATION: CDR2 of E1 light chain variable region #3
      (E1 kappa(C))

<400> SEQUENCE: 87

Gly Ala Ser Asn Arg Ala Thr
1               5

<210> SEQ ID NO 88
<211> LENGTH: 8
<212> TYPE: PRT
<213> ORGANISM: Homo sapiens
<220> FEATURE:
<223> OTHER INFORMATION: CDR3 of E1 light chain variable region #1
      (E1 kappa(A))

<400> SEQUENCE: 88

Gln Gln Phe Asn Ser Tyr Arg Thr
1               5

<210> SEQ ID NO 89
<211> LENGTH: 9

```
<212> TYPE: PRT
<213> ORGANISM: Homo sapiens
<220> FEATURE:
<223> OTHER INFORMATION: CDR3 of E1 light chain variable region #3
      (E1 kappa(C))

<400> SEQUENCE: 89

Gln Gln Tyr Gly Ser Ser Pro Trp Thr
  1               5

<210> SEQ ID NO 90
<211> LENGTH: 129
<212> TYPE: PRT
<213> ORGANISM: Homo sapiens
<220> FEATURE:
<223> OTHER INFORMATION: F19 kappa light chain variable region #1
      (F19 kappa(A))

<400> SEQUENCE: 90

Met Asp Met Arg Val Pro Ala Gln Leu Leu Gly Leu Leu Leu Leu Trp
  1               5                  10                  15

Val Pro Gly Ala Arg Cys Asp Ile Gln Leu Thr Gln Ser Pro Ser Ser
                 20                  25                  30

Leu Ser Ala Ser Val Gly Asp Arg Val Thr Ile Thr Cys Arg Val Ser
             35                  40                  45

Gln Gly Ile Ser Ser Tyr Leu Asn Trp Tyr Arg Gln Lys Pro Gly Lys
 50                  55                  60

Val Pro Lys Leu Leu Ile Tyr Ser Ala Ser Asn Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Val Ala Thr Tyr Tyr Gly Gln Arg
            100                 105                 110

Thr Tyr Asn Ala Pro Pro Thr Phe Gly Gly Gly Thr Lys Val Glu Ile
            115                 120                 125

Lys

<210> SEQ ID NO 91
<211> LENGTH: 129
<212> TYPE: PRT
<213> ORGANISM: Homo sapiens
<220> FEATURE:
<223> OTHER INFORMATION: F19 kappa light chain variable region #3
      (F19 kappa(C))

<400> SEQUENCE: 91

Met Asp Met Arg Val Pro Ala Gln Leu Leu Gly Leu Leu Leu Leu Trp
  1               5                  10                  15

Leu Pro Gly Ala Arg Cys Val Ile Trp Met Thr Gln Ser Pro Ser Leu
                 20                  25                  30

Leu Ser Ala Ser Thr Gly Asp Arg Val Thr Ile Ser Cys Arg Met Ser
             35                  40                  45

Gln Gly Ile Ser Ser Tyr Leu Ala Trp Tyr Gln Gln Lys Pro Gly Lys
 50                  55                  60

Ala Pro Glu Leu Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Cys Leu Gln Ser Glu Asp Phe Ala Thr Tyr Tyr Cys Gln Gln
            100                 105                 110
```

```
Tyr Tyr Ser Phe Pro Tyr Thr Phe Gly Gln Gly Thr Lys Leu Glu Ile
            115                 120                 125

Lys

<210> SEQ ID NO 92
<211> LENGTH: 126
<212> TYPE: PRT
<213> ORGANISM: Homo sapiens
<220> FEATURE:
<223> OTHER INFORMATION: Amino acid sequence of cDNA of F19 kappa light
      chain variable region #4 (F19 kappa(D))

<400> SEQUENCE: 92

Met Glu Ala Pro Ala Gln Leu Leu Phe Leu Leu Leu Leu Trp Leu Pro
 1               5                  10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Gly
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Pro Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp His Pro Val Arg Pro Arg Asp Gln Gly Gly Asp Ser
            115                 120                 125

<210> SEQ ID NO 93
<211> LENGTH: 11
<212> TYPE: PRT
<213> ORGANISM: Homo sapiens
<220> FEATURE:
<223> OTHER INFORMATION: CDR1 of F19 light chain variable region #1
      (F19 kappa(A))

<400> SEQUENCE: 93

Arg Val Ser Gln Gly Ile Ser Ser Tyr Leu Asn
 1               5                  10

<210> SEQ ID NO 94
<211> LENGTH: 11
<212> TYPE: PRT
<213> ORGANISM: Homo sapiens
<220> FEATURE:
<223> OTHER INFORMATION: CDR1 of F19 light chain variable region #3
      (F19 kappa(C))

<400> SEQUENCE: 94

Arg Met Ser Gln Gly Ile Ser Ser Tyr Leu Ala
 1               5                  10

<210> SEQ ID NO 95
<211> LENGTH: 11
<212> TYPE: PRT
<213> ORGANISM: Homo sapiens
<220> FEATURE:
<223> OTHER INFORMATION: CDR1 of F19 light chain variable region #4
      (F19 kappa(D))

<400> SEQUENCE: 95
```

Arg Ala Ser Gln Gly Val Ser Ser Tyr Leu Ala
1               5                   10

<210> SEQ ID NO 96
<211> LENGTH: 7
<212> TYPE: PRT
<213> ORGANISM: Homo sapiens
<220> FEATURE:
<223> OTHER INFORMATION: CDR2 of F19 light chain variable region #1
      (F19 kappa(A))

<400> SEQUENCE: 96

Ser Ala Ser Asn Leu Gln Ser
1               5

<210> SEQ ID NO 97
<211> LENGTH: 7
<212> TYPE: PRT
<213> ORGANISM: Homo sapiens
<220> FEATURE:
<223> OTHER INFORMATION: CDR2 of F19 light chain variable region #3
      (F19 kappa(C))

<400> SEQUENCE: 97

Ala Ala Ser Thr Leu Gln Ser
1               5

<210> SEQ ID NO 98
<211> LENGTH: 7
<212> TYPE: PRT
<213> ORGANISM: Homo sapiens
<220> FEATURE:
<223> OTHER INFORMATION: CDR2 of F19 light chain variable region #4
      (F19 kappa(D))

<400> SEQUENCE: 98

Asp Ala Ser Asn Arg Ala Thr
1               5

<210> SEQ ID NO 99
<211> LENGTH: 8
<212> TYPE: PRT
<213> ORGANISM: Homo sapiens
<220> FEATURE:
<223> OTHER INFORMATION: CDR3 of F19 light chain variable region #1
      (F19 kappa(A))

<400> SEQUENCE: 99

Gln Arg Thr Asn Ala Pro Pro Thr
1               5

<210> SEQ ID NO 100
<211> LENGTH: 9
<212> TYPE: PRT
<213> ORGANISM: Homo sapiens
<220> FEATURE:
<223> OTHER INFORMATION: CDR3 of F19 light chain variable region #3
      (F19 kappa(C))

<400> SEQUENCE: 100

Gln Gln Tyr Tyr Ser Phe Pro Tyr Thr
1               5

<210> SEQ ID NO 101
<211> LENGTH: 8
<212> TYPE: PRT
<213> ORGANISM: Homo sapiens
<220> FEATURE:
<223> OTHER INFORMATION: CDR3 of F19 light chain variable region #4
       (F19 kappa(D))

<400> SEQUENCE: 101

Gln Gln Arg Ser Asn Trp His Pro
 1               5

<210> SEQ ID NO 102
<211> LENGTH: 386
<212> TYPE: DNA
<213> ORGANISM: Homo sapiens
<220> FEATURE:
<223> OTHER INFORMATION: cDNA of E1 kappa light chain variable region #1
       (E1 kappa(A))

<400> SEQUENCE: 102
atggacatga gggtccccgc tcagctcctg gggcttctgc tgctctggct cccaggtgcc    60
agatgtgcca tccagttgac ccagtctcca tcctccctgt ctgcatctgt aggagacaga   120
gtcaccatca cttgccgggc aagtcagggc attagcagtg ctttagcctg gtatcagcag   180
aaaccaggga agctcctaa gctcctgatc tatgatgcct ccagtttgga aagtggggtc    240
ccatcaaggt tcagcggcag tggatctggg acagatttca ctctcaccat cagcagcctg   300
cagcctgaag attttgcaac ttattactgt caacagttta atagttaccg tacacttttg   360 gccagggga caagctggag atcaaa                                         386

<210> SEQ ID NO 103
<211> LENGTH: 384
<212> TYPE: DNA
<213> ORGANISM: Homo sapiens
<220> FEATURE:
<223> OTHER INFORMATION: cDNA of E1 kappa light chain variable region #3
       (E1 kappa(C))

<400> SEQUENCE: 103
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctaca gggccagtca gagtgttagc agcagctact tagcctggta ccagcagaaa   180
cctggccagg ctcccaggct cctcatctat ggtgcatcca cagggccac tggcatccca    240 gacaggttca gtggcagtgg gtctgggaca gacttcactc tcaccatcag cagactggag   300
cctgaagatt ttgcagtgta ttactgtcag cagtatggta gctcaccgtg acgttcggc    360 caagggacca aggtggaaat caaa                                          384

<210> SEQ ID NO 104
<211> LENGTH: 387
<212> TYPE: DNA
<213> ORGANISM: Homo sapiens
<220> FEATURE:
<223> OTHER INFORMATION: cDNA of F19 kappa light chain variable region
       #1 (F19 kappa(A))

<400> SEQUENCE: 104
atggacatga gggtccccgc tcagctcctg gggctcctac tgctctgggt cccaggtgcc    60
agatgtgaca tccagttgac ccagtctcca tcctccctgt ctgcatctgt aggagacaga   120
gtcaccatca cttgccgggt gagtcagggc attagcagtt atttaaattg gtatcggcag   180
aaaccaggga agttcctaa gctcctgatc tatagtgcat ccaatttgca atctggagtc    240
ccatctcggt tcagtggcag tggatctggg acagatttca ctctcactat cagcagcctg   300

-continued

```
cagcctgaag atgttgcaac ttattacggt caacggactt acaatgcccc tcccactttc    360
ggcggaggga ccaaggtgga gatcaaa                                        387

<210> SEQ ID NO 105
<211> LENGTH: 387
<212> TYPE: DNA
<213> ORGANISM: Homo sapiens
<220> FEATURE:
<223> OTHER INFORMATION: cDNA of F19 kappa chain variable region #3
      (F19 kappa(C))

<400> SEQUENCE: 105
atggacatga gggtccccgc tcagctcctg gggctcctgc tgctctggct cccaggtgcc     60
agatgtgtca tctggatgac ccagtctcca tccttactct ctgcatctac aggagacaga   120
gtcaccatca gttgtcggat gagtcagggc attagcagtt atttagcctg gtatcagcaa   180
aaaccaggga agcccctga gctcctgatc tatgctgcat ccactttgca aagtggggtc    240
ccatcaaggt tcagtggcag tggatctggg acagatttca ctctcaccat cagctgcctg   300
cagtctgaag attttgcaac ttattactgt caacagtatt atagtttccc gtacactttt   360
ggccagggga ccaagctgga gatcaaa                                       387

<210> SEQ ID NO 106
<211> LENGTH: 380
<212> TYPE: DNA
<213> ORGANISM: Homo sapiens
<220> FEATURE:
<223> OTHER INFORMATION: cDNA of F19 kappa chain variable region #4
      (F19 kappa(D))

<400> SEQUENCE: 106
atggaagccc cagcgcagct tctcttcctc ctgctactct ggctcccaga taccaccgga    60
gaaattgtgt tgacacagtc tccagccacc ctgtctttgt ctccagggga aagagccacc   120
ctctcctgca gggccagtca gggtgttagc agctacttag cctggtacca gcagaaacct   180
ggccaggctc ccaggctcct catctatgat gcatccaaca gggccactgg catcccagcc   240
aggttcagtg gcagtgggcc tgggacagac ttcactctca ccatcagcag cctagagcct   300
gaagattttg cagtttatta ctgtcagcag cgtagcaact ggcatcccgt tcggccaagg   360
gaccaaggtg gagattcaaa                                               380
```